US012331083B2

(12) United States Patent
Sei et al.

(10) Patent No.: US 12,331,083 B2
(45) Date of Patent: Jun. 17, 2025

(54) IMMUNOGENIC COMPOSITIONS TO TREAT AND PREVENT MICROBIAL INFECTIONS

(71) Applicant: Longhorn Vaccines and Diagnostics, LLC, Bethesda, MD (US)

(72) Inventors: Clara J. Sei, Germantown, MD (US); Luke T. Daum, San Antonio, TX (US); Gerald W. Fischer, Bethesda, MD (US)

(73) Assignee: Longhorn Vaccines and Diagnostics, LLC, Bethesda, MD (US)

( * ) Notice: Subject to any disclaimer, the term of this patent is extended or adjusted under 35 U.S.C. 154(b) by 0 days.

(21) Appl. No.: 18/527,937

(22) Filed: Dec. 4, 2023

(65) Prior Publication Data

US 2024/0166697 A1 May 23, 2024

Related U.S. Application Data

(63) Continuation of application No. 17/161,997, filed on Jan. 29, 2021, now Pat. No. 11,866,463.

(60) Provisional application No. 63/109,966, filed on Nov. 5, 2020, provisional application No. 62/971,654, filed on Feb. 7, 2020, provisional application No. 62/971,036, filed on Feb. 6, 2020.

(51) Int. Cl.
*A61K 39/02* (2006.01)
*A61K 39/145* (2006.01)
*A61K 39/395* (2006.01)
*A61K 47/54* (2017.01)
*A61K 47/69* (2017.01)
*A61P 31/16* (2006.01)
*C07K 14/11* (2006.01)
*C07K 14/195* (2006.01)
*A61K 38/00* (2006.01)

(52) U.S. Cl.
CPC .............. *C07K 14/11* (2013.01); *A61K 39/02* (2013.01); *A61K 39/145* (2013.01); *A61K 39/395* (2013.01); *A61K 47/543* (2017.08); *A61K 47/549* (2017.08); *A61K 47/6911* (2017.08); *A61P 31/16* (2018.01); *C07K 14/195* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,652,782 B2 | 2/2014 | Fischer | |
| 8,821,885 B2 | 9/2014 | Fischer | |
| 9,388,220 B2 | 7/2016 | Fischer | |
| 9,481,912 B2 | 11/2016 | Fischer | |
| 9,598,462 B2 * | 3/2017 | Fischer | C07K 14/005 |
| 9,777,045 B2 | 10/2017 | Fischer | |
| 9,821,047 B2 | 11/2017 | Fischer | |
| 10,004,799 B2 * | 6/2018 | Fischer | C07K 14/35 |
| 10,370,437 B2 | 8/2019 | Fischer | |
| 10,414,819 B2 | 9/2019 | Fischer | |
| 10,596,250 B2 | 3/2020 | Fischer | |
| 10,787,504 B2 | 9/2020 | Fischer | |
| 2008/0260773 A1 | 10/2008 | Del Giudice | |
| 2009/0081202 A1 | 3/2009 | Fischer | |
| 2009/0233309 A1 | 9/2009 | Fischer | |
| 2013/0195909 A1 * | 8/2013 | Fischer | C07K 7/08 536/23.4 |
| 2015/0056609 A1 | 2/2015 | Daum | |

OTHER PUBLICATIONS

International Preliminary Search Report and Opinion for Application No. PCT/US2021/15757 dated Jun. 9, 2021.
Landry Nathalie et al: "Influenza virus-like particle vaccines made inNicotiana benthamianaelicit durable, poly-functional and cross-reactive T cell responses to influenza HA antigens", Clinical Immunology, Elsevier, Amsterdam, NL vol. 154, No. 2, Aug. 14, 2014 (Aug. 14, 2014) , pp.
Search Report for EP Application No. 21750004 Dated Jan. 23, 2024.
Exam Report for EP Application No. 21750004 Dated Jan. 23, 2024.
W.P. Poh: "Characterization of cytotoxic 1, 2, 4-15 T-lymphocyte epitopes and immune responses to SARS coronavirus spike DNA vaccine expressing the RGD-integrin-binding motif", Journal of Medical Virology, vol. 81, No. 7, May 27, 2009 (May 27, 2009).
Search Report for EP Application No. 21750004 Dated Apr. 26, 2024.
Exam Report for EP Application No. 21750004 Dated Apr. 26, 2024.
Exam Report for KR Application No. 10-2022=7030824 Dated Dec. 11, 2024.
Exam Report for KR Application No. 10-2022=7030824 Dated Dec. 11, 2024 (translated).
Exam Report for EP Application No. 21750004.0 Dated Mar. 5, 2025.
Huang Chaolin et al: "Clinical features of patients infected with 2019 novel coronavirus in Wuhan, China", The Lancet, Elsevier, Amsterdam, NL, vol. 395, No. 10223, Jan. 24, 2020 (Jan. 24, 2020), pp. 497-506, XP086050317, ISSN: 0140-6736, DOI: 10.1016/S0140-6736(20)30183-5 [retrieved on Jan. 24, 2020].
Database EMBL [Online] EBI; Jan. 15, 2020 (Jan. 15, 2020), Zhang Y.-Z. et al: "Wuhan seafood market pneumonia virus isolate Wuhan-Hu-1, complete genome.", XP055796635, Database accession No. MN908947.

* cited by examiner

*Primary Examiner* — Agnieszka Boesen
(74) *Attorney, Agent, or Firm* — Remenick PLLC

(57) ABSTRACT

The invention relates to composite antigens comprising a peptide with contiguous amino acid sequence derived from a plurality of antigenic epitopes of one or more pathogens that induces an immune response in a mammal that is protective against infection by the one or more pathogens. In addition, the invention also relates to antibodies to composite antigens of the invention and to methods of administering vaccines comprising antigens or vaccines of antibodies for treating and/or preventing an infection.

18 Claims, 83 Drawing Sheets

Specification includes a Sequence Listing.

FIG. 1

PEPTIDE CONJUGATES IN ICR MICE VACCINE AND THERAPEUTIC APPROACHES
FEMALE ICR MICE: 24 MICE WITH 3 PER GROUP

| FLU VACCINE PROJECT LH/FLU PROJECT N ANIMAL STUDY NUMBER | FLU VACCINE PROJECT LH/FLU PROJECT N ANIMAL STUDY NUMBER | GROUPS | ANIMAL TAG ID N=24 | ADJUVANT |
|---|---|---|---|---|
| LH/N: 'FLU PEP11 + (TT T-CELL EPITOPE) CONJUGATED (MOS779.PEP63 @450ug/mL) | LH/N: FLUVAC 005.A 2020 | GROUP 8<br>PEP 63 - CRM-CONJUGATED: 'DOSE (20ug) - SQ<br>FLU PEP11 + TETANUS T-CELL EPITOPE IN C-TERMINUS | 2136<br>2137<br>2138 | ADDAVAX |
| | LH/N: FLUVAC 005.B 2020 | GROUP 9<br>PEP 63 - CRM-CONJUGATED: 'DOSE (2.5ug) - SQ<br>FLU PEP11 + TETANUS T-CELL EPITOPE IN C-TERMINUS | 2139<br>2140<br>2141 | ADDAVAX |
| LH/N: 'FLU PEP11 + (TT T-CELL EPITOPE) CONJUGATED (MOS780.PEP64 @400ug/mL) | LH/N: FLUVAC 005.C 2020 | GROUP 10<br>PEP 64 - CRM-CONJUGATED: 'DOSE (20ug) - SQ<br>FLU PEP11 + TETANUS T-CELL EPITOPE IN N-TERMINUS | 2142<br>2143<br>2144 | ADDAVAX |
| | LH/N: FLUVAC 005.D 2020 | GROUP 11<br>PEP 64 - CRM-CONJUGATED: 'DOSE (2.5ug) - SQ<br>FLU PEP11 + TETANUS T-CELL EPITOPE IN N-TERMINUS | 2145<br>2146<br>2147 | ADDAVAX |
| LH/N: 'FLU PEP11 + (TT T-CELL EPITOPE) UNCONJUGATED (PEP63 @500ug/mL) | LH/N: FLUVAC 005.E 2020 | GROUP 12<br>PEP 63 - UNCONJUGATED: 'DOSE (20ug) - SQ<br>FLU PEP11 + TETANUS T-CELL EPITOPE IN C-TERMINUS | 2148<br>2149<br>2150 | ADDAVAX |
| | LH/N: FLUVAC 005.F 2020 | GROUP 13<br>PEP 63 - UNCONJUGATED: 'DOSE (2.5ug) - SQ<br>FLU PEP11 + TETANUS T-CELL EPITOPE IN C-TERMINUS | 2151<br>2152<br>2153 | ADDAVAX |
| LH/N: 'FLU PEP11 + (TT T-CELL EPITOPE) UNCONJUGATED (PEP64 @1000ug/mL) | LH/N: FLUVAC 005.G 2020 | GROUP 14<br>PEP 64 - UNCONJUGATED: 'DOSE (20ug) - SQ<br>FLU PEP11 + TETANUS T-CELL EPITOPE IN N-TERMINUS | 2154<br>2155<br>2156 | ADDAVAX |
| | LH/N: FLUVAC 005.H 2020 | GROUP 15<br>PEP 64 - UNCONJUFATED: 'DOSE (2.5ug) - SQ<br>FLU PEP11 + TETANUS T-CELL EPITOPE IN N-TERMINUS | 2157<br>2158<br>2159 | ADDAVAX |

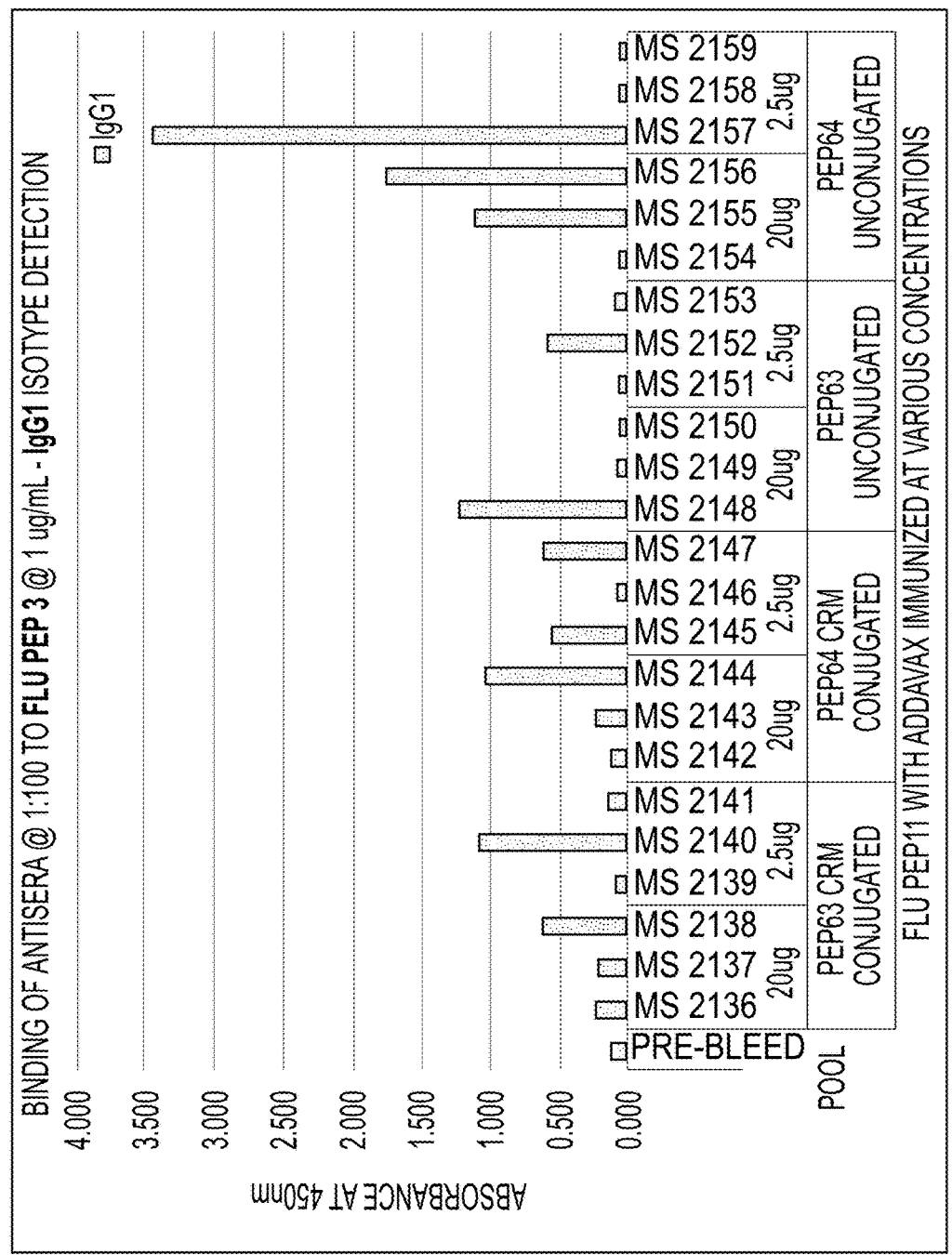
FIG. 2 (CONT. -1)

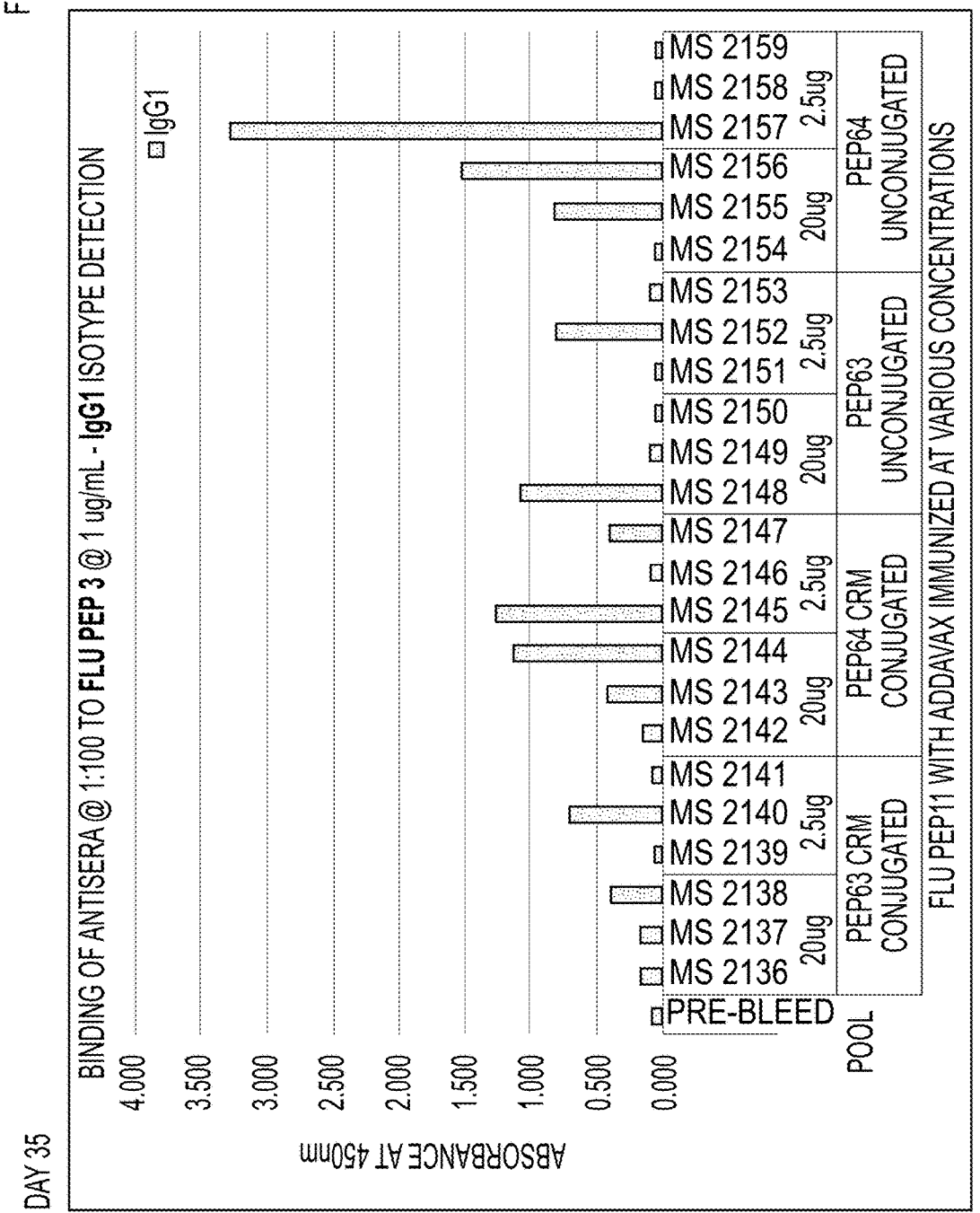
FIG. 2 (CONT. -2)

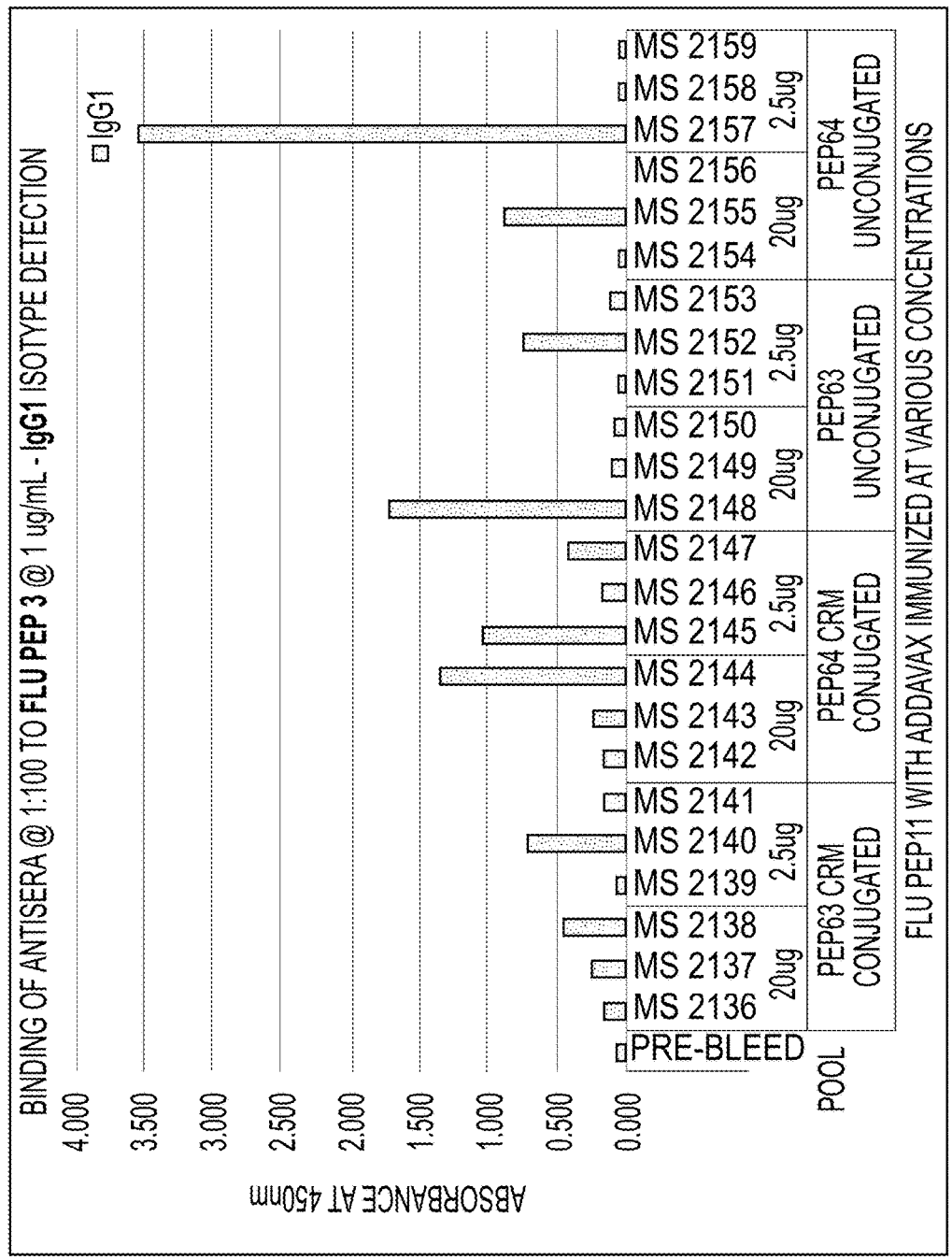
FIG. 2 (CONT. -3)

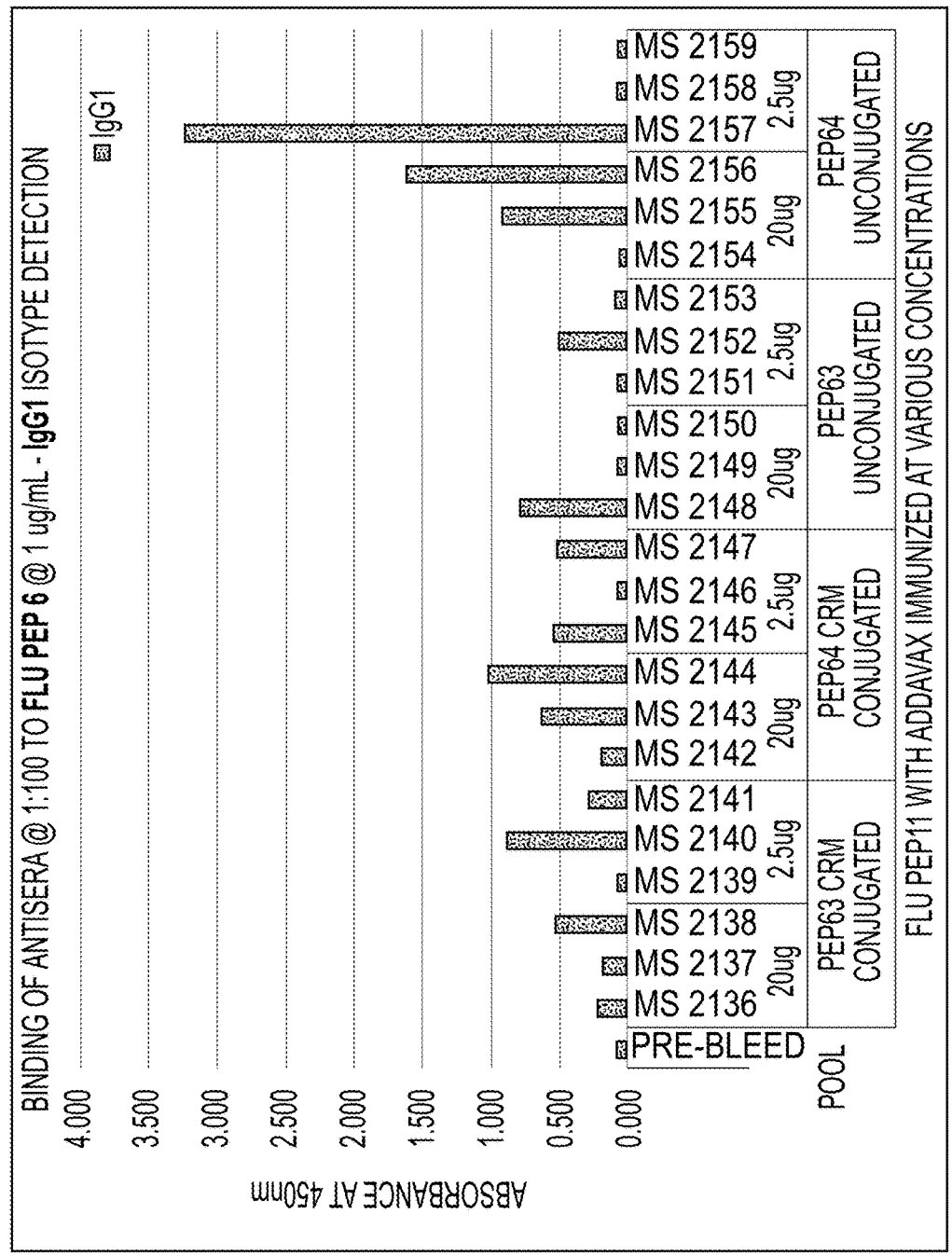
FIG. 3 (CONT. -1)

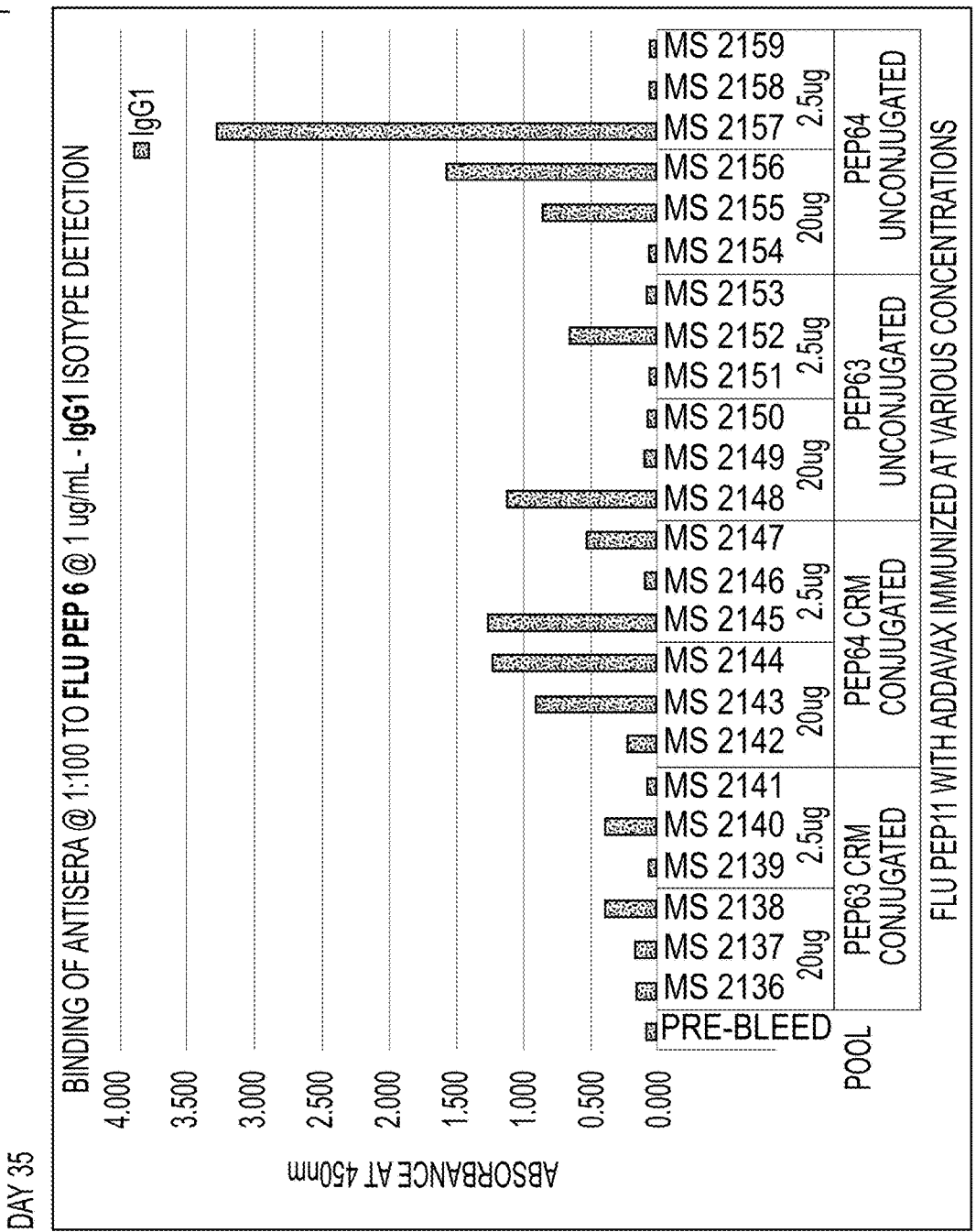
FIG. 3 (CONT. -2)

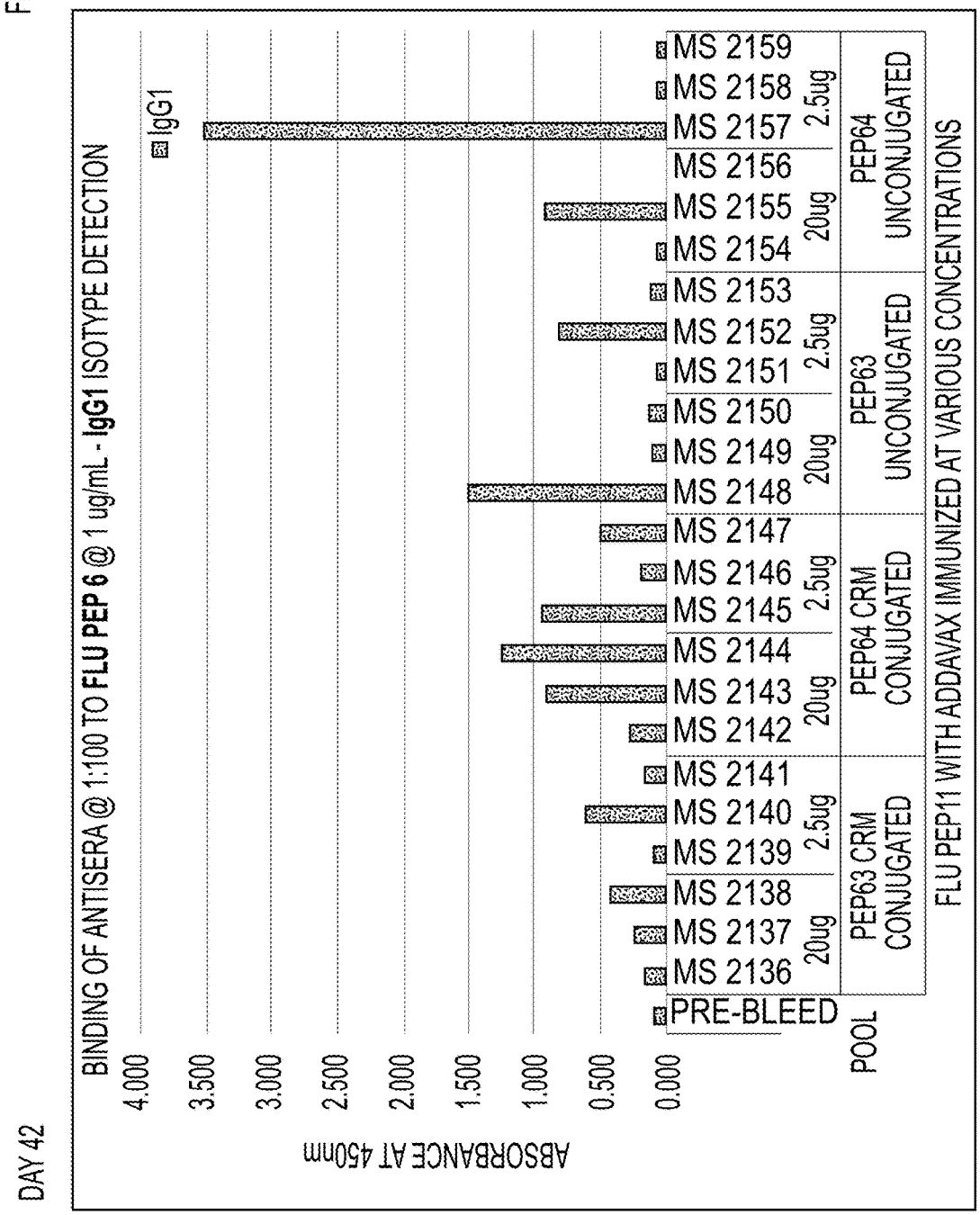
FIG. 3 (CONT. -3)

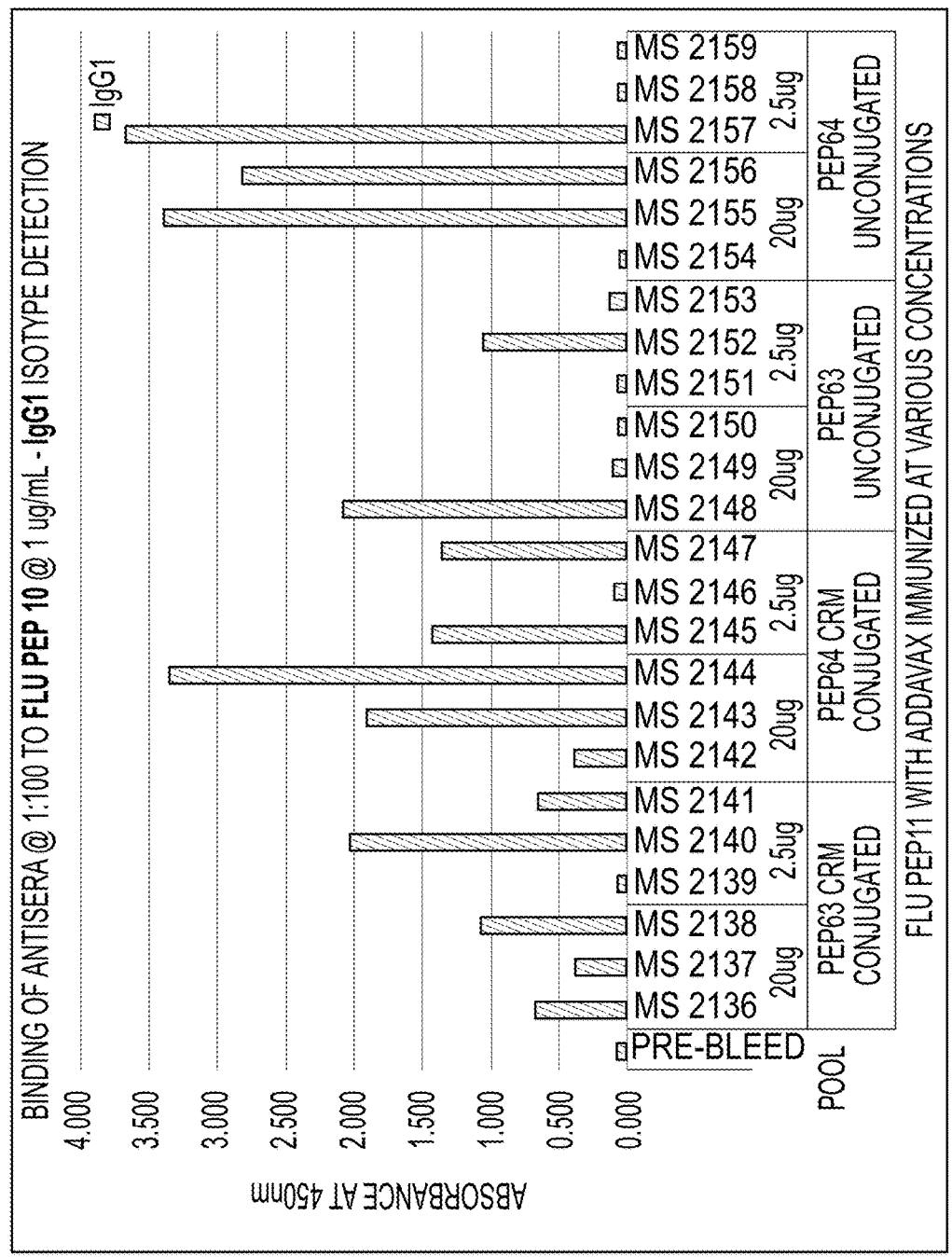
FIG. 4 (CONT. -1)

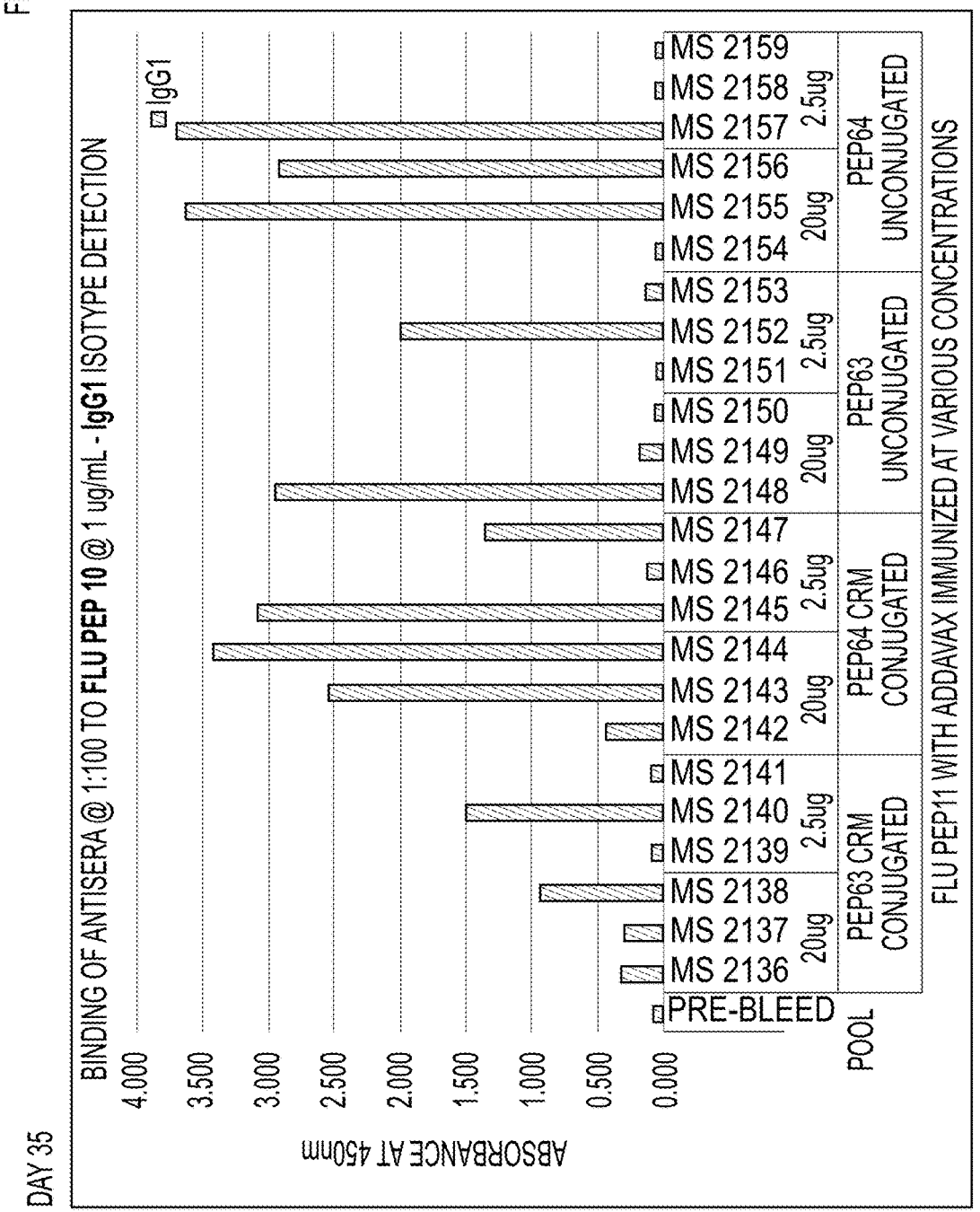
FIG. 4 (CONT. -2)

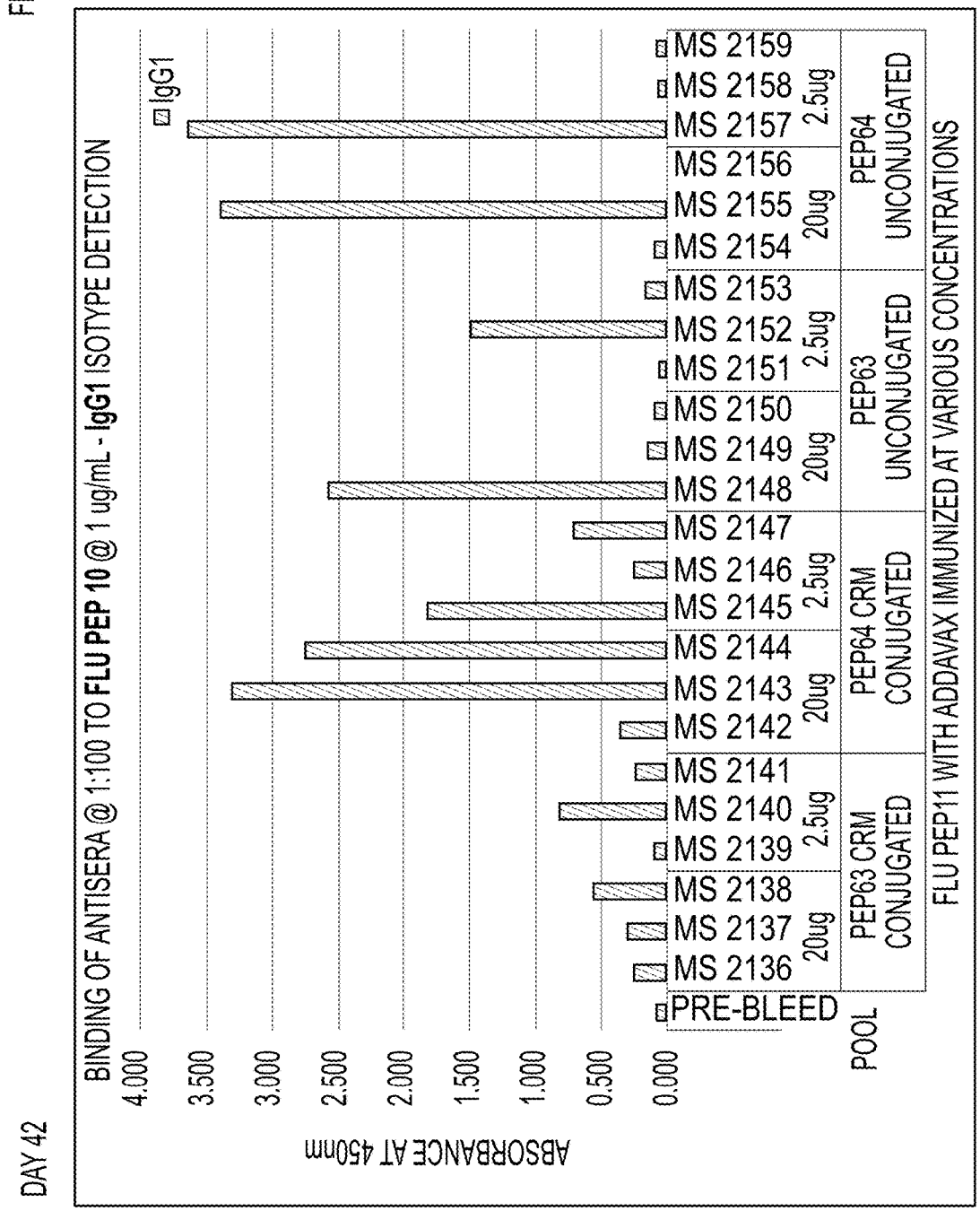
FIG. 4 (CONT. -3)

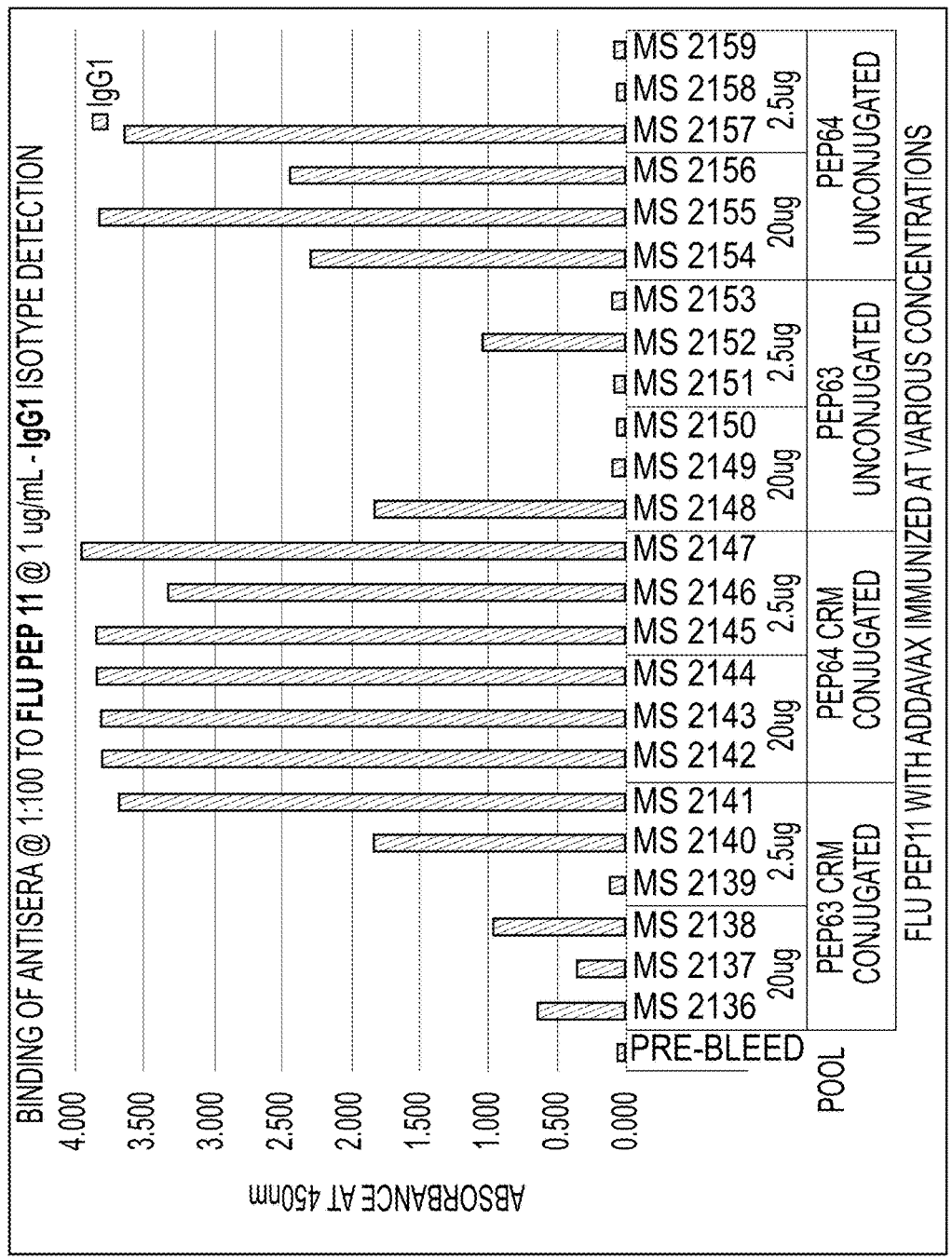
FIG. 5 (CONT. -1)

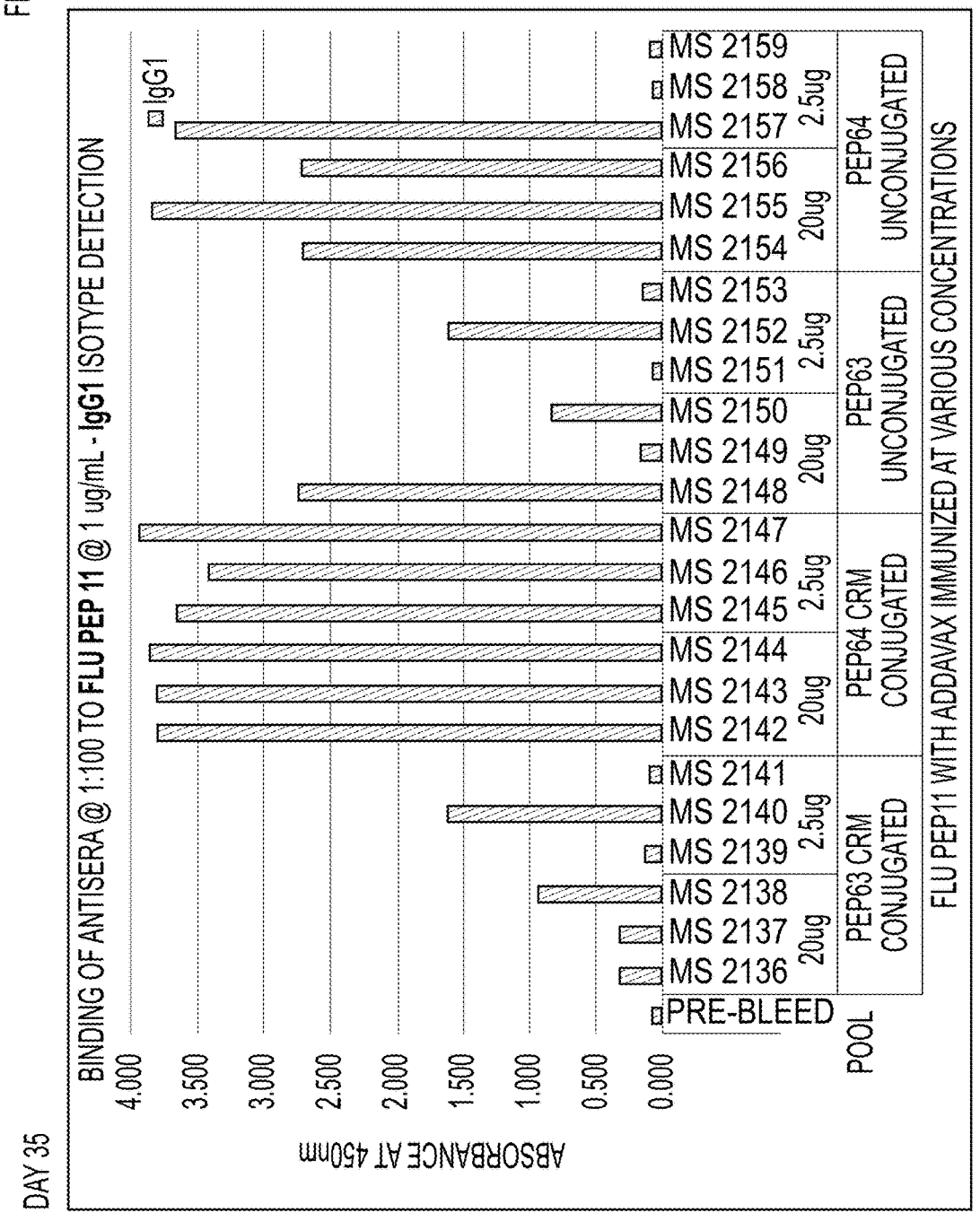
FIG. 5 (CONT. -2)

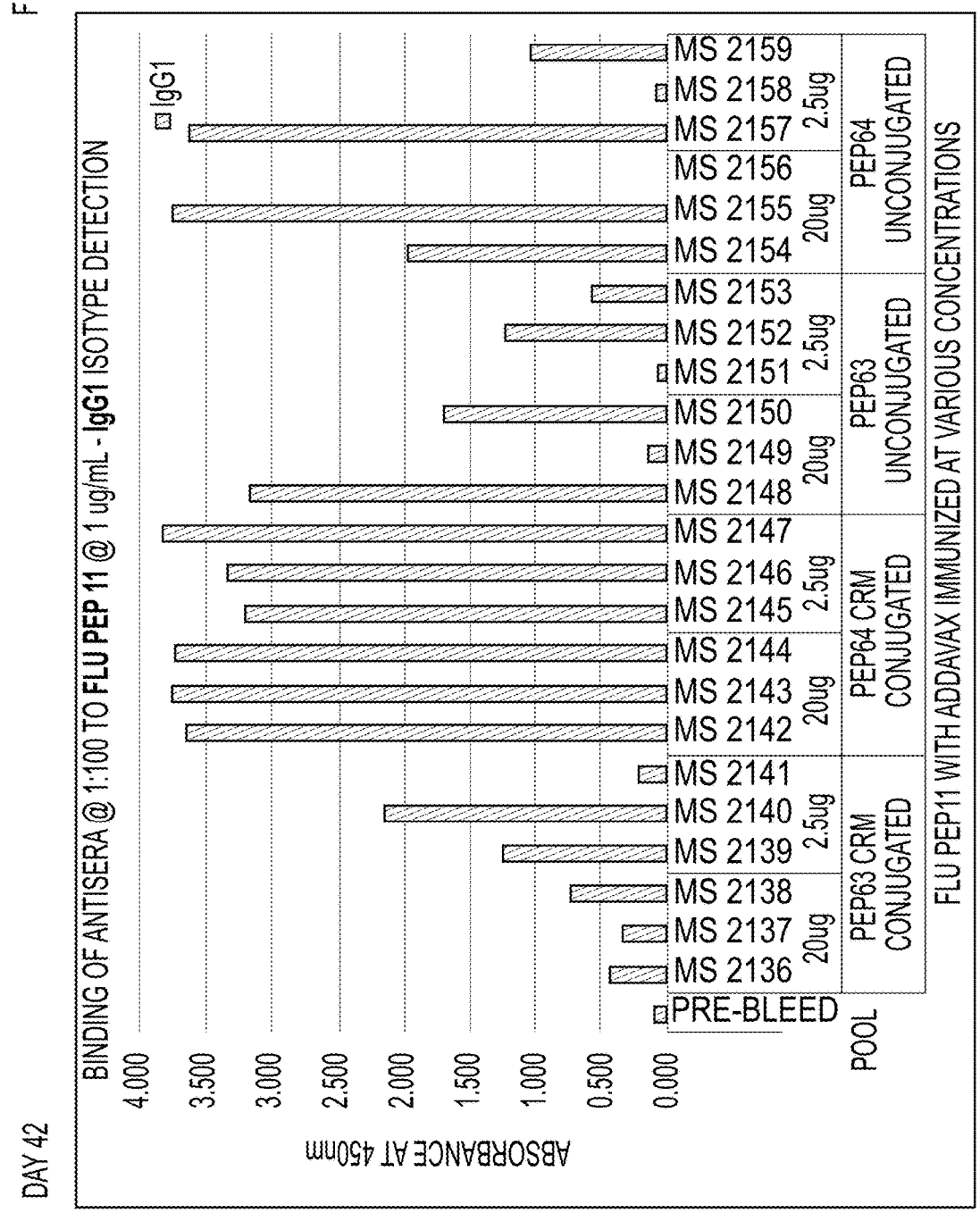
FIG. 5 (CONT. -3)

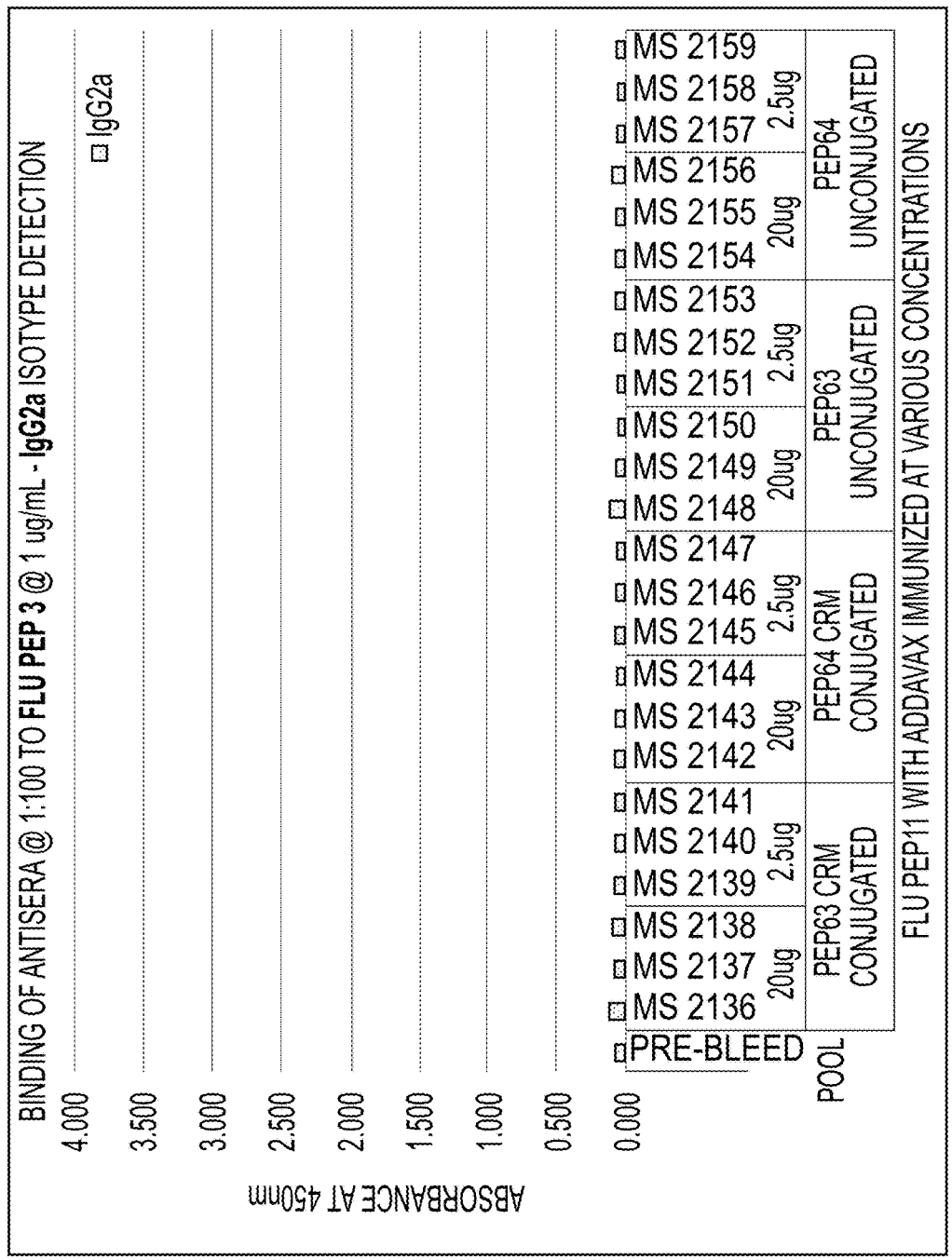
FIG. 6 (CONT. -1)

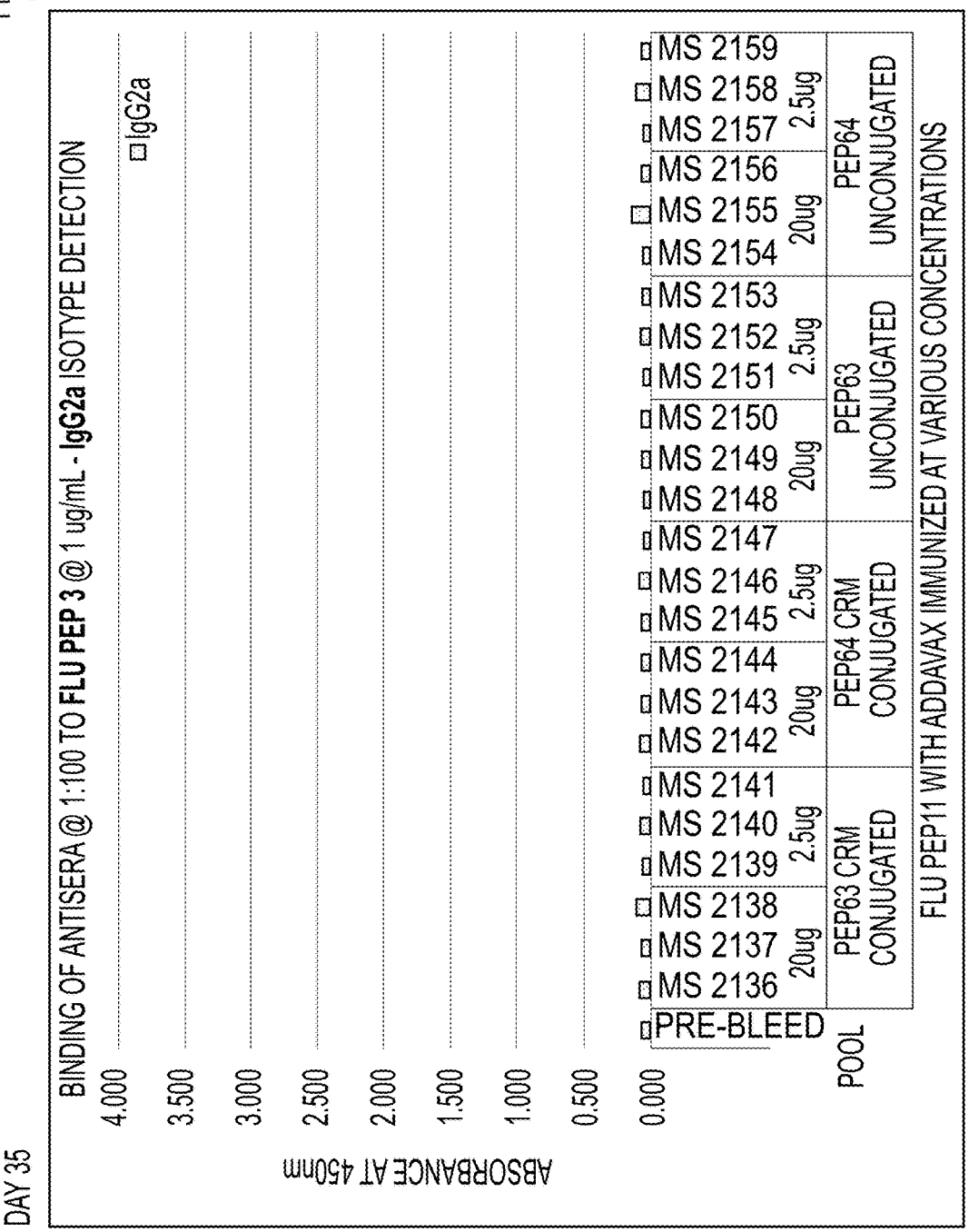
FIG. 6 (CONT. -2)

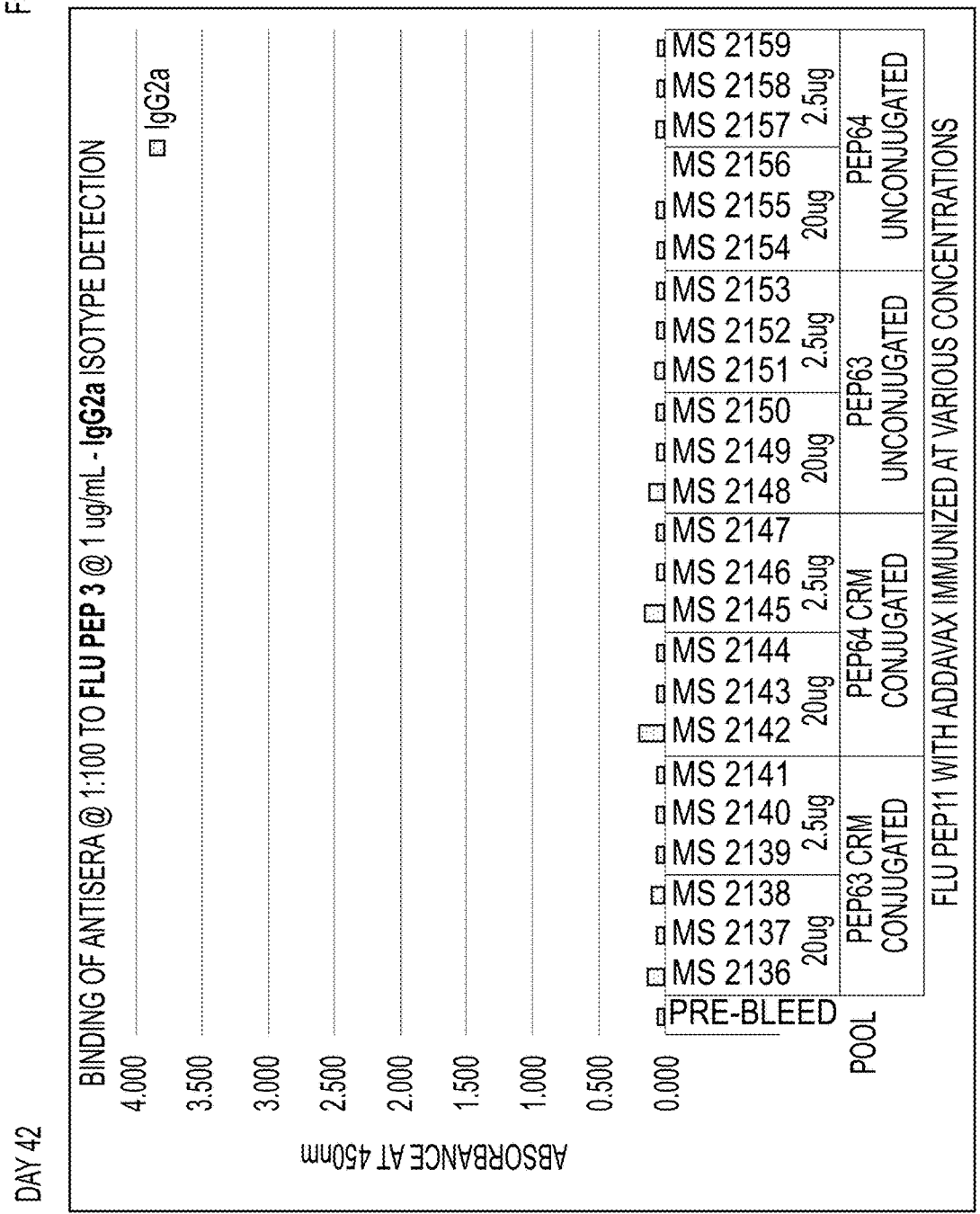
FIG. 6 (CONT. -3)

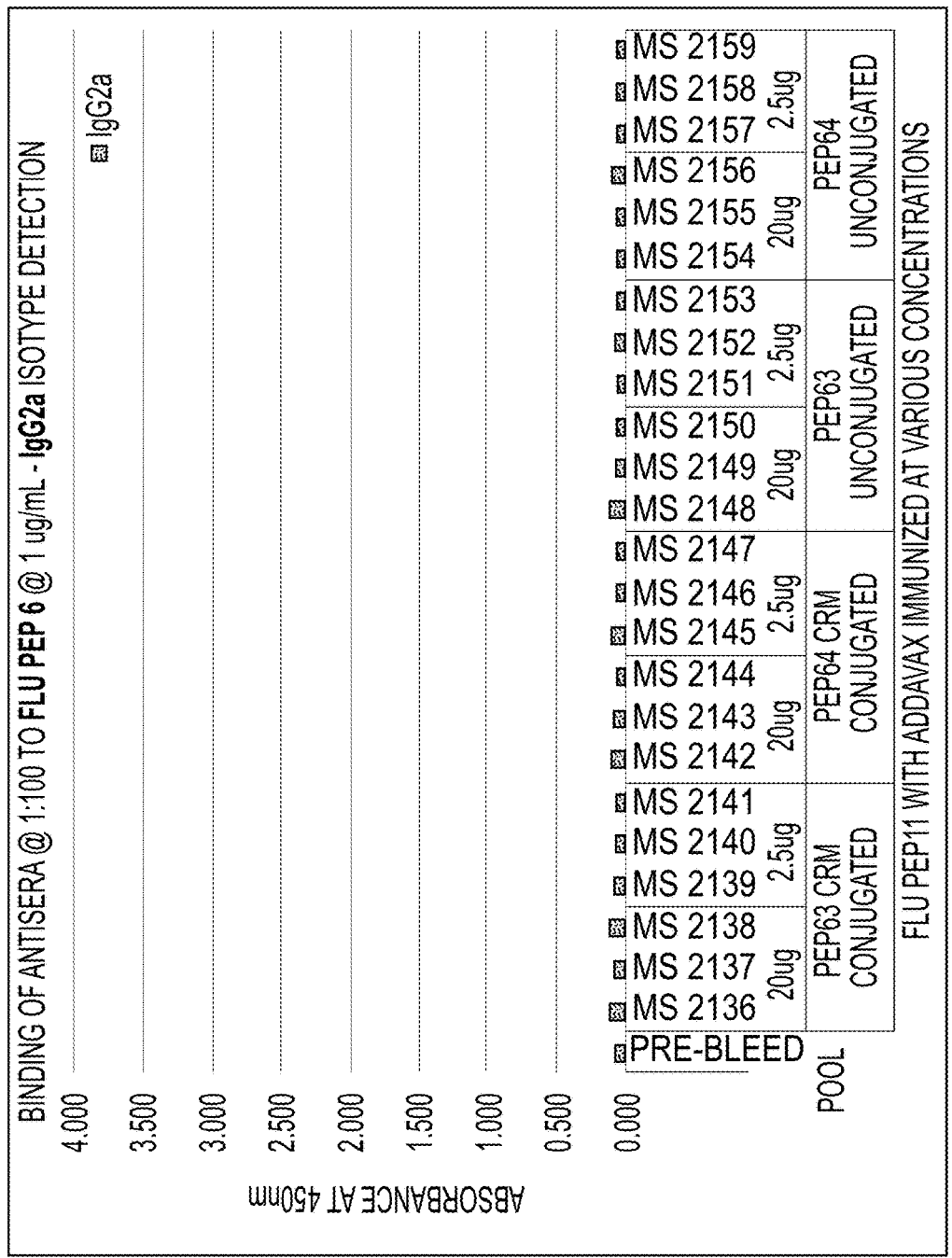
FIG. 7 (CONT. -1)

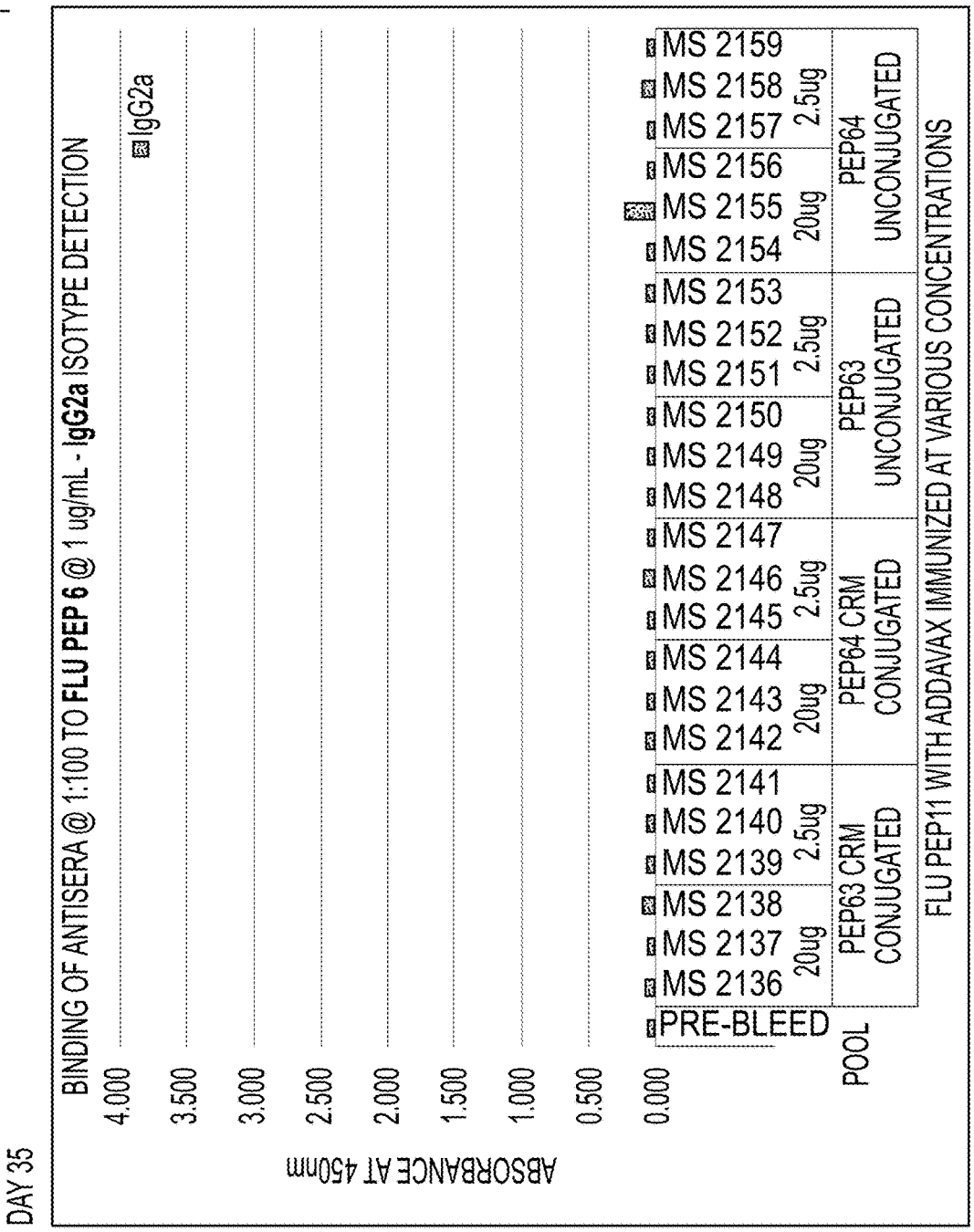
FIG. 7 (CONT. -2)

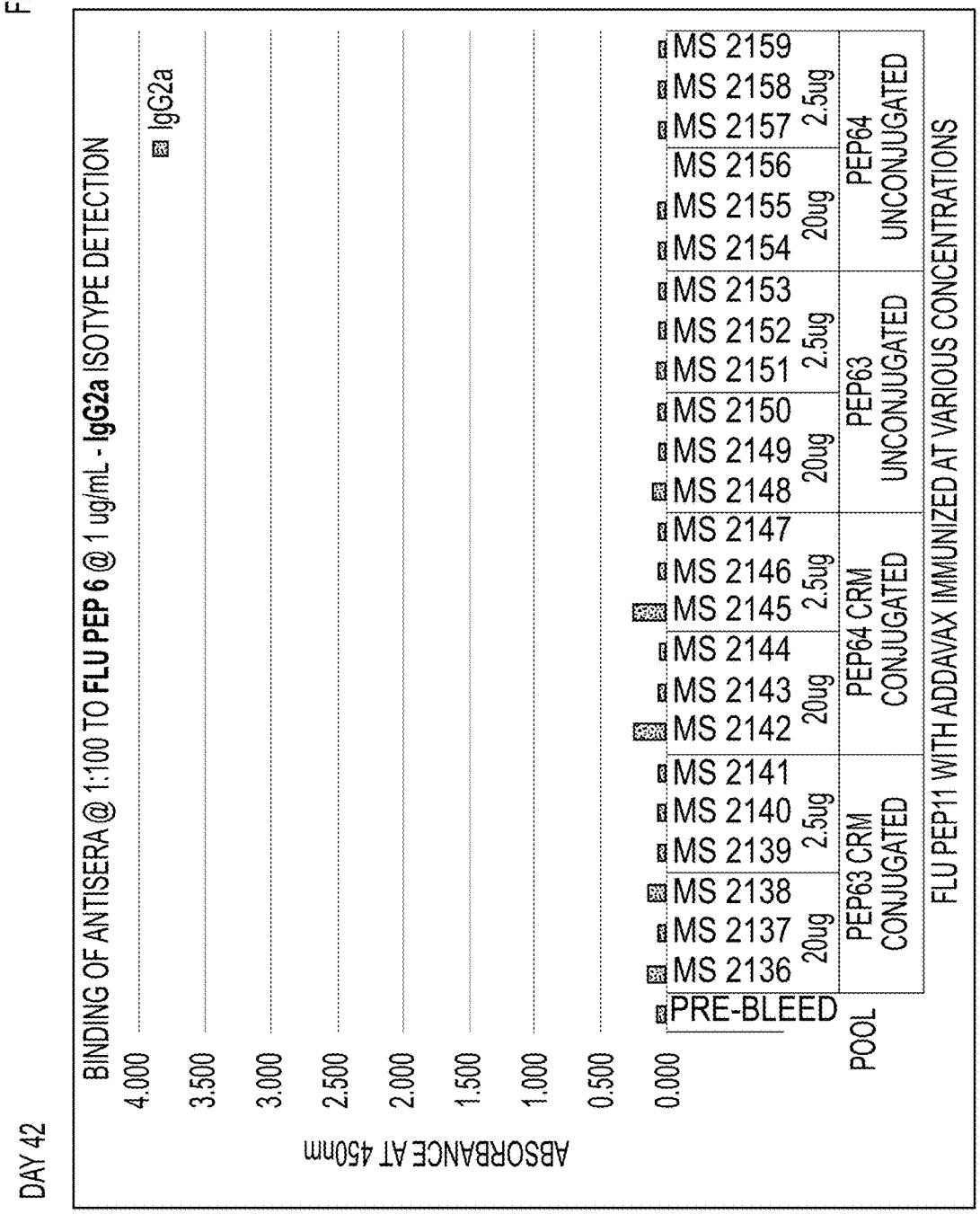
FIG. 7 (CONT. -3)

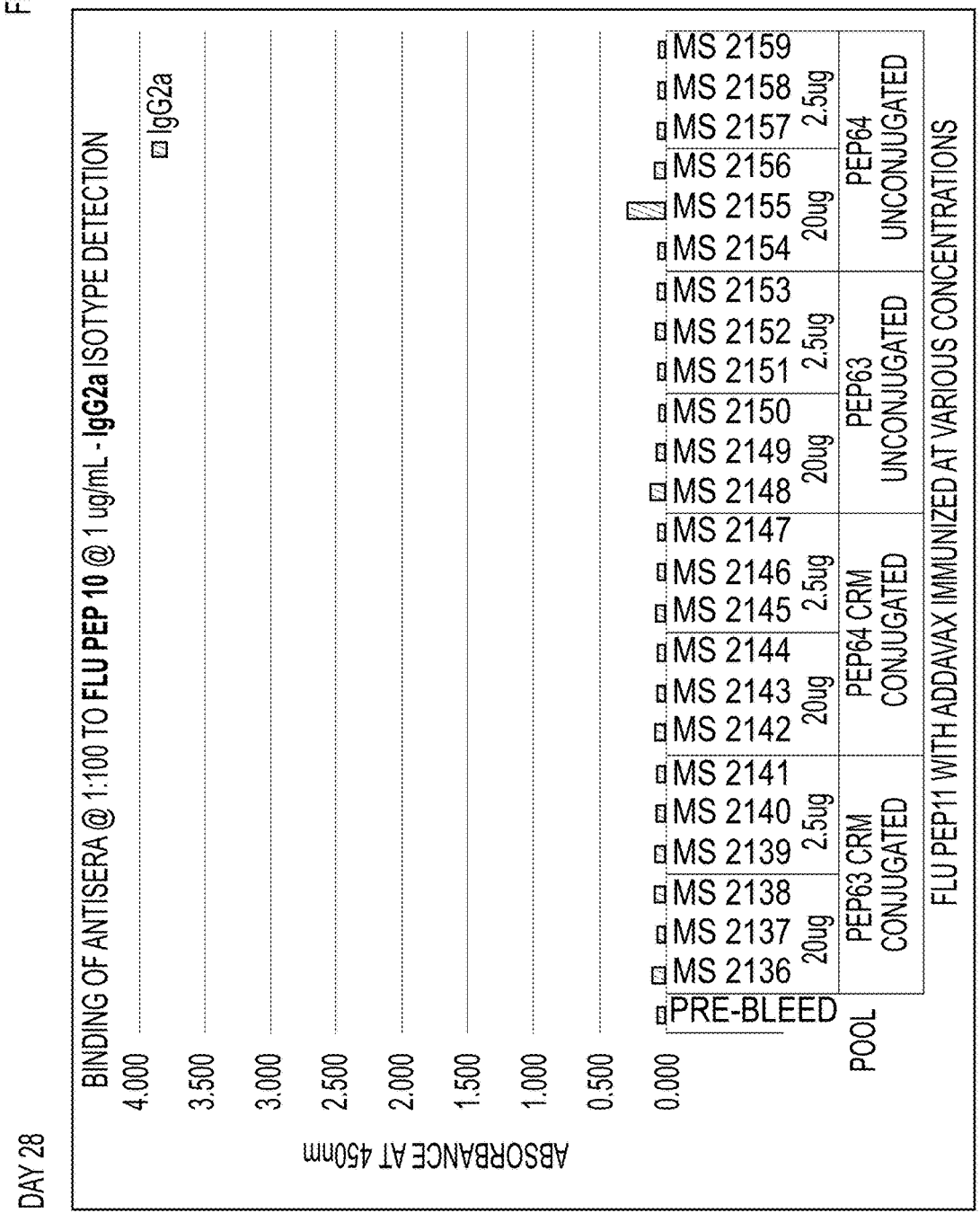
FIG. 8 (CONT. -1)

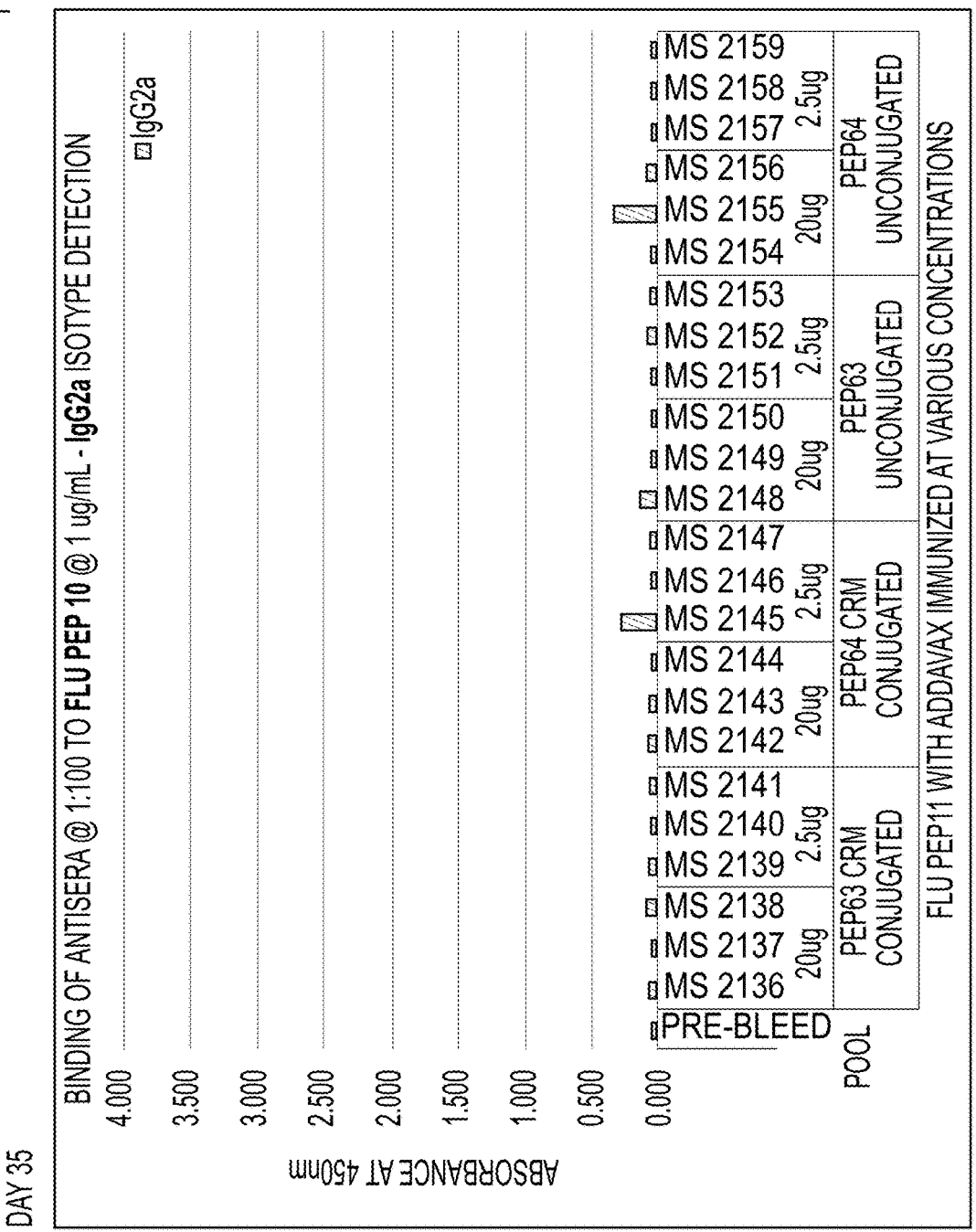
FIG. 8 (CONT. -2)

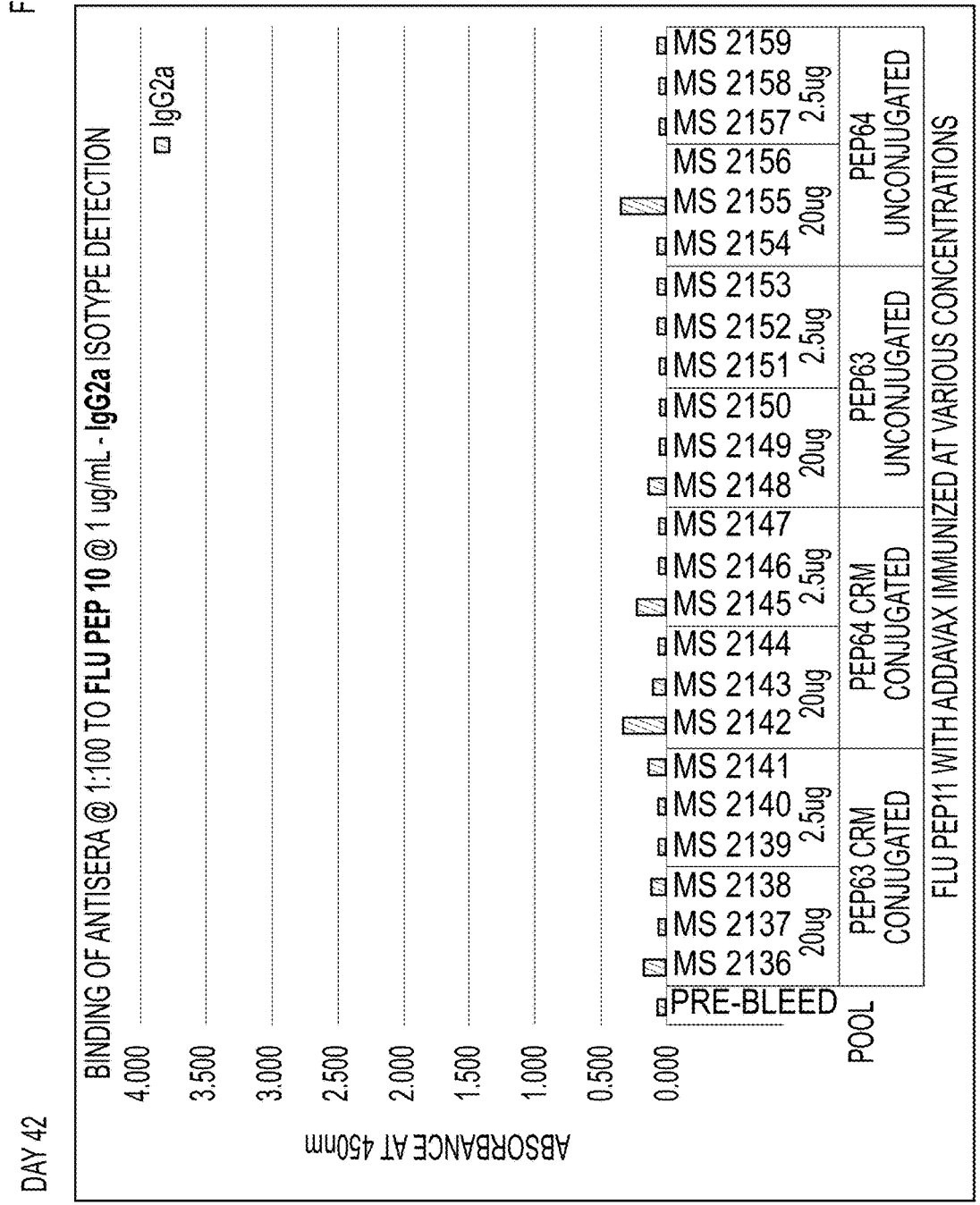
FIG. 8 (CONT. -3)

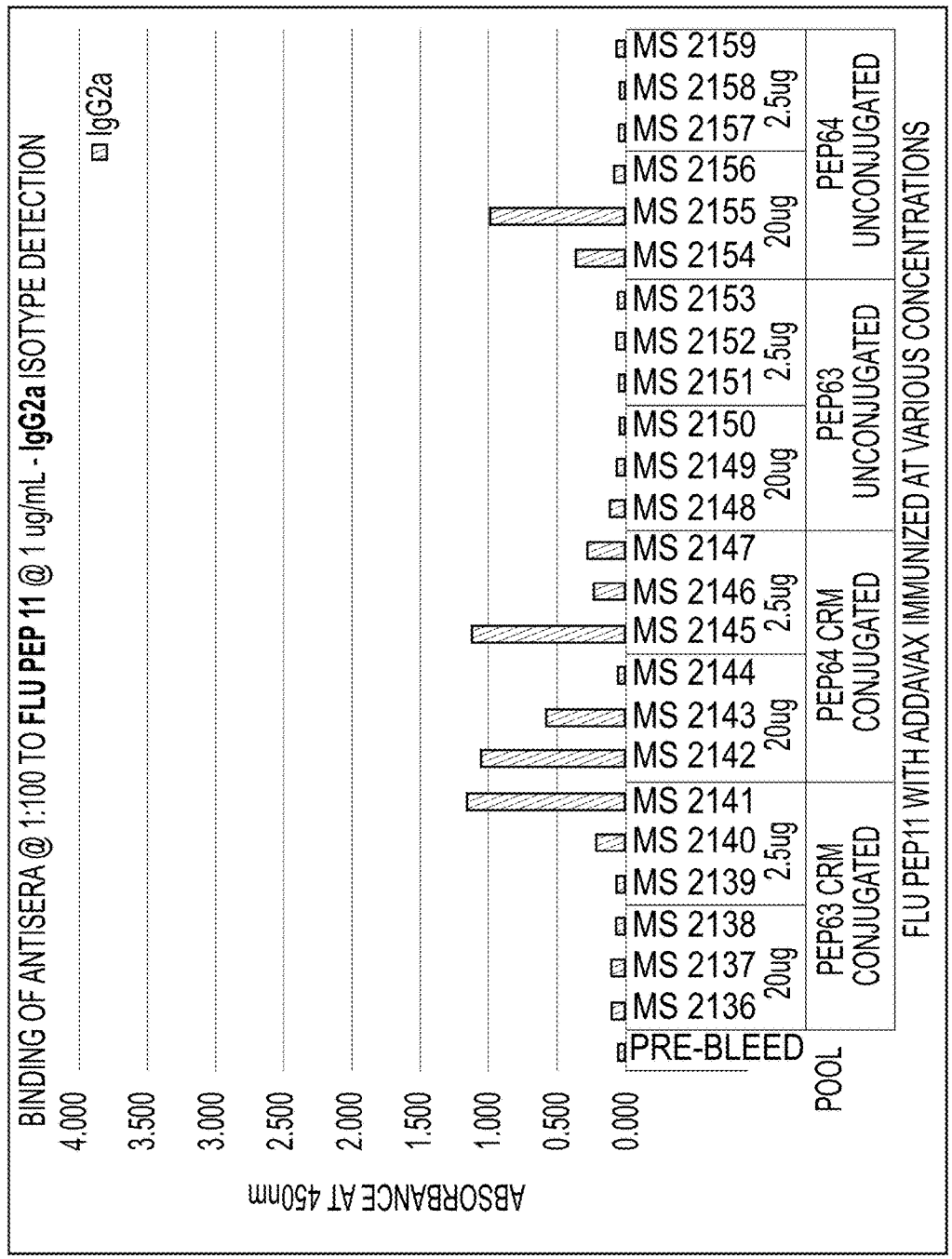
FIG. 9 (CONT. -1)

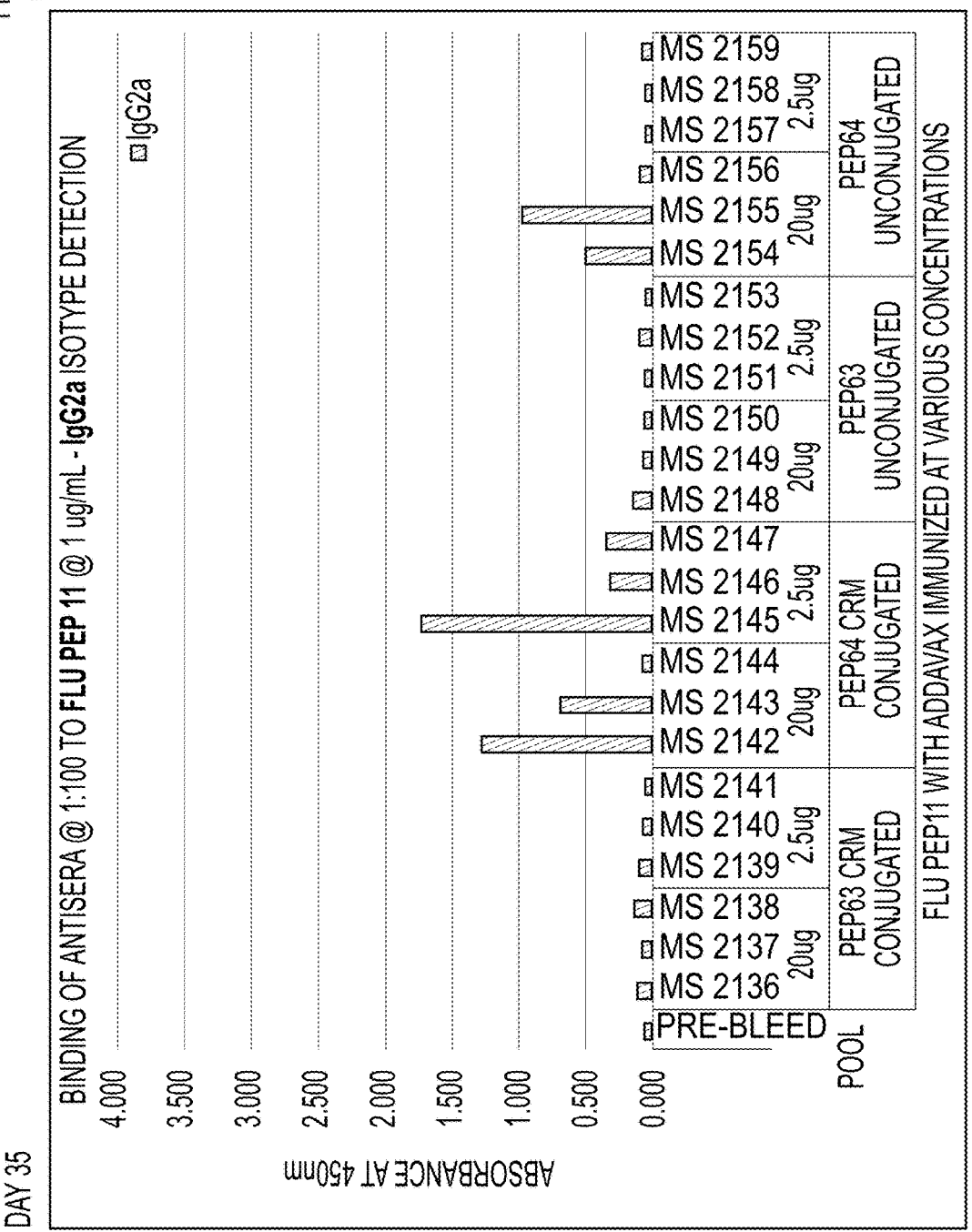
FIG. 9 (CONT. -2)

FIG. 9 (CONT. -3)

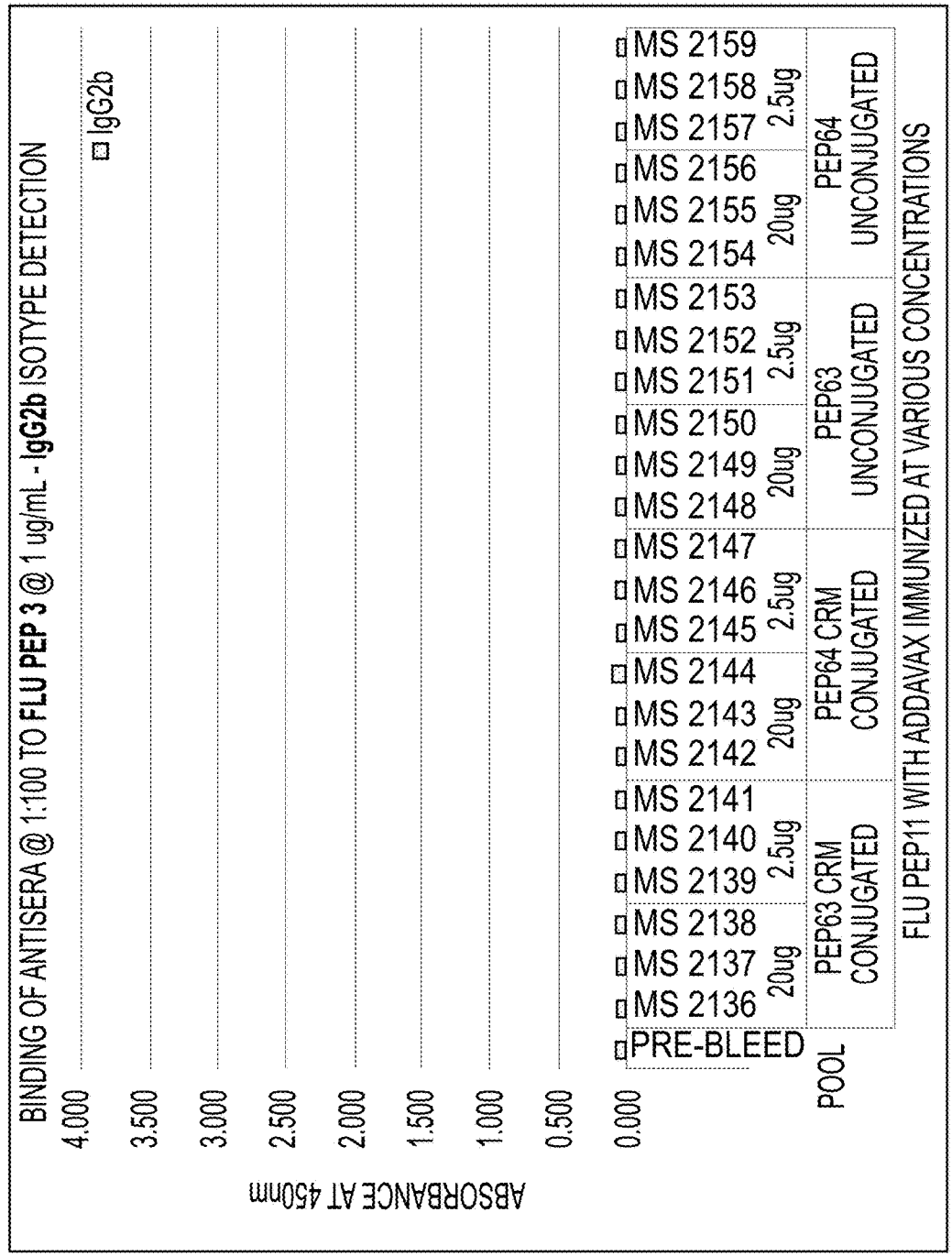

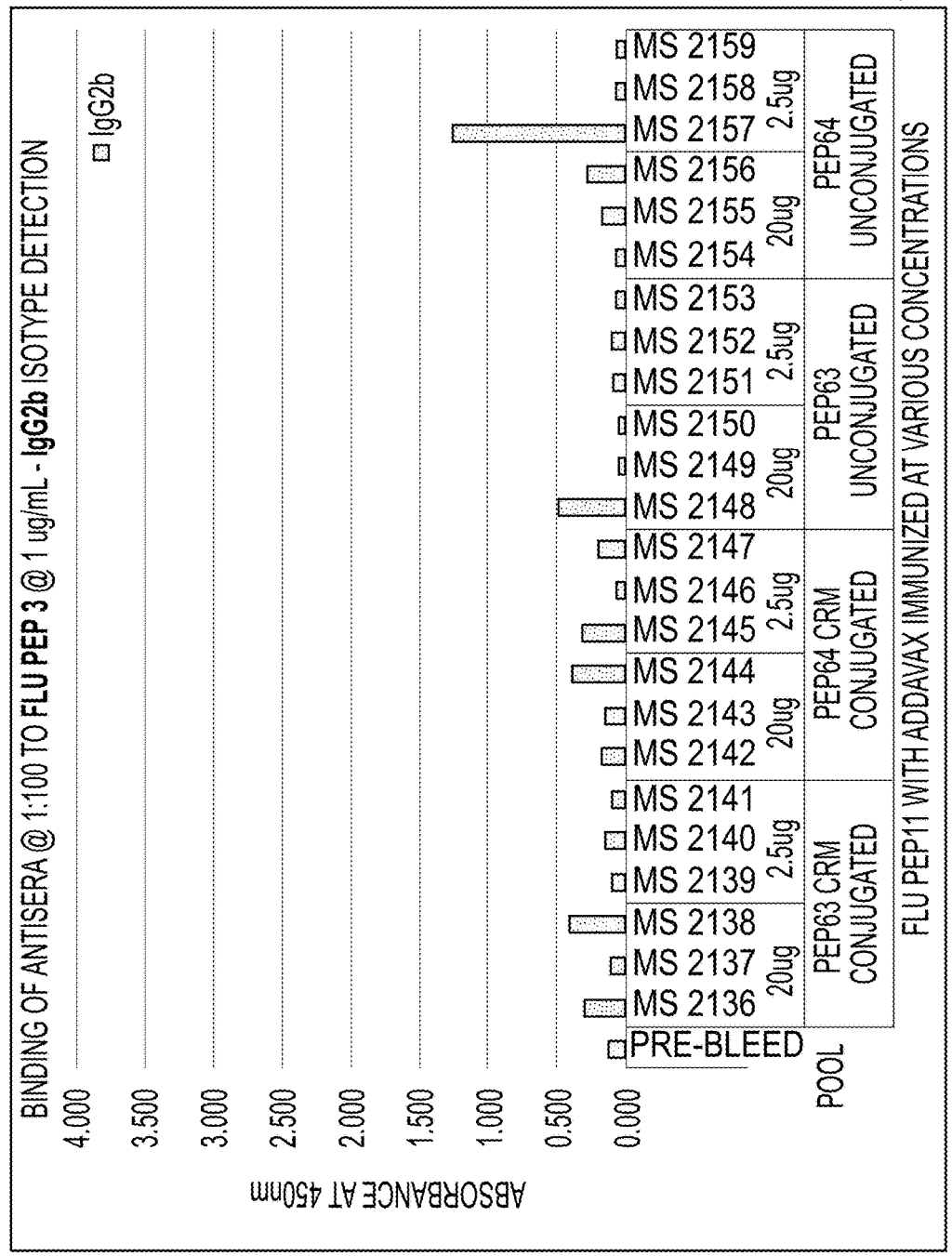
FIG. 10 (CONT. -1)

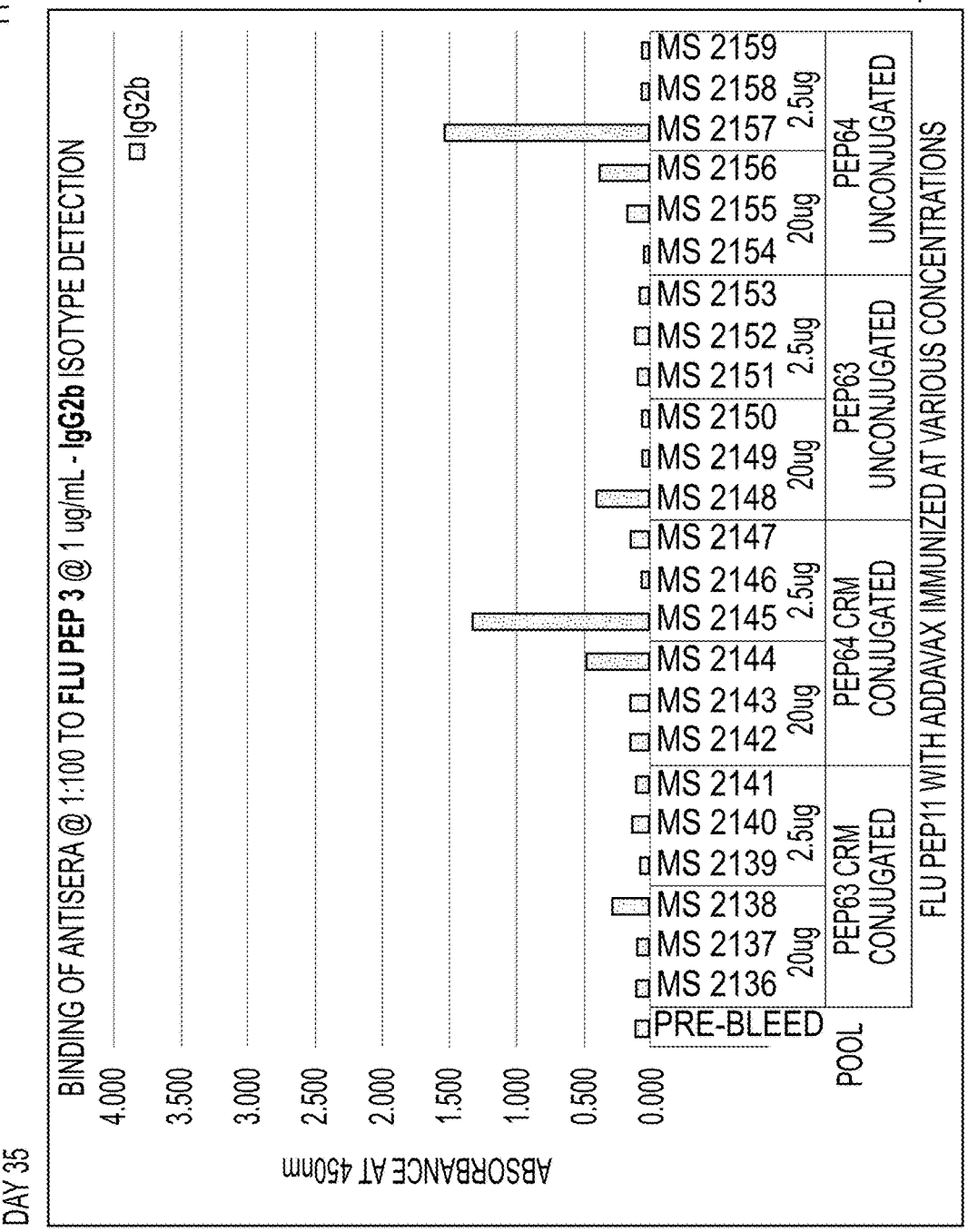
FIG. 10 (CONT. -2)

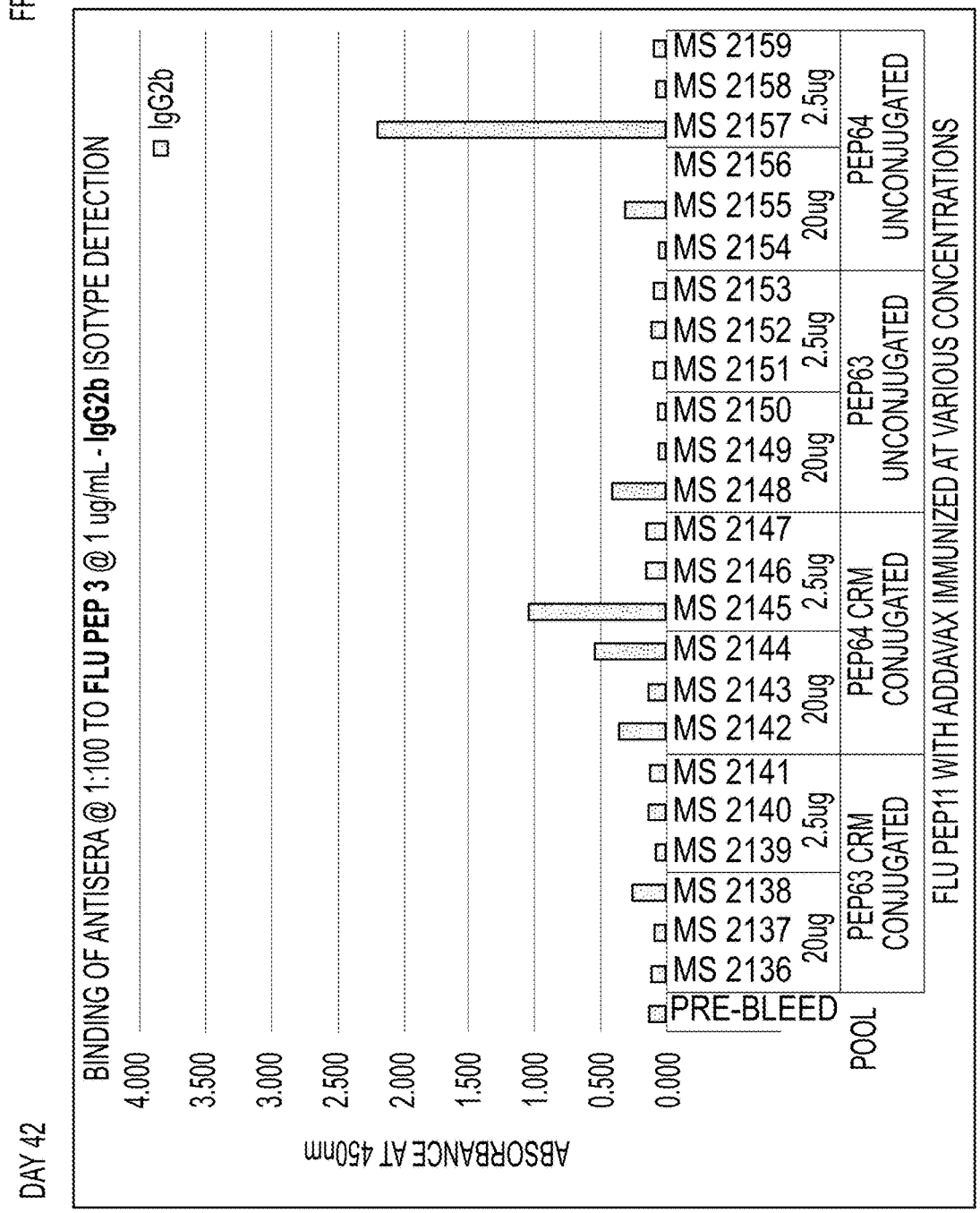
FIG. 10 (CONT. -3)

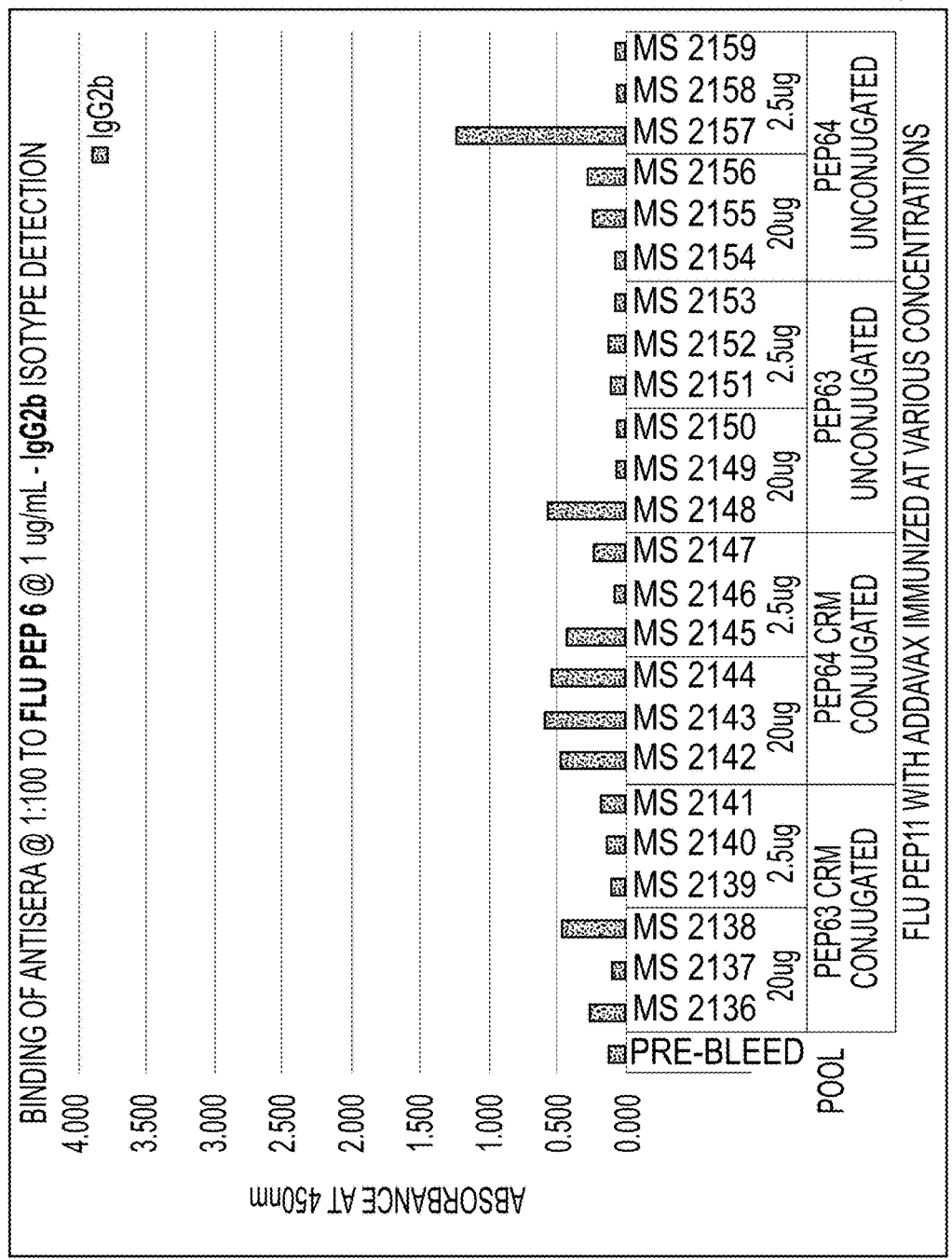
FIG. 11 (CONT. -1)

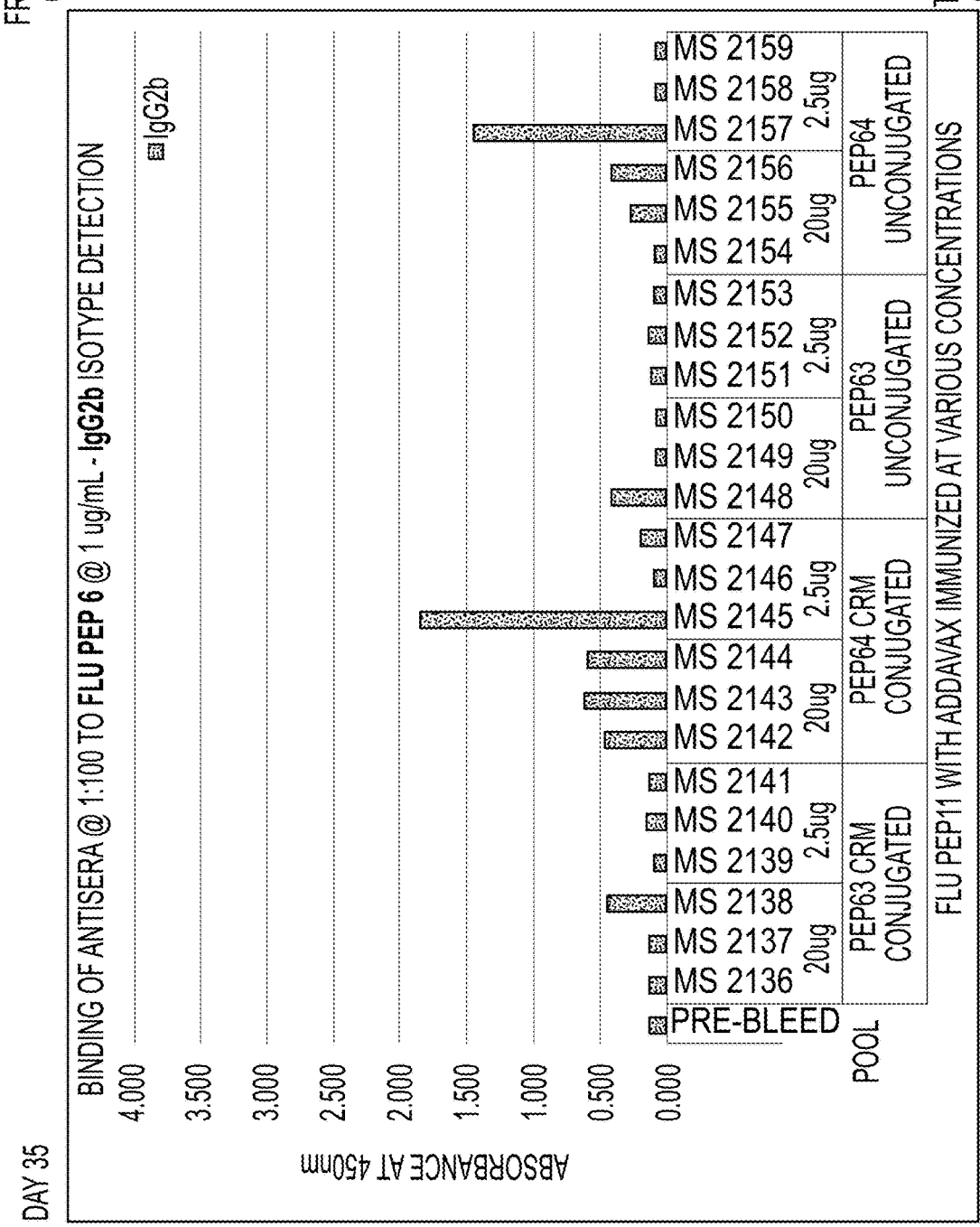
FIG. 11 (CONT. -2)

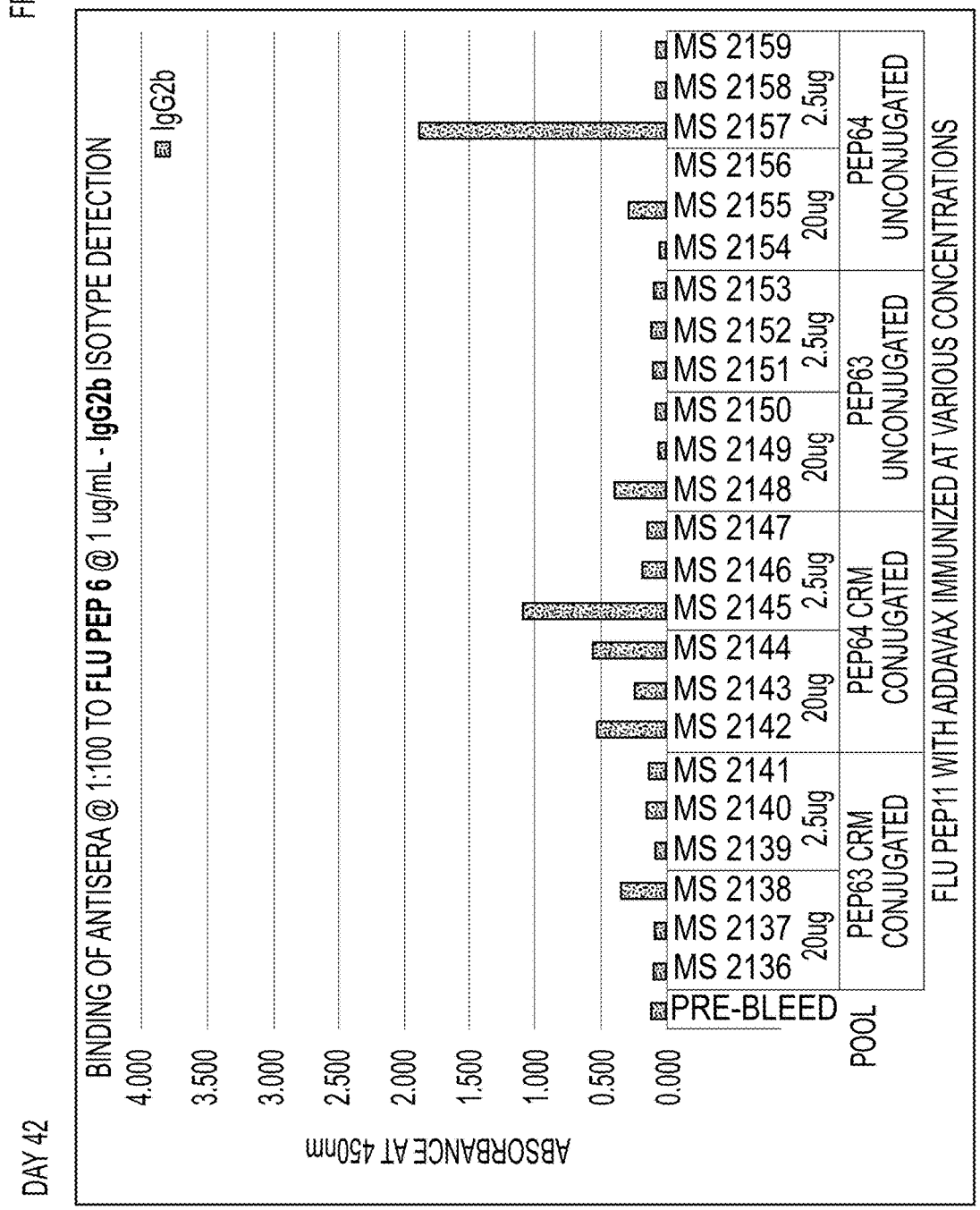
FIG. 11 (CONT. -3)

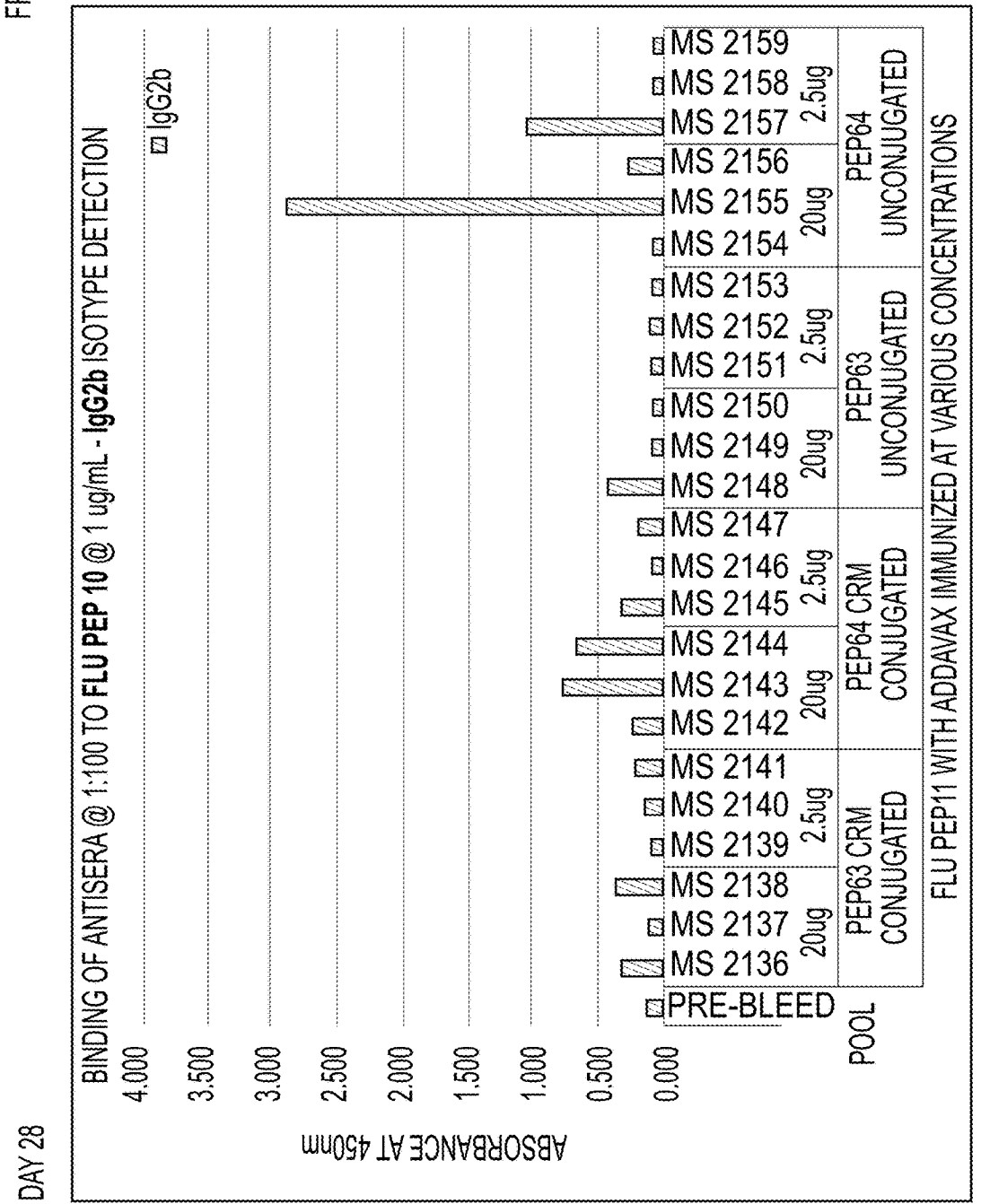
FIG. 12 (CONT. -1)

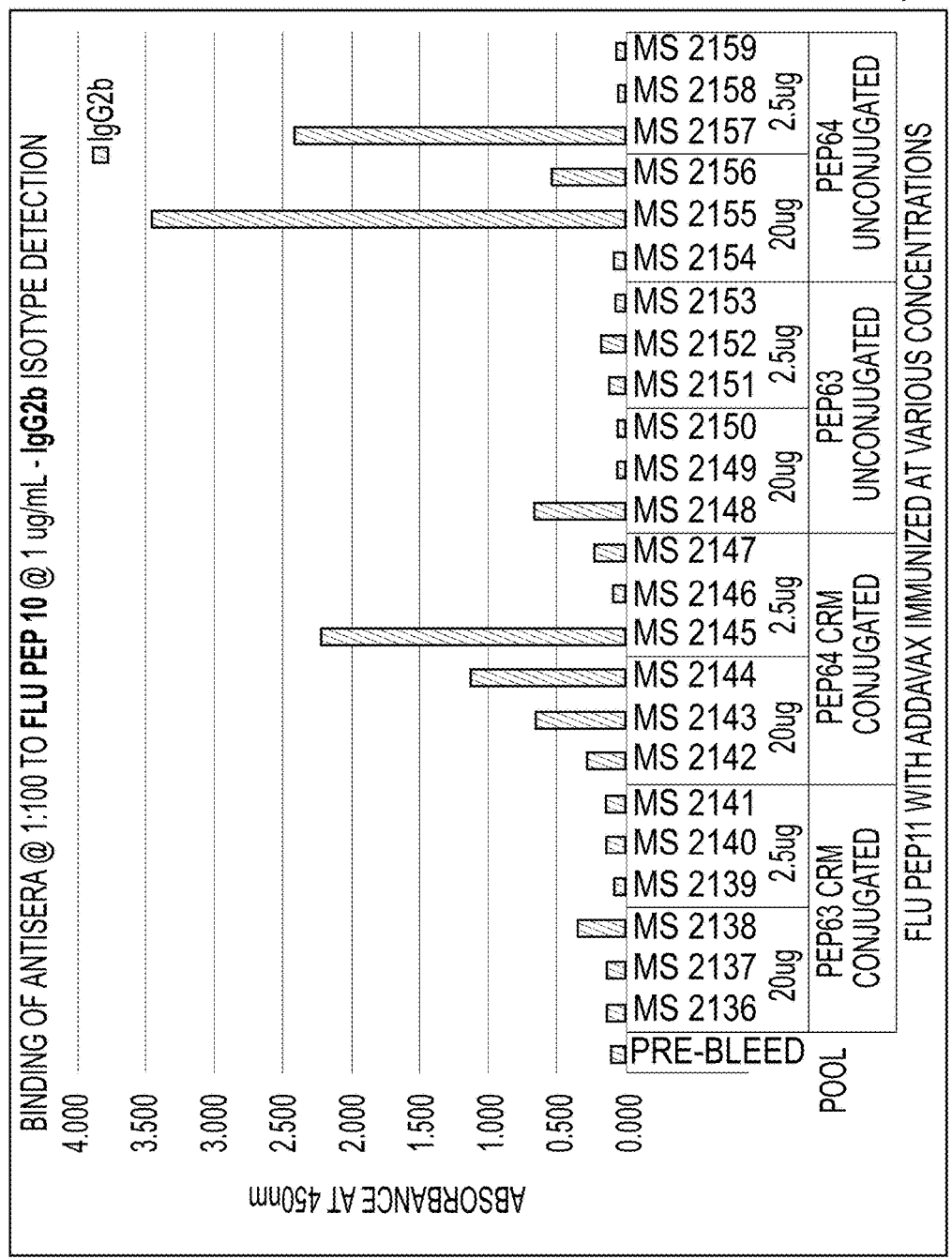
FIG. 12 (CONT. -2)

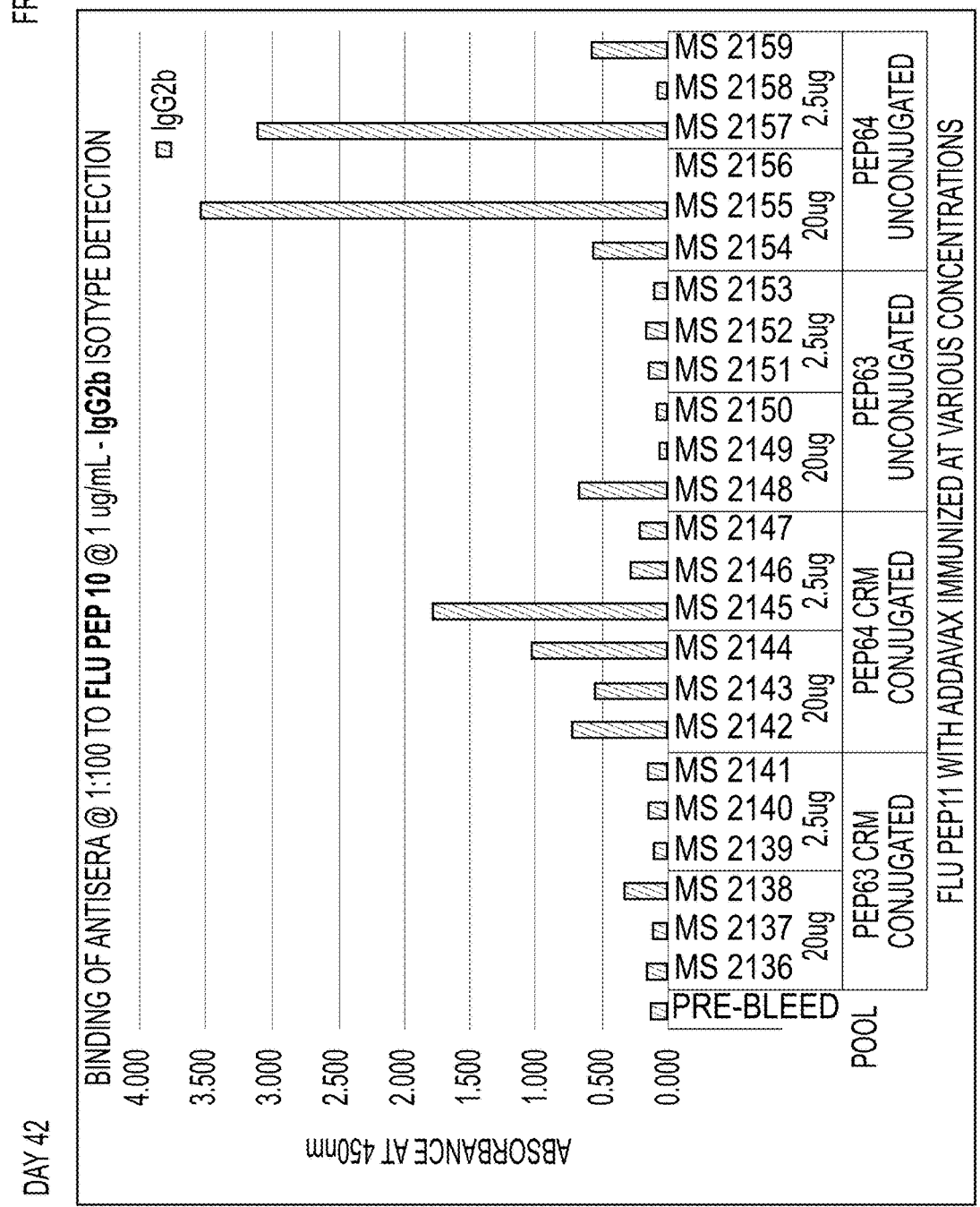
FIG. 12 (CONT. -3)

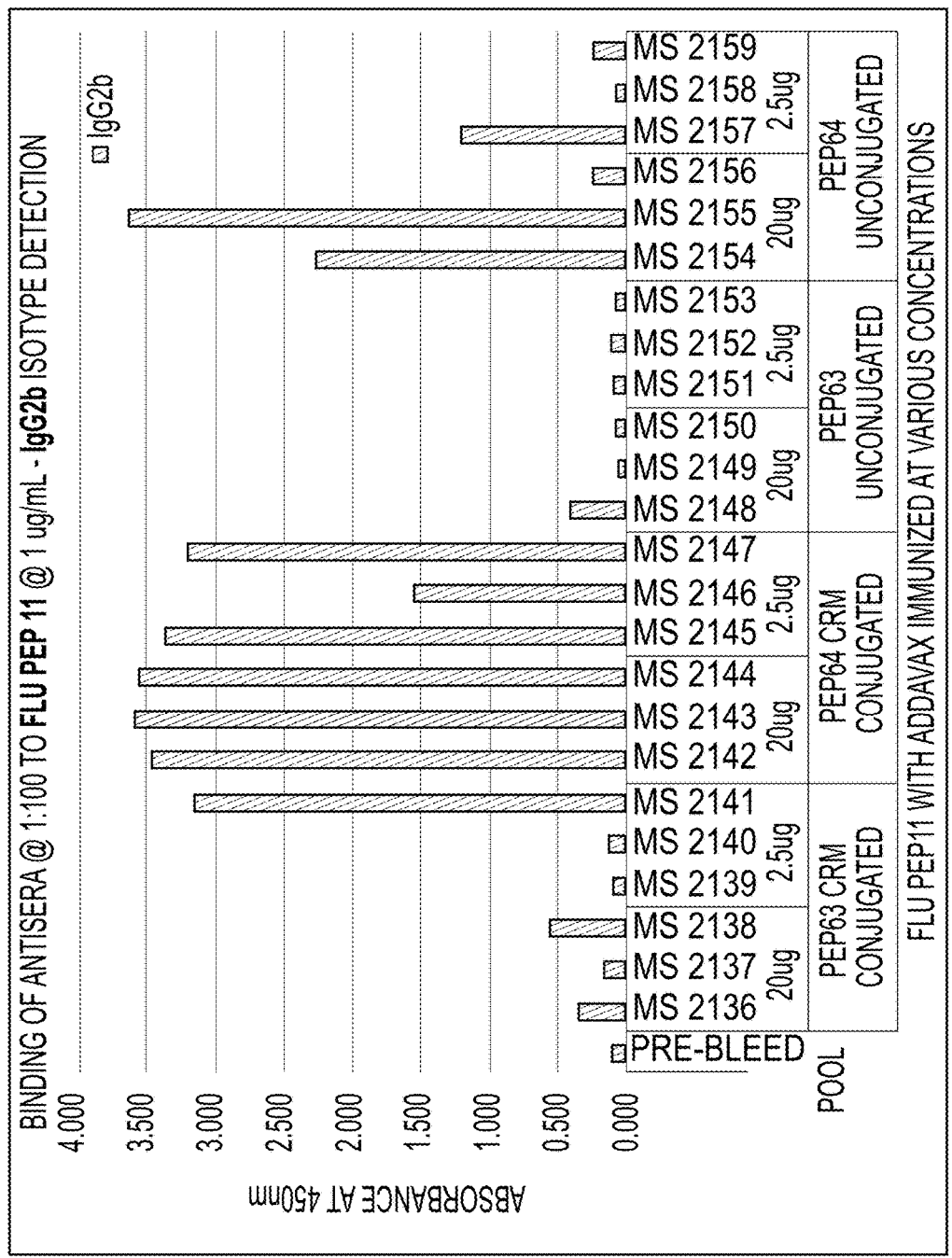
FIG. 13 (CONT. -1)

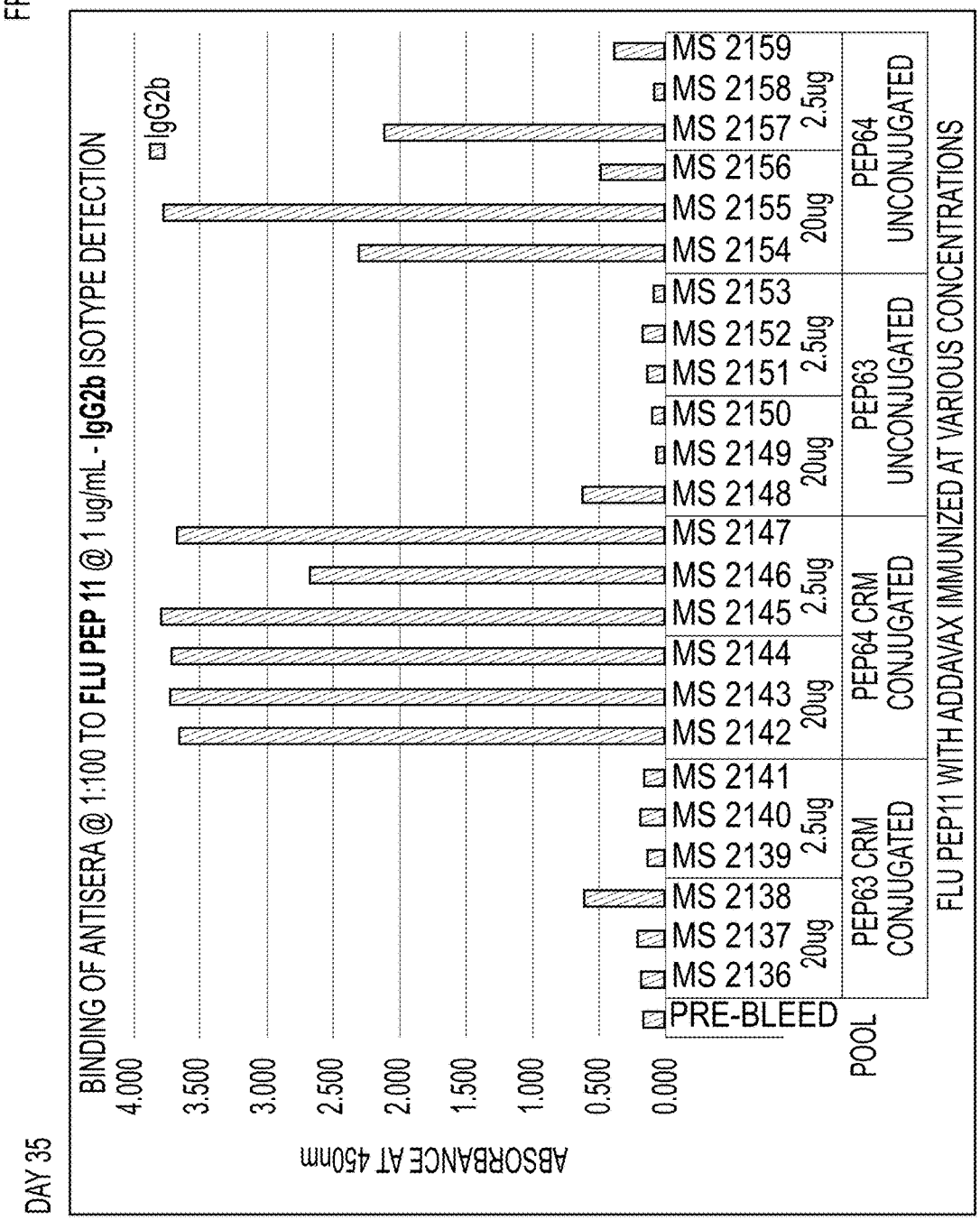
FIG. 13 (CONT. -2)

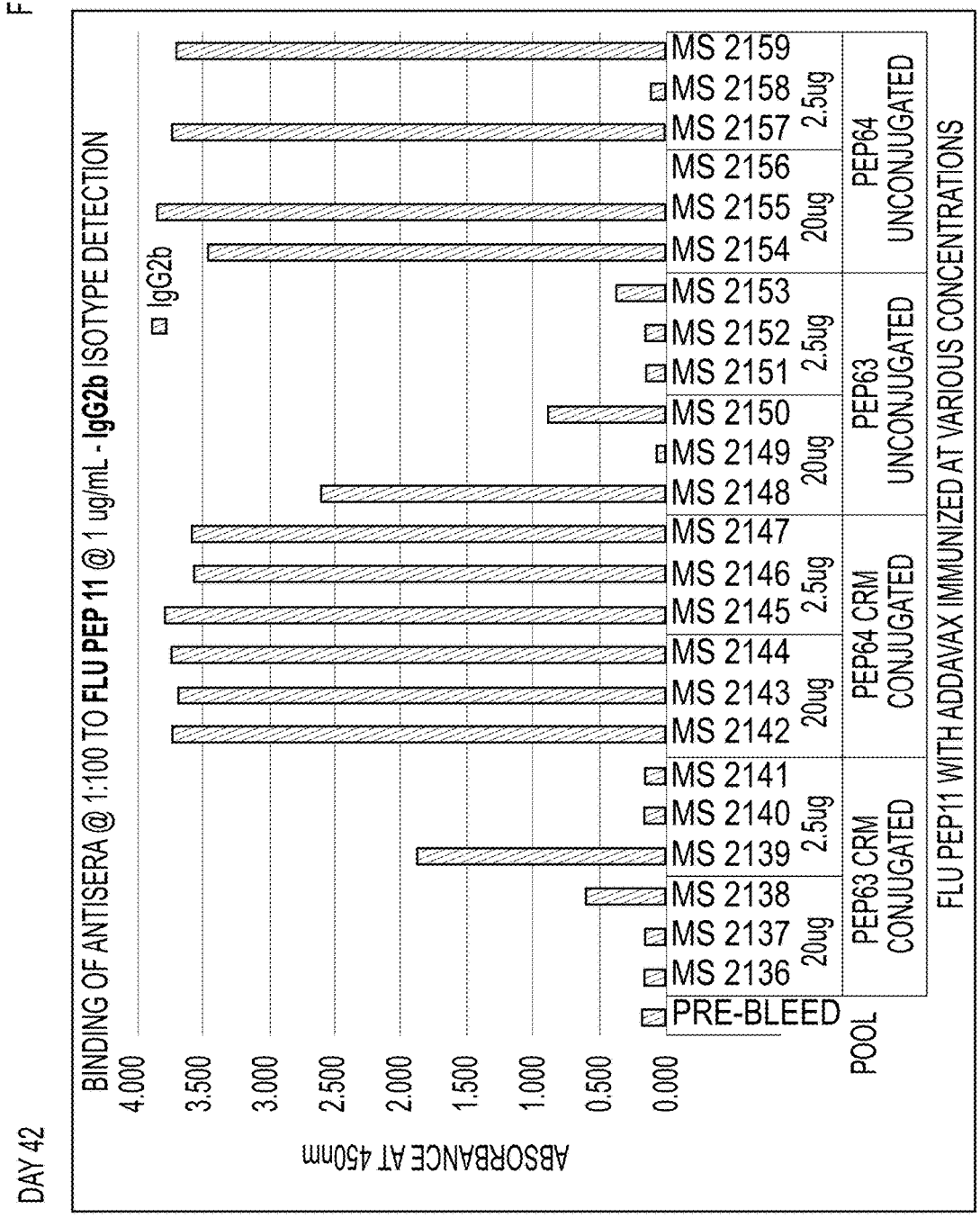
FIG. 13 (CONT. -3)

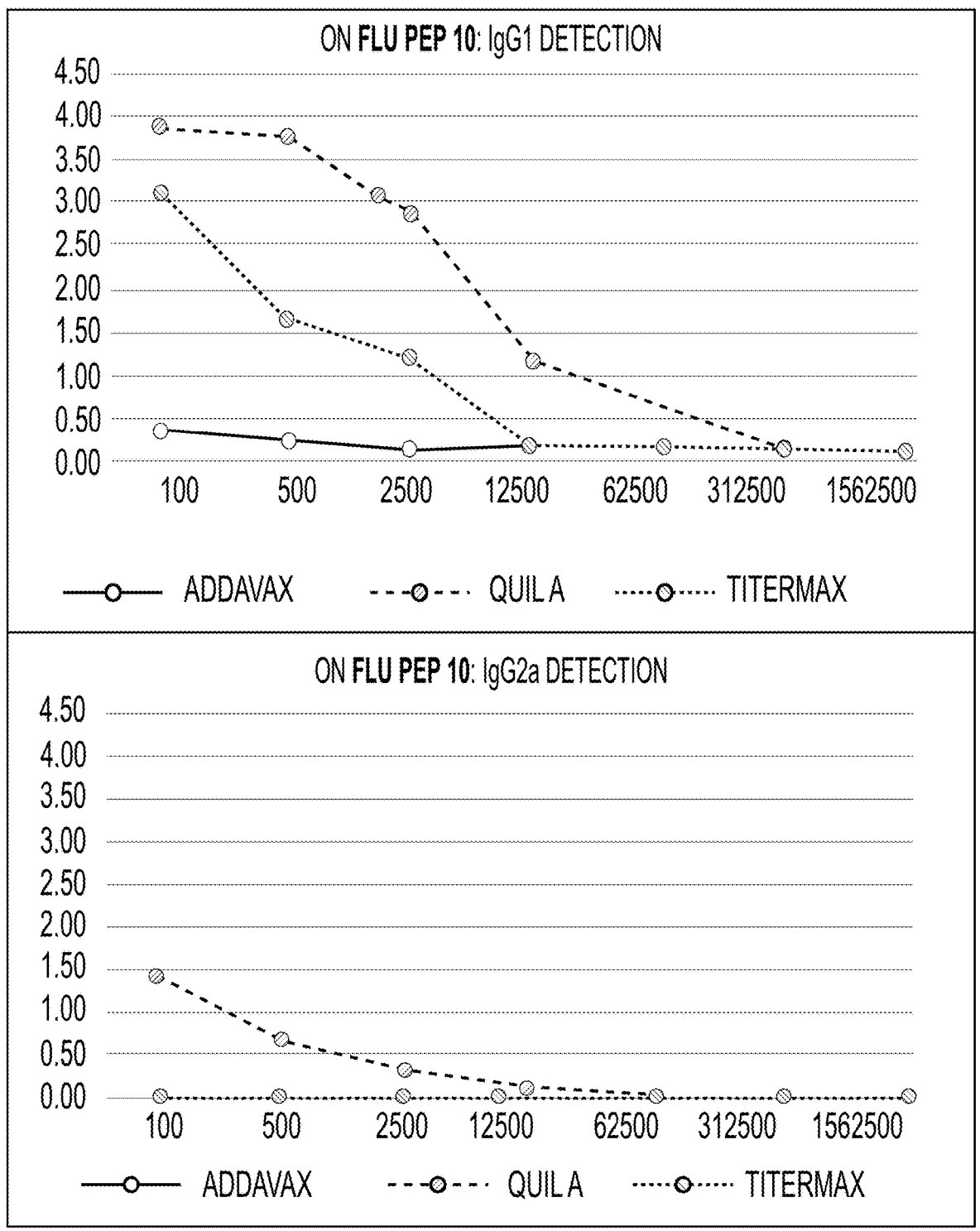
FIG. 16 (CONT. -1)

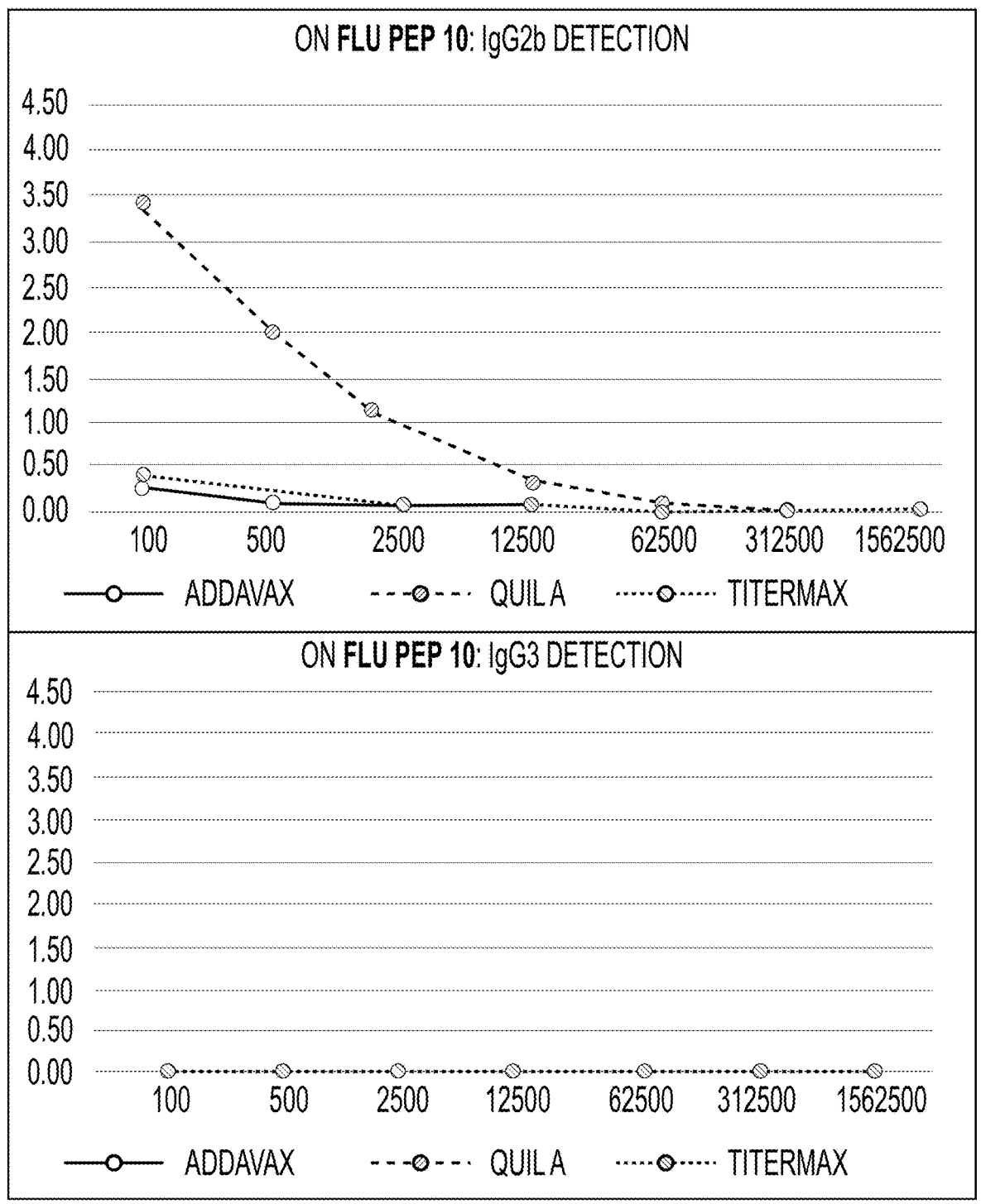
FIG. 16 (CONT. -2)

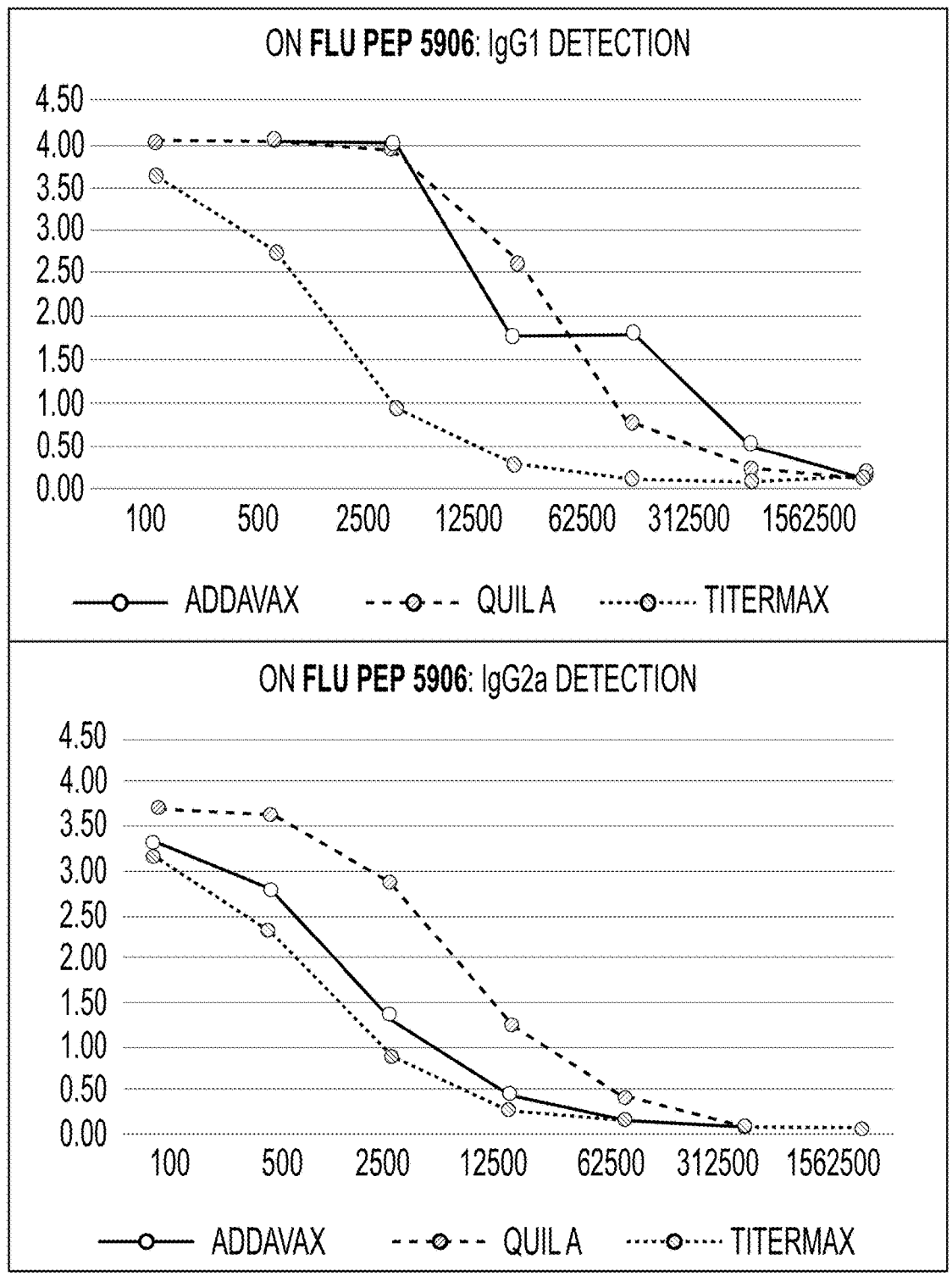
FIG. 16 (CONT. -3)

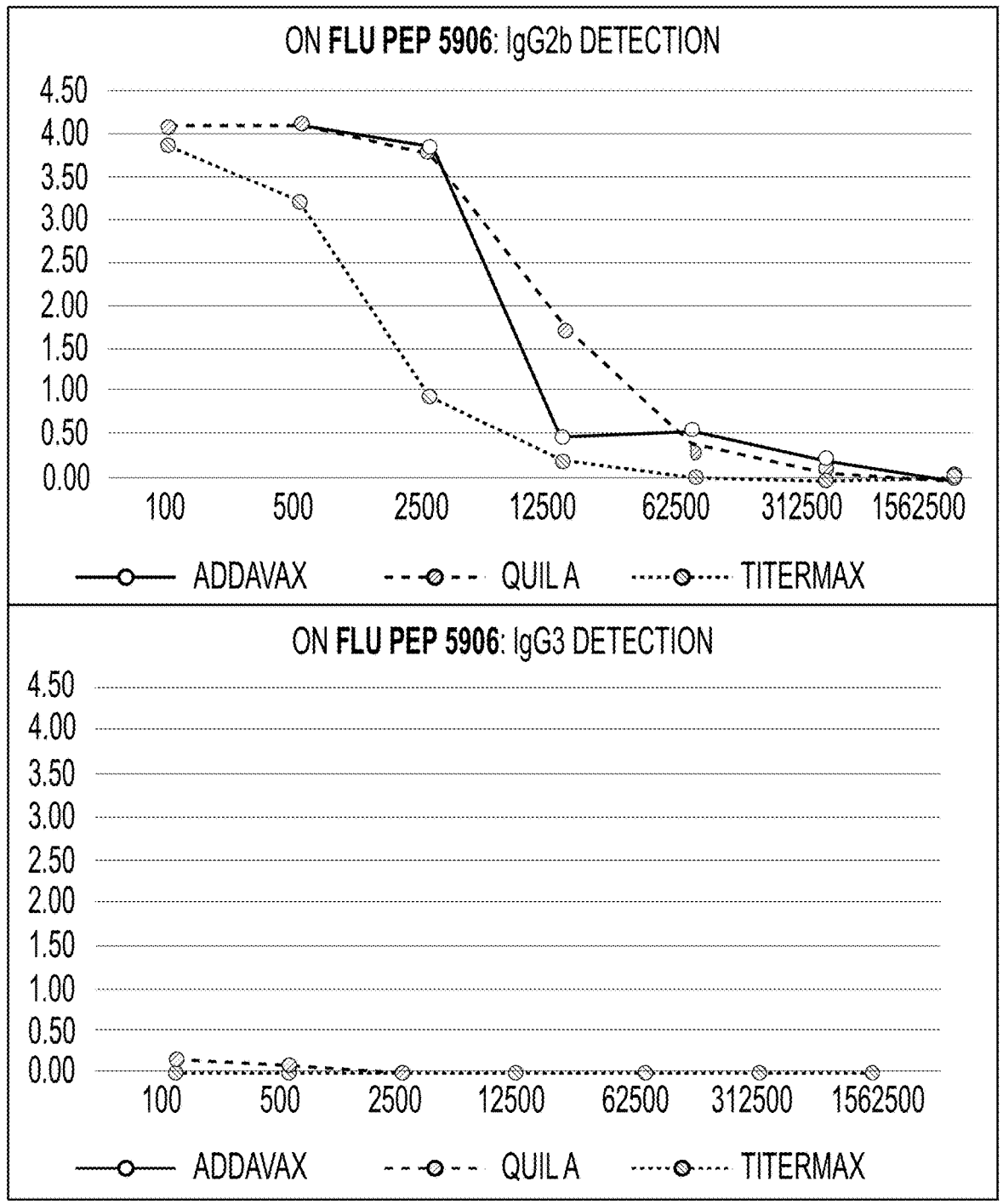
FIG. 16 (CONT. -4)

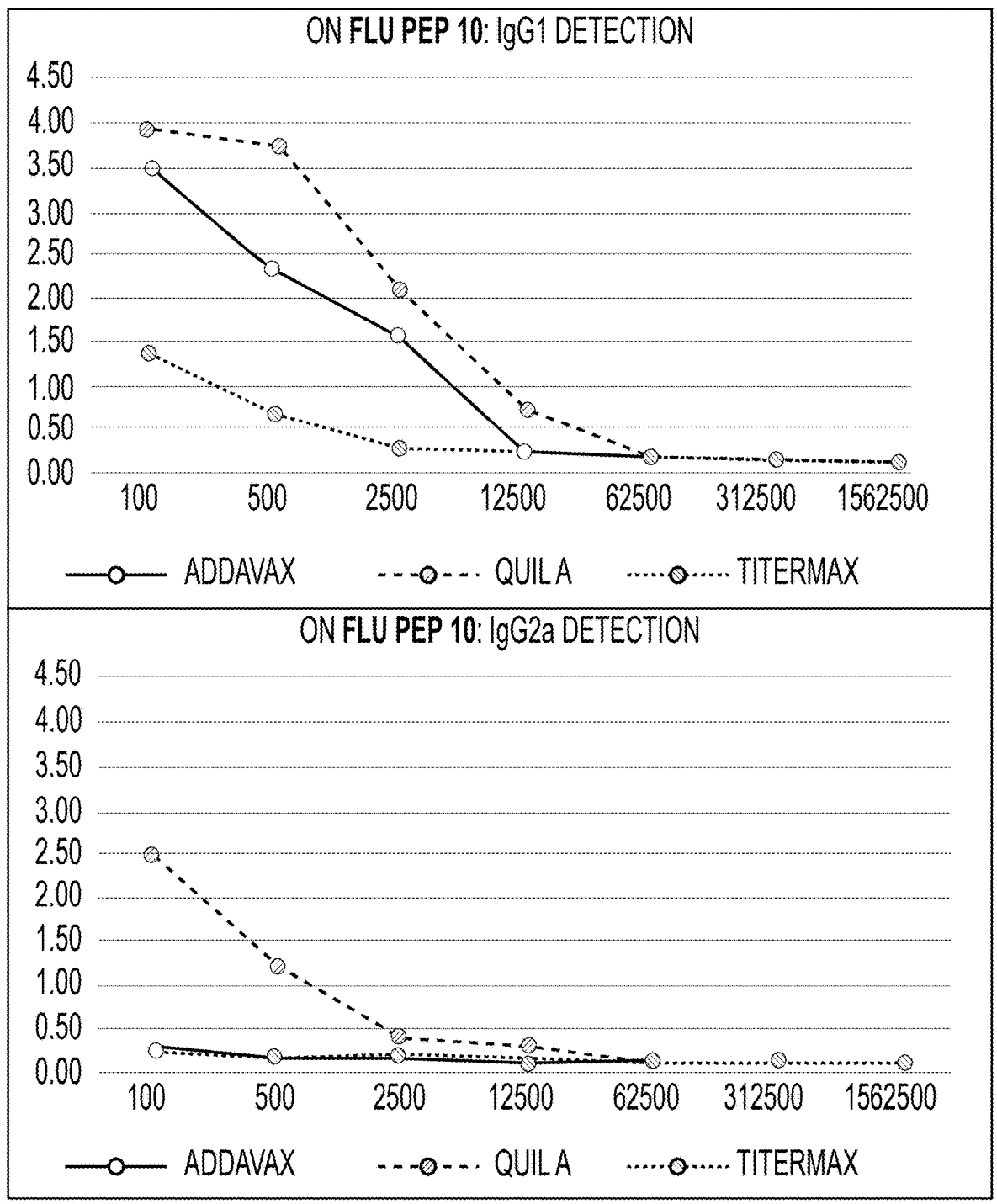
FIG. 17 (CONT. -1)

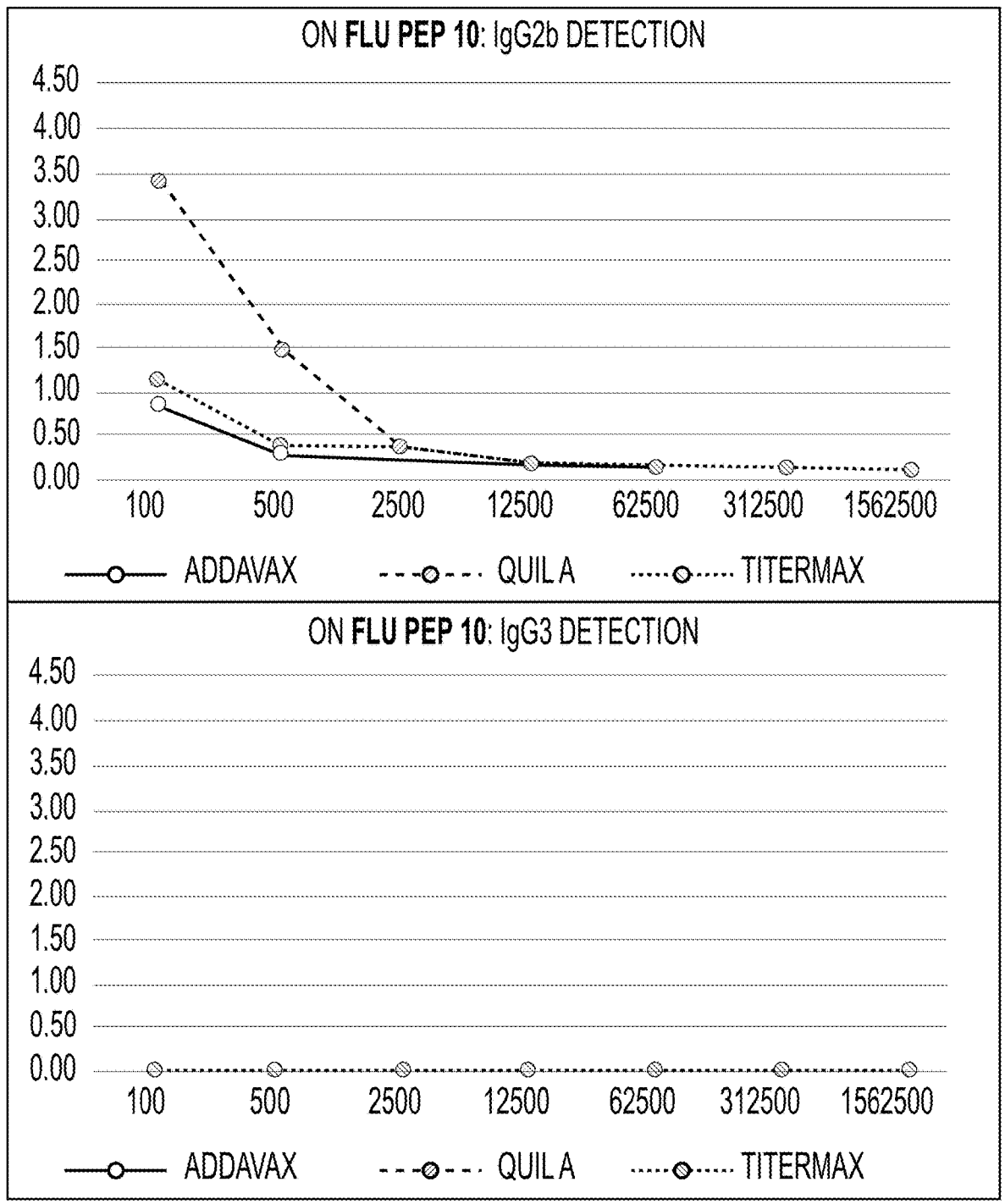
FIG. 17 (CONT. -2)

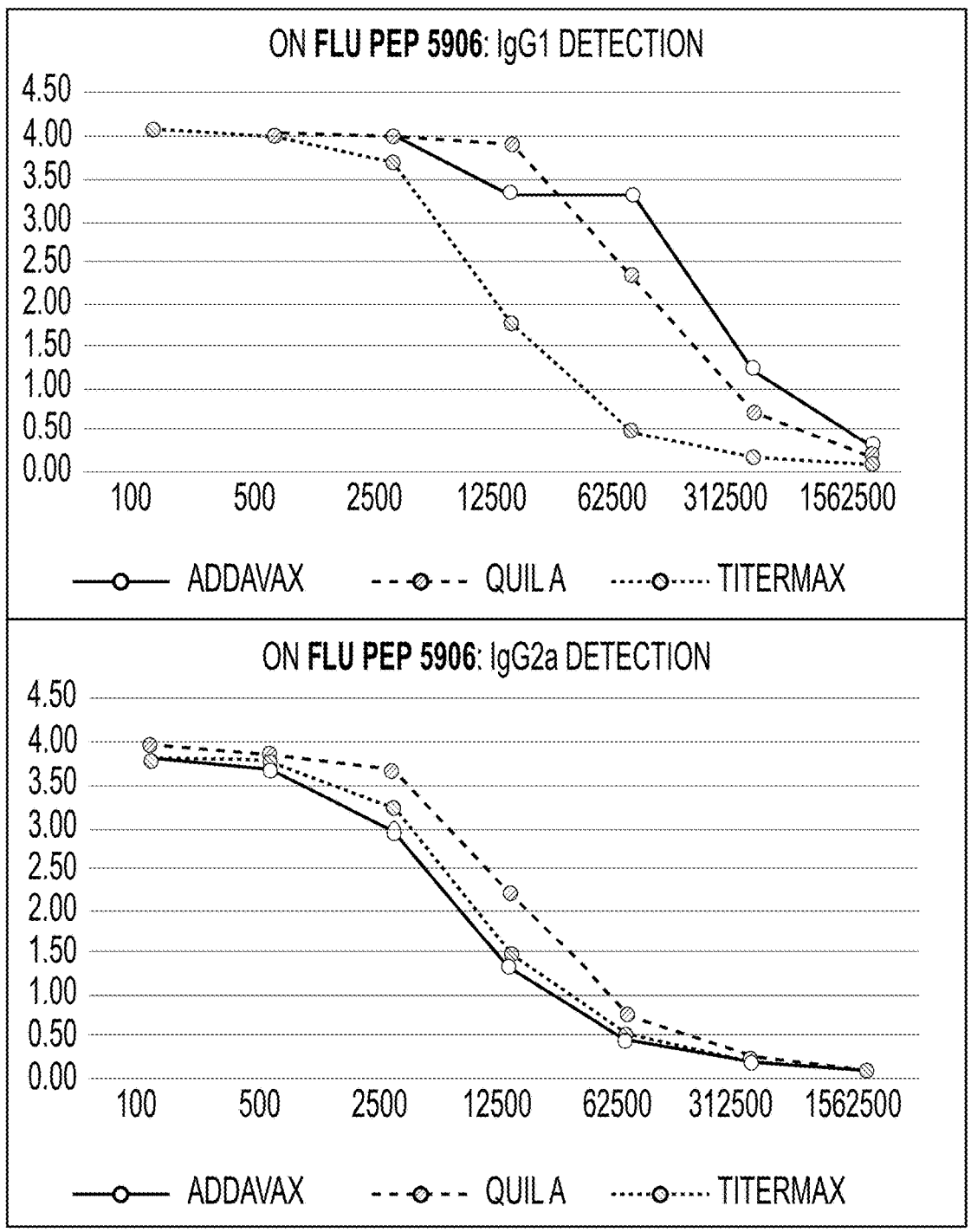
FIG. 17 (CONT. -3)

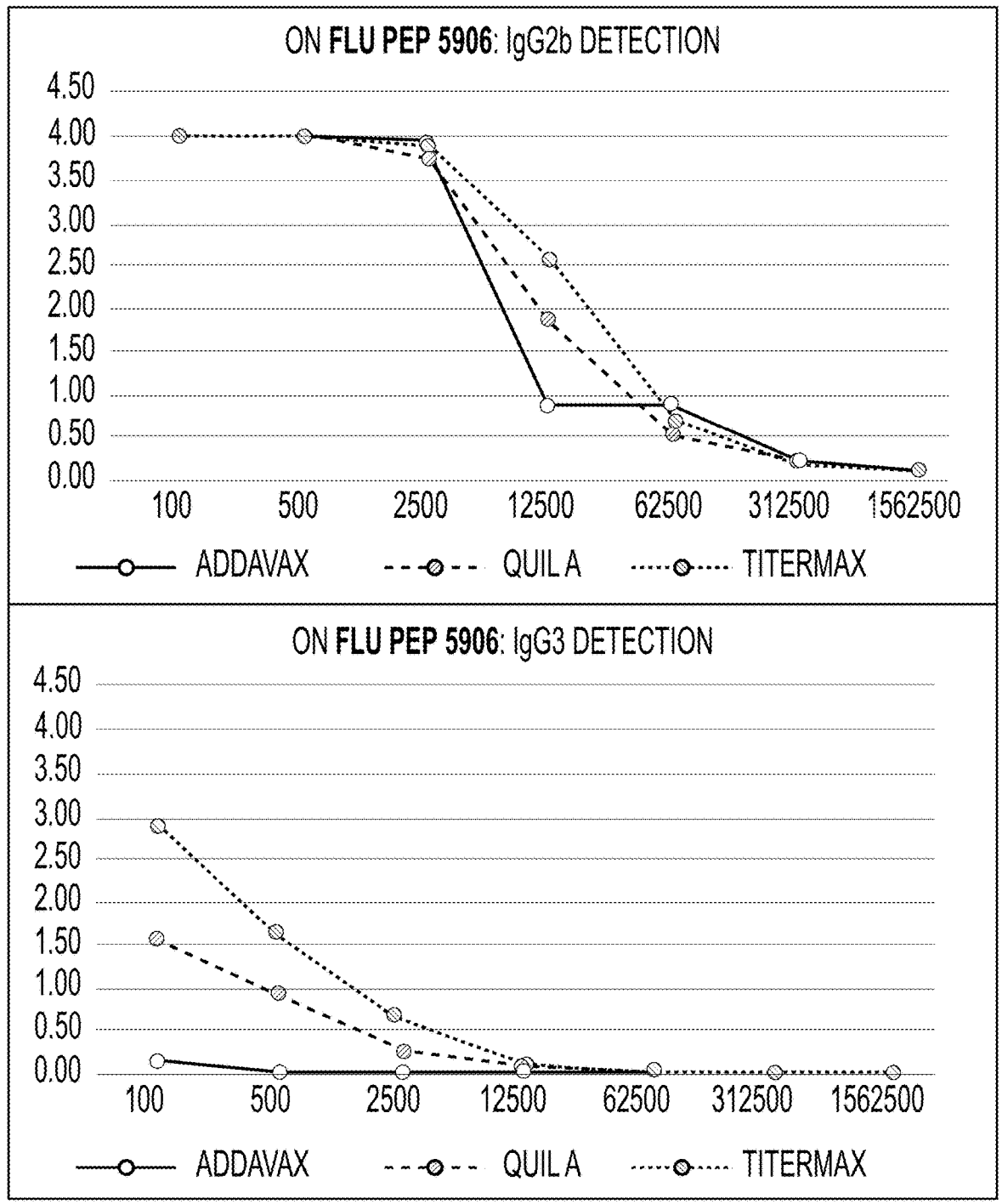
FIG. 17 (CONT. -4)

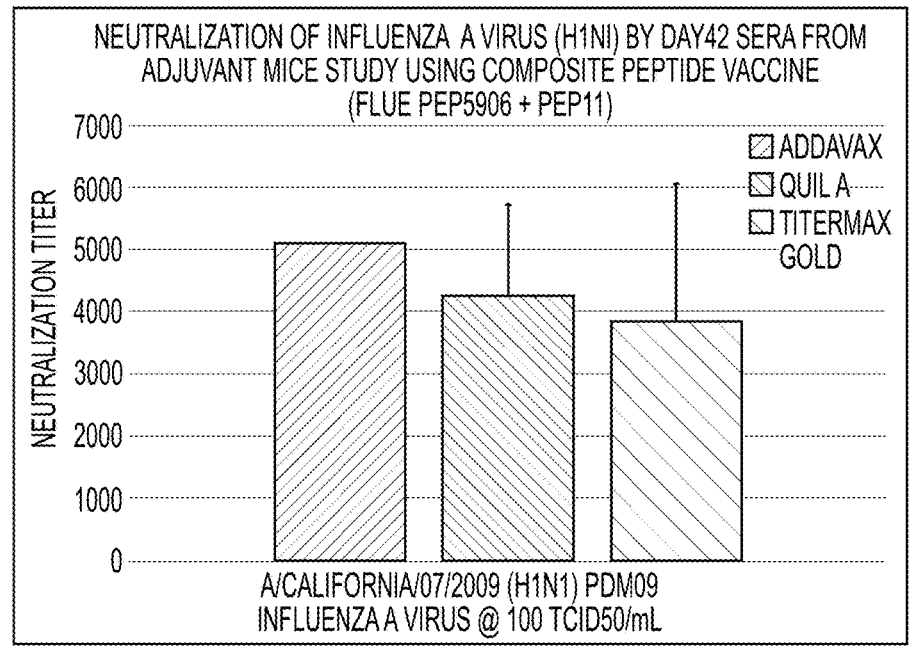

FIG. 21

| PEPTIDE | CONJUGATE | ADJUVANT | DOSE AND REGIMEN | MODE OF ADMIN | PEPTIDE SOURCE PROTEIN | ANTISERA TITERS ON PEPTIDE (OD @ 450nM) | MOUSE, MAB ID & ISOTYPE | MAB BINDING PROFILE |
|---|---|---|---|---|---|---|---|---|
| PEP 11 COMPOSITE | CRM | TITERMAX GOLD | PRIME: H3N2, $10^6$ D0, D14 BOOST: PEP: 20 μg D30, 42, 70 | H3N2: IM PEPTIDE: SQ | HEMAGGLUTININ NEURAMINIDASE | MS 2209 AG: PEP 11 D49: OD 2.8 D77: OD 3.1 | MAB EA9 (IgG1) MAB NB5(IgG2a) MAB LD9 (IgG1) | EA9 & LD9: HA NB5: NA FLU/A VIRUSES (CONT) H3N2 AND H1N1 |
| PEP 5906 COMPOSITE | CRM | FREUNDS | PRIMARY & BOOST: PEP: 50 μg D0, D21, 35, 41 | SQ | MATRIX ECTODOMAIN (M2e) | MS 1443 AG: PEP 5906 D21: OD 3.4 D42: OD 4.0 | MAB GA4 (IgG1) | MATRIX M2e FLU/A VIRUSES (CONT) H3N2 AND H1N1 |

| MOUSE ID | IMMUNOGEN | MABs GENERATED |
|---|---|---|
| M1435 | TB PEP01 - CRM, 50µg DOSE, SQ | HYBRIDOMA CLONE 1: LD7 I BB2 |
| | | SUBCLONE: LD7 I BB2 I B9 |
| | | HYBRIDOMA CLONE 2: CA6 II GA8 |
| | | SUBCLONE: CA6 II GA8 I A5 |

| OPSONOPHAGOCYTIC KILLING ACTIVITY OF ANTI-TB PEP01 MONOCLONAL ANTIBODIES AGAINST *M. SMEGMATIS* | | |
|---|---|---|
| | PERCENT KILLING (%) | |
| MAB CONCENTRATION | MAB CA6 | MAB LD7 |
| (ug/mL) | IgG2b ISOTYPE | IgG2a ISOTYPE |
| 250 | 27 | 44 |
| 200 | 58 | 76 |
| 175 | 63 | 62 |
| 150 | 10 | 72 |
| 100 | 40 | 72 |
| 75 | 46 | 76 |
| 50 | 22 | 75 |
| 25 | 51 | 52 |
| 12.5 | 43 | 56 |
| 10 | 63 | 71 |
| 5 | 55 | 74 |
| 1 | 49 | 64 |
| 0.1 | 47 | 73 |
| 0.05 | 61 | 41 |

```
                             SEQUENCE LISTING

Sequence total quantity: 114
SEQ ID NO: 1            moltype = AA  length = 20
FEATURE                 Location/Qualifiers
source                  1..20
                        mol_type = protein
                        organism = Mycobacterium tuberculosis
SEQUENCE: 1
SEFAYGSFVR TVSLPVGADE                                                     20

SEQ ID NO: 2            moltype = AA  length = 42
FEATURE                 Location/Qualifiers
REGION                  1..42
                        note = Description of Artificial Sequence: Synthetic
                         polypeptide
source                  1..42
                        mol_type = protein
                        organism = synthetic construct
SEQUENCE: 2
SEFAYGSFVR TVSLPVGADE GNLFIAPWGV IHHPHYEECS CY                             42

SEQ ID NO: 3            moltype = AA  length = 20
FEATURE                 Location/Qualifiers
REGION                  1..20
                        note = Description of Unknown: MTB/HIV epitope
source                  1..20
                        mol_type = protein
                        organism = unidentified
SEQUENCE: 3
LRPTFDTRLM RLEDEMKEGR                                                     20

SEQ ID NO: 4            moltype = AA  length = 20
FEATURE                 Location/Qualifiers
REGION                  1..20
                        note = Description of Unknown: MTB/HIV epitope
source                  1..20
                        mol_type = protein
                        organism = unidentified
SEQUENCE: 4
DPDKDVDIMV RDGQLTIKAE                                                     20

SEQ ID NO: 5            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 5
HSFKWLDSPR LR                                                             12

SEQ ID NO: 6            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 6
ISLTEWSMWY RH                                                             12

SEQ ID NO: 7            moltype = AA  length = 15
FEATURE                 Location/Qualifiers
source                  1..15
```

```
                            mol_type = protein
                            organism = Staphylococcus sp.
SEQUENCE: 7
WRMYFSHRHA HLRSP                                                            15

SEQ ID NO: 8               moltype = AA   length = 15
FEATURE                    Location/Qualifiers
source                     1..15
                            mol_type = protein
                            organism = Staphylococcus sp.
SEQUENCE: 8
WHWRHRIPLQ LAAGR                                                            15

SEQ ID NO: 9               moltype = AA   length = 7
FEATURE                    Location/Qualifiers
REGION                     1..7
                            note = Description of Unknown: Coronavirus epitope
source                     1..7
                            mol_type = protein
                            organism = unidentified
SEQUENCE: 9
YPKCDRA                                                                      7

SEQ ID NO: 10              moltype = AA   length = 9
FEATURE                    Location/Qualifiers
REGION                     1..9
                            note = Description of Unknown: Coronavirus epitope
source                     1..9
                            mol_type = protein
                            organism = unidentified
SEQUENCE: 10
WDYPKCDRA                                                                    9

SEQ ID NO: 11              moltype = AA   length = 23
FEATURE                    Location/Qualifiers
REGION                     1..23
                            note = Description of Unknown: Coronavirus epitope
source                     1..23
                            mol_type = protein
                            organism = unidentified
SEQUENCE: 11
SLDQINVTFL DLEYEMKKLE ESY                                                   23

SEQ ID NO: 12              moltype = AA   length = 14
FEATURE                    Location/Qualifiers
REGION                     1..14
                            note = Description of Unknown: Coronavirus epitope
source                     1..14
                            mol_type = protein
                            organism = unidentified
SEQUENCE: 12
KWPWYIWLGF IAGL                                                             14

SEQ ID NO: 13              moltype = AA   length = 8
FEATURE                    Location/Qualifiers
REGION                     1..8
                            note = Description of Unknown: Coronavirus epitope
source                     1..8
                            mol_type = protein
                            organism = unidentified
SEQUENCE: 13
ENQKLIAN                                                                     8

SEQ ID NO: 14              moltype = AA   length = 8
FEATURE                    Location/Qualifiers
REGION                     1..8
                            note = Description of Unknown: Influenza epitope
source                     1..8
                            mol_type = protein
                            organism = unidentified
SEQUENCE: 14
HYEECSCY                                                                     8

SEQ ID NO: 15              moltype = AA   length = 8
FEATURE                    Location/Qualifiers
REGION                     1..8
                            note = Description of Unknown: Influenza epitope
source                     1..8
                            mol_type = protein
```

```
                        -continued organism = unidentified
SEQUENCE: 15
HVEECSCY                                                           8

SEQ ID NO: 16           moltype = AA   length = 19
FEATURE                 Location/Qualifiers
REGION                  1..19
                        note = Description of Unknown: Influenza epitope
source                  1..19
                        mol_type = protein
                        organism = unidentified
SEQUENCE: 16
DWSGYSGSFV QHPELTGLD                                              19

SEQ ID NO: 17           moltype = AA   length = 16
FEATURE                 Location/Qualifiers
REGION                  1..16
                        note = Description of Unknown: Influenza epitope
source                  1..16
                        mol_type = protein
                        organism = unidentified
SEQUENCE: 17
KSCINRCFYV ELIRGR                                                 16

SEQ ID NO: 18           moltype = AA   length = 15
FEATURE                 Location/Qualifiers
REGION                  1..15
                        note = Description of Unknown: Influenza epitope
source                  1..15
                        mol_type = protein
                        organism = unidentified
SEQUENCE: 18
FVIREPFISC SHLEC                                                  15

SEQ ID NO: 19           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 19
GNLFIAP                                                            7

SEQ ID NO: 20           moltype = AA   length = 6
FEATURE                 Location/Qualifiers
REGION                  1..6
                        note = Description of Unknown: Hemagglutinin peptide
source                  1..6
                        mol_type = protein
                        organism = unidentified
SEQUENCE: 20
WFIHHP                                                             6

SEQ ID NO: 21           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 21
WGVIHHP                                                            7

SEQ ID NO: 22           moltype = AA   length = 11
FEATURE                 Location/Qualifiers
REGION                  1..11
                        note = Description of Unknown: Hemagglutinin peptide
source                  1..11
                        mol_type = protein
                        organism = unidentified
SEQUENCE: 22
DLWSYNAELL V                                                      11

SEQ ID NO: 23           moltype = AA   length = 11
FEATURE                 Location/Qualifiers
REGION                  1..11
                        note = Description of Unknown: Hemagglutinin peptide
source                  1..11
```

```
                          mol_type = protein
                          organism = unidentified
SEQUENCE: 23
DIWTYNAELL V                                                                  11

SEQ ID NO: 24             moltype = AA  length = 25
FEATURE                   Location/Qualifiers
REGION                    1..25
                          note = Description of Artificial Sequence: Synthetic peptide
source                    1..25
                          mol_type = protein
                          organism = synthetic construct
SEQUENCE: 24
SLLTEVETPI RNEWGLLTEV ETPIR                                                   25

SEQ ID NO: 25             moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct
SEQUENCE: 25
SLLTEVET                                                                      8

SEQ ID NO: 26             moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 26
ETPIRNE                                                                       7

SEQ ID NO: 27             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 27
TEVETPIRNE                                                                    10

SEQ ID NO: 28             moltype = AA  length = 13
FEATURE                   Location/Qualifiers
REGION                    1..13
                          note = Description of Artificial Sequence: Synthetic peptide
source                    1..13
                          mol_type = protein
                          organism = synthetic construct
SEQUENCE: 28
SLLTEVETPI RNE                                                                13

SEQ ID NO: 29             moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 29
SLLTEVETPI R                                                                  11

SEQ ID NO: 30             moltype = AA  length = 13
FEATURE                   Location/Qualifiers
source                    1..13
                          mol_type = protein
                          organism = Human immunodeficiency virus 1
SEQUENCE: 30
RKSIHLGPGR AFY                                                                13

SEQ ID NO: 31             moltype = AA  length = 13
FEATURE                   Location/Qualifiers
source                    1..13
                          mol_type = protein
                          organism = Human immunodeficiency virus 2
SEQUENCE: 31
```

```
KKGIAIGPGR TLY                                                         13

SEQ ID NO: 32            moltype = AA  length = 13
FEATURE                  Location/Qualifiers
source                   1..13
                         mol_type = protein
                         organism = Human immunodeficiency virus
SEQUENCE: 32
RKSIRIGPGQ AFY                                                         13

SEQ ID NO: 33            moltype = AA  length = 13
FEATURE                  Location/Qualifiers
source                   1..13
                         mol_type = protein
                         organism = Human immunodeficiency virus
SEQUENCE: 33
RKRIRVGPGQ TVY                                                         13

SEQ ID NO: 34            moltype = AA  length = 37
FEATURE                  Location/Qualifiers
REGION                   1..37
                         note = Description of Artificial Sequence: Synthetic
                          polypeptide
source                   1..37
                         mol_type = protein
                         organism = synthetic construct
SEQUENCE: 34
SLDQINVTFL DLEYEMKKLE ESYQYIKANS KFIGITE                                37

SEQ ID NO: 35            moltype = AA  length = 23
FEATURE                  Location/Qualifiers
REGION                   1..23
                         note = Description of Artificial Sequence: Synthetic peptide
source                   1..23
                         mol_type = protein
                         organism = synthetic construct
SEQUENCE: 35
WDYPKCDRAQ YIKANSKFIG ITE                                              23

SEQ ID NO: 36            moltype = AA  length = 46
FEATURE                  Location/Qualifiers
REGION                   1..46
                         note = Description of Artificial Sequence: Synthetic
                          polypeptide
source                   1..46
                         mol_type = protein
                         organism = synthetic construct
SEQUENCE: 36
WDYPKCDRAS LDQINVTFLD LEYEMKKLEE SYQYIKANSK FIGITE                      46

SEQ ID NO: 37            moltype = AA  length = 41
FEATURE                  Location/Qualifiers
REGION                   1..41
                         note = Description of Artificial Sequence: Synthetic
                          polypeptide
source                   1..41
                         mol_type = protein
                         organism = synthetic construct
SEQUENCE: 37
WDYPKCDRAT EVETPIRNEH YEECSCYQYI KANSKFIGIT E                           41

SEQ ID NO: 38            moltype = AA  length = 8
FEATURE                  Location/Qualifiers
REGION                   1..8
                         note = Description of Unknown: Highly conserved coronavirus
                          sequence
source                   1..8
                         mol_type = protein
                         organism = unidentified
SEQUENCE: 38
ARDLICAQ                                                               8

SEQ ID NO: 39            moltype = AA  length = 30
FEATURE                  Location/Qualifiers
REGION                   1..30
                         note = Description of Artificial Sequence: Synthetic
                          polypeptide
source                   1..30
                         mol_type = protein
```

```
                                 -continued organism = synthetic construct
SEQUENCE: 39
ARDLICAQKW PWYIWLGFIA GLENQKLIAN                                    30

SEQ ID NO: 40           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 40
ENQKLIANAR DLICAQ                                                   16

SEQ ID NO: 41           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 41
WDYPKCDRAE NQKLIANARD LICAQ                                         25

SEQ ID NO: 42           moltype = AA  length = 31
FEATURE                 Location/Qualifiers
REGION                  1..31
                        note = Description of Artificial Sequence: Synthetic
                          polypeptide
source                  1..31
                        mol_type = protein
                        organism = synthetic construct
SEQUENCE: 42
WDYPKCDRAE NQKLIANKWP WYIWLGFIAG L                                  31

SEQ ID NO: 43           moltype = AA  length = 39
FEATURE                 Location/Qualifiers
REGION                  1..39
                        note = Description of Artificial Sequence: Synthetic
                          polypeptide
source                  1..39
                        mol_type = protein
                        organism = synthetic construct
SEQUENCE: 43
ARDLICAQEN QKLIANWDYP KCDRAQYIKA NSKFIGITE                           39

SEQ ID NO: 44           moltype = AA  length = 76
FEATURE                 Location/Qualifiers
REGION                  1..76
                        note = Description of Artificial Sequence: Synthetic
                          polypeptide
source                  1..76
                        mol_type = protein
                        organism = synthetic construct
SEQUENCE: 44
KWPWYIWLGF IAGLWDYPKC DRAQYIKANS KFIGITEARD LICAQENQKL IANWDYPKCD    60
RAQYIKANSK FIGITE                                                   76

SEQ ID NO: 45           moltype = AA  length = 69
FEATURE                 Location/Qualifiers
REGION                  1..69
                        note = Description of Artificial Sequence: Synthetic
                          polypeptide
source                  1..69
                        mol_type = protein
                        organism = synthetic construct
SEQUENCE: 45
ARDLICAQEN QKLIANQYIK ANSKFIGITE ARDLICAQEN QKLIANWDYP KCDRAQYIKA    60
NSKFIGITE                                                           69

SEQ ID NO: 46           moltype = AA  length = 80
FEATURE                 Location/Qualifiers
REGION                  1..80
                        note = Description of Artificial Sequence: Synthetic
                          polypeptide
source                  1..80
                        mol_type = protein
                        organism = synthetic construct
SEQUENCE: 46
```

```
WDYPKCDRAT EVETPIRNEH YEECSCYQYI KANSKFIGIT EARDLICAQE NQKLIANWDY    60
PKCDRAQYIK ANSKFIGITE                                                80

SEQ ID NO: 47           moltype = AA   length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 47
HYEECSCYWD YPKCDRAVET PIRNEQYIKA NSKFIGITE                            39

SEQ ID NO: 48           moltype = AA   length = 40
FEATURE                 Location/Qualifiers
REGION                  1..40
                        note = Description of Artificial Sequence: Synthetic
                         polypeptide
source                  1..40
                        mol_type = protein
                        organism = synthetic construct
SEQUENCE: 48
ENQKLIANTE VETPIRNEHY EECSCYQYIK ANSKFIGITE                           40

SEQ ID NO: 49           moltype = AA   length = 6
FEATURE                 Location/Qualifiers
REGION                  1..6
                        note = Description of Unknown: Hemagglutinin peptide
source                  1..6
                        mol_type = protein
                        organism = unidentified
SEQUENCE: 49
GNFIAP                                                                6

SEQ ID NO: 50           moltype = AA   length = 6
FEATURE                 Location/Qualifiers
REGION                  1..6
                        note = Description of Unknown: Hemagglutinin peptide
source                  1..6
                        mol_type = protein
                        organism = unidentified
SEQUENCE: 50
GNLIAP                                                                6

SEQ ID NO: 51           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 51
GNLIFAP                                                               7

SEQ ID NO: 52           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 52
LLTEVETPIR                                                           10

SEQ ID NO: 53           moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 53
LLTEVETPIR N                                                         11

SEQ ID NO: 54           moltype = AA   length = 12
FEATURE                 Location/Qualifiers
REGION                  1..12
                        note = Description of Artificial Sequence: Synthetic peptide
```

```
                           -continued source                  1..12
                        mol_type = protein
                        organism = synthetic construct
SEQUENCE: 54
LLTEVETPIR NE                                                            12

SEQ ID NO: 55           moltype = AA   length = 18
FEATURE                 Location/Qualifiers
REGION                  1..18
                        note = Description of Unknown: N1 sequence
source                  1..18
                        mol_type = protein
                        organism = unidentified
SEQUENCE: 55
DWSGYSGSFV QHPELTGL                                                      18

SEQ ID NO: 56           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 56
EVETPIRNE                                                                9

SEQ ID NO: 57           moltype = AA   length = 38
FEATURE                 Location/Qualifiers
REGION                  1..38
                        note = Description of Unknown: Epitope sequence
source                  1..38
                        mol_type = protein
                        organism = unidentified
SEQUENCE: 57
FLLPEDETPI RNEWGLLTDD ETPIRYIKAN SKFIGITE                                 38

SEQ ID NO: 58           moltype = AA   length = 64
FEATURE                 Location/Qualifiers
REGION                  1..64
                        note = Description of Artificial Sequence: Synthetic
                         polypeptide
source                  1..64
                        mol_type = protein
                        organism = synthetic construct
SEQUENCE: 58
GNLFIAPGNL FIAPHYEECS CYHYEECSCY QYIKANSKFI GITEHYEECS CYTPIRNETP         60
IRNE                                                                     64

SEQ ID NO: 59           moltype = AA   length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 59
GNLFIAPGNL FIAPQYIKAN SKFIGITEGN LFIAP                                    35

SEQ ID NO: 60           moltype = AA   length = 48
FEATURE                 Location/Qualifiers
REGION                  1..48
                        note = Description of Unknown: Epitope sequence
source                  1..48
                        mol_type = protein
                        organism = unidentified
SEQUENCE: 60
HYEECSCYDW SGYSGSFVQH PELTGLHYEE CSCYQYIKAN SKFIGITE                      48

SEQ ID NO: 61           moltype = AA   length = 33
FEATURE                 Location/Qualifiers
REGION                  1..33
                        note = Description of Unknown: Epitope sequence
source                  1..33
                        mol_type = protein
                        organism = unidentified
SEQUENCE: 61
ITGFAPFSKD NSIRLSAGGD IWVTREPYVS CDP                                      33
```

```
SEQ ID NO: 62            moltype = AA   length = 7
FEATURE                  Location/Qualifiers
REGION                   1..7
                         note = Description of Unknown: Hemagglutinin peptide
source                   1..7
                         mol_type = protein
                         organism = unidentified
SEQUENCE: 62
IWGIHHP                                                                    7

SEQ ID NO: 63            moltype = AA   length = 7
FEATURE                  Location/Qualifiers
REGION                   1..7
                         note = Description of Unknown: Hemagglutinin peptide
source                   1..7
                         mol_type = protein
                         organism = unidentified
SEQUENCE: 63
IWGVHHP                                                                    7

SEQ ID NO: 64            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 64
IWGVIHHP                                                                   8

SEQ ID NO: 65            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 65
IWGIVHHP                                                                   8

SEQ ID NO: 66            moltype = AA   length = 27
FEATURE                  Location/Qualifiers
REGION                   1..27
                         note = Description of Unknown: Influenza M2e epitope
source                   1..27
                         mol_type = protein
                         organism = unidentified
SEQUENCE: 66
LLTEVETPIR NESLLTEVET PIRNEWG                                              27

SEQ ID NO: 67            moltype = AA   length = 13
FEATURE                  Location/Qualifiers
REGION                   1..13
                         note = Description of Unknown: Influenza M2e epitope
source                   1..13
                         mol_type = protein
                         organism = unidentified
SEQUENCE: 67
LLTEVETPIR NEW                                                             13

SEQ ID NO: 68            moltype = AA   length = 14
FEATURE                  Location/Qualifiers
REGION                   1..14
                         note = Description of Unknown: Influenza M2e epitope
source                   1..14
                         mol_type = protein
                         organism = unidentified
SEQUENCE: 68
LLTEVETPIR NEWG                                                            14

SEQ ID NO: 69            moltype = AA   length = 11
FEATURE                  Location/Qualifiers
REGION                   1..11
                         note = Description of Unknown: Influenza M2e epitope
source                   1..11
                         mol_type = protein
                         organism = unidentified
SEQUENCE: 69
LTEVETPIRN E                                                               11
```

```
SEQ ID NO: 70            moltype = AA   length = 12
FEATURE                  Location/Qualifiers
REGION                   1..12
                         note = Description of Unknown: Influenza M2e epitope
source                   1..12
                         mol_type = protein
                         organism = unidentified
SEQUENCE: 70
LTEVETPIRN EW                                                            12

SEQ ID NO: 71            moltype = AA   length = 13
FEATURE                  Location/Qualifiers
REGION                   1..13
                         note = Description of Unknown: Influenza M2e epitope
source                   1..13
                         mol_type = protein
                         organism = unidentified
SEQUENCE: 71
LTEVETPIRN EWG                                                           13

SEQ ID NO: 72            moltype = AA   length = 9
FEATURE                  Location/Qualifiers
REGION                   1..9
                         note = Description of Unknown: Influenza M2e epitope
source                   1..9
                         mol_type = protein
                         organism = unidentified
SEQUENCE: 72
MSLLTEVET                                                                 9

SEQ ID NO: 73            moltype = AA   length = 10
FEATURE                  Location/Qualifiers
REGION                   1..10
                         note = Description of Unknown: Influenza M2e epitope
source                   1..10
                         mol_type = protein
                         organism = unidentified
SEQUENCE: 73
MSLLTEVETP                                                               10

SEQ ID NO: 74            moltype = AA   length = 11
FEATURE                  Location/Qualifiers
REGION                   1..11
                         note = Description of Unknown: Influenza M2e epitope
source                   1..11
                         mol_type = protein
                         organism = unidentified
SEQUENCE: 74
MSLLTEVETP I                                                             11

SEQ ID NO: 75            moltype = AA   length = 12
FEATURE                  Location/Qualifiers
REGION                   1..12
                         note = Description of Unknown: Influenza M2e epitope
source                   1..12
                         mol_type = protein
                         organism = unidentified
SEQUENCE: 75
MSLLTEVETP IR                                                            12

SEQ ID NO: 76            moltype = AA   length = 13
FEATURE                  Location/Qualifiers
REGION                   1..13
                         note = Description of Unknown: Influenza M2e epitope
source                   1..13
                         mol_type = protein
                         organism = unidentified
SEQUENCE: 76
MSLLTEVETP IRN                                                           13

SEQ ID NO: 77            moltype = AA   length = 14
FEATURE                  Location/Qualifiers
REGION                   1..14
                         note = Description of Unknown: Influenza M2e epitope
source                   1..14
                         mol_type = protein
                         organism = unidentified
SEQUENCE: 77
```

```
MSLLTEVETP IRNE                                                           14

SEQ ID NO: 78          moltype = AA  length = 20
FEATURE                Location/Qualifiers
REGION                 1..20
                       note = Description of Unknown: Influenza M2e epitope
source                 1..20
                       mol_type = protein
                       organism = unidentified
SEQUENCE: 78
MSLLTEVETP IRNETPIRNE                                                     20

SEQ ID NO: 79          moltype = AA  length = 15
FEATURE                Location/Qualifiers
REGION                 1..15
                       note = Description of Unknown: Influenza M2e epitope
source                 1..15
                       mol_type = protein
                       organism = unidentified
SEQUENCE: 79
MSLLTEVETP IRNEW                                                          15

SEQ ID NO: 80          moltype = AA  length = 16
FEATURE                Location/Qualifiers
REGION                 1..16
                       note = Description of Unknown: Influenza M2e epitope
source                 1..16
                       mol_type = protein
                       organism = unidentified
SEQUENCE: 80
MSLLTEVETP IRNEWG                                                         16

SEQ ID NO: 81          moltype = AA  length = 24
FEATURE                Location/Qualifiers
REGION                 1..24
                       note = Description of Unknown: Influenza M2e epitope
source                 1..24
                       mol_type = protein
                       organism = unidentified
SEQUENCE: 81
MSLLTEVETP IRNEWGCRCN DSSD                                                24

SEQ ID NO: 82          moltype = AA  length = 14
FEATURE                Location/Qualifiers
REGION                 1..14
                       note = Description of Unknown: Influenza M2e epitope
source                 1..14
                       mol_type = protein
                       organism = unidentified
SEQUENCE: 82
SLLTEVETPI RNEW                                                           14

SEQ ID NO: 83          moltype = AA  length = 15
FEATURE                Location/Qualifiers
REGION                 1..15
                       note = Description of Unknown: Influenza M2e epitope
source                 1..15
                       mol_type = protein
                       organism = unidentified
SEQUENCE: 83
SLLTEVETPI RNEWG                                                          15

SEQ ID NO: 84          moltype = AA  length = 21
FEATURE                Location/Qualifiers
REGION                 1..21
                       note = Description of Unknown: Influenza M2e epitope
source                 1..21
                       mol_type = protein
                       organism = unidentified
SEQUENCE: 84
SLLTEVETPI RNEWGTPIRN E                                                   21

SEQ ID NO: 85          moltype = AA  length = 27
FEATURE                Location/Qualifiers
REGION                 1..27
                       note = Description of Unknown: Influenza M2e epitope
source                 1..27
                       mol_type = protein
                       organism = unidentified
```

```
SEQUENCE: 85
SLLTEVETPI RNEWGTPIRN ETPIRNE                                              27

SEQ ID NO: 86            moltype = AA  length = 33
FEATURE                  Location/Qualifiers
REGION                   1..33
                         note = Description of Unknown: Influenza M2e epitope
source                   1..33
                         mol_type = protein
                         organism = unidentified
SEQUENCE: 86
SLLTEVETPI RNEWGTPIRN ETPIRNETPI RNE                                       33

SEQ ID NO: 87            moltype = AA  length = 39
FEATURE                  Location/Qualifiers
REGION                   1..39
                         note = Description of Unknown: Influenza M2e epitope
source                   1..39
                         mol_type = protein
                         organism = unidentified
SEQUENCE: 87
SLLTEVETPI RNEWGLLTEV ETPIRQYIKA NSKFIGITE                                 39

SEQ ID NO: 88            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 88
TPIRNE                                                                     6

SEQ ID NO: 89            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 89
VETPIRNE                                                                   8

SEQ ID NO: 90            moltype = AA  length = 52
FEATURE                  Location/Qualifiers
REGION                   1..52
                         note = Description of Unknown: Epitope sequence
source                   1..52
                         mol_type = protein
                         organism = unidentified
SEQUENCE: 90
VTREPYVSCD PKSCINRCFY VELIRGRVTR EPYVSCDPWY IKANSKFIGI TE                  52

SEQ ID NO: 91            moltype = AA  length = 6
FEATURE                  Location/Qualifiers
REGION                   1..6
                         note = Description of Unknown: Hemagglutinin peptide
source                   1..6
                         mol_type = protein
                         organism = unidentified
SEQUENCE: 91
WGIHHP                                                                     6

SEQ ID NO: 92            moltype = AA  length = 6
FEATURE                  Location/Qualifiers
REGION                   1..6
                         note = Description of Unknown: Hemagglutinin peptide
source                   1..6
                         mol_type = protein
                         organism = unidentified
SEQUENCE: 92
WGVHHP                                                                     6

SEQ ID NO: 93            moltype = AA  length = 7
FEATURE                  Location/Qualifiers
REGION                   1..7
                         note = Description of Artificial Sequence: Synthetic peptide
source                   1..7
                         mol_type = protein
```

```
                                          -continued
                              organism = synthetic construct
SEQUENCE: 93
WGIVHHP                                                                        7

SEQ ID NO: 94           moltype = AA   length = 8
FEATURE                 Location/Qualifiers
REGION                  1..8
                        note = Description of Unknown: Hemagglutinin peptide
source                  1..8
                        mol_type = protein
                        organism = unidentified
SEQUENCE: 94
YIWGIHHP                                                                       8

SEQ ID NO: 95           moltype = AA   length = 8
FEATURE                 Location/Qualifiers
REGION                  1..8
                        note = Description of Unknown: Hemagglutinin peptide
source                  1..8
                        mol_type = protein
                        organism = unidentified
SEQUENCE: 95
YIWGVHHP                                                                       8

SEQ ID NO: 96           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 96
YIWGVIHHP                                                                      9

SEQ ID NO: 97           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 97
YIWGIVHHP                                                                      9

SEQ ID NO: 98           moltype = AA   length = 14
FEATURE                 Location/Qualifiers
REGION                  1..14
                        note = Description of Unknown: T cell epitope
source                  1..14
                        mol_type = protein
                        organism = unidentified
SEQUENCE: 98
QYIKANSKFI GITE                                                               14

SEQ ID NO: 99           moltype = AA   length = 15
FEATURE                 Location/Qualifiers
REGION                  1..15
                        note = Description of Unknown: Epitope sequence
source                  1..15
                        mol_type = protein
                        organism = unidentified
SEQUENCE: 99
PIRNEWGCRC NDSSD                                                              15

SEQ ID NO: 100          moltype = AA   length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 100
GNLFIAPWGV IHHPHYEECS CY                                                      22

SEQ ID NO: 101          moltype = AA   length = 22
FEATURE                 Location/Qualifiers
REGION                  1..22
                        note = Description of Artificial Sequence: Synthetic peptide
source                  1..22
```

```
                              mol_type = protein
                              organism = synthetic construct
SEQUENCE: 101
WGVIHHPGNL FIAPHYEECS CY                                          22

SEQ ID NO: 102      moltype = AA  length = 294
FEATURE             Location/Qualifiers
source              1..294
                    mol_type = protein
                    organism = Mycobacterium tuberculosis
SEQUENCE: 102
SRPGLPVEYL QVPSPSMGRD IKVQFQSGGA NSPALYLLDG LRAQDDFSGW DINTPAFEWY  60
DQSGLSVVMP VGGQSSFYSD WYQPACGKAG CQTYKWETFL TSELPGWLQA NRHVKPTGSA  120
VVGLSMAASS ALTLAIYHPQ QFVYAGAMSG LLDPSQAMGP TLIGLAMGDA GGYKASDMWG  180
PKEDPAWQRN DPLLNVGKLI ANNTRVWVYC GNGKPSDLGG NNLPAKFLEG FVRTSNIKFQ  240
DAYNAGGGHN GVFDFPDSGT HSWEYWGAQL NAMKPDLQRA LGATPNTGPA PQGA        294

SEQ ID NO: 103      moltype = AA  length = 336
FEATURE             Location/Qualifiers
REGION              1..336
                    note = Description of Artificial Sequence: Synthetic
                     polypeptide
source              1..336
                    mol_type = protein
                    organism = synthetic construct
SEQUENCE: 103
SEFAYGSFVR TVSLPVGADE GNLFIAPWGV IHHPHYEECS CYSRPGLPVE YLQVPSPSMG  60
RDIKVQFQSG GANSPALYLL DGLRAQDDFS GWDINTPAFE WYDQSGLSVV MPVGGQSSFY  120
SDWYQPACGK AGCQTYKWET FLTSELPGWL QANRHVKPTG SAVVGLSMAA SSALTLAIYH  180
PQQFVYAGAM SGLLDPSQAM GPTLIGLAMG DAGGYKASDM WGPKEDPAWQ RNDPLLNVGK  240
LIANNTRVWV YCGNGKPSDL GGNNLPAKFL EGFVRTSNIK FQDAYNAGGG HNGVFDFPDS  300
GTHSWEYWGA QLNAMKPDLQ RALGATPNTG PAPQGA                           336

SEQ ID NO: 104      moltype = AA  length = 13
FEATURE             Location/Qualifiers
REGION              1..13
                    note = Description of Unknown: Hemagglutinin peptide
source              1..13
                    mol_type = protein
                    organism = unidentified
SEQUENCE: 104
GNLIAPWGVI HHP                                                    13

SEQ ID NO: 105      moltype = AA  length = 14
FEATURE             Location/Qualifiers
REGION              1..14
                    note = Description of Unknown: Hemagglutinin peptide
source              1..14
                    mol_type = protein
                    organism = unidentified
SEQUENCE: 105
GNLFIAPWGV IHHP                                                   14

SEQ ID NO: 106      moltype = AA  length = 28
FEATURE             Location/Qualifiers
REGION              1..28
                    note = Description of Unknown: Hemagglutinin peptide
source              1..28
                    mol_type = protein
                    organism = unidentified
SEQUENCE: 106
GNLFIAPWGV IHHPGNLFIA PWGVIHHP                                    28

SEQ ID NO: 107      moltype = AA  length = 22
FEATURE             Location/Qualifiers
REGION              1..22
                    note = Description of Unknown: Hemagglutinin peptide
source              1..22
                    mol_type = protein
                    organism = unidentified
SEQUENCE: 107
HYEECSCYGN LFIAPWGVIH HP                                          22

SEQ ID NO: 108      moltype = AA  length = 22
FEATURE             Location/Qualifiers
REGION              1..22
                    note = Description of Unknown: Hemagglutinin peptide
source              1..22
                    mol_type = protein
```

```
                                organism = unidentified
SEQUENCE: 108
GNLFIAPHYE ECSCYWGVIH HP                                              22

SEQ ID NO: 109          moltype = AA   length = 12
FEATURE                 Location/Qualifiers
REGION                  1..12
                        note = Description of Unknown: Hemagglutinin peptide
source                  1..12
                        mol_type = protein
                        organism = unidentified
SEQUENCE: 109
GNLFIAPRYA FA                                                         12

SEQ ID NO: 110          moltype = AA   length = 11
FEATURE                 Location/Qualifiers
REGION                  1..11
                        note = Description of Unknown: Hemagglutinin peptide
source                  1..11
                        mol_type = protein
                        organism = unidentified
SEQUENCE: 110
GNLVVPRYAF A                                                          11

SEQ ID NO: 111          moltype = AA   length = 11
FEATURE                 Location/Qualifiers
REGION                  1..11
                        note = Description of Unknown: Hemagglutinin peptide
source                  1..11
                        mol_type = protein
                        organism = unidentified
SEQUENCE: 111
GNLIAPRYAF A                                                          11

SEQ ID NO: 112          moltype = AA   length = 6
FEATURE                 Location/Qualifiers
REGION                  1..6
                        note = Description of Unknown: Hemagglutinin peptide
source                  1..6
                        mol_type = protein
                        organism = unidentified
SEQUENCE: 112
GNLVVP                                                                 6

SEQ ID NO: 113          moltype = AA   length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 113
GNLFIAPWGV IHHPHYEECS CYQYIKANSK FIGITE                               36

SEQ ID NO: 114          moltype = AA   length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 114
QYIKANSKFI GITEGNLFIA PWGVIHHPHY EECSCY                               36
```

IMMUNOGENIC COMPOSITIONS TO TREAT AND PREVENT MICROBIAL INFECTIONS

REFERENCE TO RELATED APPLICATIONS

This application is a Continuation of U.S. application Ser. No. 17/161,997 filed Jan. 29, 2021, which claims priority to U.S. Provisional Application No. 63/109,966, filed Nov. 5, 2020, U.S. Provisional Application No. 62/971,654, filed Feb. 7, 2020, and U.S. Provisional Application No. 62/971,036, filed Feb. 6, 2020, each of which is entirely and specifically incorporated by reference.

SEQUENCE LISTING

The instant application contains a Sequence Listing which has been submitted electronically in XML format and is hereby incorporated by reference in its entirety. Said XML copy, created on Jan. 26, 2023, is named 3022_045_USDV_SL.txt and is 141 kbytes in size.

BACKGROUND

1 Field of the Invention

The present invention is directed to composite antigens composed of a plurality of epitopes, and to tools and methods for generating an immune response with the composite antigens of the invention. The invention is also directed to antigenic sequences obtained or derived from one or more microbes and, in particular, bacterial and/or viral sequences, coupled with a T cell stimulating component for the development of novel vaccines and to the immunogenic composition, vaccines and methods developed. The invention is also directed to antibodies that bind to antigenic sequences of the invention.

2 Description of the Background

Microbial and viral pathogens are a primary source of infectious disease in animals. Pathogens and their hosts constantly adapt to one another in an endless competition for survival and propagation. Certain pathogens have become enormously successful at infecting mammalian hosts and surviving exposure to the host immune response, even over periods of years or decades. Examples of extremely successful mammalian pathogens are influenza virus, coronavirus, and Mycobacteria.

Three genera of influenza viruses currently comprise the Orthomyxoviridae Family: Influenza virus A, Influenza virus B, and Influenza virus C. Each of these genera contains a single species of influenza virus. The genus Influenza virus A consists of a single species, influenza A virus, which includes all of the influenza virus strains currently circulating among humans, including, for example, but not limited to, H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7 serotypes. In virus classification, influenza viruses are RNA viruses. The genus Influenza virus B consists of a single species, influenza B virus, of which there is currently only one known serotype. Influenza B virus is almost exclusively a human pathogen but is significantly less common and less genetically diverse than influenza A strains. Because of this limited genetic diversity, most humans acquire a certain degree of immunity to influenza B virus at an early age; however, the mutation frequency of the virus is sufficiently high enough to prevent lasting immunity by most humans, but not high enough to permit pandemic infection by influenza B virus across human populations. The genus Influenza virus C also consists of a single species, denoted influenza C virus, of which there is also currently only one known serotype. This serotype is known to infect both primates and porcine, and while infections of influenza C virus are rare, the resulting illness can be severe. Epidemics of influenza C virus are not uncommon in exposed populations, however, due to its rapid transmissibility in humans having close contact.

A fourth family of influenza viruses was identified in 2016—Influenza D, which was first isolated in 2011. Hemagglutinin (HA) and neuraminidase (NA) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to HA and NA. These different types of HA and NA form the basis of the H and N distinctions in, for example, H5N1. There are 18 HA and 11 NA subtypes known, but only HA 1, 2 and 3, and NA 1 and 2 are commonly found in humans. Influenza A virus, in particular, has many different serotypes, upwards of 144 possible "HN" serotypes based on variations within these two proteins alone. Only a small number of these combinations are believed to be circulating within susceptible populations at any given time.

Influenza viruses are etiologic agents for a contagious respiratory illness (commonly referred to as the flu) that primarily affects humans and other vertebrates. Influenza is highly infectious and an acute respiratory disease that has plagued the human race since ancient times. Infection is characterized by recurrent annual epidemics and periodic major worldwide pandemics. Influenza virus infection can cause mild to severe illness and can even lead to death. Every year in the United States, 5 to 20 percent of the population, on average, contracts the flu with more than 200,000 hospitalizations from complications and over 36,000 deaths. Because of the high disease-related morbidity and mortality, direct and indirect social economic impacts of influenza are enormous. Four pandemics occurred in the last century, together causing tens of millions of deaths worldwide.

Coronaviruses are a group of RNA viruses that cause diseases in mammals and birds. Coronaviruses are viruses in the subfamily Orthocoronavirinae in the family Coronaviridae, in the order Nidovirales. Coronaviruses are enveloped viruses with a positive-sense single-stranded RNA genome and with a nucleocapsid of helical symmetry. The genomic size of coronaviruses ranges from approximately 26 to 32 kilobases, the largest for an RNA virus. The name "coronavirus" is derived from the Latin corona, meaning crown or halo, which refers to the characteristic appearance of the virus particles (virions): they have a fringe reminiscent of a royal crown or of the solar corona. In humans, the viruses cause respiratory infections including what is referred to as the common cold. Coronavirus is also the etiological agent of SARS, MERS, and the 2019-20-Wuhan outbreak.

Influenza virus and coronavirus spread from host to host through coughing or sneezing. Airborne droplets are the primary transmission vectors between individuals. In humans, the virus typically spreads directly from person to person, although persons can also be infected from indirect contact with surfaces harboring the virus. Infected adults become infectious to others beginning as little as one day before primary symptoms of the disease develop. Thereafter, these persons remain infectious for up to 5 days or more after. Uncomplicated illness is often characterized by an abrupt onset of constitutional and respiratory symptoms, including fever, myalgia, headache, malaise, nonproductive cough, sore throat, rhinitis, or a combination of one or more of these symptoms.

Currently, the spread of pathogenic influenza virus is controlled in animal populations by vaccination and/or treatment with one or more anti-viral compounds. Vaccines containing inactivated influenza virus or simply influenza antigen are currently in use worldwide and especially promoted for use by high-risk groups such as infants, the elderly, those without adequate health care and immunocompromised individuals. Most all viruses for vaccine use are propagated in fertile hen's eggs, inactivated by chemical means, and the antigens purified. The vaccines are usually trivalent, containing representative influenza A viruses (H1N1 and H3N2) and influenza B strains. The World Health Organization (WHO) regularly updates the specific strains targeted for vaccine development to those believed to be most prevalent and thereby maximize overall world efficacy. During inter-pandemic periods, it typically takes eight months or more before an updated influenza vaccine is ready for market. Historically, viral pandemics are spread to most continents within four to six months, and future viral pandemics are likely to spread even faster due to increased international travel. It is likely inevitable that an effective vaccine made by conventional means will be unavailable or in very short supply during the first wave of any future widespread outbreak or pandemic. There are currently no antiviral drugs approved for prevention or treatment or coronavirus.

Annual influenza outbreaks occur as a result of "antigenic drift." Antigenic drift is caused by mutations within antigenic (i.e., immunity stimulating) portions of viral proteins within viral subtypes circulating in host populations that alter the host's ability to recognize and defend effectively against the infecting virus, even when the virus has been circulating in the community for several years. Antigenic shift occurs when there is an abrupt or sudden, major change in a virus. Antigenic shift is typically caused by the occurrence of new combinations of the HA and/or NA, proteins on the surface of the virus, i.e., the creation of a new Influenza subtype, or variations in the structure of the spike protein in the case of coronavirus. The antigenic drift that diminishes existing immunity in a host population generally occurs within so-called immunodominant antigens or regions. Immunodominant antigens are those antigens belonging to a pathogen that are the most-easily and most-quickly recognized by the host immune system and, consequently, account for the vast majority of immune response to the invading pathogen. Typically, immunodominant antigens exist within regions of the pathogen that are most exposed to the environment, i.e., are on the external surfaces or on protruding elements of the pathogen, and so are most readily accessible to the host immune system.

In the case of influenza, the immunodominant HA and NA proteins protrude from the central capsid of the viral particle, and so they tend to interact most strongly with the host's internal environment and dominate the host immune response. Mutations occurring in the microbial genome that protect the microbe from the host immune system, these mutations are most readily found to affect the immunodominant antigens. The appearance of a new influenza A virus subtype, to which most of the world's population is naïve, is the first step toward a pandemic. If the new Influenza subtype also has the capacity to spread easily from person to person, then a full-blown pandemic may be expected resulting in a global influenza outbreak infecting millions of humans.

Proteins that contribute to the overall structure of all coronaviruses are the spike (S), envelope (E), membrane (M), and nucleocapsid (N), and also internal proteins such as polymerase (P). The immunodominant proteins is believed to be the spike protein as it interacts with the host's internal environment and dominate the host immune response.

Non-immunodominant antigens are those that are capable of raising a host immune response but account for only a small amount of the total immune response. This is thought to happen because the non-immunodominant antigens are at least partially shielded from the host immune system, as in the case of an antigen that is located in a cleft or fold of the microbial surface or is surrounded by protruding elements of the microbe. In the case of influenza, non-immunodominant antigens occurring near the capsid surface are shielded from the host immune system by the immunodominant HA and NA spikes protruding from the surface. Non-immunodominant antigens tend to show less mutation in response to host immune pressure than do immunodominant antigens.

The CDC and the leading authorities on disease prevention in the world recommend the single best way of preventing a viral respiratory infection is through regular vaccinations. Conventional vaccines typically target the immunodominant proteins, HA and NA antigens for influenza. These vaccines have not been universally protective or 100 percent effective at preventing the disease. Antigenic shift prevents flu vaccines from being universally protective or from maintaining effectiveness over many years. The ineffectiveness of conventional vaccines may also be due, in part, to antigenic drift and the resulting variation within antigenic portions of the HA and NA proteins most commonly recognized by the immune system (i.e., immunodominant antigens). As a result, many humans may find themselves susceptible to the flu virus without an effective method of treatment available since influenza is constantly improving its resistant to current treatments. This scenario is particularly concerning with respect to the H5N1 virus, which is highly virulent but for which there is currently no widely available commercial vaccine to immunize susceptible human populations.

Currently, flu vaccines are reformulated each year due to the yearly emergence of new strains, and generally induce limited immunity. In addition, to achieve a protective immune response, some vaccines are administered with high doses of antigen. This is particularly true for H5N1 vaccines. In addition, influenza vaccines, including H5N1 vaccines, typically present epitopes in the same order as the epitopes are found in nature, generally presenting as whole-viral proteins; consequently, relatively large amounts of protein are required to make an effective vaccine. As a result, each administration includes an increased cost associated with the dose amount, and there is increased difficulty in manufacturing enough doses to vaccinate the general public. Further, the use of larger proteins elevates the risk of undesirable immune responses in the recipient host.

*Mycobacterium tuberculosis* (MTB) is a pathogenic bacterial species in the family Mycobacteriaceae and the causative agent of most cases of tuberculosis (TB). *M. smegmatis*, another microbe of the same family, is often utilized in laboratory studies as a surrogate for MTB. Another species of this genus is *M. leprae*, the causative agent of leprosy. MTB was first discovered in 1882 by Robert Koch, *M. tuberculosis* has an unusual, complex, lipid rich, cell wall which makes the cells impervious to Gram staining. Acid-fast detection techniques are used to make the diagnosis instead. The physiology of *M. tuberculosis* is highly aerobic and requires significant levels of oxygen to remain viable. Primarily a pathogen of the mammalian respiratory system, MTB is generally inhaled and, in five to ten percent of individuals, will progress to an acute pulmonary infection. The remaining individuals will either clear the infection completely or the infection may become latent. It is not clear how the immune system controls MTB, but cell mediated immunity is believed to play a critical role (Svenson et al., Human Vaccines, 6-4:309-17, 2010). Common diagnostic methods for TB are the tuberculin skin test, acid-fast stain and chest radiographs.

*M. tuberculosis* requires oxygen to proliferate and does not retain typical bacteriological stains due to high lipid content of its cell wall. While mycobacteria do not fit the Gram-positive category from an empirical standpoint (i.e., they do not retain the crystal violet stain), they are classified as acid-fast Gram-positive bacteria due to their lack of an outer cell membrane.

*M. tuberculosis* has over one hundred strain variations and divides every 15-20 hours, which is extremely slow compared to other types of bacteria that have division times measured in minutes (*Escherichia coli* can divide roughly every 20 minutes). The microorganism is a small *bacillus* that can withstand weak disinfectants and survive in a dry state for weeks. The cell wall of MTB contains multiple components such as peptidoglycan, mycolic acid and the glycolipid lipoarabinomannan. The role of these moieties in pathogenesis and immunity remain controversial. (Svenson et al., Human Vaccines, 6-4:309-17, 2010).

When in the lungs, *M. tuberculosis* is taken up by alveolar macrophages, but these macrophages are unable to digest the bacteria because the cell wall of the bacteria prevents the fusion of the phagosome with a lysosome. Specifically, *M. tuberculosis* blocks the bridging molecule, early endosomal autoantigen 1 (EEA1); however, this blockade does not prevent fusion of vesicles filled with nutrients. As a consequence, bacteria multiply unchecked within the macrophage. The bacteria also carry the UreC gene, which prevents acidification of the phagosome, and also evade macrophage-killing by neutralizing reactive nitrogen intermediates.

The BCG vaccine (Bacille de Calmette et Guérin) against tuberculosis is prepared from a strain of the attenuated, but live bovine tuberculosis *bacillus, Mycobacterium bovis*. This strain lost its virulence to humans through in vitro subculturing in Middlebrook 7H9 media. As the bacteria adjust to subculturing conditions, including the chosen media, the organism adapts and in doing so, loses its natural growth characteristics for human blood. Consequently, the bacteria can no longer induce disease when introduced into a human host. However, the attenuated and virulent bacteria retain sufficient similarity to provide immunity against infection of human tuberculosis. The effectiveness of the BCG vaccine has been highly varied, with an efficacy of from zero to eighty percent in preventing tuberculosis for duration of fifteen years, although protection seems to vary greatly according to geography and the lab in which the vaccine strain was grown. This variation, which appears to depend on geography, generates a great deal of controversy over use of the BCG vaccine yet has been observed in many different clinical trials. For example, trials conducted in the United Kingdom have consistently shown a protective effect of sixty to eighty percent, but those conducted in other areas have shown no or almost no protective effect. For whatever reason, these trials all show that efficacy decreases in those clinical trials conducted close to the equator. In addition, although widely used because of its protective effects against disseminated TB and TB meningitis in children, the BCG vaccine is largely ineffective against adult pulmonary TB, the single most contagious form of TB.

A 1994 systematic review found that the BCG reduces the risk of getting TB by about fifty percent. There are differences in effectiveness, depending on region due to factors such as genetic differences in the populations, changes in environment, exposure to other bacterial infections, and conditions in the lab where the vaccine is grown, including genetic differences between the strains being cultured and the choice of growth medium.

The duration of protection of BCG is not clearly known or understood. In those studies showing a protective effect, the data are inconsistent. The MRC study showed protection waned to 59% after 15 years and to zero after 20 years; however, a study looking at Native Americans immunized in the 1930s found evidence of protection even 60 years after immunization, with only a slight waning in efficacy. Rigorous analysis of the results demonstrates that BCG has poor protection against adult pulmonary disease, but does provide good protection against disseminated disease and TB meningitis in children. Therefore, there is a need for new vaccines and vaccine antigens that can provide solid and long-term immunity to MTB.

The role of antibodies in the development of immunity to MTB is controversial. Current data suggests that T cells, specifically $CD4^+$ and $CD8^+$ T cells, are critical for maximizing macrophage activity against MTB and promoting optimal control of infection (Slight et al, JCI 123(2):712, February 2013). However, these same authors demonstrated that B cell deficient mice are not more susceptible to MTB infection than B cell intact mice suggesting that humoral immunity is not critical. Phagocytosis of MTB can occur via surface opsonins, such as C3, or nonopsonized MTB surface mannose moieties. Fc gamma receptors, important for IgG facilitated phagocytosis, do not seem to play an important role in MTB immunity (Crevel et al., Clin Micro Rev. 15(2), April 2002; Armstrong et al., J Exp Med. 1975 Jul. 1; 142(1):1-16). IgA has been considered for prevention and treatment of TB, since it is a mucosal antibody. A human IgA monoclonal antibody to the MTB heat shock protein HSPX (HSPX) given intra-nasally provided protection in a mouse model (Balu et al, J of Immun. 186:3113, 2011). Mice treated with IgA had less prominent MTB pneumonic infiltrates than untreated mice. While antibody prevention and therapy may be hopeful, the effective MTB antigen targets and the effective antibody class and subclasses have not been established (Acosta et al, Intech, 2013).

Cell wall components of MTB have been delineated and analyzed for many years. Lipoarabinomannan (LAM) has been shown to be a virulence factor and a monoclonal antibody to LAM has enhanced protection to MTB in mice (Teitelbaum, et al., Proc. Natl. Acad. Sci. 95:15688-15693, 1998, Svenson et al., Human Vaccines, 6-4:309-17, 2010). The mechanism whereby the MAB enhanced protection was not determined, and the MAB did not decrease bacillary burden. It was postulated that the MAB possibly blocked the effects of LAM induced cytokines. The role of mycolic acid for vaccines and immune therapy is unknown. It has been used for diagnostic purposes, but has not been shown to have utility for vaccine or other immune therapy approaches.

While MTB infected individuals may develop antibodies to mycolic acid, there is no evidence that antibodies in general, or specifically mycolic acid antibodies, play a role in immunity to MTB. Antibiotic resistance and latency are problems for treating and preventing MTB infections. The BCG vaccine against TB does not provide protection from acquiring TB to a significant degree.

Within an immune response, T cells are important tools of the immune system and a major source of the cascade of cytokines that occurs following an immune response. Two of the principal forms of T cells are identified by the presence of the cell surface molecules CD4 and CD8. T cells that express CD4 are generally referred to as helper T cells. T helper cells include the subsets Th1 and Th2, and the cytokines they produce are known as Th1-type cytokines and Th2-type cytokines, both sets of which are of critical importance in developing an immune response. The Th1-type cytokines produce a pro-inflammatory response stimulating the opsonization of intracellular parasites, basically the humoral immune response. Interferon gamma is one of the principal Th1 cytokines. The Th2-type cytokines include interleukins 4, 5, 10 and 13, which are closely associated with the promotion of a cellular immune response. Against an infection, a balanced Th1 and Th2 response is most desired.

Accordingly, it would be advantageous to administer a vaccine that provides protection against a microbial infection over a broad range of different strains and/or variations of a pathogen, and a vaccine that is effective against multiple pathogens. It would also be advantageous to administer a single or limited number of vaccinations that would provide effective protection across a selection of different pathogens without loading a patient's system with secondary components generally associated with administering multiple single vaccine doses (e.g., T cell stimulating agents, CRM, components associated with vaccine manufacture, minor contaminants). Preferably the immunogenic composition and vaccine would not generate an inflammatory response upon administration.

It would also be advantageous to administer a vaccine that could be effective in those individuals with limited immune system function. Such vaccines would be useful to treat many individuals and populations and may be useful to compliment conventional vaccines, all to provide comprehensive protection to as many individuals as possible against existing as well as new and emerging pathogens across a population without loading a patient's system with secondary components which may themselves generate a negative immune response.

SUMMARY OF THE INVENTION

The present invention provides new and useful compositions, as well as tools and methods for generating an immune response against a microbial infection. In particular, the invention provides vaccines and methods developed from multiple antigenic regions of one or more pathogens, with or without a T cell epitope, with a single or fewer doses than conventionally required.

One embodiment of the invention is directed to peptides containing multiple epitopes of one or more pathogens, with or without a T cell stimulating epitope. Preferably the pathogens are obtained or derived from one or more viral type, strain and/or serotype, and/or one or more pathogenic bacteria, type, strain and/or serotype. Preferably the T cell stimulating epitope is obtained or derived from tetanus toxin, tetanus toxin heavy chain proteins, diphtheria toxoid, CRM, recombinant CRM, tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus *influenzae* protein D, Flagellin Fli C, Horseshoe crab Haemocyanin, and/or a fragment, derivative, or modification thereof. Preferably one or more of the T cell stimulating epitopes is at the N-terminus, the C-terminus, within the peptide, or any combination thereof. Peptides of the invention may comprise multiple influenza virus epitopes and/or multiple T cell stimulating epitopes. Peptide may be part of an immunogenic composition which may optionally contain an adjuvant such as, for example, Freund's, a liposome, saponin, lipid A, squalene, and derivatives and combinations thereof. Preferably, the immunogenic composition is a vaccine that treats or prevents infection of the one or more pathogens.

Another embodiment of the invention is directed to peptides containing an influenza virus epitope, a coronavirus epitope, and/or an MTB epitope, with or without a T cell stimulating epitope. Preferably the influenza virus epitope is obtained or derived from an HA protein, an NA protein, an M1 protein, an M2 protein, an M2e protein of the influenza virus, and/or a fragment, derivative, or modification thereof. Preferably the coronavirus epitope is obtained or derived from a spike protein (S), an envelope protein (E), a membrane protein (M), a polymerase protein (P), and/or a nucleocapsid protein (N) of coronavirus and/or a fragment, derivative, or modification thereof. Preferably the MTB epitope is obtained or derived from a heat shock protein, an MTB surface antigen, an MTB internal antigen, peptidoglycan, mycolic acid, lipoarabinomannan, and/or a fragment, derivative, or modification thereof. Also preferably, the T cell stimulating epitope is obtained or derived from tetanus toxin, tetanus toxin heavy chain proteins, diphtheria toxoid, CRM, recombinant CRM, tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus *influenzae* protein D, Flagellin Fli C, Horseshoe crab Haemocyanin, and/or a fragment, derivative, or modification thereof. Preferably one or more of the T cell stimulating epitopes is at the N-terminus, the C-terminus, within the peptide, or any combination thereof. Peptides of the invention may comprise multiple influenza virus epitopes and/or multiple T cell stimulating epitopes. Peptide may be part of an immunogenic composition which may optionally contain an adjuvant such as, for example, Freund's, a liposome, saponin, lipid A, squalene, and derivatives and combinations thereof. Preferably, the immunogenic composition is a vaccine that treats or prevents influenza virus infection.

Another embodiment of the invention is directed to antibodies that are specifically reactive to the peptides of the invention. Preferably the antibody is a monoclonal antibody and, accordingly, the invention includes a hybridoma that expresses the monoclonal antibody.

Another embodiment of the invention is directed to methods to treat or prevent a viral or bacterial infection, such as, for example, an MTB infection, an influenza virus infection, and/or corona virus infection by administering the immunogenic composition to a mammal suspected of being or determined to be infected with MTB, an influenza virus and/or a corona virus. Preferably the immunogenic composition produces a viral neutralizing response and/or an opsonophagocytic immune response by the mammal. Preferably the response includes Th1-type cytokines and/or Th2-type cytokines such as, for example, interleukins 4, 5, 10 and/or 13.

Another embodiment of the invention is directed to a composite antigen comprising a peptide with contiguous amino acid sequence derived from a plurality of antigenic epitopes of one or more pathogens that induces an immune response in a mammal that is protective against infection by the one or more pathogens. Preferably the plurality of epitopes contains one or more composite epitopes. Preferably the composite antigen contains a plurality of antigenic epitopes, comprising one or more repetitions of a same epitope, one or more repetitions of different epitopes, one or more repetitions of composite epitopes, or a combination thereof. Also preferably, the amino acid sequence of at least one epitope of the composite antigen does not exist naturally. Composite antigens can be used to treat or preferably prevent infection and disease associated with one or more pathogens including but not limited to viruses, bacteria, parasites, yeast, fungi, or a combination thereof. Preferably the pathogen is an influenza virus and the one or more antigenic epitopes are amino acid sequences of M1, M2, HA, NA, PB1, or PB2 protein, or a combination thereof, or the pathogen is a coronavirus and one or more antigenic epitopes are amino acid sequences of the spike (S), envelope (E), membrane (M), and nucleocapsid (N). Preferably, the composite is coupled with an antigen that stimulates T-cells such as, for example, tetanus toxin, tetanus toxin heavy chain proteins, diphtheria toxoid (e.g., recombinant or native CRM197), tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, *Hemophilus influenzae* protein D, Flagellin Fli C, Horseshoe crab Haemocyanin, and fragments, derivatives, and modifications thereof.

Another embodiment of the invention is directed to composite antigens that contain epitopes from both influenza virus and coronavirus. Preferably, the composite is coupled with an antigen that stimulates T-cells.

Another embodiment of the invention is directed to immunogenic compositions and vaccines for the treatment and/or prevent of infections and symptoms attributable to microbial infection, including but not limited to coronavirus, influenza virus, MTB, and other pathogenic organisms. Immunogenic compositions include antigens of the invention and antibodies that bind to antigens of the invention.

Another embodiment of the invention is directed to antibodies that are specifically reactive to the composite antigens of the invention.

Another embodiment of the invention is directed to polynucleotides that encode composite antigens of the invention.

Another embodiment of the invention is directed to methods for generating an immune response in a mammal comprising administering to the mammal the composite antigen of the invention. Administration may be via any route including but not limited to i.v., i.c., i.m., nasal, and oral. Preferably the immune response generated is protective against a number of different strains, serotypes or species of the one or more pathogens.

Other embodiments and advantages of the invention are set forth in part in the description, which follows, and in part, may be obvious from this description, or may be learned from the practice of the invention.

DESCRIPTION OF THE FIGURES

FIG. 1 Vaccine and therapeutic study design in ICR mice immunized with peptides, conjugated or unconjugated, with Tetanus T-cell epitope in the C or N-terminus.

FIG. 21 Combination Flu Pep11+5906 CRM-Conjugated vaccine with various adjuvants neutralization of H1N1 influenza viruses.

FIG. 22 Individual Flu Pep11 and Flu Pep 5906 CRM-conjugated vaccines and monoclonal antibody identification.

DESCRIPTION OF THE INVENTION

Figure 2:
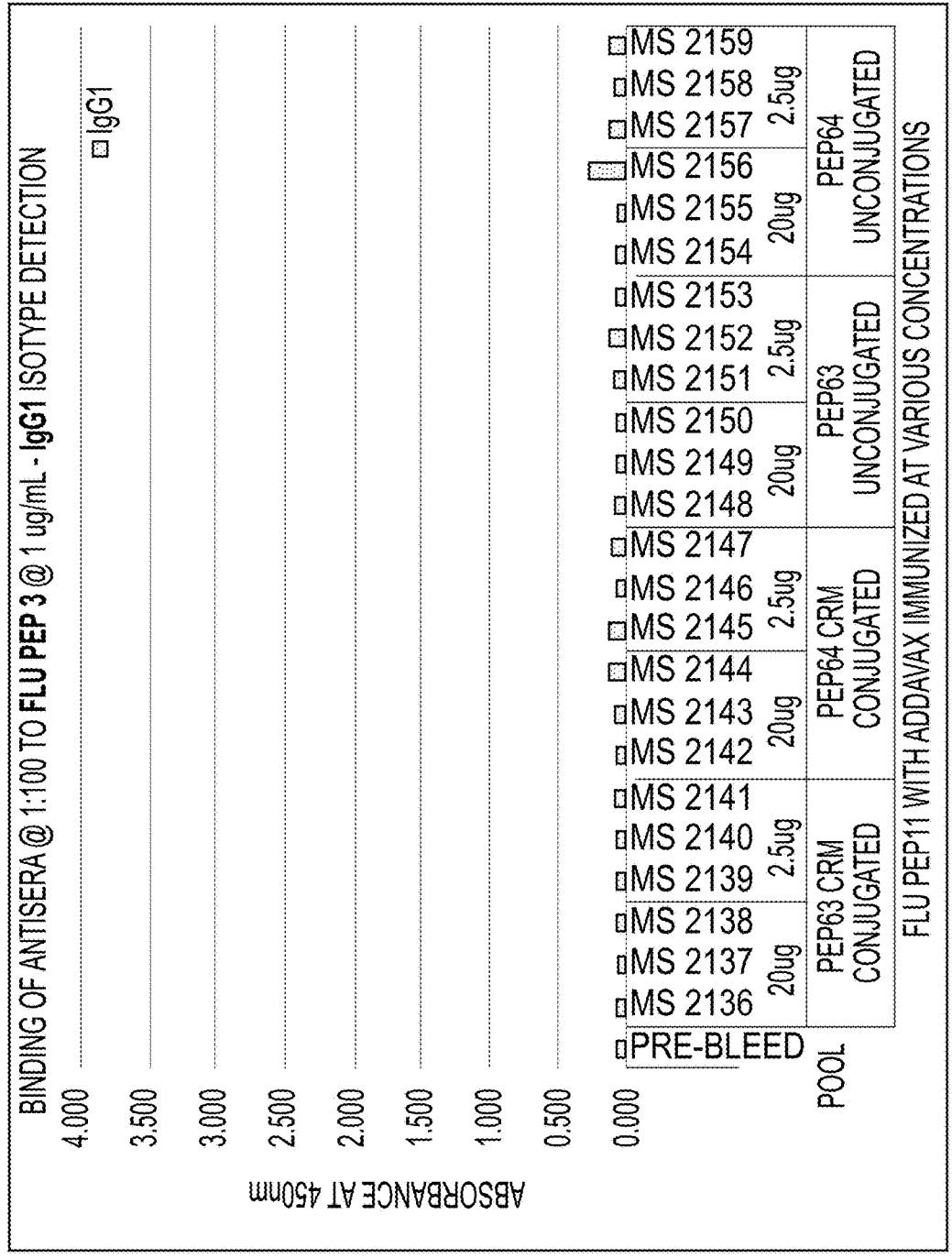
FIG. 2 Day 7-42 Serum antibody responses to Flu Pep 3: IgG1 isotype detection.
Figure 2:
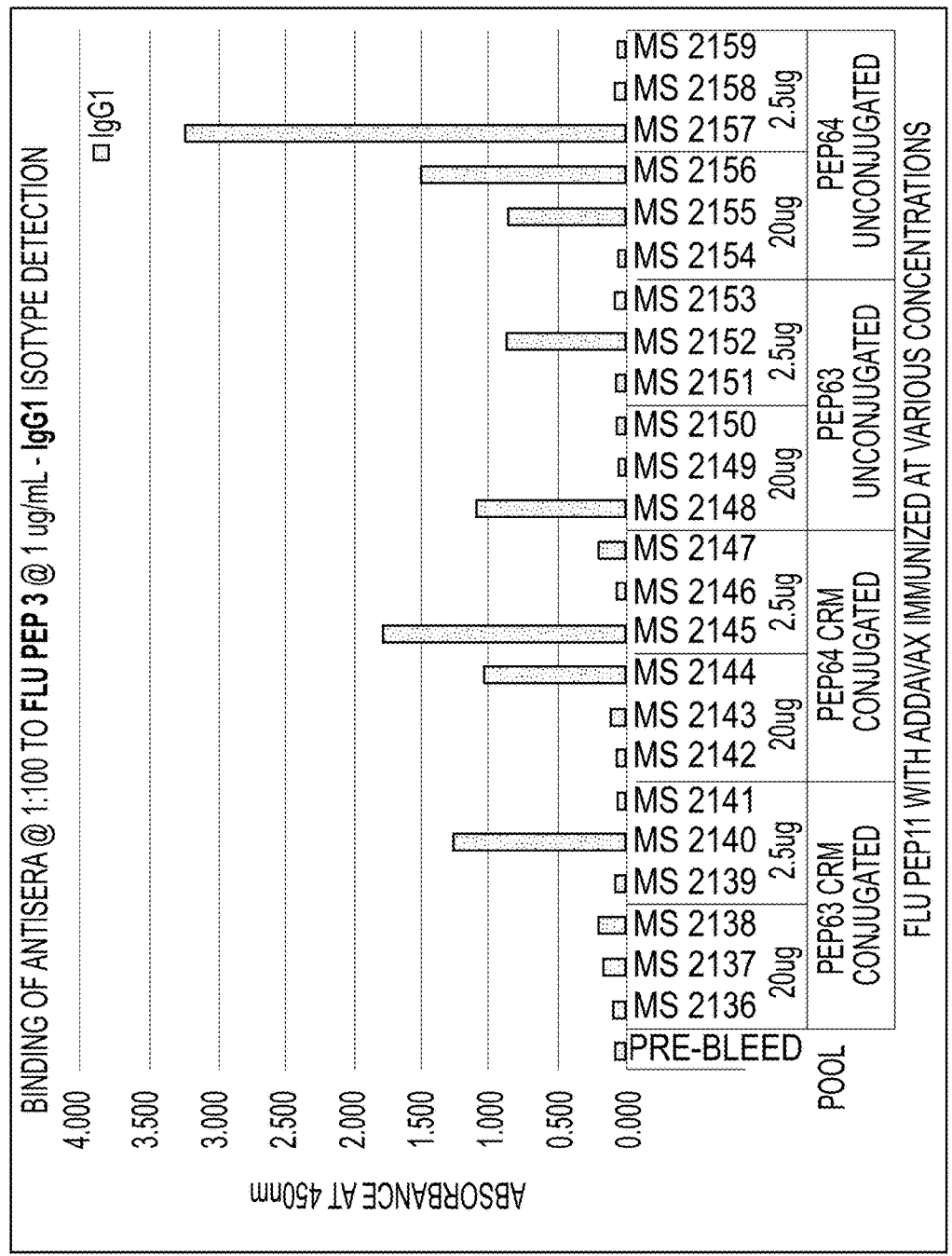

Vaccinations and vaccines are often the best mechanism for avoiding an infection and preventing the spread of debilitating and dangerous pathogens. With respect to viral infections and many bacterial infections, vaccinations are often the only effective option as treatment options are few and those that are available provide only limited effectiveness. Conventional vaccinations require a priori understanding or general identification of the existing antigenic regions of the pathogen. The pathogen itself is propagated and a suitable vaccine developed from heat-killed or otherwise attenuated microorganisms. Alternatively, an antigen or collection of antigens is identified that will generate a protective immune response upon administration. The need for a vaccine is especially urgent with respect to preventing infection by certain bacteria and viruses. Many microbes and especially certain viruses mutate constantly often rendering the vaccine developed to the prior or originating microbe useless against the new strains that emerge. As a consequence, vaccines against infections are reformulated yearly and often administered at fairly high doses. The development and manufacturing costs are high and administering vaccines pose a great many complications and associated risks to patients.

It has been surprisingly discovered that an effective vaccine can be produced from an antigen or a composite antigen of the invention (when referred to herein, antigens of the invention may comprise composite, non-composite or both types of sequences). Composite antigens are antigens that contains or are derived from a plurality of antigenic regions (e.g. epitopes) of a pathogen or of different pathogens. Composite antigens of the invention may contain an antigenic region that represents a combination of all or parts of two or more epitopes (e.g., a composite peptide), or a plurality of immunologically responsive regions derived from one or multiple antigenic sources (e.g., microbial epitopes such as epitopes of virus particles, parasites, bacteria, fungi, cells). These immunological regions are amino acid sequences or epitopes that are representative of sequences found at those antigenic regions of a pathogen or other antigen associated with an infection or a disease or, importantly, associated with stimulation of the immune system to provide protection against the pathogen. As peptide vaccines are synthetically produced, they avoid egg culture and can be rapidly and efficiently manufactured.

One embodiment of the invention is directed to antigens and/or composite antigens. Composite antigens of the invention contain non-naturally occurring amino acid sequences that do not exist in nature and are otherwise artificially constructed, preferable as a continuous sequence. Each sequence of a composite antigen contains a plurality of immunologically responsive regions or epitopes of one or more pathogens, which are artificially arranged, preferably along a single amino acid sequence or peptide. The plurality may contain multiples of the same epitope, although generally not in a naturally occurring order, or multiples of a variety of different epitopes from one or more pathogens. Epitopes may be identical to known immunological regions of a pathogen, or entirely new constructs that have not previously existed and therefore artificially constructed. Preferably, the composite antigen of the invention induces a Th1 and/or Th2 response in immunological system the host, basically a cellular and humoral response. Preferably that response include the production of killer T-cell (Tc or CTL) responses, helper T-cell (TH) responses, macrophages (MP), and specific antibody production in an inoculated mammal. Preferably the pathogenic epitopes and T cell stimulating epitopes are on a continuous sequence.

A "composite" antigen may be artificially created from two or more epitopes, such that the resulting antigen has physical and/or chemical properties that differ from or are additive of the individual epitopes. Preferable the composite antigen, when exposed to the immune system of a mammal, is capable of simultaneously generating an immunological response to each of the constituent epitope of the composite and preferably to a greater degree (e.g., as measurable from a cellular or humoral response to an identified pathogen) than the individual epitopes. In addition, the composite antigen preferably provides the added function of generating a protective immunological response in a patient when used as a vaccine and against each of the constituent epitopes. Preferably, the composite has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Another embodiment of the invention is directed to a peptide and/or a composite peptide that contains a composite epitope that represent two or more epitopes with epitope sequences only similar to the epitope sequences from which they were derived. Epitopes are regions obtained or derived from a protein or peptide of a pathogen that elicit a robust immunological response when administered to a mammal. Preferably, that robust response provides the mammal with an immunological protection against developing disease from exposure to the pathogen. A preferred example is a composite epitope, which is one artificially created from a combination of two or more highly conserved, although not identical, amino acid sequences of two or more different, but otherwise related pathogens. The pathogens may be of the same type, but of a different strain, serotype, or species or other relation. In this example, the composite antigen contains the conserved region that is in common between the related epitopes, and also contains the variable regions which differ. The sequences of a composite antigen that represents a combination of two conserved, but not identical sequences, may be illustrated as follows:

Sequence of Epitope 1 . . . AAAAABAAAAA . . .
Sequence of Epitope 2 . . . AAAAACAAAAA . . .
Composite Epitope . . . AAAAABCAAAAA . . .

wherein, "A" represents the amino acids in common between the two highly conserved epitopes, "B" and "C" represent the amino acids that differ, respectively, between two epitopes, each of "A", "B" and "C" can be any amino acid and any number of amino acids. Preferably the conserved region contains about 20 or less amino acids on each side of the variable amino acids, preferably about 15 or less, preferably about 10 or less, preferably about 8 or less, preferably about 6 or less, and more preferably about 4 or less. Preferably the amino acids that vary between two similar, but not identical conserved regions are 5 or less, preferably 4 or less, preferably 3 or less, preferably 2 or less, and more preferably only 1.

A "composite epitope," similar to the composite antigen, is an engineered, artificially created single epitope made from two or more constituent epitopes, such that the resulting composite epitope has physical and/or chemical properties that differ from or are additive of the constituent epitopes. Preferable the composite epitope, when exposed to the immune system of a mammal, is capable of simultaneously generating an immunological response to each of the constituent epitopes of the composite and preferably to a greater degree than that achieved by either of the constituent epitopes individually. In addition, the composite epitope provides the added function of generating a protective immunological response in a patient when used as a vaccine and against each of the constituent epitopes. Preferably, the composite has the additional function of providing protection against not only the pathogens from which the constituents were derived, but related pathogens as well. These related pathogenic organisms may be strains or serotypes of the same species of organism, or different species of the same genus of organism, or different organisms entirely that are only related by a common epitope.

Composite epitopes of the invention are entirely artificial molecules, each a single continuous sequence that does not otherwise exist in nature and to which an immune system has not been otherwise exposed. Preferably, these conserved immunological regions that are combined as a composite epitope represent immunologically responsive regions of proteins and/or polypeptides that are highly conserved between related pathogens. Although a vaccine can be developed from a single composite epitope, in many instances the most effective vaccine may be developed from multiple, different composite epitopes.

Composite antigens of the invention may contain one or more epitopes or composite epitopes, which may include and/or one or more known epitopes to provide an effective vaccine against one or more pathogens. Although composite antigens may comprise a single composite epitope, a composite antigen would not comprise only a single known epitope. Preferably, the immunological response achieved from a vaccination with a composite antigen, or group of composite antigens, provides protection against infection caused by the original strains from which the sequence of the composite antigen was derived, and also provides immunological protection against other strains, serotypes and/or species that share one or more of the general conserved regions represented in the composite antigen. Thus, the resulting immune response achieved from a vaccination with a composite antigen is more broadly protective than can be achieved from a conventional single antigen vaccination against multiple strains, serotypes, and species or otherwise related pathogens regardless of antigenic drift that may take place in the evolution of the pathogen. Preferably, vaccines developed from composite antigens of the invention avoid any need for repeated or annual vaccinations, the associated complications and expenses of manufacture, and the elevated risks to the patient. These vaccines are useful to treat individuals and populations, thereby preventing infection, mortality and pandemics, and are useful to compliment conventional vaccines.

As discussed herein, the composite antigen preferably comprises a single chain of amino acids with a sequence derived from one or more epitopes or a plurality of epitopes, that may be the same or different. Epitope sequences may be repeated consecutively and uninterrupted along a composite sequence or interspersed among other sequences that may be single or a few amino acids as spacers or sequences that encode peptides (collectively spacers such as PEG spacers) and may be nonimmunogenic or immunogenic and capable of inducing a cellular (T cell) or humoral (B cell) immune response in a mammal. T-cell stimulating antigens include, for example, tetanus toxin, tetanus toxin heavy chain proteins, diphtheria toxoid (e.g., recombinantly engineered or purified CRM197), tetanus toxoid, *Pseudomonas* exoprotein A, *Pseudomonas aeruginosa* toxoid, *Bordetella pertusis* toxoid, *Clostridium perfringens* toxoid, *Escherichia coli* heat-labile toxin B subunit, *Neisseria meningitidis* outer membrane complex, Hemophilus *influenzae* protein D, Flagellin Fli C, Horseshoe crab Haemocyanin, and fragments, derivatives, and modifications thereof. Peptides sequence from unrelated microbes may be combined into a single composite antigen. For example, viral sequences of selected immune-responsive peptides may be interspersed with conserved sequences or epitopes selected from other microbes, such as, for example, bacteria such as *S. pneumococcus, P. auriginosa* or *S. aureus*. Preferred viral proteins, from which preferred epitopes may be selected, include, but are not limited to the influenza virus proteins PspA, PspC, HA, NA, M2e, *H. influenza* protein D, and coagulase, and/or coronavirus proteins spike (S), envelope (E), membrane (M), polymerase protein (P), and nucleocapsid (N). Preferably antigen portions of MTB include epitopes obtained or derived from a heat shock protein, an MTB surface antigen, an MTB internal antigen, peptidoglycan, mycolic acid, lipoarabinomannan, and/or a fragment, derivative, or modification thereof and also MTP epitopes created upon treatment of bacteria with, for example, heat, chemicals or sonication. Under these conditions, epitopes not otherwise accessible are exposed (e.g., cryptic epitopes). Composite antigens containing cryptic epitopes of viral or bacterial origin coupled with T cell stimulating epitopes.

An epitope of the composite antigen may be of any sequence and size, but is preferable composed of natural amino acids or mimetopes and is more than 5 but less than 100 amino acids in length, preferably less than 80, preferably less than 70, preferably less than 60, preferably less than 50, preferably less than 40, preferably less than 30, preferably between 5 and 25 amino acids in length, preferably between 8 and 20 amino acids in length, and more preferably between 5 and 15 amino acids in length. Composite antigens preferably contain any number of composite and/or other epitopes. The most effective number of epitopes of a composite antigen against a particular pathogen, pathogen family, or group of pathogens may be determined by one skilled in the art from the disclosures of this application and using routine testing procedures. Composite antigens may be effective with one epitope, preferably with 2 or more, 3 or more 4 or more, 5 or more or greater. Optionally, composite antigens may include one or more spacers between epitopes which may be sequences of antigenic regions derived from the same or from one or more different pathogens, or sequences that serve as immunological primers or that otherwise provide a boost to the immune system. That boost may be generated from a sequence of amino acids that are known to stimulate the immune system, either directly or as an adjuvant. Preferred adjuvants comprise analgesic adjuvants, inorganic compounds such as alum, aluminum hydroxide, aluminum phosphate, calcium phosphate hydroxide, mineral oil such as paraffin oil, bacterial products such as killed bacteria *Bordetella pertussis, Mycobacterium bovis*, toxoids, nonbacterial organics such as squalene, detergents (Quil A), plant saponins such as *Quillaja*, soybean, *Polygala senega*, cytokines such as IL-1, IL-2, IL-12, Freund's complete adjuvant, Freund's incomplete adjuvant, food-based oil, Adjuvant 65, which is a product based on peanut oil, and derivatives, modifications and combinations thereof.

In one preferred embodiment, composite antigens useful to generate an immunological response against influenza virus comprise epitopes of HA and/or NA proteins, and/or new epitopes derived from similar conserved regions of different serotypes and strains of influenza virus, and/or from the S protein of coronavirus. Also preferred are composite antigens containing epitopes of proteins of *Mycobacterium tuberculosis* and *Clostridium tetani*, and/or new epitopes derived from similar conserved regions of different serotypes of these bacteria.

Another embodiment of the invention is directed to a contiguous sequence of one or more epitopes, which may comprise composite and/or known epitopes, from one or more pathogens in a sequence that does not exist naturally and must be artificially constructed. Preferably, a contiguous sequence of the invention contains one or more conserved and/or composite epitopes, which is a combination of the sequences of the conserved regions of epitopes that are common to multiple pathogens plus those amino acids that differ between the two conserved regions. For example, where two pathogens contain similar conserved regions that differ by only a single amino acid, the composite sequences would include the conserved region amino acids and each of the amino acids that differ between the two regions as discussed herein.

It is also preferable that an antigen of the invention contain a plurality of repeated epitopes and, optionally, epitopes conjugated with linker regions between or surrounding each epitope, and the plurality of epitopes be the same or different. Preferred linkers include amino acid sequences of antigenic regions of the same or of different pathogens, or amino acids sequences that aid in the generation of an immune response. Preferred examples include, but are not limited to, any of the various antigenic regions of bacteria such as, but not limited to tuberculosis and virus such as, but not limited to influenza and coronavirus. It is also preferred that antigens contain one or more epitopes that generate a T cell response, a B cell response, or both in conjunction with a specific response to the pathogen.

Another embodiment of the invention is directed to immunizing mammals with the antigens of the invention. Antisera obtained from the immunized mammals are reactive against the pathogens from which the composite antigen was derived. Another embodiment of the invention is therefore antisera obtained from the immunized mammals, which may be further purified for testing or utilized therapeutically for administration to another mammal and thereby provides protection against infection from the one or more pathogens. It is also preferred that the antisera obtained provide a broad protection, not just against the pathogens from which the composite antigen was derived, but also from additional pathogens that may differ by strain, serotype, or even species.

Another embodiment of the invention is a vaccine composed of the antigen or antisera containing the desired antibodies developed from the antigens of the invention. Preferably, the vaccines of the invention (which can be passive such as antibody vaccines or active such as antigen vaccines) are less susceptible to variation of antigenicity due to antigenic shift of pathogens which reduces or eliminates the need for annual or repeated vaccination to maintain protection of patient populations against potential outbreaks of infection from new viral isolates. In addition, the vaccines of the invention generally and advantageously provide increased safety considerations, both in their manufacture and administration (due in part to a substantially decreased need for repeated administration), a relatively long shelf life in part due to minimized need to reformulate due to strain-specific shift and drift, an ability to target immune responses with high specificity for particular microbial epitopes, and an ability to prepare a single vaccine that is effective against multiple pathogens, each of which may be a different but know strain or species of the same pathogen. The invention encompasses antigenic and antibody compositions, methods of making such compositions, and methods for their use in the prevention, treatment, management, and/or prophylaxis of an infection. The compositions disclosed herein, as well as methods employing them, find particular use in the treatment or prevention of viral, bacterial, parasitic and/or fungal pathogenesis and infection using immunogenic compositions and methods superior to conventional treatments presently available in the art.

Another embodiment of the invention is directed to methods of preventing or controlling infection, such as, for example, an outbreak of viral, parasitic, fungal, or bacterial infection, preferably but not limited to an influenza virus, coronavirus, and/or a tuberculosis bacterial infection, in a selected mammalian population. The method includes at least the step of providing an immunologically effective amount of one or more of the disclosed immunogenic or vaccine compositions to a susceptible or an at-risk member of the population, for a time sufficient to prevent, reduce, lessen, alleviate, control, or delay the outbreak of such an infection in the general population.

Another embodiment of the invention is directed to methods for producing a protective immune response against infection, for example by influenza virus or coronavirus, in a mammal in need thereof. Such a method generally includes a step of providing to a mammal in need thereof, an immunologically-effective amount of one or more of the immunogenic compositions disclosed herein under conditions and for a time sufficient to produce such a protective immune response against one or more species, strains, or serotypes of an infectious organism. Additionally, the invention also provides a method for administering a prophylactic antiviral or antimicrobial composition to at least a first cell, tissue, organ, or organ system in a mammal that generally involves providing to such a mammal a prophylactically-effective amount of at least a first immunogenic composition as disclosed herein. Immunogenic compositions include antigens of the invention and antibodies that bind to antigens of the invention.

Another embodiment of the invention is directed to an immunogenic composition comprising the antigens of the invention having one or more repeated peptide sequences, or fragments, variants, or derivatives of such peptide sequences that are conserved across a plurality of proteins in the same or different pathogen. The conserved regions from which the sequence is derived may be conserved within subtypes of the same pathogen or different pathogens. Preferred pathogens include, but are not limited to bacteria, viruses, parasites, fungi and viruses.

Antigens of the invention may also be obtained or derived from the sequences of bacteria such as, for example, multiple or combined epitopes of the proteins and/or polypeptides of, for example, but not limited to *Streptococcus, Pseudomonas, Mycobacterium* such as *M. tuberculosis, Shigella, Campylobacter, Salmonella, Haemophilus influenza, Chlamydophila pneumonia, Corynebacterium diphtheriae, Clostridium tetani, Mycoplasma pneumonia, Staphylococcus aureus, Moraxella catarrhalis, Legionella pneumophila, Bordetella pertussis, Escherichia coli*, such as *E. coli* 0157, and multiple or combined epitomes of conserved regions of any of the foregoing. Exemplary parasites from which sequences may be obtained or derived include but are not limited to *Plasmodium* such as *Plasmodium falciparum* and *Trypanosoma*. Exemplary fungi include, but are not limited to, *Aspergillus fumigatus* or *Aspergillus flavus*. Exemplary viruses include, but are not limited to arena viruses, bunyaviruses, coronaviruses, filoviruses, hepadna viruses, herpes viruses, orthomyxoviruses, parvoviruses, picaviruses, picornaviruses, papillomaviruses, reoviruses, retroviruses, rhabdoviruses, and togaviruses. Preferably, the virus epitopes are obtained or derived from sequences of Influenza viruses (e.g., the paramyxoviruses).

In another preferred embodiment, the antigens contain a conserved region derived from an influenza virus subtypes (e.g., influenza viruses with varying HA or NA compositions, such as H1N1, H5N1, H3N2, and H2N2). Epitopes of conserved regions on NA or HA may also confer cross-subtype immunity. As an example, conserved epitopes on NA(N1) may confer enhanced immunity to H5N1 and H1N1. With respect to similar or homologous chemical compounds among influenza A subtypes and/or strains within a subtype, preferably these are at least about 80 percent, more preferably at least about 90 percent, more preferably at least about 95 percent identical, more preferably at least about 96 percent identical, more preferably at least about 97 percent identical, more preferably at least about 98 percent identical, more preferably at least about 99 percent identical, and even more preferably 100 percent identical (invariant). Preferably, at least one peptide sequence within the antigen is also conserved on homologous proteins (e.g., protein subunits) of at least two viral particles, preferably influenza particles. Proteins of influenza virus include, for example, expressed proteins in the virus structure, such as HA, NA, protein polymerases (PB1, PB2, PA), matrix proteins (M1, M2), and nucleoprotein ("NP"). Preferably, the conserved peptide sequences are conserved on at least two or more of the M1, M2, HA, NA, or one or more polymerase proteins.

In a preferred example, a selected sequence in the M1 and M2 proteins of the H5N1 influenza virus corresponds to the M1 and M2 proteins found in other H5N1 particles, and to the same sequence in the M1 and M2 proteins of the H3N2 influenza virus. In addition, while HA and NA proteins have highly variable regions, conserved sequences from HA and NA are found across many influenza strains and many subtypes (e.g., HA and NA sequences are conserved across H5N1 and H1N1). In a preferred embodiment of the invention, the sequences is derived from a conserved sequence present within variants or strains (viral isolates expressing substantially the same HA and NA proteins, but wherein the HA and NA protein amino acid sequences show some minor drift), of a single influenza virus subtype and more preferably across at least two influenza virus subtypes, e.g., subtypes of influenza A virus.

In another embodiment, the invention provides a peptide or polypeptide, which may contain a composite sequence, that includes at least one sequence, which comprises one or more repeatedly occurring epitopes, each of which is conserved across a plurality of homologous proteins that is conserved in a population of influenza virus strains or serotypes, and a pharmaceutically acceptable carrier. In exemplary composite antigens, at least one epitopic sequence is repeated at least once, preferably at least twice times, more preferably at least three times. In other embodiments, the at least one epitopic sequence is repeated four or more times. Preferably, the sequences are identical with the sequences in the homologous protein subunits of at least two circulating viral isolates. In each embodiment, the compositions may include a pharmaceutically acceptable carrier.

In additional preferred embodiments, the peptide sequences include sequences derived from genome (i.e., RNA) segment 7 of the influenza virus, while in a more preferred embodiment, the sequences include at least portions of the M1 and M2 proteins. In other preferred embodiments, the sequences include sequences expressed from genome segments encoding the HA or NA proteins. Such sequences are less affected by subtype drift and more broadly protective against infections.

In additional embodiments, the antigen includes one or more T-cell stimulating epitopes, such as diphtheria toxoid, tetanus toxoid, a polysaccharide, a lipoprotein, or a derivative or any combination thereof (including fragments or variants thereof). Typically, the at least one repeated sequence of the antigen is contained within the same molecule as the T-cell stimulating epitopes. In the case of protein-based T-cell stimulating epitopes, the at least one repeated sequence of the antigen may be contained within the same polypeptide as the T-cell stimulating epitopes, may be conjugated thereto, or may be associated in other ways. Preferably, one or more T-cell stimulating epitopes are positioned at the N-Terminus, the C-Terminus, within the peptide, or in any combination thereof of the antigen of the invention.

In additional embodiments, the antigens, with or without associated T-cell stimulating epitopes may include one or more polysaccharides or portions thereof. In preferred embodiments, at least one sequence of an antigen is conjugated to one or more polysaccharides. In other embodiments, one or more polysaccharides are conjugated to other portions of the antigen. Certain embodiments of the present invention are selected from polysaccharide vaccines, protein-polysaccharide conjugate vaccines, or combinations thereof.

Antigens of the invention may be synthesizing by in vitro chemical synthesis, solid-phase protein synthesis, and in vitro (cell-free) protein translation, or recombinantly engineered and expressed in bacterial cells, fungi, insect cells, mammalian cells, virus particles, yeast, and the like.

A preferred antigen includes at least one of the following elements: at least one conserved epitope; optionally at least one T-cell epitope; optionally at least one polysaccharide (sugars); optionally at least one structural component; or a combination thereof. The at least one structural component may include one or more of: at least one linker segment; at least one sugar-binding moiety; at least one nucleotide-binding moiety; at least one protein-binding moiety; at least one enzymatic moiety; or a combination thereof. The invention encompasses methods of preparing an immunogenic composition, preferably a pharmaceutical composition, more preferably a vaccine, wherein a target antigen of the present invention is associated with a pharmaceutically acceptable diluent, excipient, or carrier, and may be used with most any adjuvant.

Within the context of the present invention, that a relatively small number of conservative or neutral substitutions (e.g., 1 or 2) may be made within the sequence of the antigen or epitope sequences disclosed herein, without substantially altering the immunological response to the peptide. In some cases, the substitution of one or more amino acids in a particular peptide may in fact serve to enhance or otherwise improve the ability of the peptide to elicit an immune or T-cell response in an animal that has been provided with a composition that comprises the modified peptide, or a polynucleotide that encodes the peptide. Suitable substitutions may generally be identified using computer programs and the effect of such substitutions may be confirmed based on the reactivity of the modified peptide with antisera and/or T-cells. Accordingly, within certain preferred embodiments, a peptide for use in the disclosed diagnostic and therapeutic methods may comprise a primary amino acid sequence in which one or more amino acid residues are substituted by one or more replacement amino acids, such that the ability of the modified peptide to react with antigen-specific antisera and/or T-cell lines or clones is not significantly less than that for the unmodified peptide.

As described above, preferred peptide variants are those that contain one or more conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Examples of amino acid substitutions that represent a conservative change include: (1) replacement of one or more Ala, Pro, Gly, Glu, Asp, Gln, Asn, Ser, or Thr; residues with one or more residues from the same group; (2) replacement of one or more Cys, Ser, Tyr, or Thr residues with one or more residues from the same group; (3) replacement of one or more Val, Ile, Leu, Met, Ala, or Phe residues with one or more residues from the same group; (4) replacement of one or more Lys, Arg, or His residues with one or more residues from the same group; and (5) replacement of one or more Phe, Tyr, Trp, or His residues with one or more residues from the same group. A variant may also, or alternatively, contain non-conservative changes, for example, by substituting one of the amino acid residues from group (1) with an amino acid residue from group (2), group (3), group (4), or group (5). Variants may also (or alternatively) be modified by, for example, the deletion or addition of amino acids that have minimal influence on the immunogenicity, secondary structure and hydropathic nature of the peptide.

Epitopes may be arranged in any order relative to one another in the sequence. The number of spacer amino acids between two or more of the epitopic sequences can be of any practical range, including, for example, from 1 or 2 amino acids to 3, 4, 5, 6, 7, 8, 9, or even 10 or more amino acids between adjacent epitopes.

Another embodiment of the invention is directed to polynucleotides including DNA, RNA and PNA constructs that encode the sequences of the invention. These polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials. As is appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention. Polynucleotides that encode an immunogenic peptide may generally be used for production of the peptide, in vitro or in vivo. Any polynucleotide may be further modified to increase stability in vivo. Possible modifications include, but are not limited to, the addition of flanking sequences at the 5' and/or 3'-ends; the use of phosphorothioate or 2'-o-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Another embodiment of the invention encompasses methods of vaccinating a subject against Influenza that includes administering to a patient in need of influenza vaccination a therapeutically or prophylactically effective amount of an influenza vaccine, which influenza vaccine includes a, immunogenic and/or composite antigen comprising one or more composite or other sequences, each of which is conserved across a plurality of homologous proteins in a plurality of influenza virus particles, and a pharmaceutically acceptable carrier, to provide a detectable immune response in the patient against influenza.

Another embodiment of the invention is directed to nucleotide or DNA vaccines encoding composite antigens of the invention. A DNA vaccine of the invention contains the genetic sequence of a composite antigen, plus other necessary sequences that provide for the expression of the composite antigen in cells. By injecting the mammal with the genetically engineered DNA, the composite antigen is produced in or preferably on cells, which the mammal's immune system recognizes and thereby generates a humoral or cellular response to the composite antigen, and therefore the pathogen. DNA vaccines have a number of advantages over conventional vaccines, including the ability to induce a more general and complete immune response in the mammal. Accordingly, DNA vaccines can be used to protect a mammal against disease caused from many different pathogenic organisms of viral, bacterial, and parasitic origin as well as certain tumors.

DNA and RNA vaccines typically comprise a bacterial DNA or RNA, respectively, that encodes the composite antigen contained in vectors or plasmids that have been genetically modified to transcribe and/or translate the composite antigenic sequences into specific protein sequences derived from a pathogen. By way of example, the vaccine DNA or RNA is injected into the cells of the body, where the cellular machinery transcribed and translates the DNA or translates the RNA into the composite antigen. Composite antigens, being non-natural and unrecognized by the mammalian immune system, are processed by cells and the processed proteins, preferably the epitopes, displayed on cell surfaces. Upon recognition of these composite antigens as foreign, the mammal's immune system generates an appropriate immune response that protects the mammal from infection. In addition, DNA and RNA vaccines of the invention are preferably codon optimized for expression in the mammalian cells of interest, such as but not limited to mouse or human cells. In a preferred embodiment, codon optimization involves selecting a desired codon usage bias (the frequency of occurrence of synonymous codons in coding DNA or RNA) for the particular cell type so that the desired peptide sequence is expressed.

Another embodiment of the invention is directed to therapeutic and prophylactic agents in a pharmaceutically acceptable composition for administration to a cell or an animal, either alone, or in combination with one or more other modalities of prophylaxis and/or therapy. Therapeutic and prophylactic agents of the invention include non-composite and composite antigens, epitopes, compositions containing antigens and epitopes, sequences, DNA vaccines of the invention, antibodies of the invention, and/or T cells primed or exposed to antigens of the invention. The formulation of pharmaceutically-acceptable excipients and carrier solutions is well known to those of ordinary skill in the art, as is the development of suitable dosing and treatment regimens for using the particular compositions described herein in a variety of treatment regimens.

The amount(s) of immunogenic composition(s) and the time needed for the administration of such immunogenic composition(s) (e.g., antigens and/or antibodies to the antigen) will be within the purview of the ordinary-skilled artisan having benefit of the present teachings. The administration of a therapeutically-effective, pharmaceutically-effective, and/or prophylactically-effective amount of the disclosed immunogenic compositions may be achieved by a single administration, such as for example, a single injection of a sufficient quantity of the delivered agent to provide the desired benefit to the patient undergoing such a procedure. Alternatively, in some circumstances, it may be desirable to provide multiple, or successive administrations of the immunogenic compositions, either over a relatively short, or even a relatively prolonged period of time, as may be determined by the medical practitioner overseeing the administration of such compositions to the selected individual. Administration may be by any appropriate route.

The immunogenic compositions and vaccines of the present invention (e.g., antigens and/or antibodies) are preferably administered in a manner compatible with the dosage formulation, and in such an amount as will be prophylactically or therapeutically effective and preferably immunogenic. The quantity to be administered depends on the subject to be treated, including, e.g., the capacity of the patient's immune system to mount an immune response, and the degree of protection desired. Suitable dosage ranges may be on the order of several hundred micrograms (μg) of active ingredient per vaccination with a preferred range from about 0.1 μg to 2000 μg (even though higher amounts, such as, e.g., in the range of about 1 to about 10 mg are also contemplated), such as in the range from about 0.5 μg to 1000 μg, preferably in the range from about 1 μg to about 500 μg and especially in the range from about 10 μg to about 100 μg. Suitable regimens for initial administration and booster shots are also variable but are typified by an initial administration followed by optional but preferred subsequent inoculations or other periodic administrations.

In certain embodiments, the dose would consist of the range of about 1 μg to about 1 mg total protein or target antigen. In one exemplary embodiment, the vaccine dosage range is about 0.1 μg to about 10 mg. However, one may prefer to adjust dosage based on the amount of peptide delivered. In either case, these ranges are merely guidelines from which one of ordinary skill in the art may deviate according to conventional dosing techniques. Precise dosages may be determined by assessing the immunogenicity of the conjugate produced in the appropriate host so that an immunologically effective dose is delivered. An immunologically effective dose is one that stimulates the immune system of the patient to establish an immune response to the immunogenic composition or vaccine. Preferably, a level of immunological memory sufficient to provide long-term protection against disease caused by microbial infection is obtained. The immunogenic compositions or vaccines of the invention may be preferably formulated with an adjuvant. By "long-term" it is preferably meant over a period of time of at least about 6 months, over at least about 1 year, over at least about 2 to 5 or even at least about 2 to about 10 years or longer.

Another embodiment of the invention is directed to antibodies that are specific for the antigens as described here and conservative variants thereof. Antibodies specific for these polypeptides are useful, e.g., in both diagnostic and therapeutic purposes, e.g., related to the activity, distribution, and expression of target polypeptides. Antibodies of the invention may be classes IgG, IgM, IgA, IgD or IgE and include, but are not limited to, polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Antibodies specific for the peptides of the invention can be generated by methods well known in the art. Such antibodies can include, but are not limited to, polyclonal, monoclonal, chimeric, humanized, single chain, Fab fragments and fragments produced by an Fab expression library. Numerous methods for producing polyclonal and monoclonal antibodies are known to those of skill in the art, and can be adapted to produce antibodies specific for the polypeptides of the invention, and/or encoded by the polynucleotide sequences of the invention (see, e.g., Coligan Current Protocols in Immunology Wiley/Greene, NY; Paul (ed.) (1991); (1998) Fundamental Immunology Fourth Edition, Lippincott-Raven, Lippincott Williams & Wilkins; Harlow and Lane (1989) Antibodies: A Laboratory Manual, Cold Spring Harbor Press, NY, USA; Stites et al. (Eds.) Basic and Clinical Immunology (4th ed.) Lange Medical Publications, Los Altos, CA, USA and references cited therein; Goding, Monoclonal Antibodies: Principles and Practice (2d ed.) Academic Press, New York, NY, USA; 1986; and Kohler and Milstein (1975).

The following examples illustrate embodiments of the invention but should not be viewed as limiting the scope of the invention.

EXAMPLES

Example 1 Antibodies to Composite Influenza Sequences

Influenza vaccine strategies focus on inducing antibodies to multiple key proteins to promote broad influenza immunity across seasonal and pandemic strains. In humans, HA-reactive antibodies constitute a subset of neutralizing antibodies important in protection. Neuraminidase drifts independently of HA and immunity to NA correlates with protection. The extracellular domain of Matrix 2 (M2e) protein is a highly conserved region in influenza A viruses. Immunity to influenza induced by M2e includes both adaptive and innate immune responses and can be an important target for developing a universal influenza vaccine. The HA and NA peptides are located near or at the protein surface where the receptor binding sites reside. These epitopes classically are impacted by induction of antibodies through the adaptive immune system and a major target for influenza vaccines. Additionally, the extracellular portion of the M2 matrix protein (M2e) is highly conserved and constitutes a set of epitopes that may function through different mechanisms and the innate immune system. Other immunologic mechanisms are important for antibodies to M2e, such as NK cell mediated ADCC. The M2e epitope is also an important target for developing a universal influenza A vaccine. To supplement the current annually updated vaccine, composite peptide vaccines were developed derived from multiple, highly conserved HA, NA, and matrix (M2e) surface antigen epitopes from influenza A viruses. Combining multiple conserved antigenic sites provided broad influenza neutralization to be effective for seasonal and pandemic viruses. As peptide vaccines are synthetically produced, such vaccines avoid egg culture allowing for broad administration and rapid and efficient manufacturing.

Figure 14:
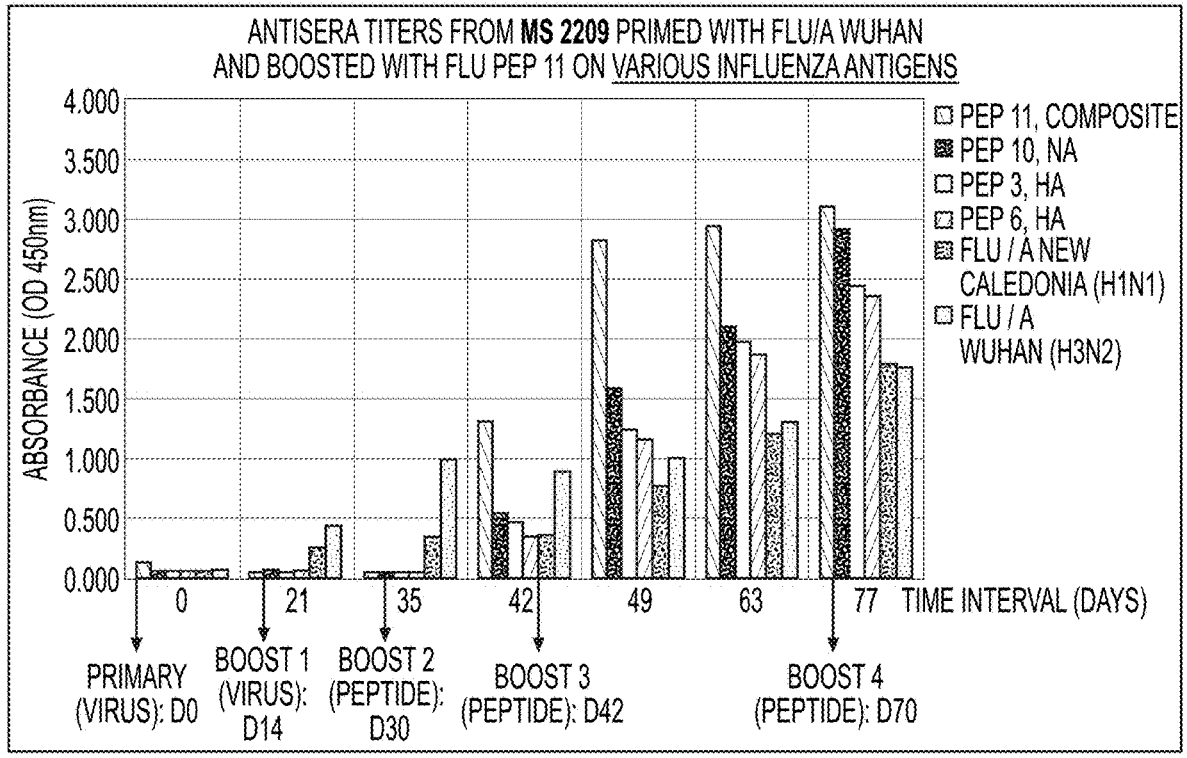
FIG. 14 Individual Flu Pep11 CRM-Conjugated vaccine (MS 2209) with TiterMax adjuvant: antisera titers.
Figure 15:
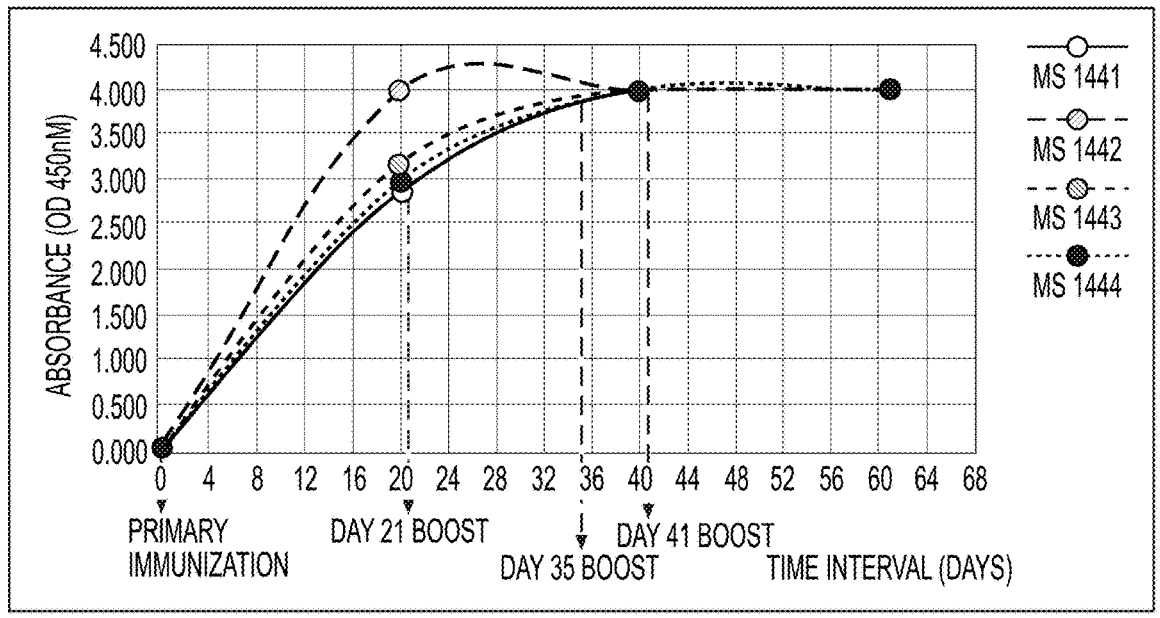
FIG. 15 Individual Flu Pep5906 CRM-Conjugated vaccine with Freund's adjuvant (MS 1443): antisera titers.

Composite peptide influenza vaccines induce antibodies that recognize the individual peptides in the composite vaccines, bind to native epitopes on Group 1 and Group 2 influenza A viruses (see FIG. 14). Saponin adjuvanted composite peptide vaccines induced robust serum IgG antibodies to composite vaccine peptides that also bound to native epitopes on Group 1 and Group 2 influenza viruses (see FIGS. 16-19). These antibodies also were strongly neutralizing for influenza viruses (see FIGS. 20-21). FIG. 14 shows that using mouse 2209 as an example of exposure to live influenza virus (like most children and adults) prior to immunization with composite influenza vaccines did not develop a strong antibody response to influenza viruses or the conserved peptides. One immunization with the composite peptides, increased antibodies to influenza virus. Serum antibodies to the conserved HA and NA epitopes in the vaccine did increase after two composite vaccine immunization and by day 63, good antibody titers to all peptides were observed (see FIG. 14). Concomitant with the rise in antibodies that bound to the peptides, a rise in antibodies that bound to live Group 1 and Group 2 influenza viruses was observed. FIG. 15 shows serum antibodies to the conserved M2e epitopes in the Flu Pep5906 CRM-conjugated vaccine administered to mice 1441-1444 and demonstrates a marked increase in the antibody response after one immunization. A booster immunization on day 21 exhibited strong antibody responses to M2e which were sustained at absorbance ($OD_{450nM}$) levels above 3.50 through day 63 (see FIG. 15). In this study, the adjuvant Titermax was used and shows that immunization with a composite influenza matrix peptide (M2e) vaccine without prior virus exposure, but with Freunds adjuvant, rapidly induced serum antibodies to the composite matrix peptide that were boosted with a second immunization (see FIG. 15).

Figure 16:
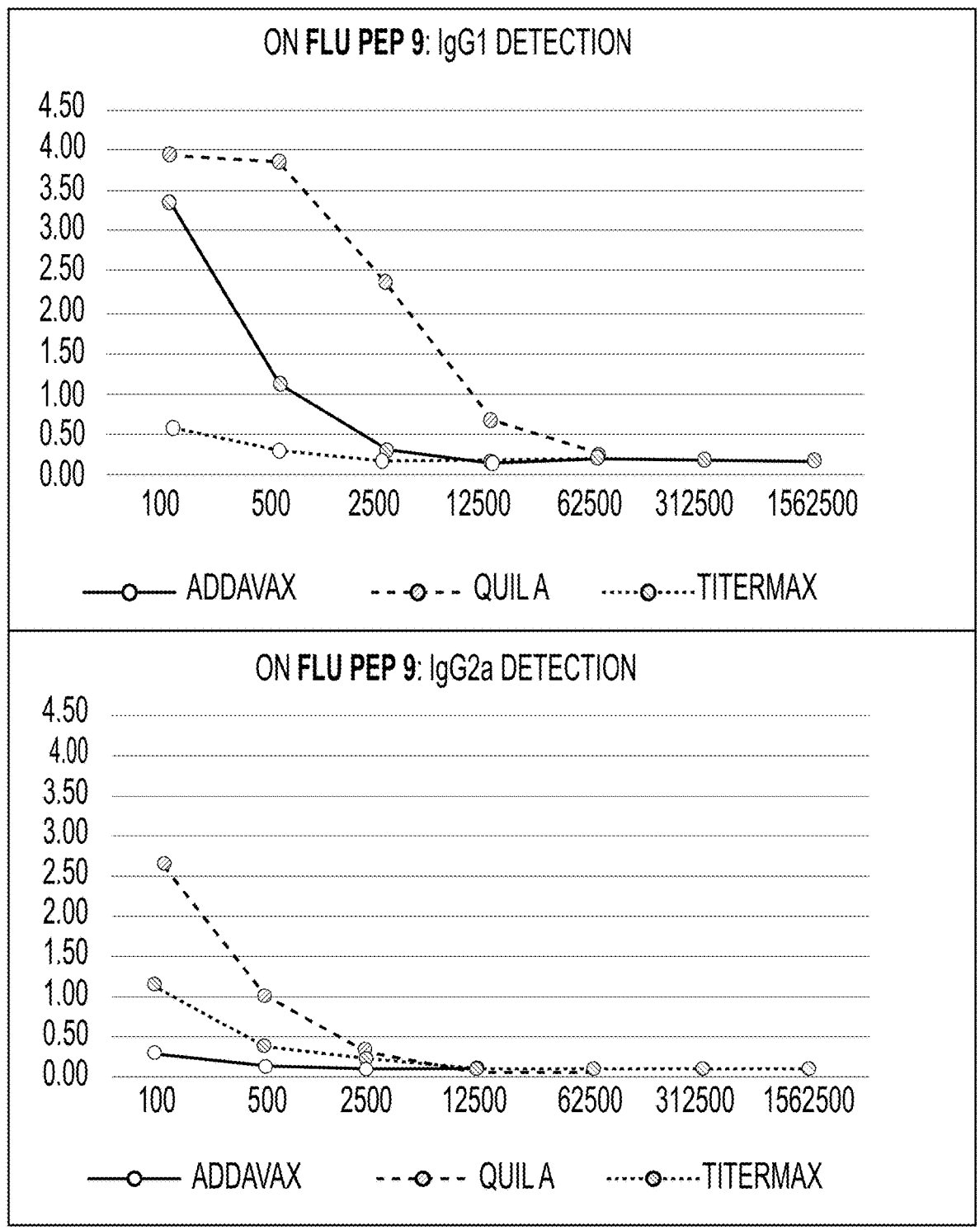
FIG. 16 Combination Flu Pep11+5906 CRM-Conjugated vaccine with various adjuvants immunologic responses in ICR mice: (Day 28) Serum titers on Flu Peptides 9 (HA), 10 (NA), 5906 (M2e).
Figure 16:
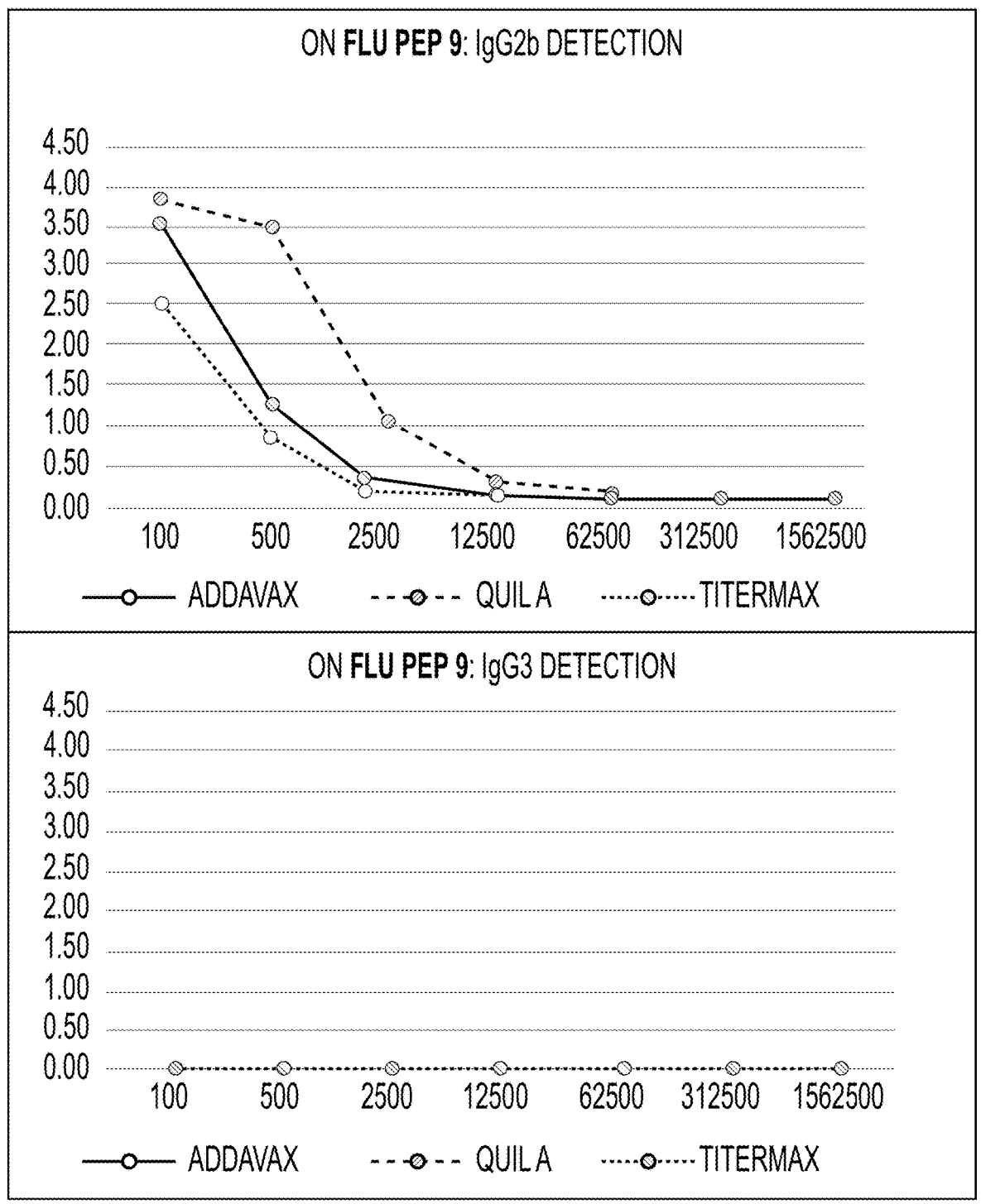
Figure 17:
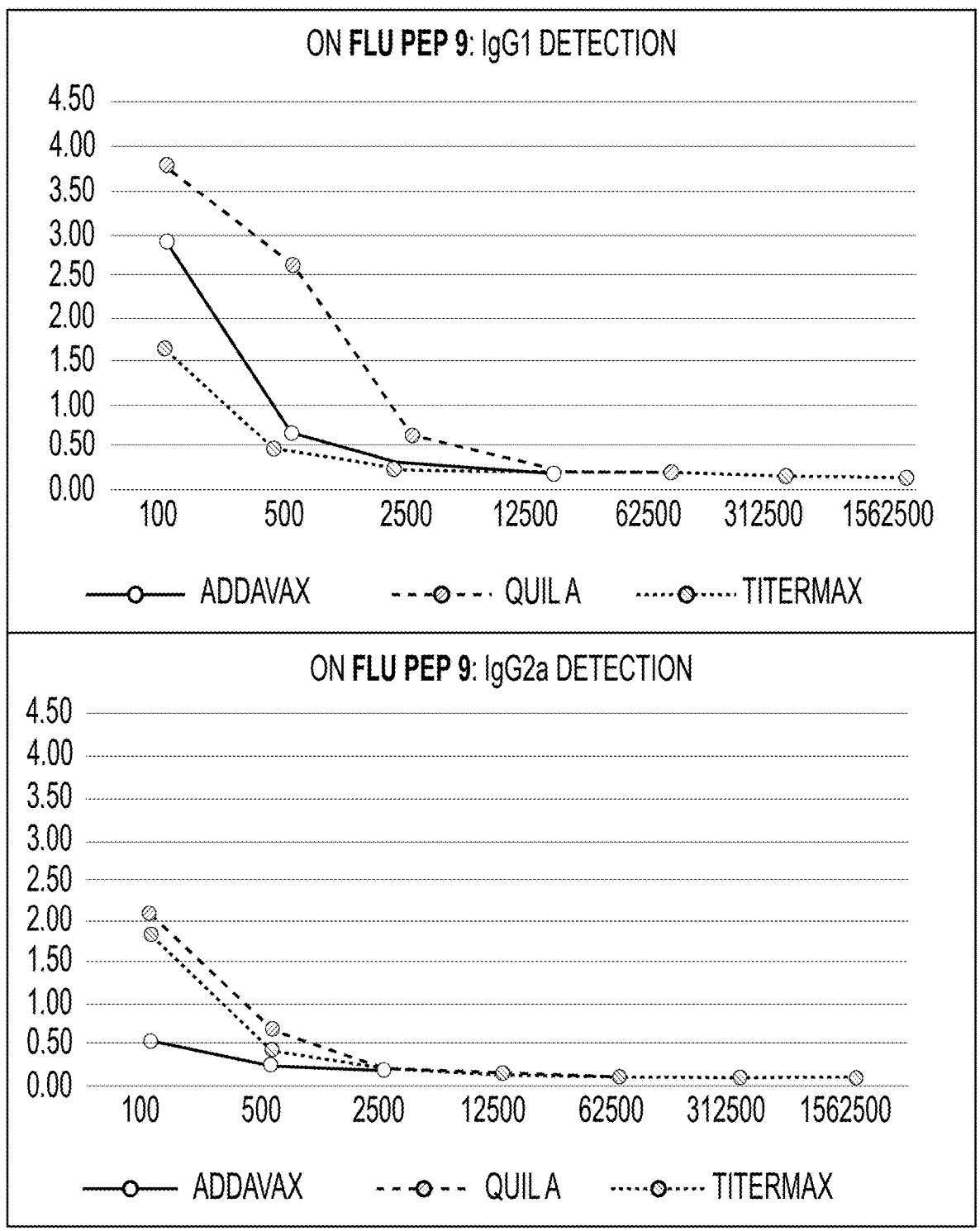
FIG. 17 Combination Flu Pep11+5906 CRM-Conjugated vaccine with various adjuvants immunologic responses in ICR Mice: (Day 42) Serum titers on Flu Peptides 9 (HA), 10 (NA), 5906 (M2e).
Figure 17:
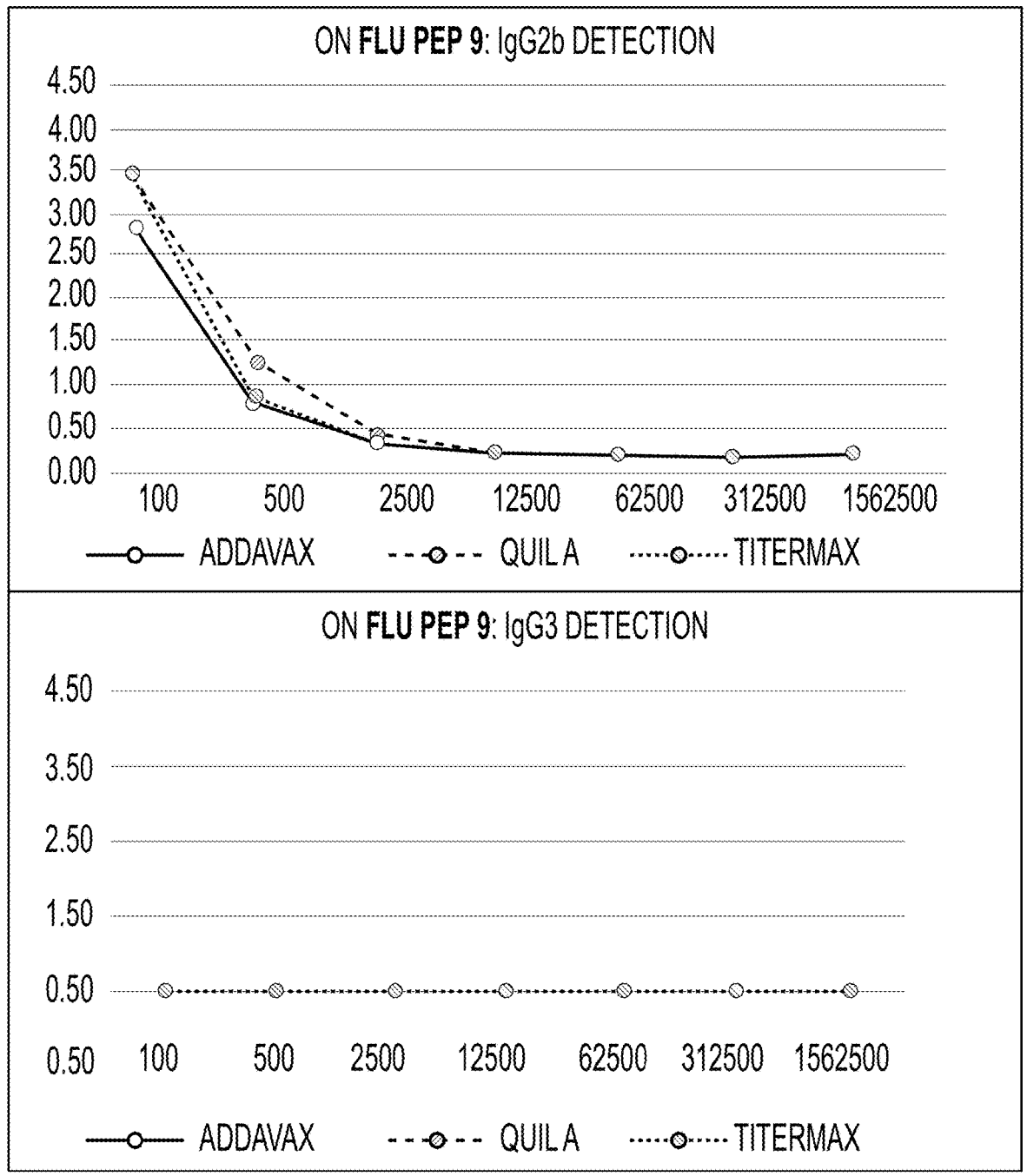
Figure 18:
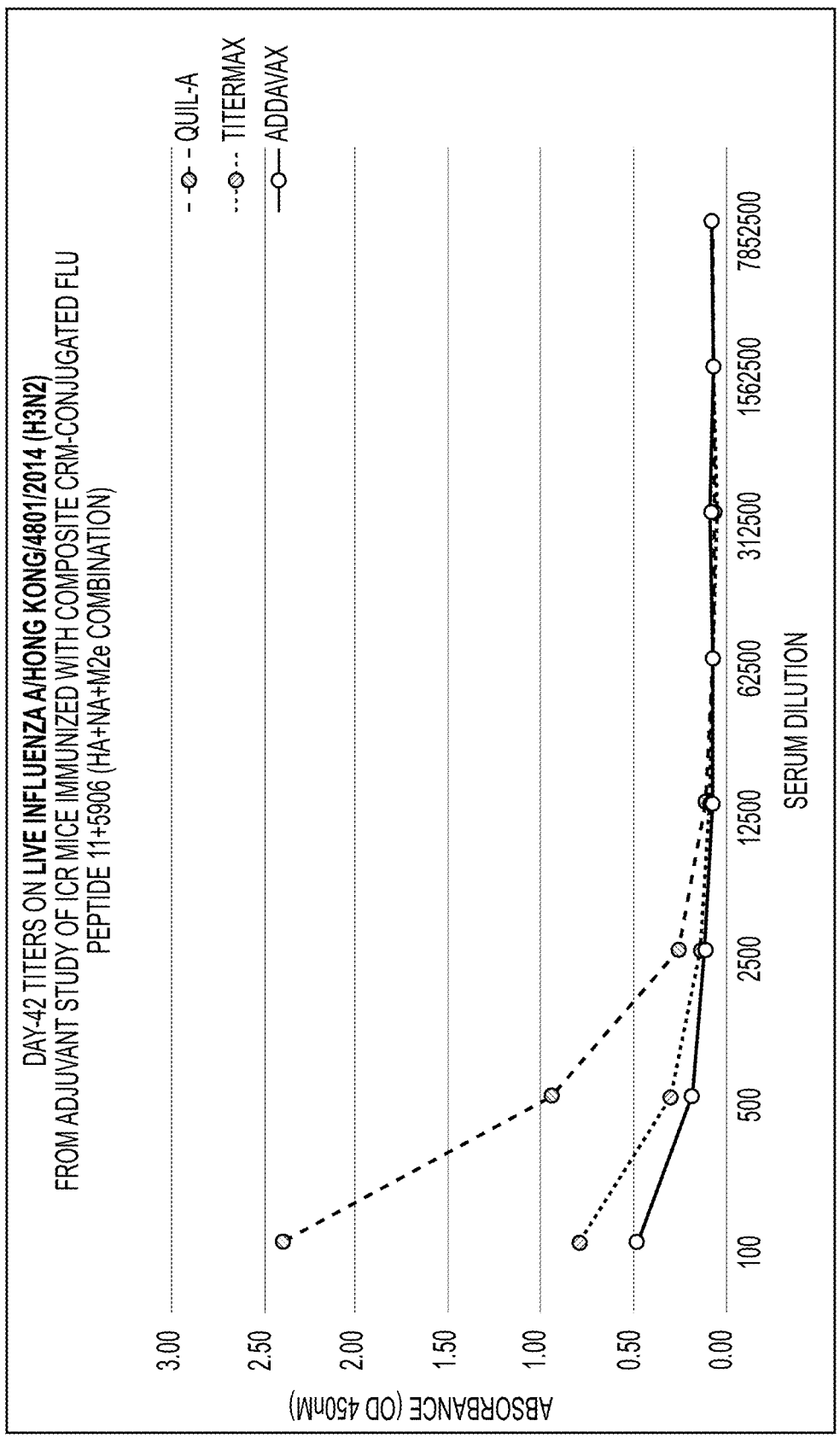
FIG. 18 Combination Flu Pep11+5906 CRM-Conjugated vaccine with various adjuvants immunologic responses in ICR Mice: (Day 42) Serum titers on live influenza viruses.
Figure 19:
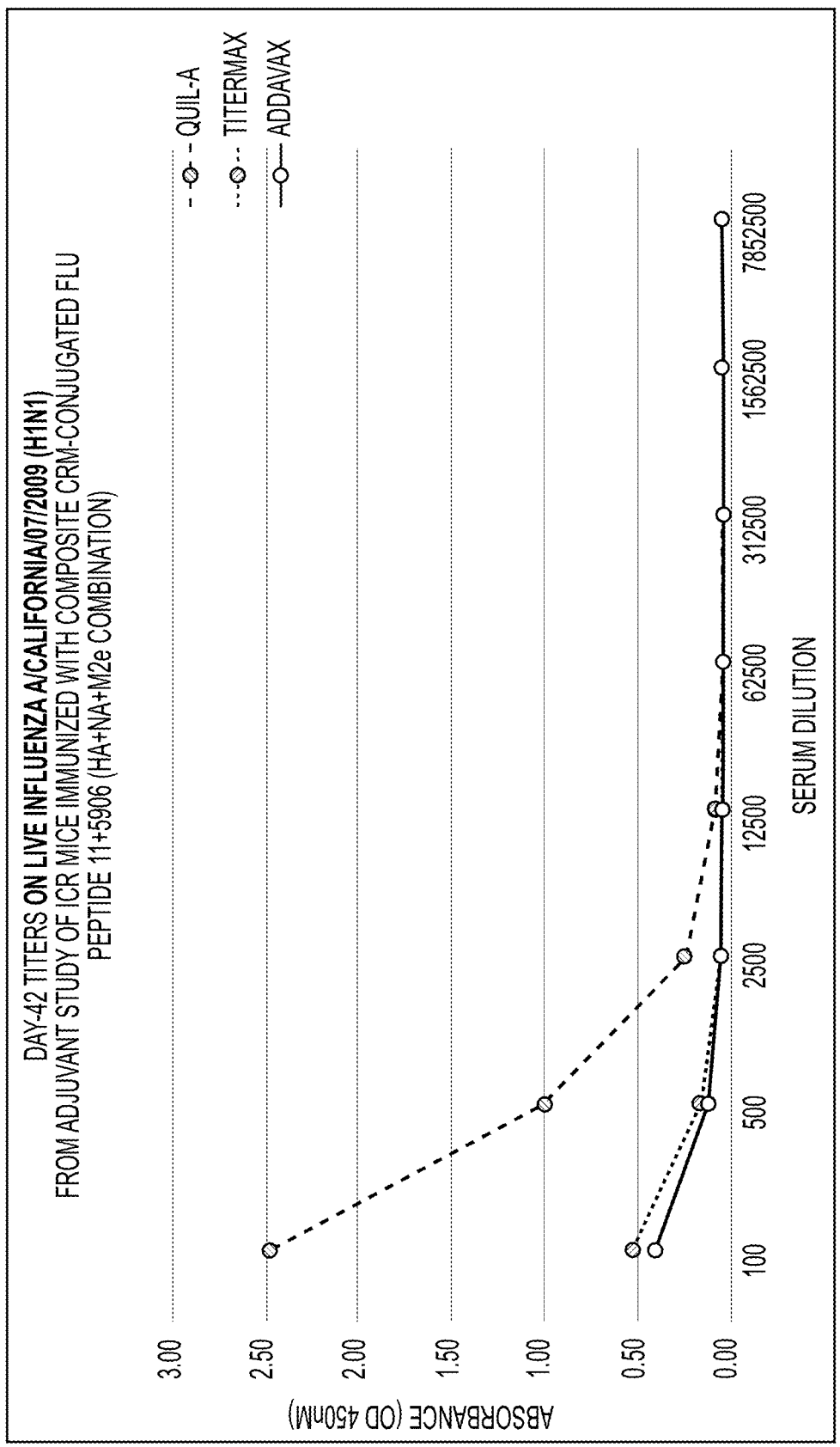
FIG. 19 Combination Flu Pep11+5906 CRM-Conjugated Vaccine with Various Adjuvants Immunologic Responses in ICR Mice: (Day 42) Serum titers on live influenza viruses.
Figure 20:
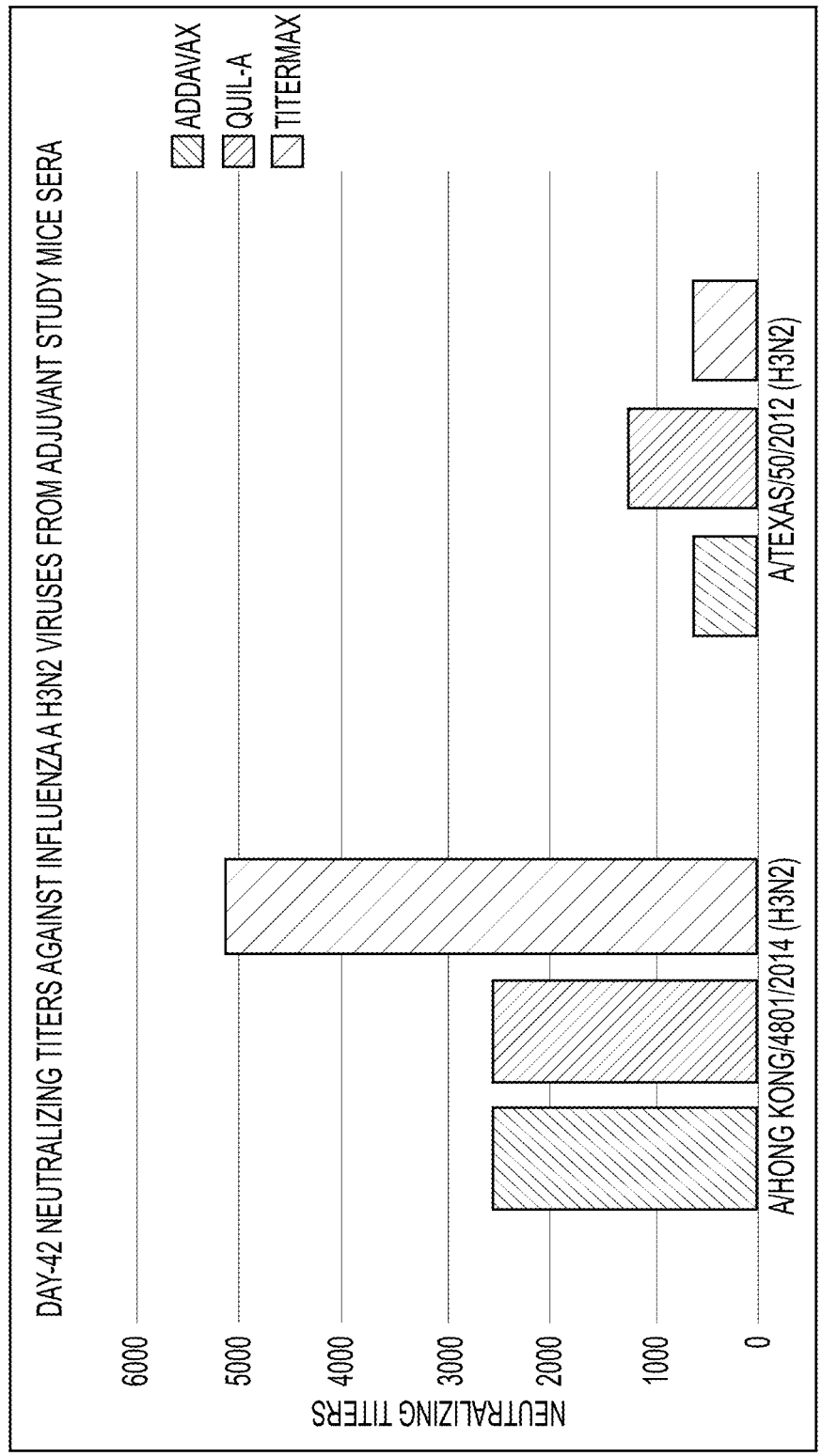
FIG. 20 Combination Flu Pep11+5906 CRM-Conjugated vaccine with various adjuvants neutralization of H3N2 influenza viruses.
Figure 23:
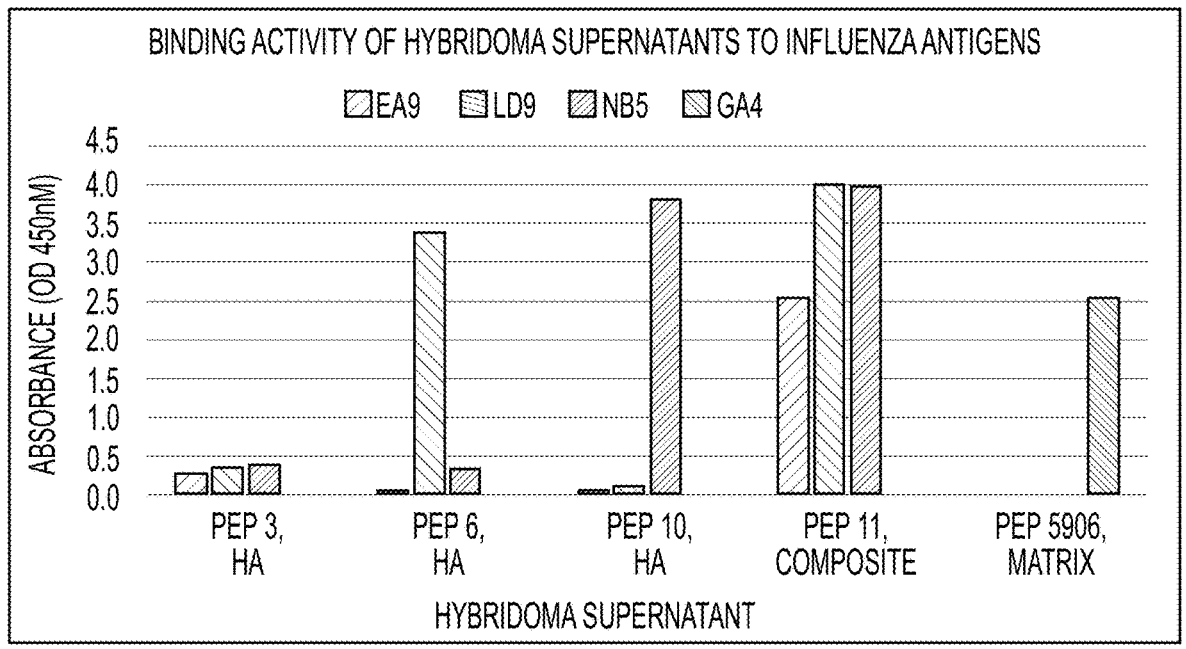
FIG. 23 Hybridoma binding activity to Influenza Peptides 3, 6 (both HA), 10 (NA), 11 (HA+NA), and 5906 (M2e).
Figure 24:
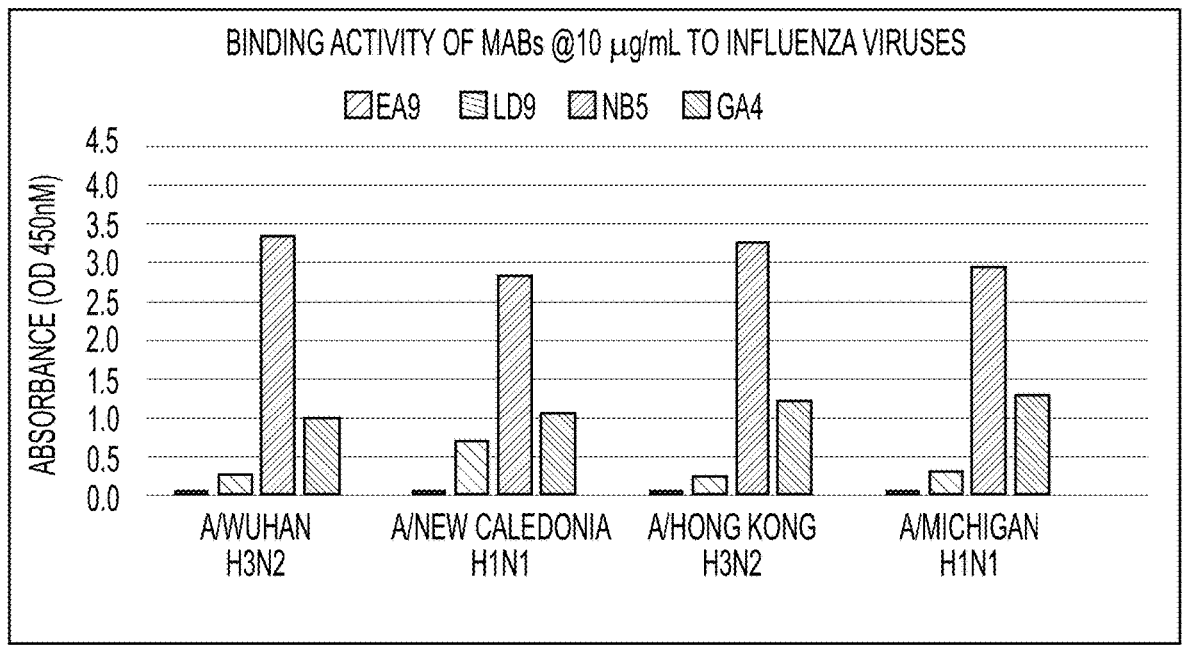
FIG. 24 Monoclonal antibody binding activity to Live H3N2 & H1N1 Influenza viruses.
Figure 25:
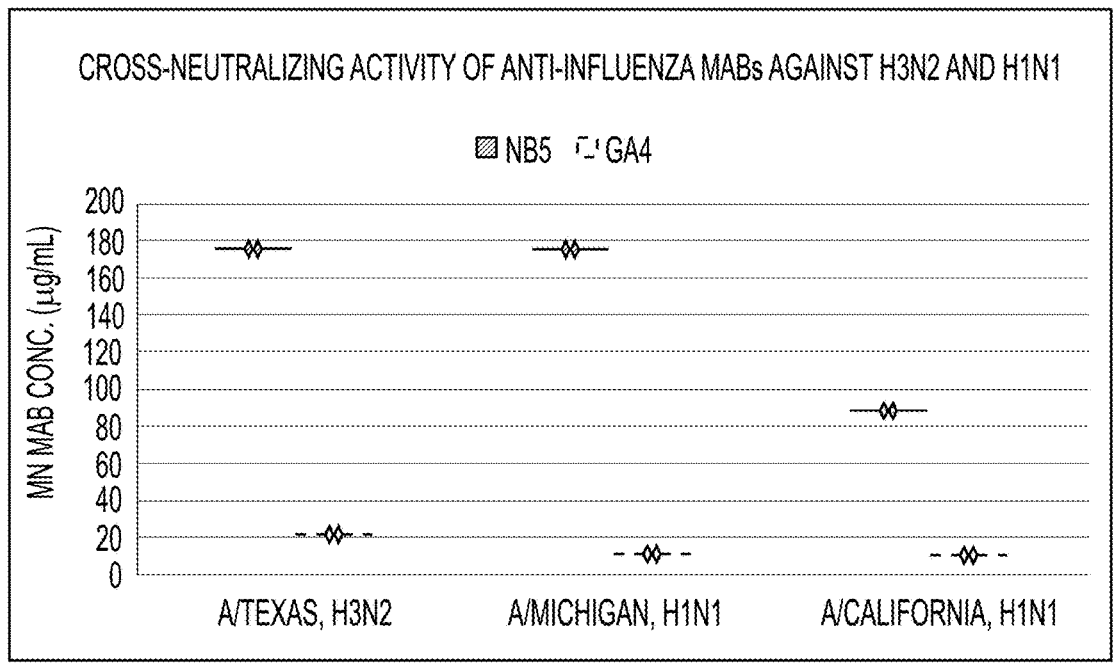
FIG. 25 Monoclonal antibody neutralizing activity against H3N2 and H1N1 Influenza viruses.
Figure 26:
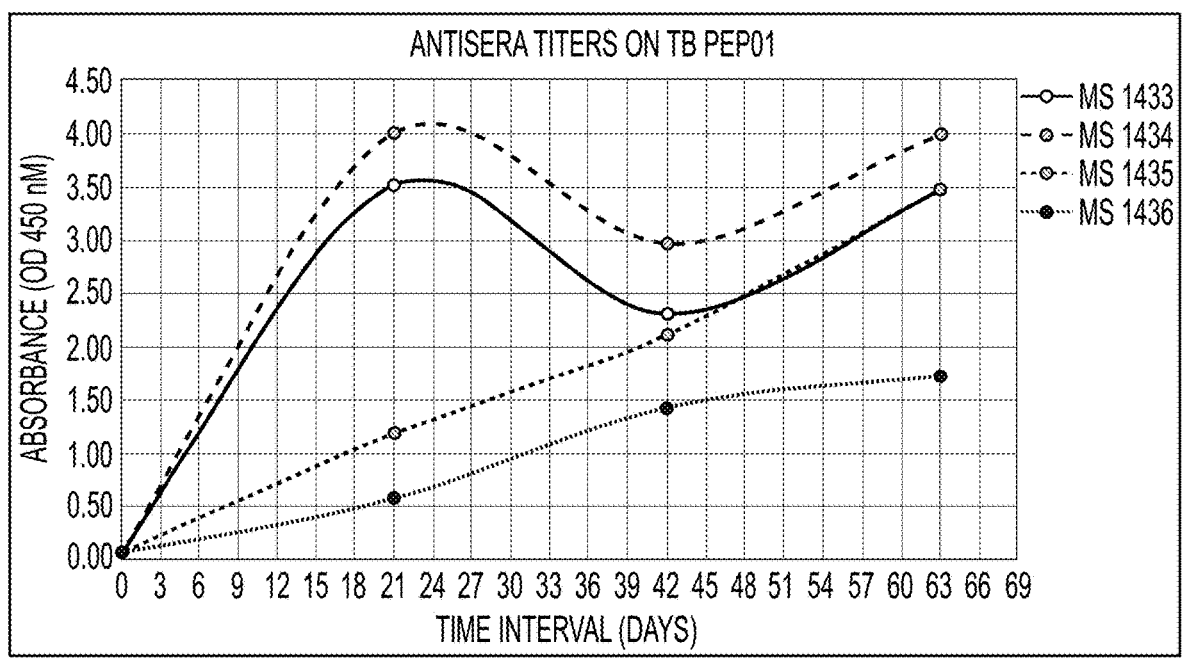
FIG. 26 TB Pep01 CRM-Conjugated vaccine with Freunds Adjuvant: Antisera Titers.
Figures 27, 28:
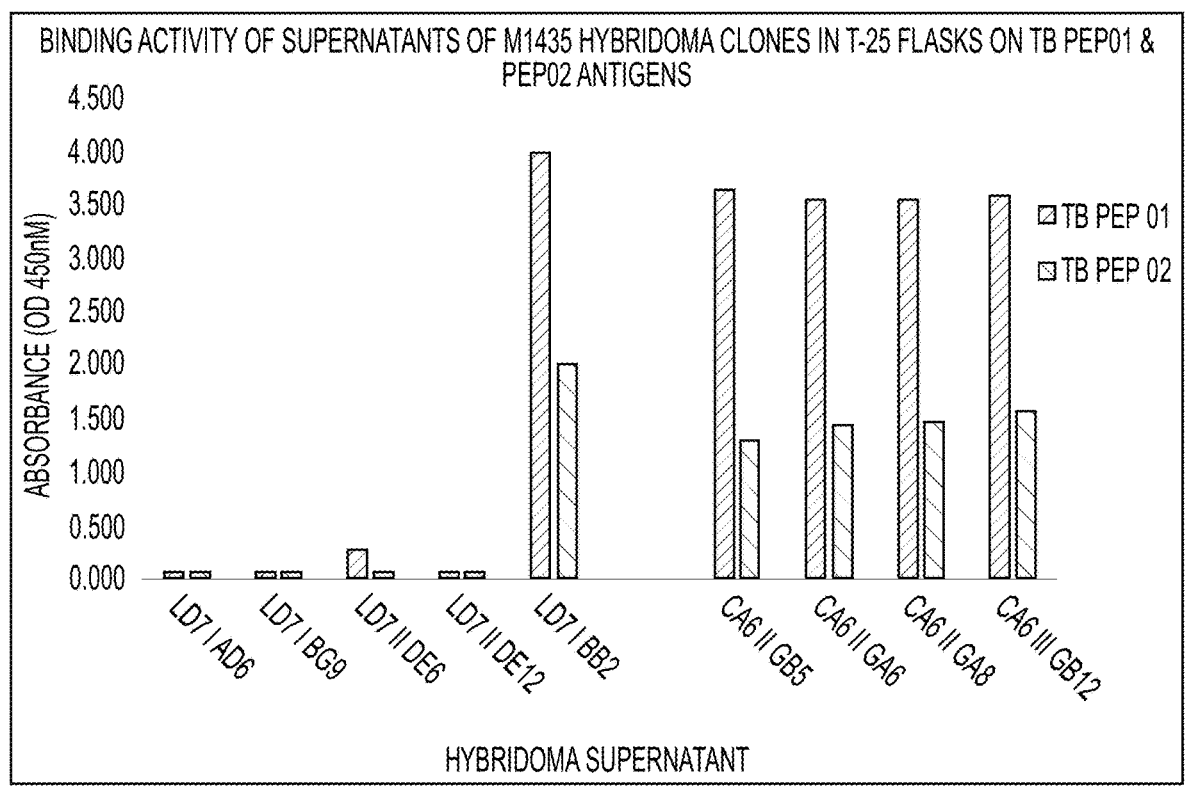
FIG. 27 Hybridoma identification from TB Pep01-CRM conjugated vaccine.
FIG. 28 Hybridoma binding activity to MTB peptide TB Pep01 (Alpha crystallin HSP) and TB Pep02 (TB Pep01+Flu Pep11).
Figures 29, 30:
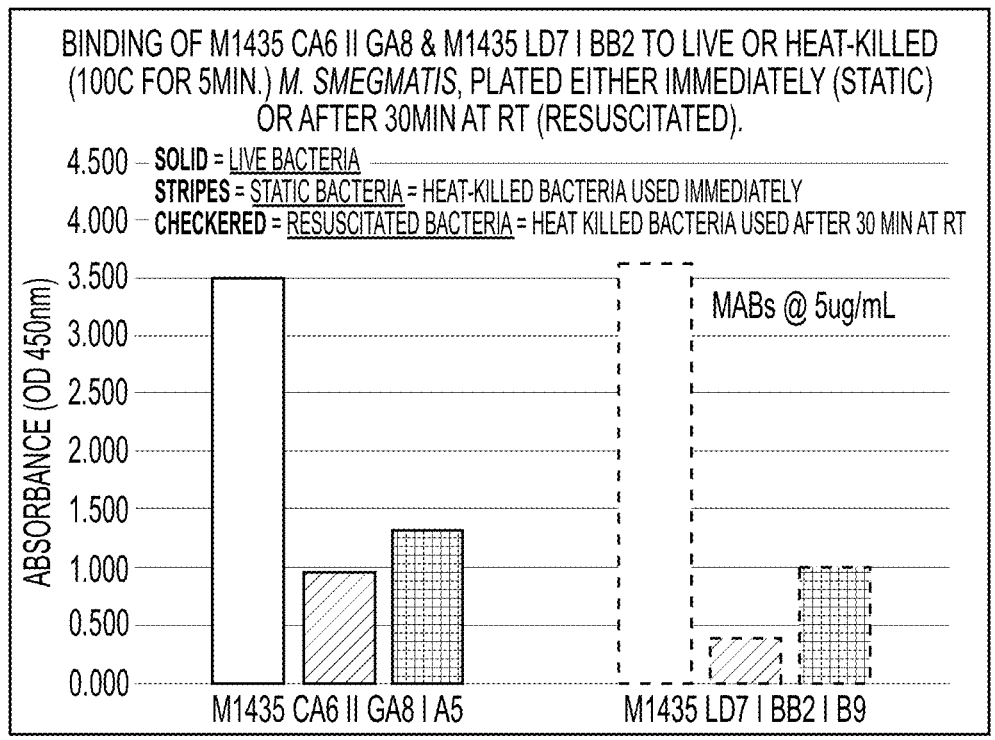
FIG. 29 Monoclonal antibody Binding Activity to Live *M. smegmatis*.
FIG. 30 Monoclonal antibody Opsonophagocytic Killing Activity against *M. smegmatis*.
Figure 31:
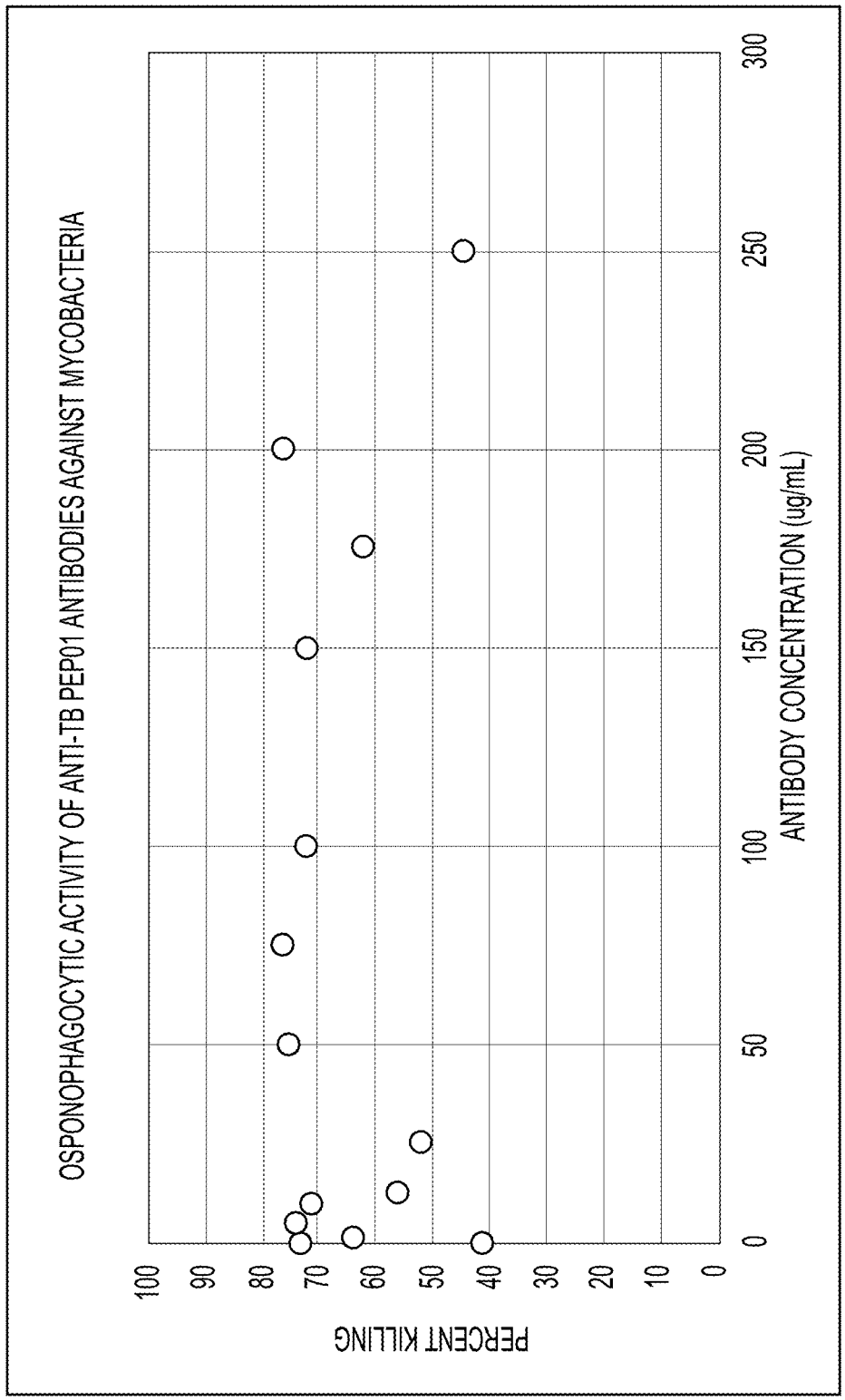
FIG. 31 Monoclonal antibody Opsonophagocytic Killing Activity against Mycobacteria.

To determine the effect of different types of adjuvants and to determine if the HA, NA and Matrix peptide composite vaccines could be delivered together without immune interference, the effects of combining the CRM-conjugated composite vaccines was analyzed using three different adjuvants. Titermax—an emulsion containing block copolymer, squalene and sorbitol monooleate; Addavax—a squalene oil in water nano-emulsion; Quill A—a purified and concentrated saponin adjuvant. The composite peptide vaccines were each CRM-conjugated and given individually with these different adjuvants. FIG. 16 shows that immunization with composite influenza peptides (both M2e and HA, NA together) induced peptide and isotype specific serum IgG responses after 2 immunizations (booster immunization on day 21). Saponin adjuvant Quill A induced robust serum IgG titers equal to or better than squalene emulsion adjuvants across IgG isotypes and HA, NA and M2e peptides. FIG. 17 shows that the superior effects of the saponin adjuvant persisted after a second booster dose on day 35. FIGS. 18 and 19 show that the influenza composite vaccines induce antibodies that not only bind to the highly conserved NA, HA and M2e peptides, but the induced serum antibodies also bind to the native epitopes on H1N1 and H3N2 live influenza, crossing Group 1 and 2 influenza viruses. FIGS. 20 and 21 show that the serum antibodies induced by the composite influenza vaccines not only bind to the conserved epitopes on live influenza virus, but that the induced antibodies neutralize influenza viruses in groups 1 and 2. For both influenza strains, that circulated 2 years apart, strong neutralization was observed and Quill A promoted induction of antibodies that demonstrated influenza virus neutralization at greater than a 1:1000 titer for both H3N2 viruses and greater than 1:3000 for H1N1 viruses. Monoclonal antibodies (mAbs) developed from mice 2209 (mAbs EA9, NB5 and LD9) and 1443 (mAb GA4) shown in FIGS. 23 and 24, and identified in FIG. 22, not only bound to conserved epitopes of HA Pep 3 and Pep 6, and NA Pep 10, and the composite HA+NA Pep 11, and the matrix epitope 5906, but also to live Group 1 and 2 influenza viruses. mAb EA9 at 10 μg/ml bound poorly, but at 25 μg/ml bound well to Pep 3 and live influenza A viruses (see FIGS. 23-24). These monoclonal antibodies also neutralized influenza viruses in groups 1 and 2 (see FIG. 25). Hybridoma cell lines that express MABs EA9 and LD9 were deposited with the ATCC (Manassas, Virginia) on Oct. 13, 2023. Hybridoma EA9 was assigned Accession No. PTA-127659, and hybridoma LD9 was assigned Accession No. PTA-127662. Hybridoma cell lines that express MABs NB5 and GA4 were deposited with the ATCC (Manassas, Virginia) on Mar. 13, 2024. Hybridoma NB5 was assigned Accession No. PTA-127714, and hybridoma GA4 was assigned Accession No. PTA-127713.

These studies using composite peptide conjugate vaccines show strong humoral responses in mice. Broadly reactive serum antibodies against the peptides and live influenza viruses were detected. These vaccines individually or in combination, induced antibodies that demonstrated functional activity against contemporary influenza strains in Group 1 and 2. Additionally, evaluation of the abilities of three different adjuvants (Saponin-derived, Squalene-based sorbitan-trioleate, and Squalene-based block copolymer) to promote robust immune responses against influenza antigens (HA, NA and M2e peptides) demonstrated that the Saponin-derived adjuvant with our composite peptide CRM-conjugate vaccine induced broadly reactive serum antibodies across surface peptides, matrix and live influenza viruses and also demonstrated a robust humoral response across isotypes. Furthermore, functional activity against contemporary influenza strains was greater for the Saponin-derived group, compared to Squalene-based groups. Saponin-derived adjuvants plays an important role in the induction of key immune responses that are critical for immunity to influenza.

Example 2 Flu Pep11—TT Study Design

The position of the T-cell epitope in the composite antigen can affect the immune enhancement of the epitopes in the composite antigen. The Pep 11 composite peptide was synthesized with a T-cell epitope (tetanus toxoid {TT}) on either the N-terminus (Pep 64) or C-terminus (Pep 63). Mice were immunized with the peptides Pep 63 and Pep 64 both as conjugated to CRM or unconjugated, all with Addavax as adjuvant. Booster injections were given at day 21 and day 35. The overall study design is shown in FIG. 1. Mouse number 2156 was euthanized after day 35 bleed, prior to the completion of the study.

Example 3 Study Results at Day 7, 21, 28, 35 and 42 for IgG Isotypes

Serum was obtained from mice immunized with the composite influenza peptides Pep 63 and Pep 64 both in conjugated and unconjugated forms. These serum sample were tested for IgG1, IgG2a and IgG2b activity against Pep 3, Pep 6, Pep 10, and Pep 11 (Pep 11—the composite 3, 6 and 10 peptides).

Figure 3:
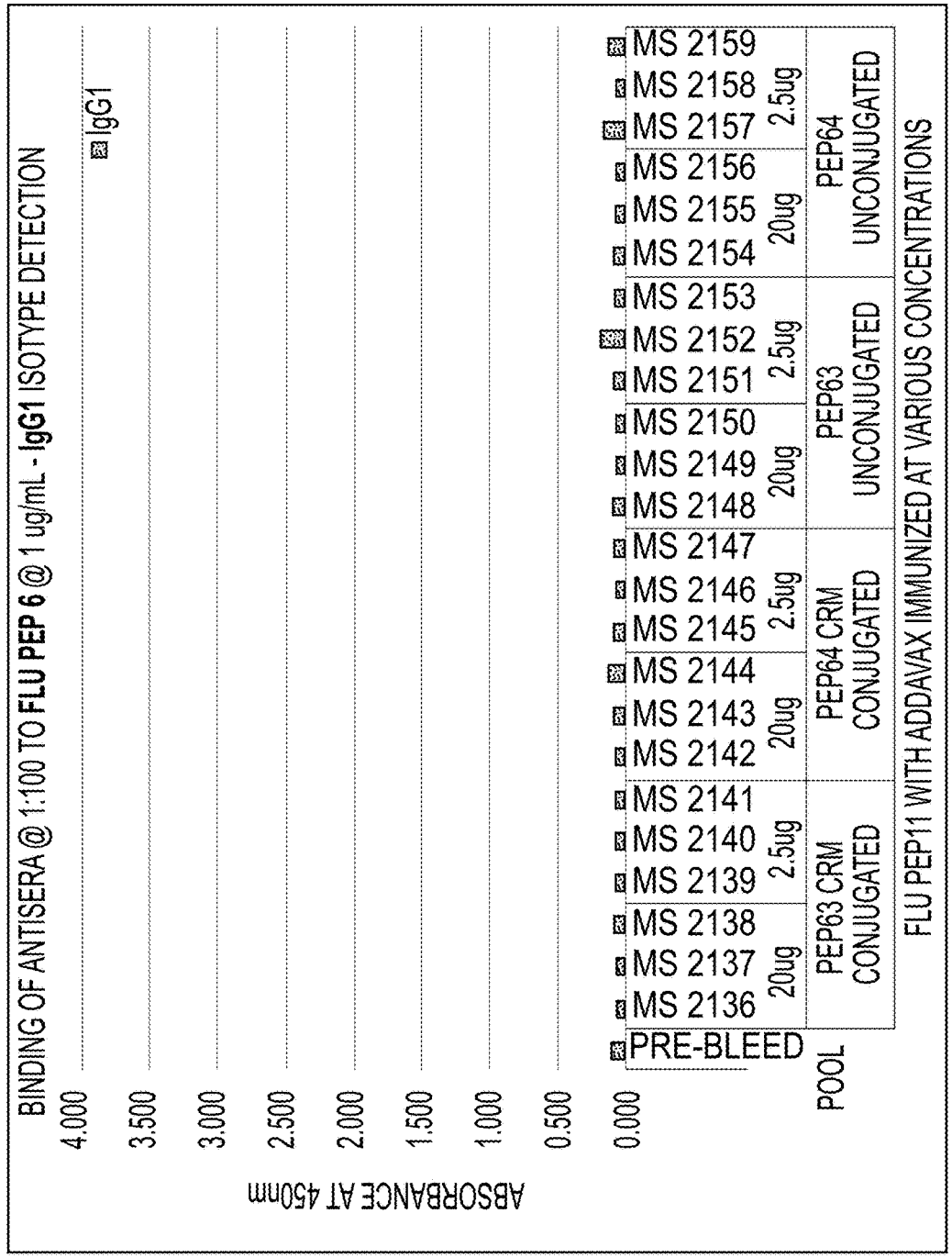
FIG. 3 Day 7-42 Serum antibody responses to Flu Pep 6: IgG1 isotype detection.
Figure 3:
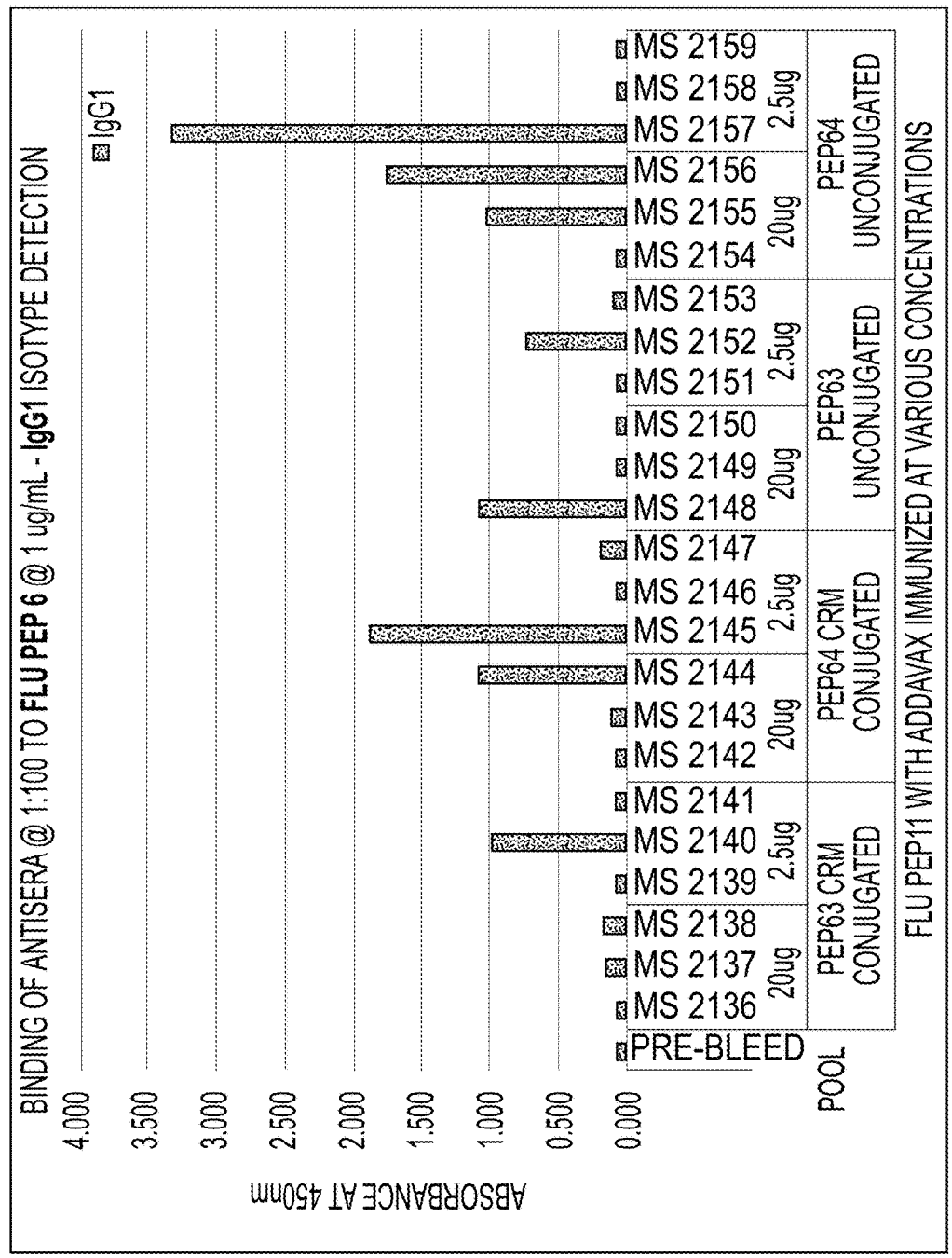
Figure 4:
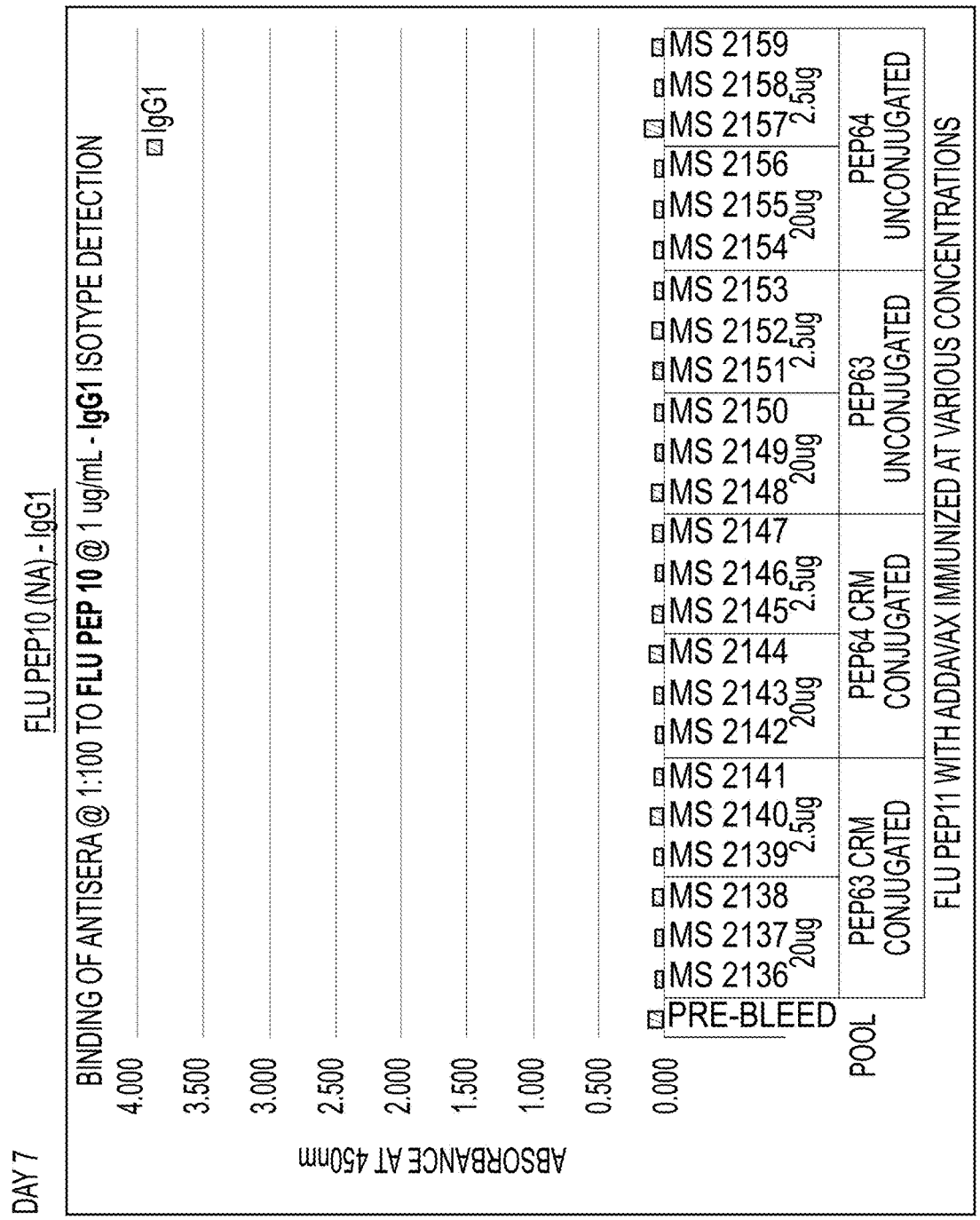
FIG. 4 Day 7-42 Serum antibody responses to Flu Pep 10: IgG1 isotype detection.
Figure 4:
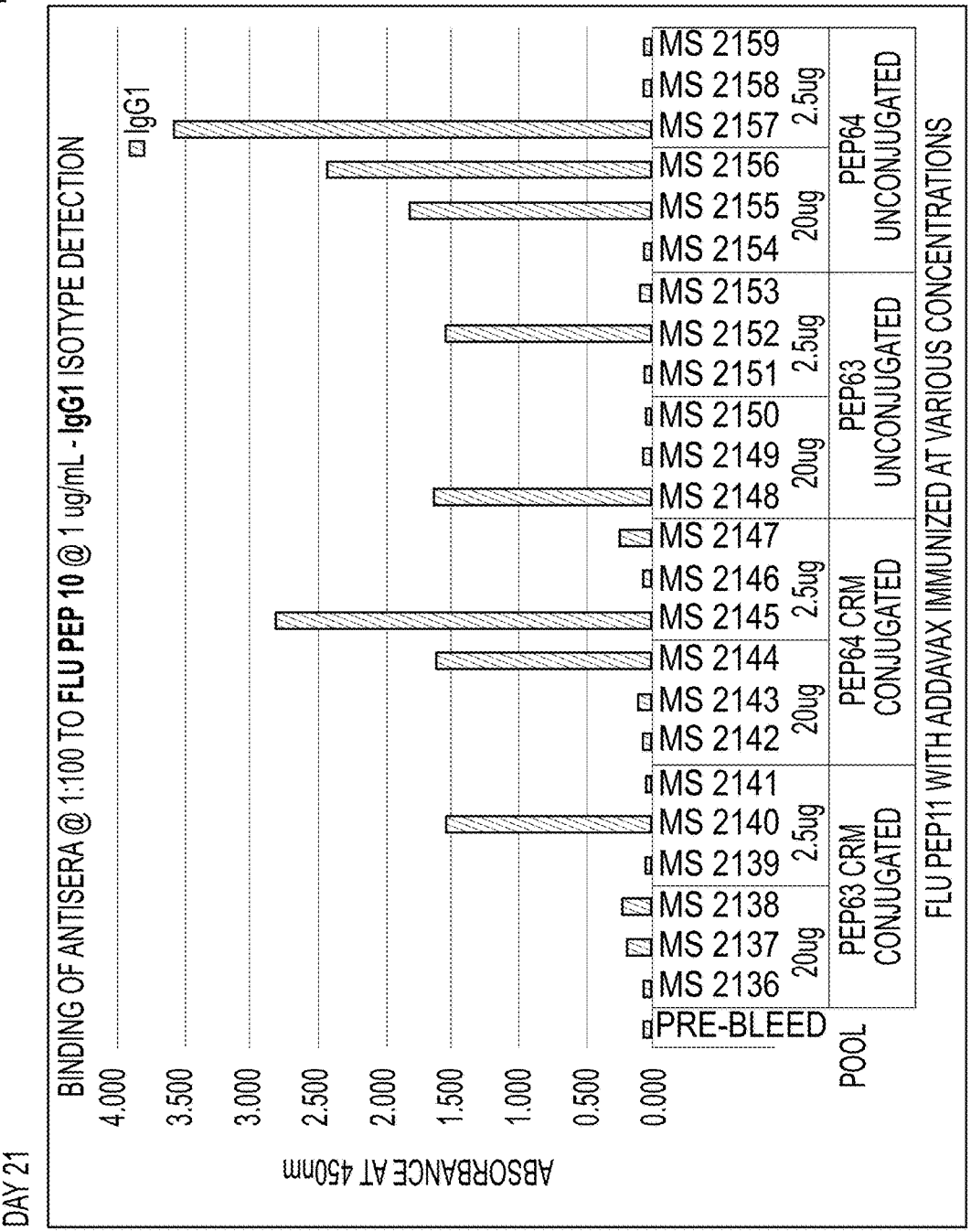
Figure 5:
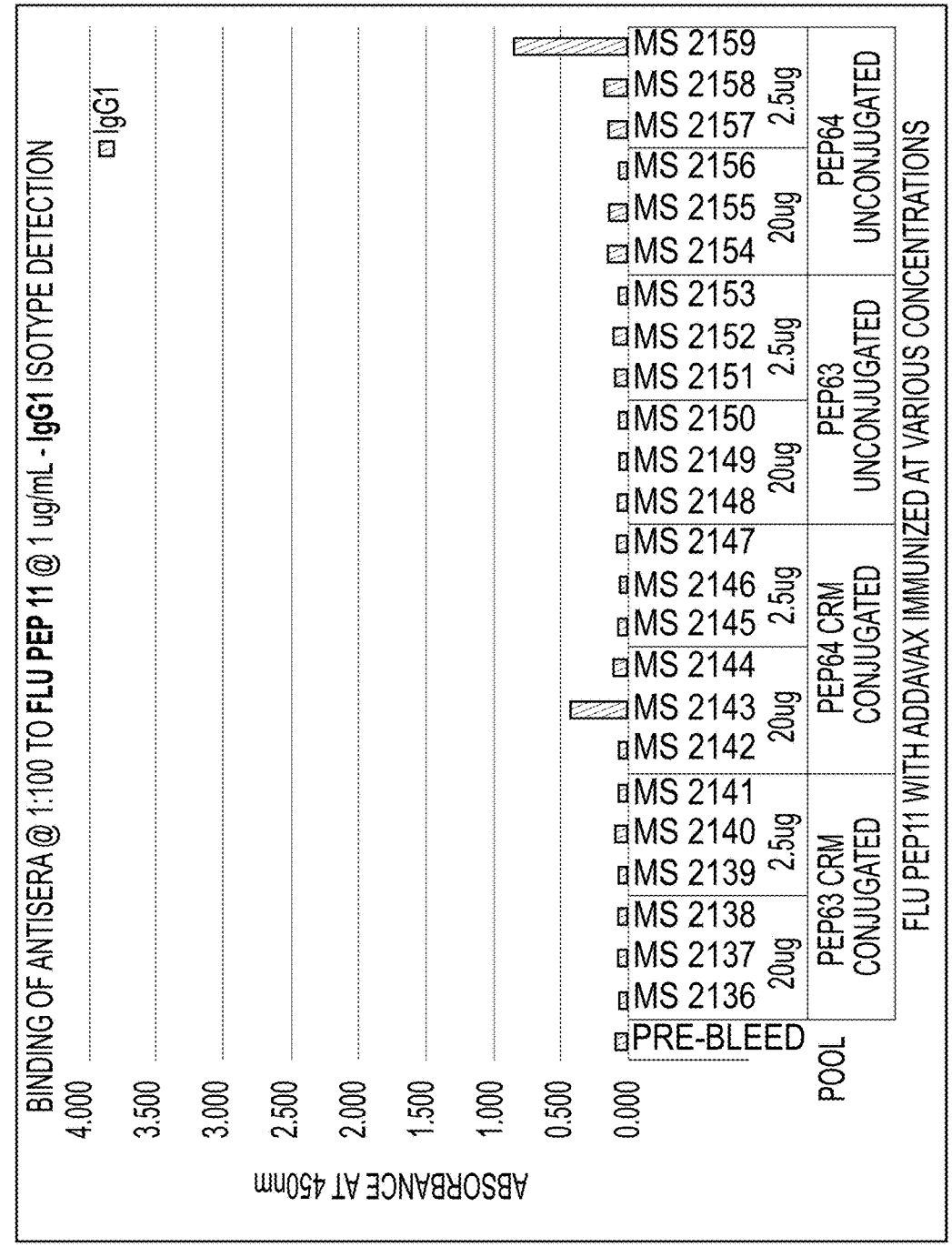
FIG. 5 Day 7-42 Serum antibody responses to Flu Pep 11: IgG1 isotype detection.
Figure 5:
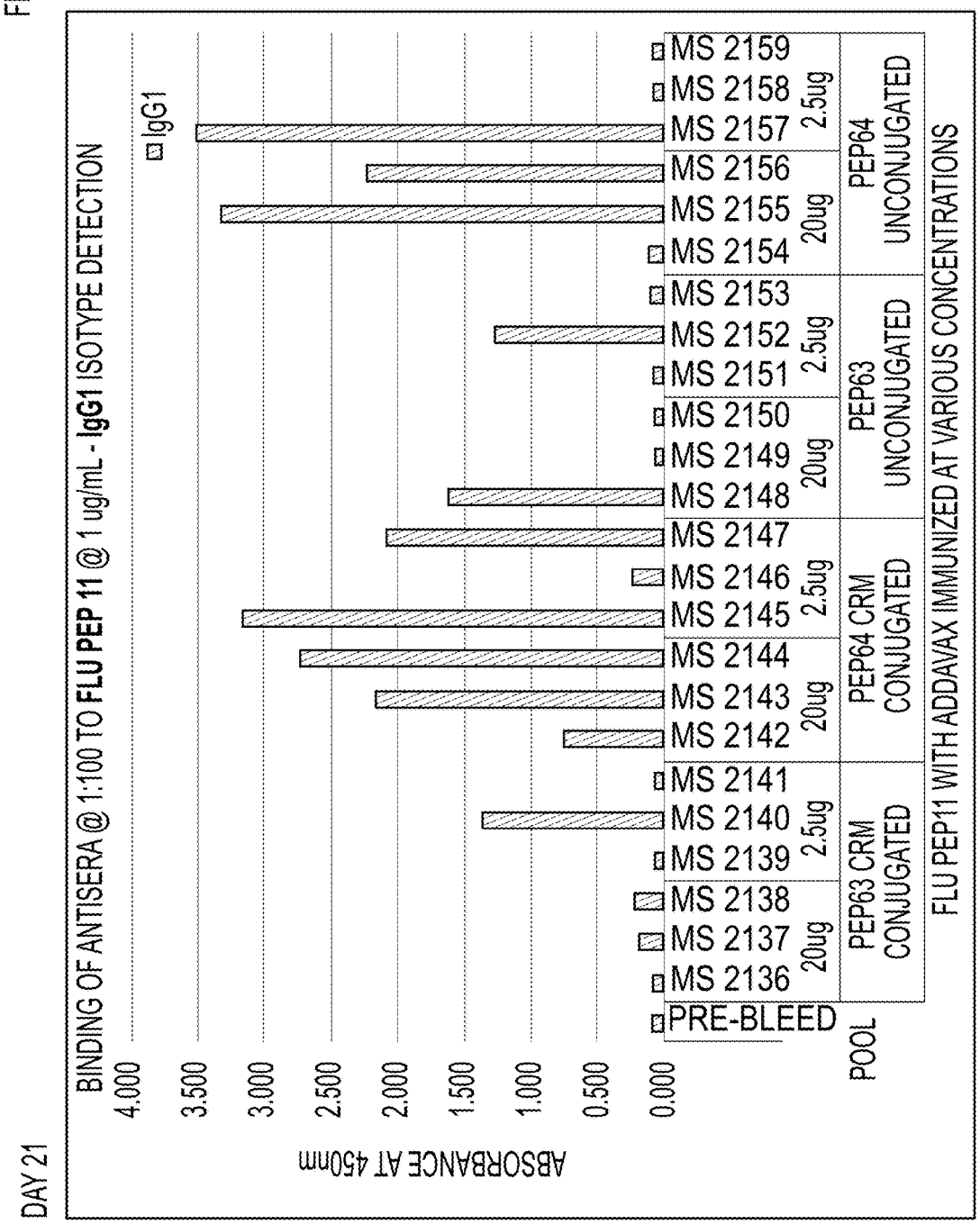

With regard to Pep 3, Pep 6, Pep 10, and Pep 64, both conjugated and unconjugated, as compared to Pep 63 showed an overall greater IgG1 response (FIGS. 2, 3 and 4). With regard to Pep 11, Pep 64, both conjugated and unconjugated, as compared to Pep 63 also showed a greater IgG1 response (FIG. 5).

Figure 6:
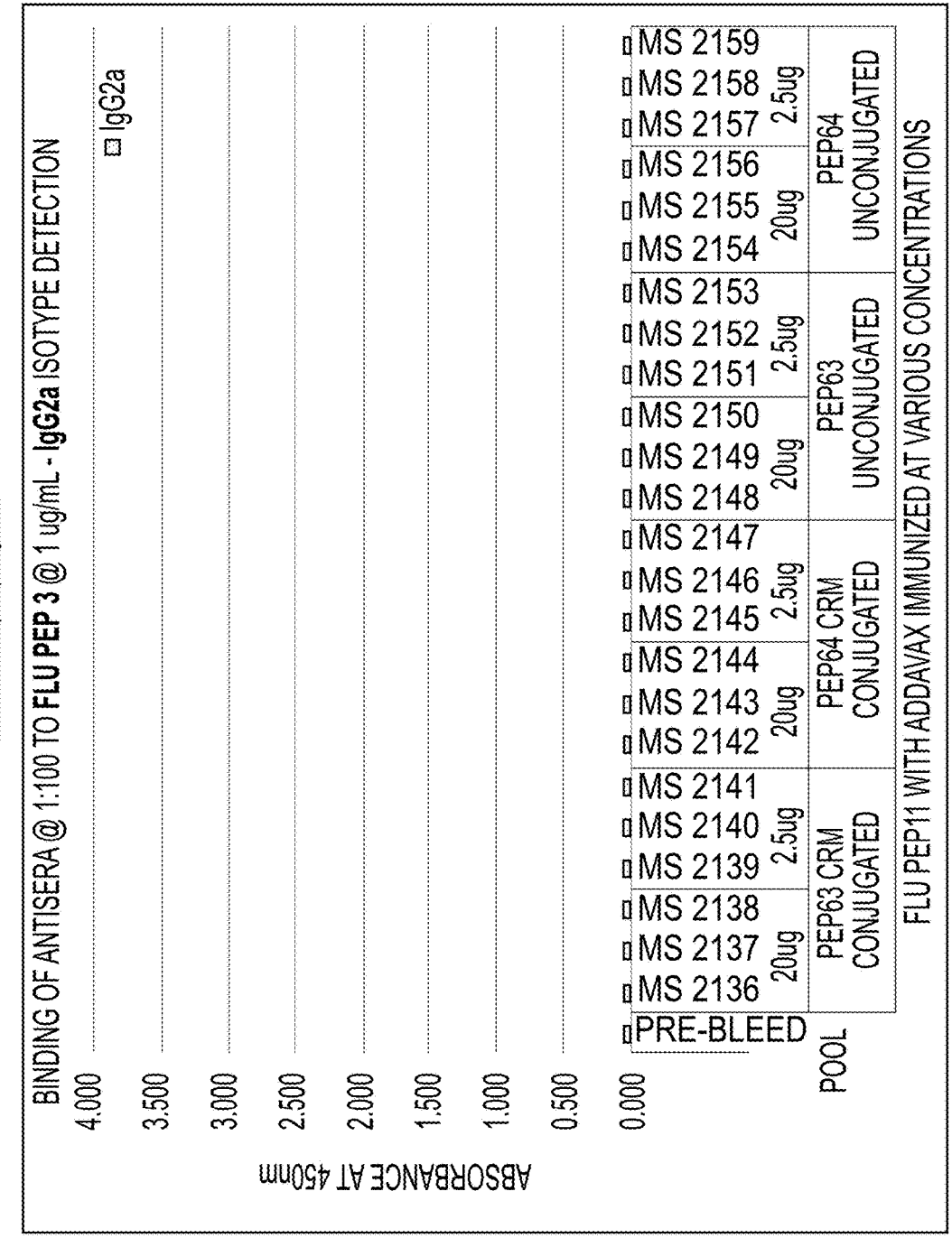
FIG. 6 Day 7-42 Serum antibody responses to Flu Pep 3: IgG2a isotype detection.
Figure 6:
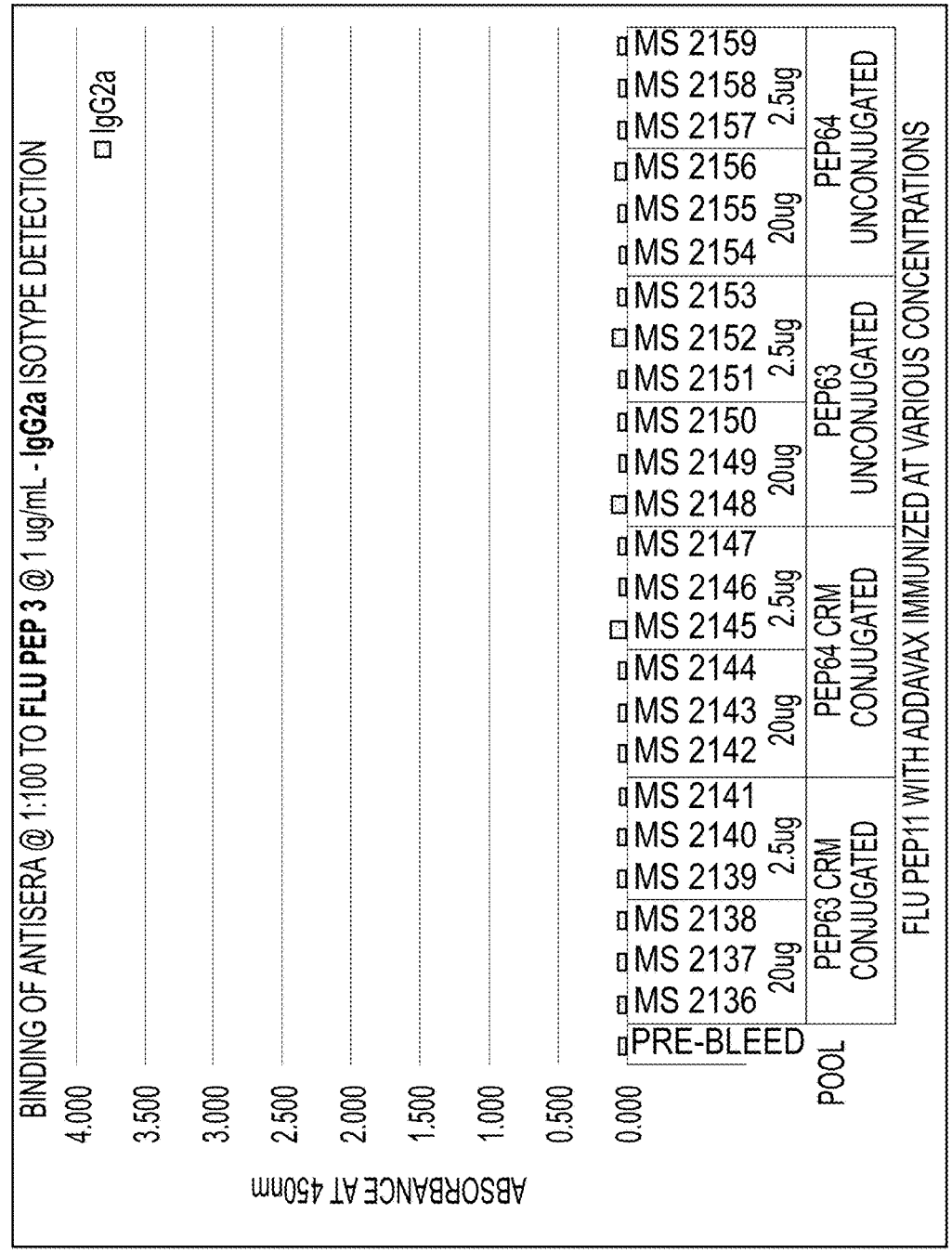
Figure 7:
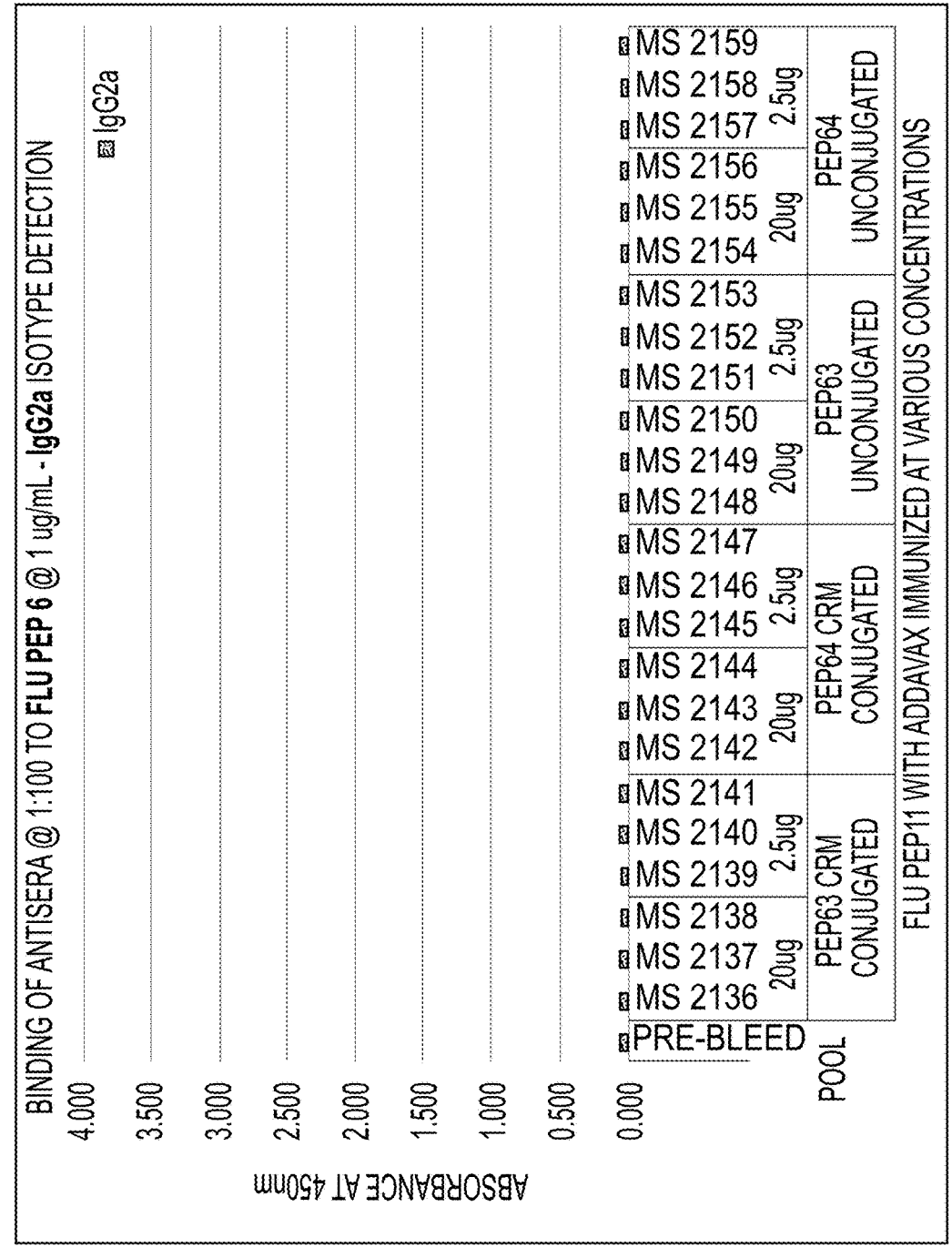
FIG. 7 Day 7-42 Serum antibody responses to Flu Pep 6: IgG2a isotype detection.
Figure 7:
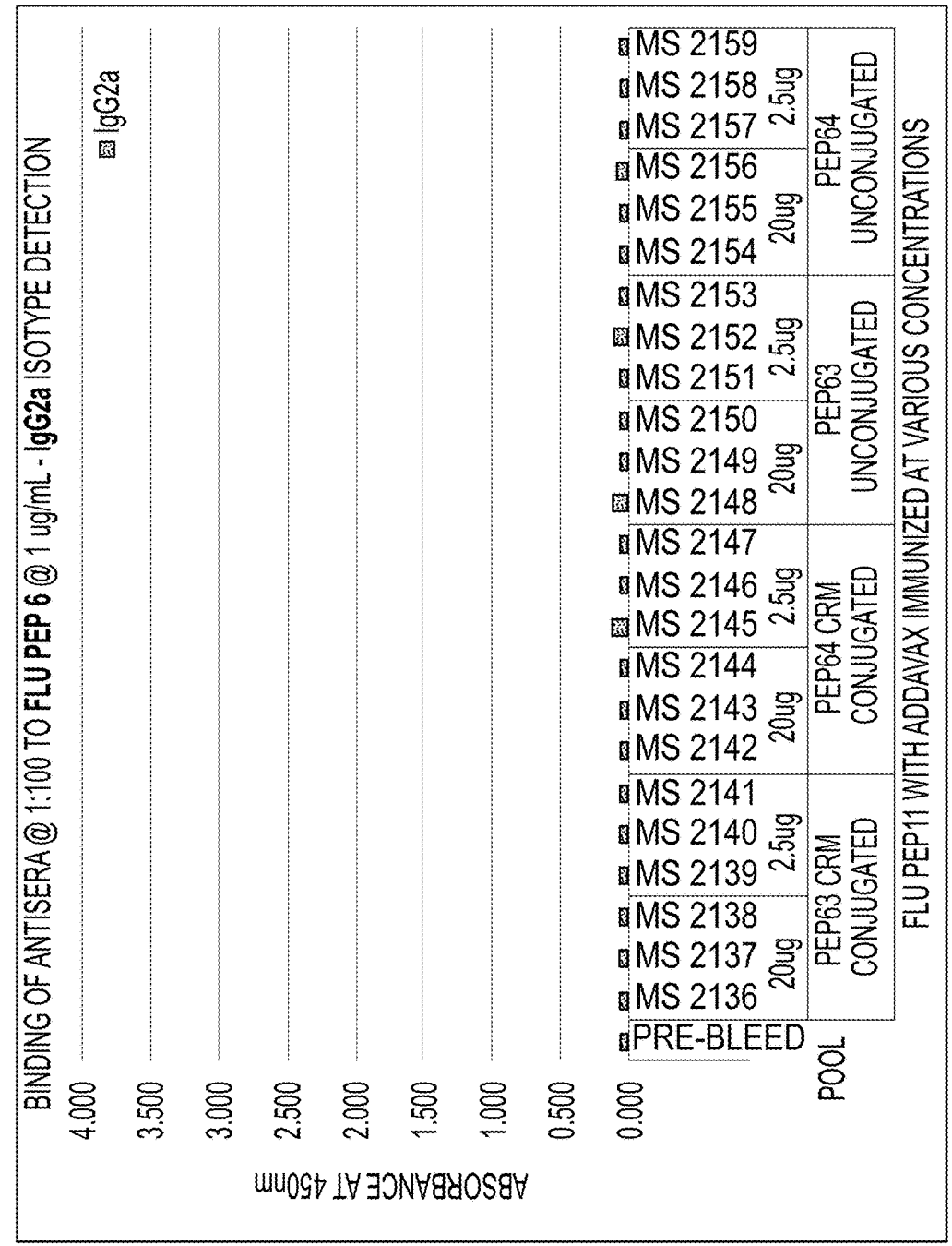
Figure 8:
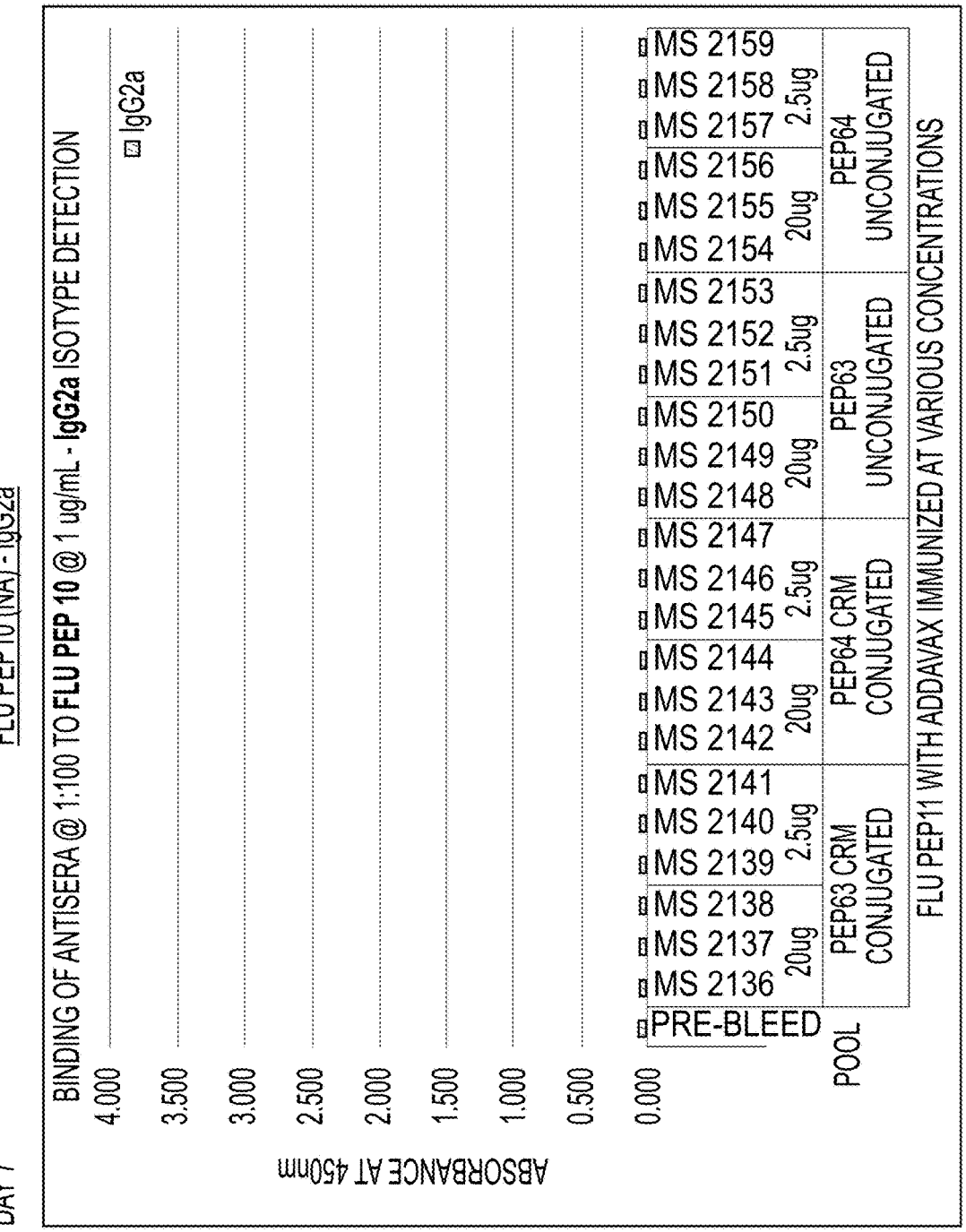
FIG. 8 Day 7-42 Serum antibody responses to Flu Pep 10: IgG2a isotype detection.
Figure 8:
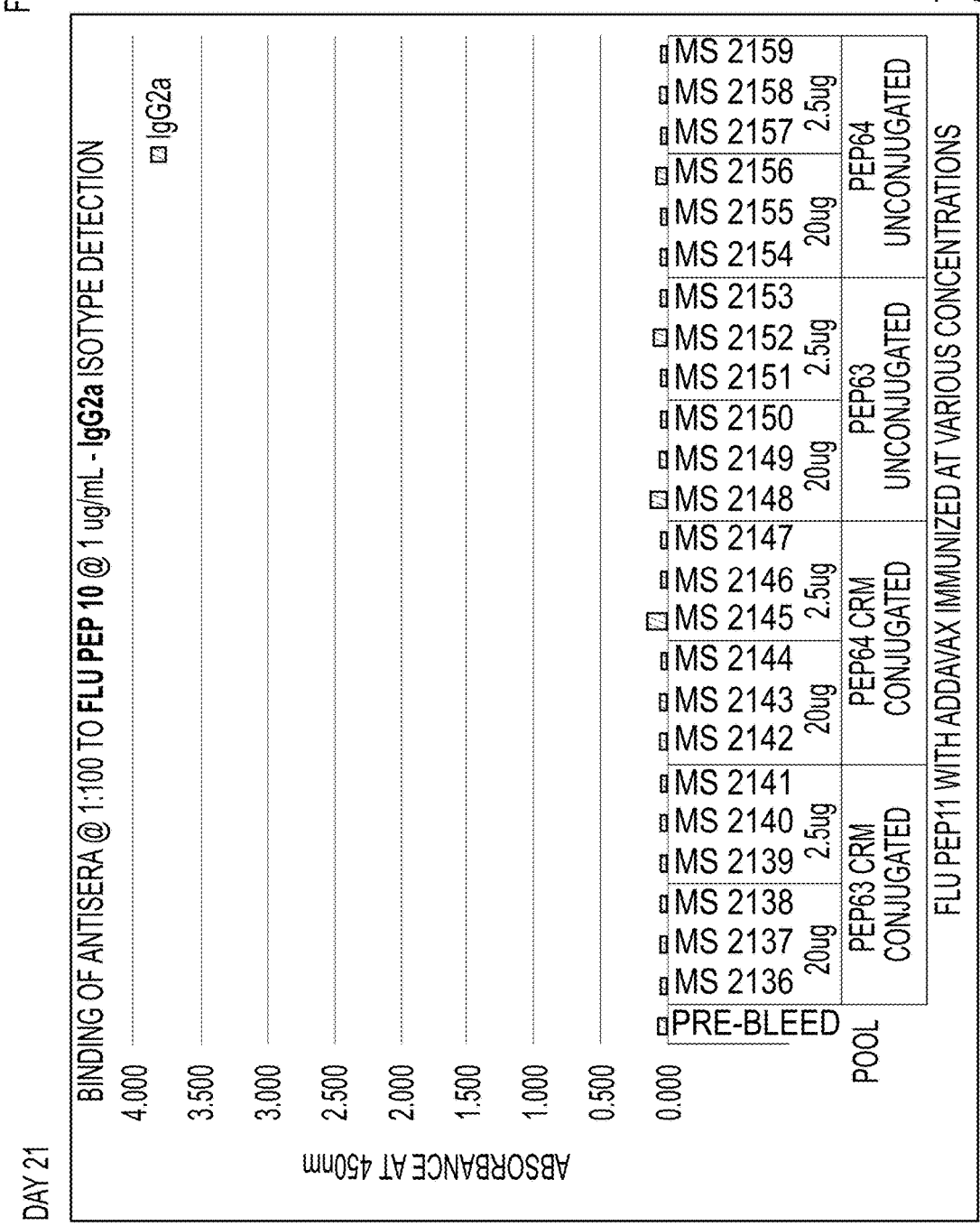
Figure 9:
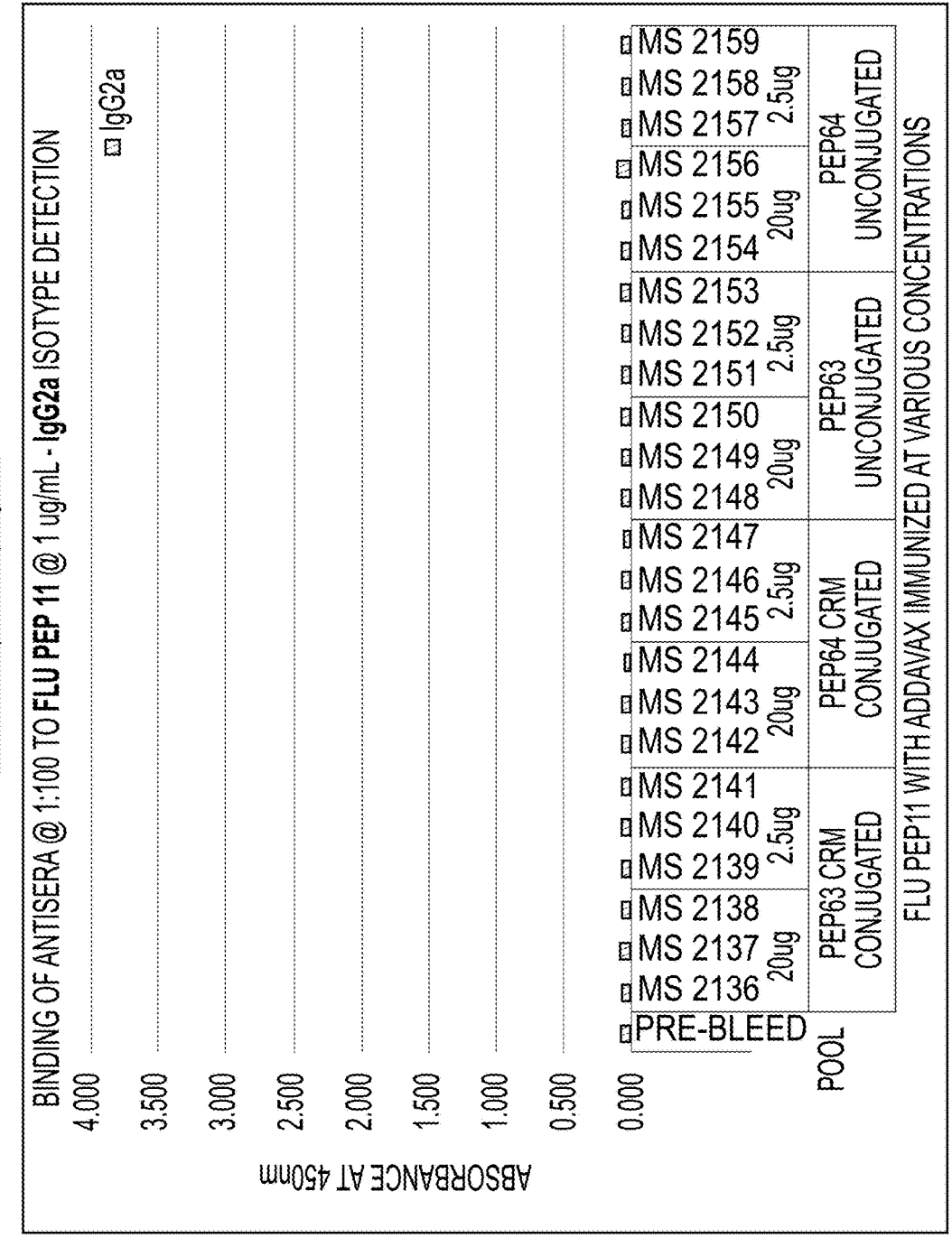
FIG. 9 Day 7-42 Serum antibody responses to Flu Pep 11: IgG2a isotype detection.
Figure 9:
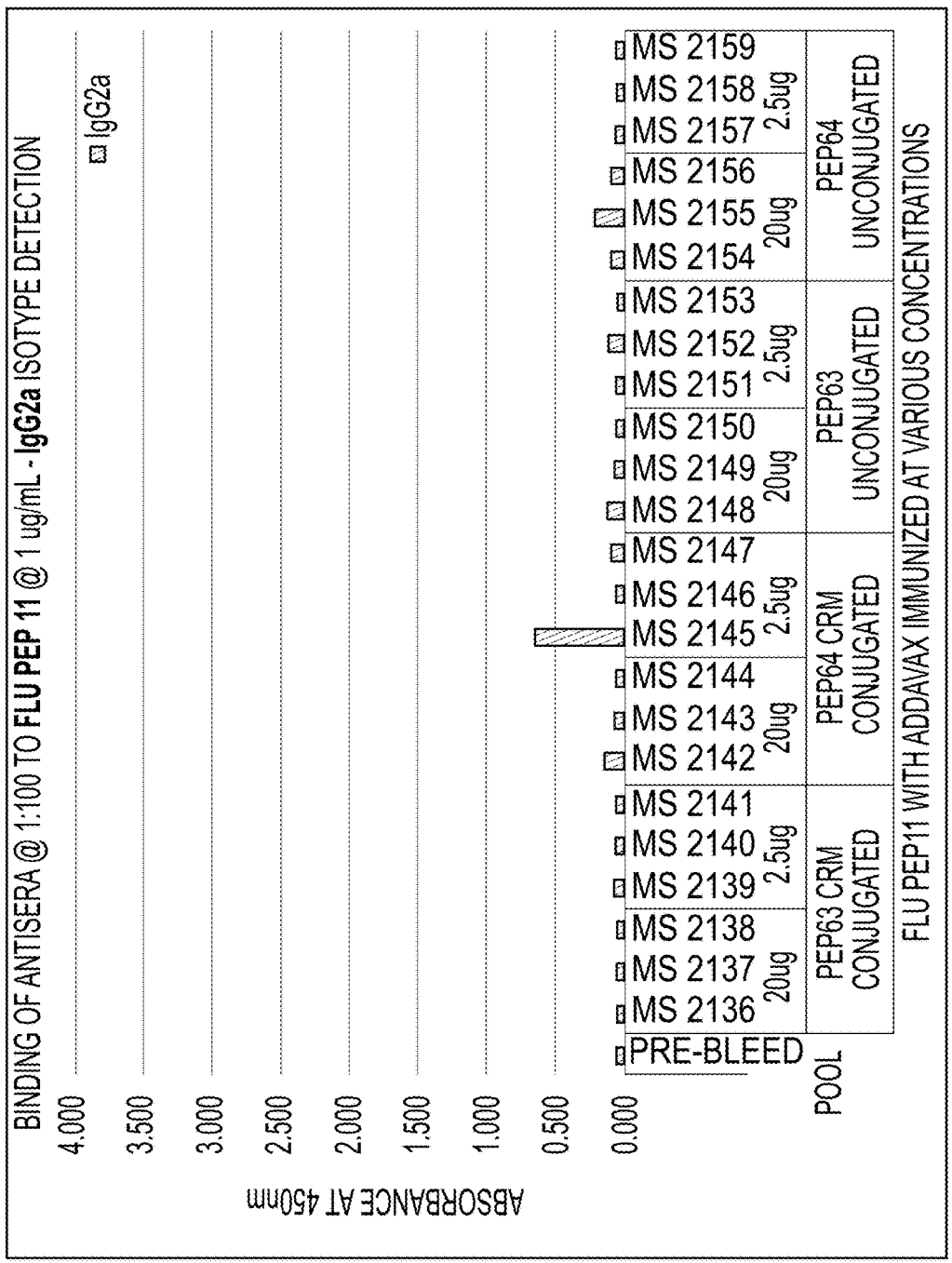

With regard to Pep 3, Pep 6, and Pep 10, there was a minimal IgG2a response to either Pep 63 or Pep 64, whether in conjugated or unconjugated form (FIGS. 6-8). With regard to Pep 11, Pep 64, conjugated and unconjugated showed only a weak IgG2a response; conjugated greater than unconjugated (FIG. 9).

Figure 10:
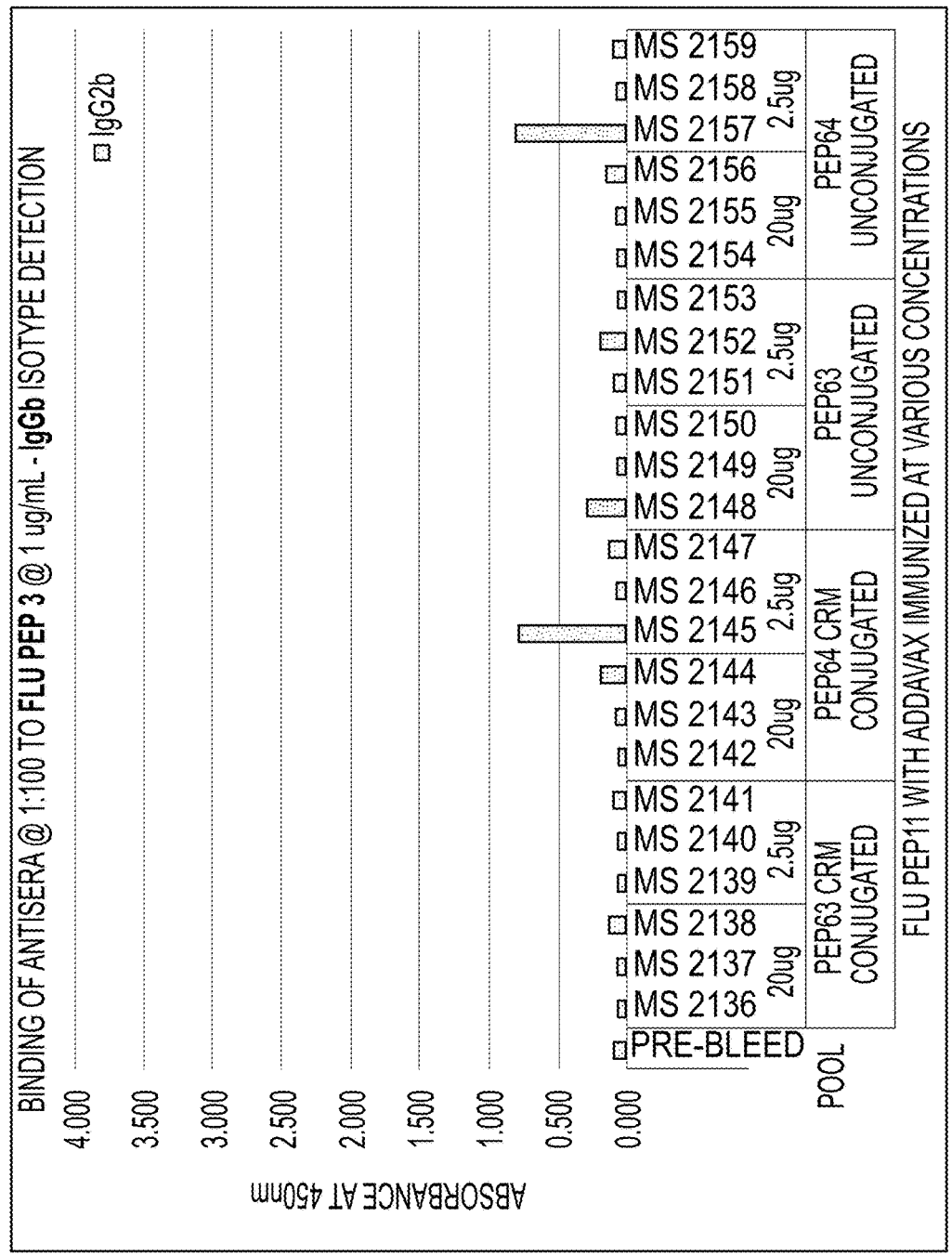
FIG. 10 Day 7-42 Serum antibody responses to Flu Pep 3: IgG2b isotype detection.
Figure 11:
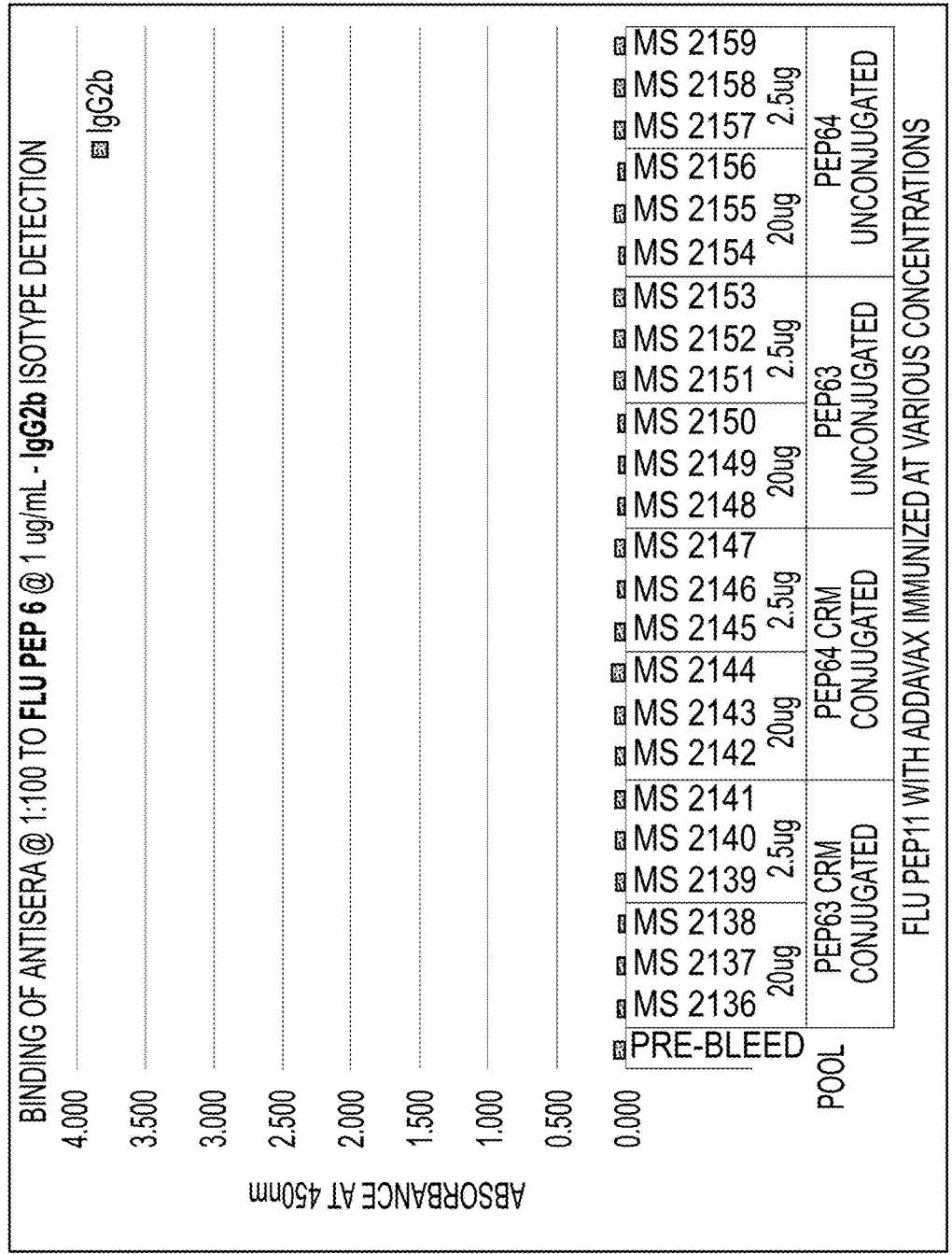
FIG. 11 Day 7-42 Serum antibody responses to Flu Pep 6: IgG2b isotype detection.
Figure 11:
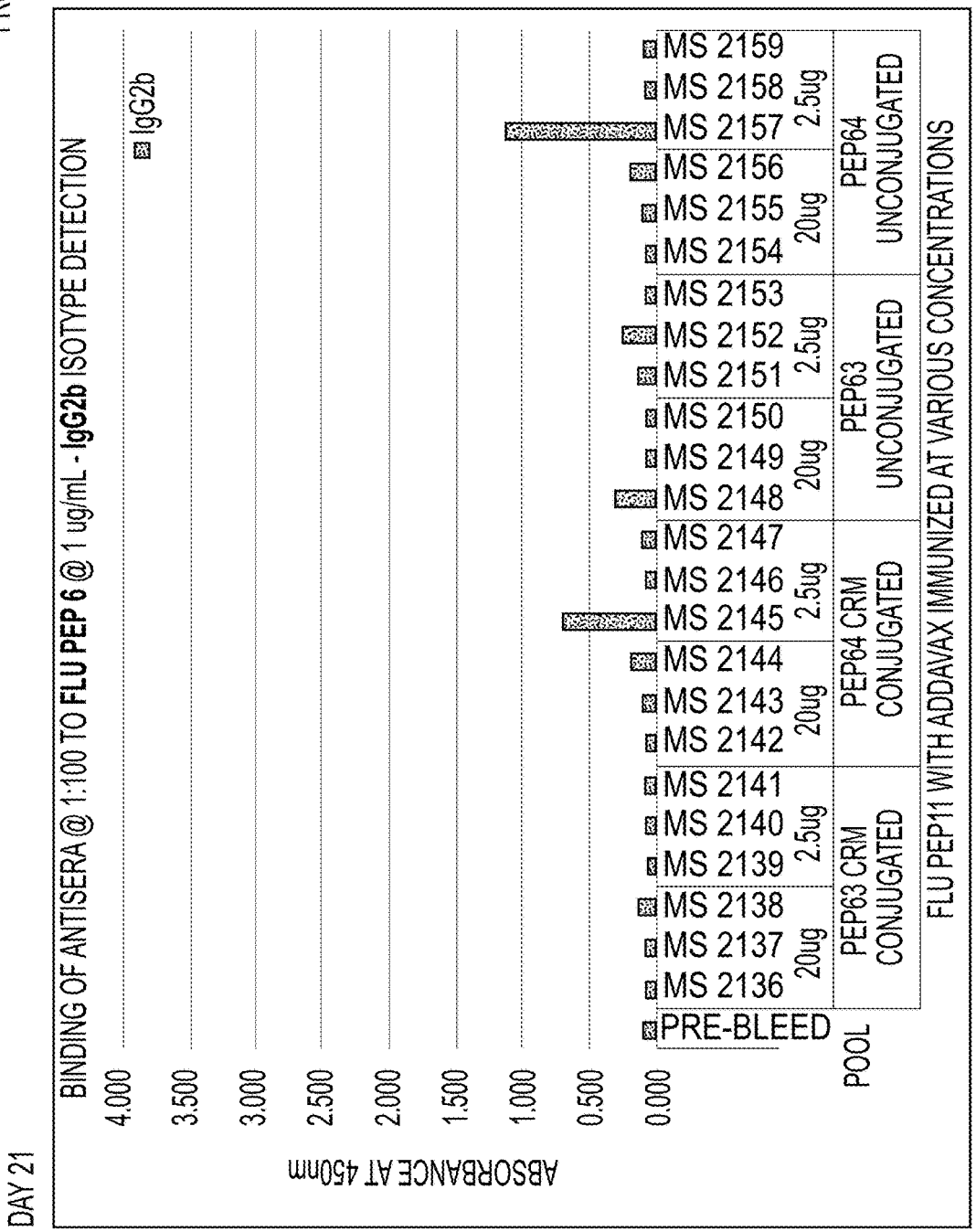
Figure 12:
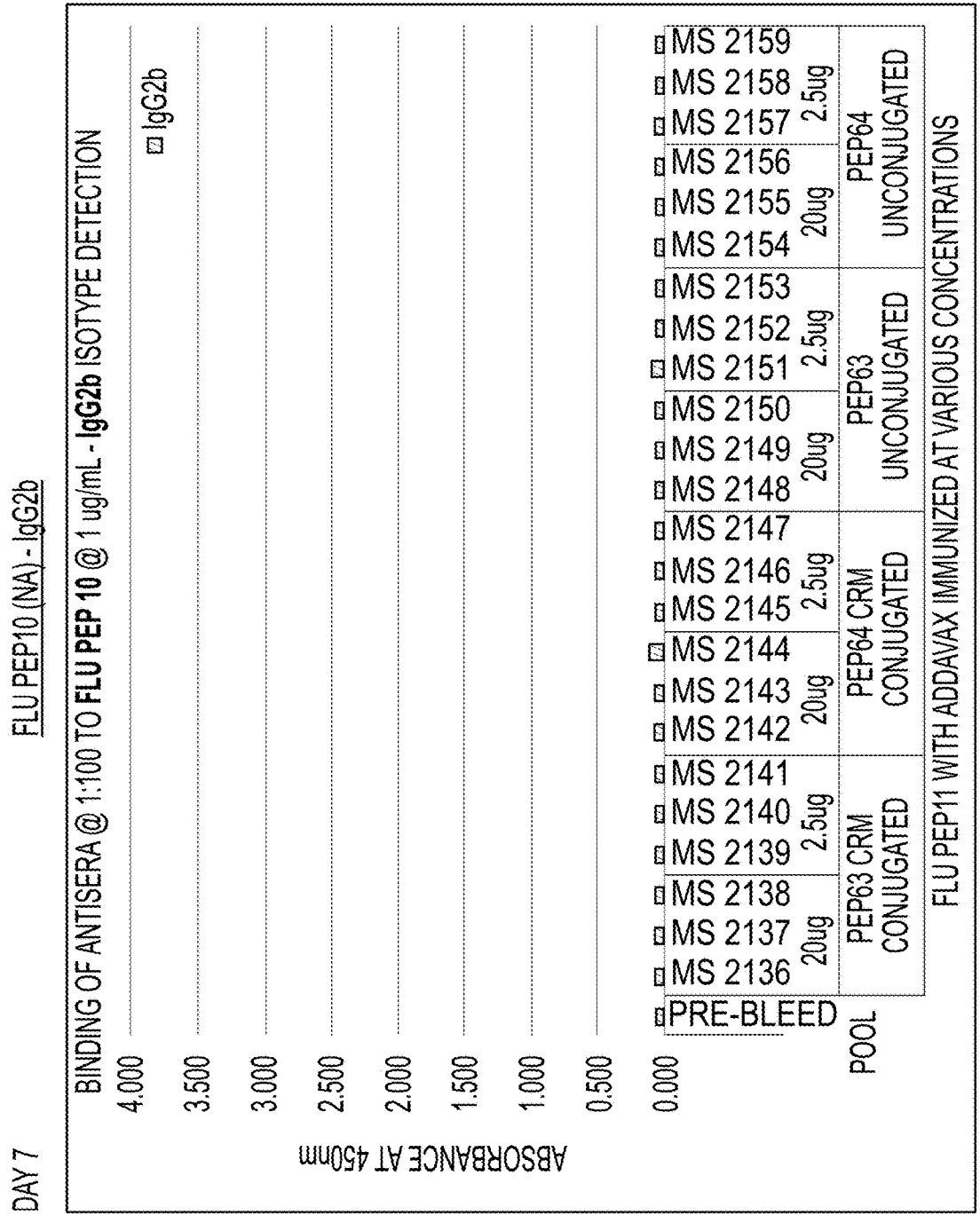
FIG. 12 Day 7-42 Serum antibody responses to Flu Pep 10: IgG2b isotype detection.
Figure 12:
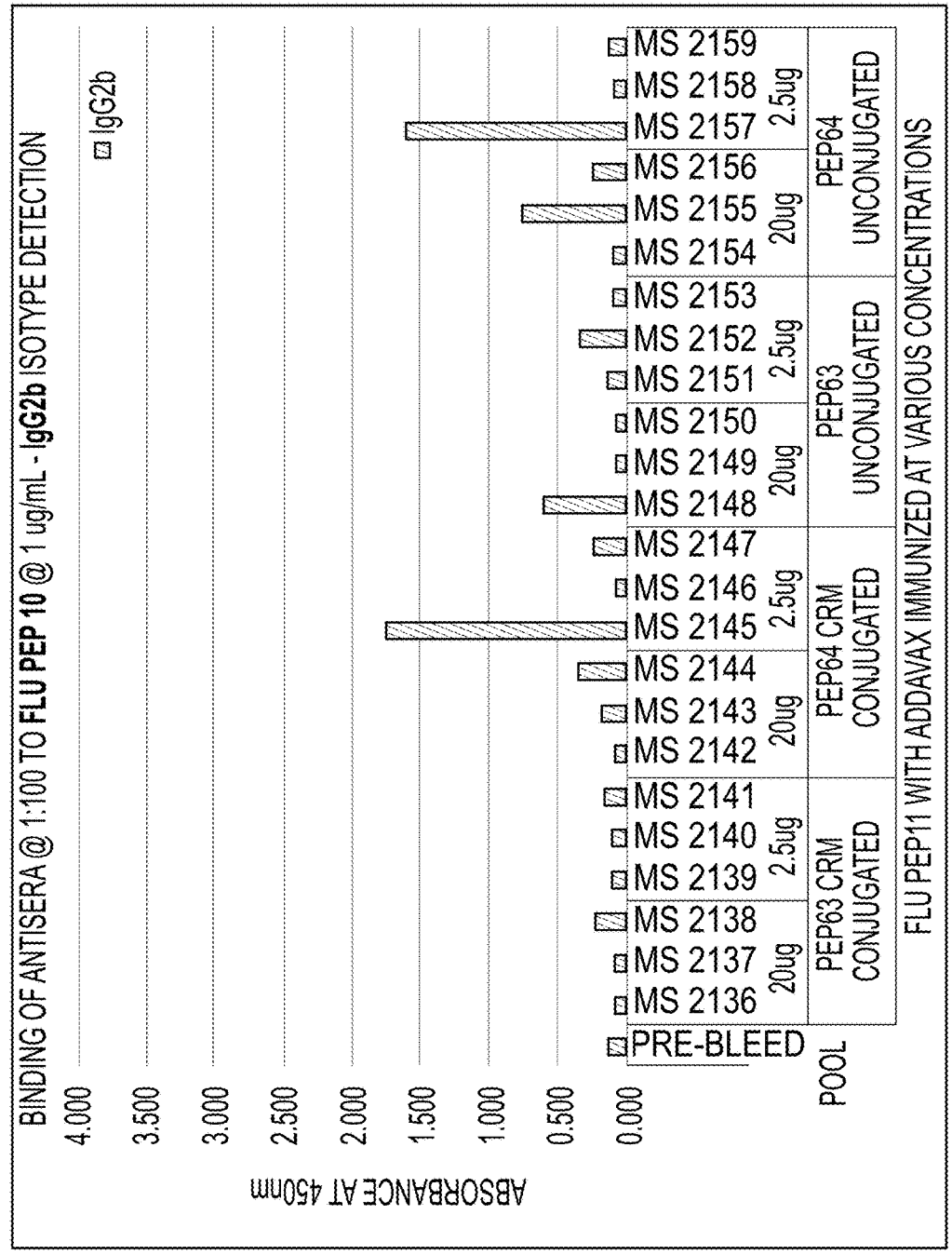
Figure 13:
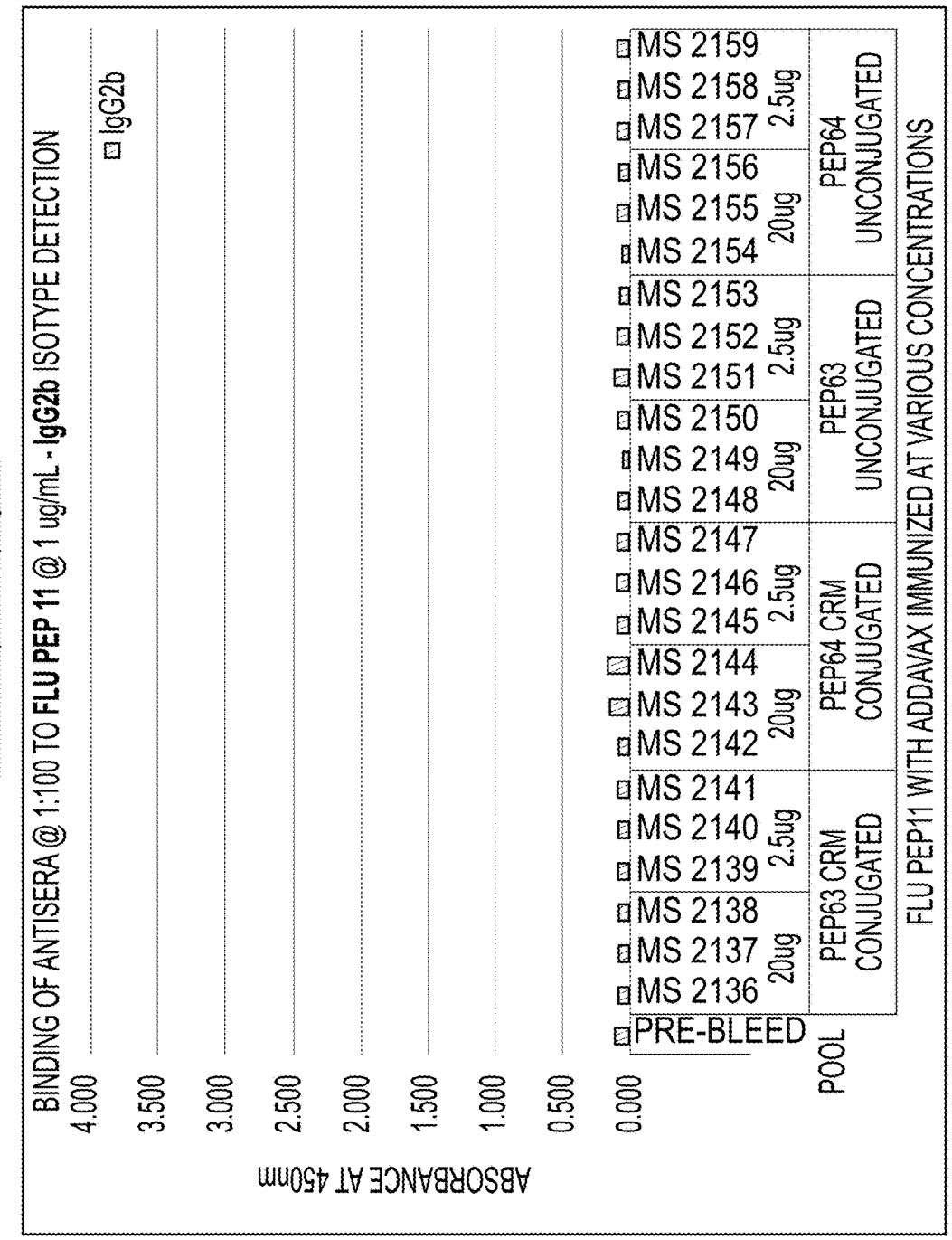
FIG. 13 Day 7-42 Serum antibody responses to Flu Pep 11: IgG2b isotype detection.
Figure 13:
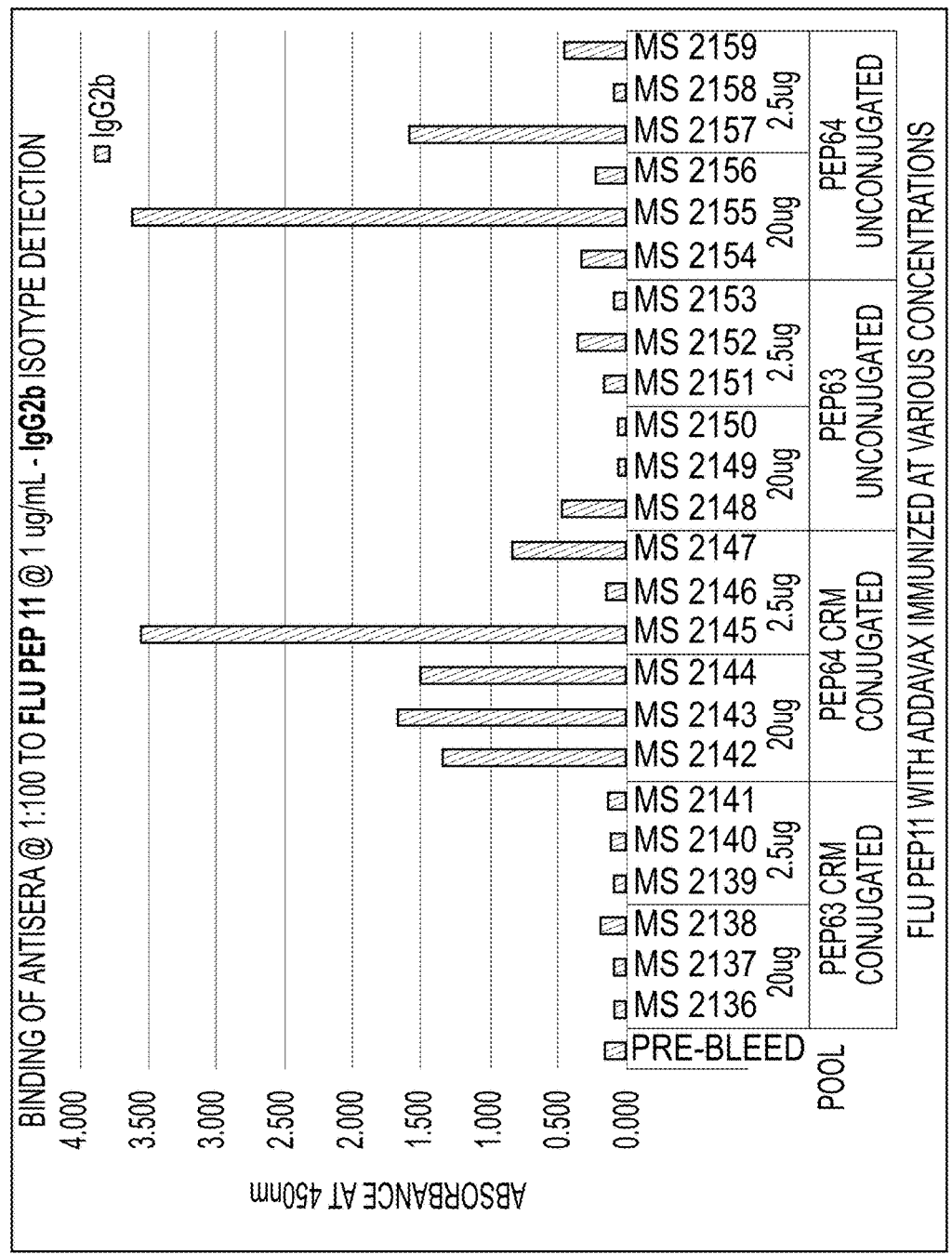

With regard to Pep 3, Pep 6, Pep 10 there was a greater IgG2b response to Pep 64, conjugated, as compared to Pep 63 which mostly appeared after booster was administered (FIGS. 10-12). With regard to Pep 11, Pep 64, conjugated, showed a very large IgG2b response that was enhanced after the booster was administered (FIG. 13).

Pep 64 (both conjugated and unconjugated) with the T-cell epitope at the N-terminal end induced increased serum antibody responses to the individual peptides across IgG1 and IgG2b isotypes, but not IgG2a. What this data clearly shows is that the location of the T cell epitope on an antigen can have a significant effect of how the antigen is seen and responded to by the host immune system. These data also indicate that T cell epitope placement can have a profound effect on both the Th-1 and Th-2 responses.

Example 4 Antibodies to Composite MTB Sequences

Composite MTB peptide vaccines induce antibodies that recognize the conserved MTB Alpha Crystallin HSP epitope (designated as TB Pep01) derived from *Mycobacterium tuberculosis* H37Rv (NC_000962.2).

Serum antibodies from mice 1433-1436 (see FIG. 26) immunized with 50 μg TB Pep01 CRM-conjugated vaccine demonstrated good responses to the conserved MTB epitope (alpha crystallin HSP), TB Pep01. Mouse 1435 (see FIG. 27), selected for fusion, produced hybridomas LD7 I BB2 and CA6 II GA8 that demonstrated good binding activity to TB Pep01 and TB Pep02 epitopes (FIG. 28). Monoclonal antibodies LD7 I BB2 I B9 and CA6 II GA8 I A5 (hereafter referred to as mAb LD7 and CA6) that were developed from the hybridomas not only bound to TB Pep01, but also to live *M. smegmatis* (see FIG. 29). Importantly, mAbs LD7 and CA6 promoted opsonophagocytic killing of mycobacteria (see FIGS. 30 and 31).

Example 5 Sequences

The following is a list of exemplary amino acid sequences that can be utilized as antigenic portions, reverse translated to RNA sequences, or reverse transcribed to DNA sequences for use as compounds, compositions, and/or vaccines. Sequences also may be combined with each other, with T cell stimulating sequences, with other sequences, and/or any combination of the preceding. Sequences may include linkers for couplings, such as for example, CAGA for coupling to CRM protein, and may be included at the N-terminus or the C-terminus. Sequences may also be combined as described herein as composite sequences as well.

```
MTB/VIRAL EPITOPES
SEQ ID NO 1:
SEFAYGSFVRTVSLPVGADE
(Conserved MTB Alpha Crystallin HSP epitope
derived from Mycobacterium tuberculosis H37Rv
(NC_000962.2))

SEQ ID NO 2:
SEFAYGSFVRTVSLPVGADEGNLFIAPWGVIHHPHYEECSCY
(MTB Alpha
Crystallin HSP and 2 conserved influenza HA
Peptides and 1 conserved NA Peptide)

SEQ ID NO 3:
LRPTFDTRLMRLEDEMKEGR

SEQ ID NO 4:
DPDKDVDIMVRDGQLTIKAE

LAM MIMETOPES
SEQ ID NO 5:
HSFKWLDSPRLR
(Conserved MTB Lipoarabinomanin mimetope)

SEQ ID NO 6:
ISLTEWSMWYRH
(Conserved MTB Lipoarabinomanin mimetope)

STAPHYLOCOCCUS LTA EPITOPES
(bind to opsonic Mabs)
SEQ ID NO 7:
WRMYFSHRHAHLRSP
(LTA Epitope)

SEQ ID NO 8:
WHWRHRIPLQLAAGR
(LTA Epitope)

CORONAVIRUS EPITOPES
SEQ ID NO 9:
YPKCDRA
(RNA Polymerase Region)

SEQ ID NO 10:
WDYPKCDRA
(RNA Polymerase Region; corona conserved
seq-polymerase)
neutralizing Ab)

SEQ ID NO 11:
SLDQINVTFLDLEYEMKKLEESY
(Spike Protein Conserved Region)

SEQ ID NO 12:
KWPWYIWLGFIAGL
(Highly conserved spike protein region)

SEQ ID NO 13:
ENQKLIAN
(Highly conserved spike protein region;
attachment area for all
coronaviruses)

INFLUENZA EPITOPES
Neuraminidase Peptides
SEQ ID NO 14:
HYEECSCY
(N1 and N5 active sialic acid catalytic
site, Pep 10)

SEQ ID NO 15:
HVEECSCY
(N1 and N2)
```

SEQ ID NO 16:
DWSGYSGSFVQHPELTGLD
(longest conserved sequence; N1 and N5)

SEQ ID NO 17:
KSCINRCFYVELIRGR
(N3 conserved epitope)

SEQ ID NO 18:
FVIREPFISCSHLEC
(Pep 5; N1 and N5 conserved sialic acid
binding region)

Hemagglutinin Peptides
SEQ ID NO 19:
GNLFIAP
(Composite combining GNLIAP (SEQ ID NO: 50)
AND GNFIAP (SEQ ID NO: 49),
HA conserved epitopes of H1, H3 and H5)

SEQ ID NO 20:
WFIHHP
(H5)

SEQ ID NO 21:
WGVIHHP
(Composite combining WGVHHP (SEQ ID NO: 92)
AND

WGIHHP (SEQ ID NO: 91),
HA conserved epitopes)

SEQ ID NO 22:
DLWSYNAELLV
(Stem Peptide)

SEQ ID NO 23:
DIWTYNAELLV
(Stem Peptide)

Matrix Peptides M1 and M2e
SEQ ID NO 24:
SLLTEVETPIRNEWGLLTEVETPIR
(M1/M2e conserved region)

SEQ ID NO 25:
SLLTEVET
(highly conserved region M1/M2e)

SEQ ID NO 26:
ETPIRNE
(mostly M2e)

SEQ ID NO 27:
TEVETPIRNE
(M1/M2e)

SEQ ID NO 28:
SLLTEVETPIRNE
(M1/M2e)

SEQ ID NO 29:
SLLTEVETPIR
(M1/M2e)

HIV Peptides
(GP120 V3 Crown Variable Region Conserved
Peptides targeted by cross-clade
neutralizing Mabs)

SEQ ID NO 30:
RKSIHLGPGRAFY
(HIV1) UG1033

SEQ ID NO 31:
KKGIAIGPGRTLY
(HIV2) NY5

SEQ ID NO 32:
RKSIRIGPGQAFY
(HIV3) ZAM18

SEQ ID NO 33:
RKRIRVGPGQTVY
(HIV4) NDF

CORONAVIRUS EPITOPES WITH AND
WITHOUT T CELL EPITOPES
SEQ ID NO 34:
SLDQINVTFLDLEYEMKKLEESYQYIKANSKFIGITE
(spike protein with
tetanus toxoid T cell epitope)

SEQ ID NO 35:
WDYPKCDRAQYIKANSKFIGITE
(POL + tetanus T cell epitope)

SEQ ID NO 36:
WDYPKCDRASLDQINVTFLDLEYEMKKLEESYQYIKANSKFIGITE
(Cor POL + SP + Tet)

SEQ ID NO 37:
WDYPKCDRATEVETPIRNEHYEECSCYQYIKANSKFIGITE
(Cor POL-M2e-Flu NA-Tetanus T cell;
one coronavirus conserved epitope and
two Flu conserved epitopes
that is a broader pandemic vaccine)

CORONAVIRUS AND COMPOSITE CORONAVIRUS/
INFLUENZA EPITOPES
SEQ ID NO 38:
ARDLICAQ
(highly conserved cor seq-
spike attachment same is all three-Cor
MERS SARS)

SEQ ID NO 39:
ARDLICAQKWPWYIWLGFIAGLENQKLIAN
(combinations or conserved
seqs w/o T cell epitope)

SEQ ID NO 40:
ENQKLIANARDLICAQ
(combinations or conserved seqs
w/o T cell epitope)

SEQ ID NO 41:
WDYPKCDRAENQKLIANARDLICAQ
(combinations or conserved seqs w/o
T cell epitope)

SEQ ID NO 42:
WDYPKCDRAENQKLIANKWPWYIWLGFIAGL
(combinations or conserved
seqs w/o T cell epitope)

SEQ ID NO 43:
ARDLICAQENQKLIANWDYPKCDRAQYIKANSKFIGITE
(combinations of corona
(Cor) conserved seqs w/ T cell epitope)

SEQ ID NO 44:
KWPWYIWLGFIAGLWDYPKCDRAQYIKANSKFIGITEARDLICAQEN

QKLIANWDYPKCDRAQYIKANSKFIGITE
(combinations of Cor conserved seqs w/ T cell
epitope)

SEQ ID NO 45:
ARDLICAQENQKLIANQYIKANSKFIGITE ARDLICAQENQKLIAN

WDYPKCDRAQYIKANSKFIGITE
(combinations of Cor conserved seqs
w/ T cell epitope)

-continued

SEQ ID NO 46:
WDYPKCDRATEVETPIRNEHYEECSCY<ins>QYIKANSKFIGITE</ins>

ARDLICAQENQKLIANWDYPKCDRAQYIKANSKFIGITE
(combinations of Cor plus Influ
conserved seqs w/ T cell epitope; bold = Cor;
Italicized = m2e; Underlined = Flu;
Bold and underlined—T-cell SEQ ID NO 47:
HYEECSCYWDYPKCDRAVETPIRNEQYIKANSKFIGITE
(combinations of
Cor plus Influ conserved seqs w/ T cell epitope)

SEQ ID NO 48:
ENQKLIANTEVETPIRNEHYEECSCY<ins>QYIKANSKFIGITE</ins>
(combinations of
Cor plus Influ conserved seqs w/ T cell epitope)

OTHER EPITOPES AND COMPOSITE SEQUENCES
SEQ ID NO 49:
GNFIAP
(HA epitope; Pep 1)

SEQ ID NO 50:
GNLIAP
(HA epitope; Pep 2)

SEQ ID NO 51:
GNLIFAP
(composite sequence of HA epitopes
Pep 1 and 2)

SEQ ID NO 52:
LLTEVETPIR
(M1/M2e)

SEQ ID NO 53:
LLTEVETPIRN
(M1/M2e)

SEQ ID NO 54:
LLTEVETPIRNE
(M1/M2e)

SEQ ID NO 55:
DWSGYSGSFVQHPELTGL
(NA epitope of H1 and N5 serotypes)

SEQ ID NO 56:
EVETPIRNE
(M1/M2e)

SEQ ID NO 57:
FLLPEDETPIRNEWGLLTDDETPIRYIKANSKFIGITE

SEQ ID NO 58:
GNLFIAPGNLFIAPHYEECSCYHYEECSCYQYIKANSKFIGITEHY

EECSCYTPIRNETPIRNE
(composite of HA epitopes and T cell epitope)

SEQ ID NO 59:
GNLFIAPGNLFIAPQYIKANSKFIGITEGNLFIAP
(composite of HA epitopes
and T cell epitope)

SEQ ID NO 60:
HYEECSCYDWSGYSGSFVQHPELTGLHYEECSCYQYIKANSKFI

GITE

SEQ ID NO 61:
ITGFAPFSKDNSIRLSAGGDIWVTREPYVSCDP

SEQ ID NO 62:
IWGIHHP
(HA epitope)

SEQ ID NO 63:
IWGVHHP
(HA epitope)

SEQ ID NO 64:
IWGVIHHP
(composite of HA epitopes)

SEQ ID NO 65:
IWGIVHHP
(composite of HA epitopes)

SEQ ID NO 66:
LLTEVETPIRNESLLTEVETPIRNEWG
(M2e epitope)

SEQ ID NO 67:
LLTEVETPIRNEW
(M2e epitope)

SEQ ID NO 68:
LLTEVETPIRNEWG
(M2e epitope)

SEQ ID NO 69:
LTEVETPIRNE
(M2e epitope)

SEQ ID NO 70:
LTEVETPIRNEW
(M2e epitope)

SEQ ID NO 71:
LTEVETPIRNEWG
(M2e epitope)

SEQ ID NO 72:
MSLLTEVET
(M2e epitope)

SEQ ID NO 73:
MSLLTEVETP
(M2e epitope)

SEQ ID NO 74:
MSLLTEVETPI
(M2e epitope)

SEQ ID NO 75:
MSLLTEVETPIR
(M2e epitope)

SEQ ID NO 76:
MSLLTEVETPIRN
(M2e epitope)

SEQ ID NO 77:
MSLLTEVETPIRNE
(M2e epitopes)

SEQ ID NO 78:
MSLLTEVETPIRNETPIRNE
(M2e epitope)

SEQ ID NO 79:
MSLLTEVETPIRNEW
(M2e epitope)

SEQ ID NO 80:
MSLLTEVETPIRNEWG
(M2e epitope)

SEQ ID NO 81:
MSLLTEVETPIRNEWGCRCNDSSD
(M2e epitope)

-continued

SEQ ID NO 82:
SLLTEVETPIRNEW
(M2e epitope)

SEQ ID NO 83:
SLLTEVETPIRNEWG
(M2e epitope)

SEQ ID NO 84:
SLLTEVETPIRNEWGTPIRNE
(M2e epitope)

SEQ ID NO 85:
SLLTEVETPIRNEWGTPIRNETPIRNE
(M2e epitope)

SEQ ID NO 86:
SLLTEVETPIRNEWGTPIRNETPIRNETPIRNE
(M2e epitopes)

SEQ ID NO 87:
SLLTEVETPIRNEWGLLTEVETPIRQYIKANSKFIGITE
(M2e epitope)

SEQ ID NO 88:
TPIRNE
(M1/M2e)

SEQ ID NO 89:
VETPIRNE
(M1/M2e)

SEQ ID NO 90:
VTREPYVSCDPKSCINRCFYVELIRGRVTREPYVSCDPWYIK
ANSKFIGITE

SEQ ID NO 91:
WGIHHP
(HA conserved region; Pep 5)

SEQ ID NO 92:
WGVHHP
(HA conserved region; Pep 4)

SEQ ID NO 93:
WGIVHHP
(composite of HA epitopes; Pep 7)

SEQ ID NO 94:
YIWGIHHP
(HA epitope)

SEQ ID NO 95:
YIWGVHHP
(HA epitope)

SEQ ID NO 96:
YIWGVIHHP
(composite of HA epitopes)

SEQ ID NO 97:
YIWGIVHHP
(composite of HA epitopes)

SEQ ID NO 98:
QYIKANSKFIGITE
(T cell epitope)

SEQ ID NO 99:
PIRNEWGCRCNDSSD

SEQ ID NO 100:
GNLFIAPWGVIHHPHYEECSCY
(composite of HA and NA epitopes; Pep 11)

SEQ ID NO 101:
WGVIHHPGNLFIAPHYEECSCY
(composite of NA and HA epitopes)

SEQ ID NO 102:
SRPGLPVEYLQVPSPSMGRDIKVQFQSGGANSPALYLLDG

LRAQDDFSGWDINTPAFEWYDQSGLSVVMPVGGQSSFYSD

WYQPACGKAGCQTYKWETFLTSELPGWLQANRHVKPTGSA

VVGLSMAASSALTLAIYHPQQFVYAGAMSGLLDPSQAMGP

TLIGLAMGDAGGYKASDMWGPKEDPAWQRNDPLLNVGKLI

ANNTRVWVYCGNGKPSDLGGNNLPAKFLEGFVRTSNIKFQ

DAYNAGGGHNGVFDFPDSGTHSWEYWGAQLNAMKPDLQRA

LGATPNTGPAPQGA
(TB coding region sequence of 85a; Pep 64)

SEQ ID NO 103:
SEFAYGSFVRTVSLPVGADEGNLFIAPWGVIHHPHYEECS

CYSRPGLPVEYLQVPSPSMGRDIKVQFQSGGANSPALYLL

DGLRAQDDFSGWDINTPAFEWYDQSGLSVVMPVGGQSSFY

SDWYQPACGKAGCQTYKWETFLTSELPGWLQANRHVKPTG

SAVVGLSMAASSALTLAIYHPQQFVYAGAMSGLLDPSQAM

GPTLIGLAMGDAGGYKASDMWGPKEDPAWQRNDPLLNVGK

LIANNTRVWVYCGNGKPSDLGGNNLPAKFLEGFVRTSNIK

FQDAYNAGGGHNGVFDFPDSGTHSWEYWGAQLNAMKPDLQ

RALGATPNTGPAPQGA
(336 amino acid sequence comprising HSPx,
Pep 11 and TB 85a)

SEQ ID NO 104:
GNLIAPWGVIHHP
(HA epitopes)

SEQ ID NO 105:
GNLFIAPWGVIHHP
(HA epitopes)

SEQ ID NO 106:
GNLFIAPWGVIHHPGNLFIAPWGVIHHP
(HA epitopes)

SEQ ID NO 107:
HYEECSCYGNLFIAPWGVIHHP
(HA epitopes)

SEQ ID NO 108:
GNLFIAPHYEECSCYWGVIHHP
(HA epitopes)

SEQ ID NO 109:
GNLFIAPRYAFA
(HA epitopes)

SEQ ID NO 110:
GNLVVPRYAFA
(HA epitopes)

SEQ ID NO 111:
GNLIAPRYAFA
(HA epitopes)

SEQ ID NO 112:
GNLVVP
(HA epitopes)

-continued

SEQ ID NO 113:
GNLFIAPWGVIHHPHYEECSCYQYIKANSKFIGITE
(Pep 11 with C
terminal T cell epitope+ = Pep 63)

SEQ ID NO 114:
QYIKANSKFIGITEGNLFIAPWGVIHHPHYEECSCY
(Pep 11 with N
terminal T cell epitope+ = Pep 64)

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. An immunogenic peptide containing a plurality of microbial epitopes, wherein the plurality comprises one or more epitopes of a *Mycobacterium* and one or more epitopes of an influenza virus wherein the plurality is contained in a contiguous peptide sequence, and the immunogenic peptide contains one or more sequences selected from the group consisting of SEQ ID NOs. 3-8, 15, 20, 22-24, 29, 37, 46-48, and 61.

2. The peptide of claim 1, wherein the one or more influenza virus epitopes are selected from the group consisting of epitopes of an HA protein, an NA protein, an M1 protein, an M2 protein, an M2e protein of the influenza virus, and fragments, derivatives, and modifications thereof.

3. The peptide of claim 1, wherein the one or more epitopes of a *Mycobacterium* are selected from the group consisting of epitopes of a peptidoglycan, a mycolic acid, a heat shock protein, a cell surface protein, an internal antigen, a lipoarabinomannan, and fragments, derivatives, and modifications thereof.

4. The peptide of claim 1, which comprises at least one T cell stimulating epitope.

5. The peptide of claim 4, wherein the T cell stimulating epitope is an epitope of tetanus toxin, tetanus toxin heavy chain proteins, diphtheria toxoid, CRM, recombinant CRM, tetanus toxoid, *Pseudomonas* exoprotein A, *Pseudomonas aeruginosa* toxoid, *Bordetella pertussis* toxoid, *Clostridium perfringens* toxoid, *Escherichia coli* heat-labile toxin B subunit, *Neisseria meningitidis* outer membrane complex, Hemophilus *influenzae* protein D, Flagellin Fli C, Horseshoe crab Haemocyanin, and/or a fragment, derivative, or modification thereof.

6. The peptide of claim 4, wherein the T cell stimulating epitope is at the N-terminus of the peptide.

7. The peptide of claim 4, wherein the T cell stimulating epitope is at the C-terminus of the peptide.

8. The peptide of claim 4, wherein the T cell stimulating epitope is at an internal region of the peptide.

9. A composition comprising the peptide of claim 1 and a pharmaceutically acceptable diluent, excipient, or carrier.

10. The composition of claim 9, further comprising an adjuvant.

11. The composition of claim 10, wherein the adjuvant is selected from the group consisting of Freund's, a liposome, saponin, lipid A, squalene, and derivatives and combinations thereof.

12. A vaccine comprising the peptide of claim 1.

13. An immunogenic peptide containing a plurality of microbial epitopes, wherein the plurality comprises one or more epitopes of peptidoglycan of a *Mycobacterium* and one or more epitopes of a neuraminidase protein of an influenza virus wherein the plurality is contained in a contiguous peptide sequence, and the immunogenic peptide contains one or more sequences selected from the group consisting of SEQ ID NOs. 3, 4, 15, 37, 46, 47, and 48.

14. An immunogenic peptide containing a plurality of microbial epitopes, wherein the plurality comprises one or more epitopes of a heat shock protein of a *Mycobacterium* and one or more epitopes of a matrix protein of an influenza virus wherein the plurality is contained in a contiguous peptide sequence, and the immunogenic peptide contains one or more sequences selected from the group consisting of SEQ ID NOs. 20, 24, 29, 37, 46, and 61.

15. An immunogenic peptide containing as a contiguous sequence a sequence selected from the group consisting of SEQ ID NOs. 113 and 114.

16. A composition containing the peptide of claim 15 plus a pharmaceutically acceptable diluent, excipient, or carrier.

17. The composition of claim 15, further comprising an adjuvant.

18. The composition of claim 17, wherein the adjuvant is selected from the group consisting of Freund's, a liposome, saponin, lipid A, squalene, and derivatives and combinations thereof.

* * * * *